(12) United States Patent
Nakatani

(10) Patent No.: US 10,766,937 B2
(45) Date of Patent: Sep. 8, 2020

(54) COMPOSITIONS AND METHODS OF TREATING CANCER

(75) Inventor: Yoshihiro Nakatani, Chestnut Hill, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 384 days.

(21) Appl. No.: 14/343,022

(22) PCT Filed: Sep. 6, 2012

(86) PCT No.: PCT/US2012/053959
§ 371 (c)(1),
(2), (4) Date: May 21, 2014

(87) PCT Pub. No.: WO2013/036636
PCT Pub. Date: Mar. 14, 2013

(65) Prior Publication Data
US 2015/0045308 A1 Feb. 12, 2015

Related U.S. Application Data

(60) Provisional application No. 61/531,433, filed on Sep. 6, 2011.

(51) Int. Cl.
*C07K 14/47* (2006.01)
*A61K 38/00* (2006.01)

(52) U.S. Cl.
CPC ...... *C07K 14/4747* (2013.01); *C07K 14/4702* (2013.01); *A61K 38/00* (2013.01)

(58) Field of Classification Search
None
See application file for complete search history.

(56) References Cited

U.S. PATENT DOCUMENTS 5,596,072 A   1/1997   Culpepper et al.
7,067,646 B2 *  6/2006   Nakatani ............ 536/23.5

OTHER PUBLICATIONS

EMBL Database (Accession No. AK302623, retrieved from http://www.ebi.ac.uk/Tools/dbfetch/emblfetch?style=html&id=AK302623&Submit=Go, last updated Jul. 24, 2008).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Wakamatsu et al., Database EMBL, Database accession No. AK302623, Jul. 24, 2008, abstract.
"SubName: Full=E3 ubiquitin-protein ligase UBR4, SubName: Full=CDNA FLJ53484, highly similar to *Homo sapiens* ubiquitin protein ligase E3 component n-recognin 4 (UBR4), mRNA"; retrieved from EBI accession No. B4DYV5 sequence.
Nakatani Yoshihiro et al.: "p600, a unique protein required for membrane morphogenesis and cell survival", *Proceedings of the National Academy of Science of the United States of America*, vol. 102, No. 42, Oct. 2005, pp. 15093-15098, abstract.
Sakai Hiroshi et al., "Inhibition of p600 Expression Suppresses Both Invasiveness and Anoikis Resistance of Gastric Cancer", *Annals of Surgical Oncology*, Springer-Verlag, NE, vol. 18, No. 7, Feb. 24, 2011, pp. 2057-2065.
DeMasi Joseph et al., "Bovine papillomavirus E7 transformation function correlates with cellular p600 protein binding", *Proceedings of the National Academy of Sciences of the United States of America*, vol. 102, No. 32, Aug. 2005, pp. 11486-11491.
Huh Kyung-Won et al., "Association of the human papillomavirus type 16 E7 oncoprotein with the 600-kDa retinoblastoma protein-associated factor, p600", *Proceedings of the National Academy of Sciences of the United States of America*, vol. 102, No. 32, Aug. 2005, pp. 11492-11497.
Moody Cary et al., "Human papillomavirus oncoproteins: pathways to transformation", *Nature Reviews Cancer*, vol. 10, No. 8, Aug. 2010, pp. 550-560.
International Search Report issued for application No. PCT/US2012/053959, dated Feb. 18, 2013.

* cited by examiner

*Primary Examiner* — Brian Gangle
*Assistant Examiner* — Andrea K McCollum
(74) *Attorney, Agent, or Firm* — Baker Donelson

(57) ABSTRACT

The present invention provides compositions and methods of treating various disorders associated with aberrant cell growth.

9 Claims, 15 Drawing Sheets

Specification includes a Sequence Listing.

COMPOSITIONS AND METHODS OF TREATING CANCER

RELATED APPLICATIONS

This application is a national stage application, filed under 35 U.S.C. § 371, of International Application No. PCT/US2012/053959, filed Sep. 6, 2012, which claims the benefit of provisional application U.S. Ser. No. 61/531,433, filed on Sep. 6, 2011, the contents which are herein incorporated by reference in their entireties.

GOVERNMENT SUPPORT

This invention was made with government support under grant number R01 CA138866 awarded by The National Institutes of Health. The government has certain rights in the invention.

INCORPORATION OF SEQUENCE LISTING

The contents of the text file named "20363-061001WO_ST25.txt," which was created on Sep. 5, 2012 and is 317 KB in size, are hereby incorporated by reference in their entirety.

FIELD OF THE INVENTION

The present invention relates generally to fragments of p600 and their use in inducing cell death to treat proliferative disorders, such as cancer.

BACKGROUND OF THE INVENTION

Although chemotherapy has been responsible for curing many people of cancer in the latter half of the 20th century, there still remain a large number of patients whose tumors either show little response to treatment, or respond initially only to recur later. For these patients, the current treatments are clearly inadequate. Thus, a need exists for better treatments of cancer.

SUMMARY OF THE INVENTION

The invention is based upon the discovery that truncated forms of p600 induce cell death. Accordingly, the invention features p600 nucleic acid fragments between 700 and 3000 nucleotides in length. The nucleic acid encodes a polypeptide that when expressed in a cell induces cell death.

In some embodiments the fragment contains nucleic acid residues 1-2499 of SEQ ID NO: 1; 5041-7203 of SEQ ID NO: 1; 5317-6765 of SEQ ID NO: 1; 5317-7203 of SEQ ID NO: 1; 5317-8160 of SEQ ID NO: 1; 9685-11838 of SEQ ID NO: 1; 10075-11838 of SEQ ID NO: 1; 10249-12114 of SEQ ID NO: 1; 13438-15549 of SEQ ID NO: 1; or 13729-155549 of SEQ ID NO: 1.

In yet another embodiment the fragment contains nucleic acid residues 5590-7203 of SEQ ID NO: 1; 6049-6765 of SEQ ID NO: 1; 5590-6765 of SEQ ID NO: 1; 6049-7203 of SEQ ID NO: 1; 8851-10980 of SEQ ID NO: 1; 9685-10980 of SEQ ID NO: 1; 9685-10626 of SEQ ID NO: 1; 9685-11124 of SEQ ID NO: 1; 14098-15549 of SEQ ID NO: 1; or 13438-15360 of SEQ ID NO: 1.

In another embodiment the fragment contains nucleic acid residues 1915-3348 of SEQ ID NO: 1; 2227-3348 of SEQ ID NO: 1; 2449-3870 of SEQ ID NO: 1; 4687-5439 of SEQ ID NO: 1; 5317-6471 of SEQ ID NO: 1; 5317-6240 of SEQ ID NO: 1; 10075-10980 of SEQ ID NO: 1; 10138-10980 of SEQ ID NO: 1; 10249-10980 of SEQ ID NO: 1; 10603-11838 of SEQ ID NO: 1; 11089-12114 of SEQ ID NO: 1; 11728-13503 of SEQ ID NO: 1; 13051-14460 of SEQ ID NO: 1; 11728-13977 of SEQ ID NO: 1; 12181-14553 of SEQ ID NO: 1; 12181-13977 of SEQ ID NO: 1; 13438-14943 of SEQ ID NO: 1; 13438-15105 of SEQ ID NO: 1; or 13438-15228 of SEQ ID NO: 1.

Also included in the invention are polypeptides encoded by the nucleic acids of the invention.

The invention further provides compositions containing any of the nucleic acids and polypeptides of the invention and a pharmaceutically acceptable carrier. Optionally, the composition further contains a nanoparticle or a nanosphere.

Also included in the invention are methods of inducing cell death by contacting a cell with any of the nucleic acids and polypeptides or the invention. The cell is a cancer cell.

The invention provides methods of treating cancer in a subject in need thereof by administering to the subject any of the composition of the invention in an amount sufficient to induce death of a cancer cell.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1:
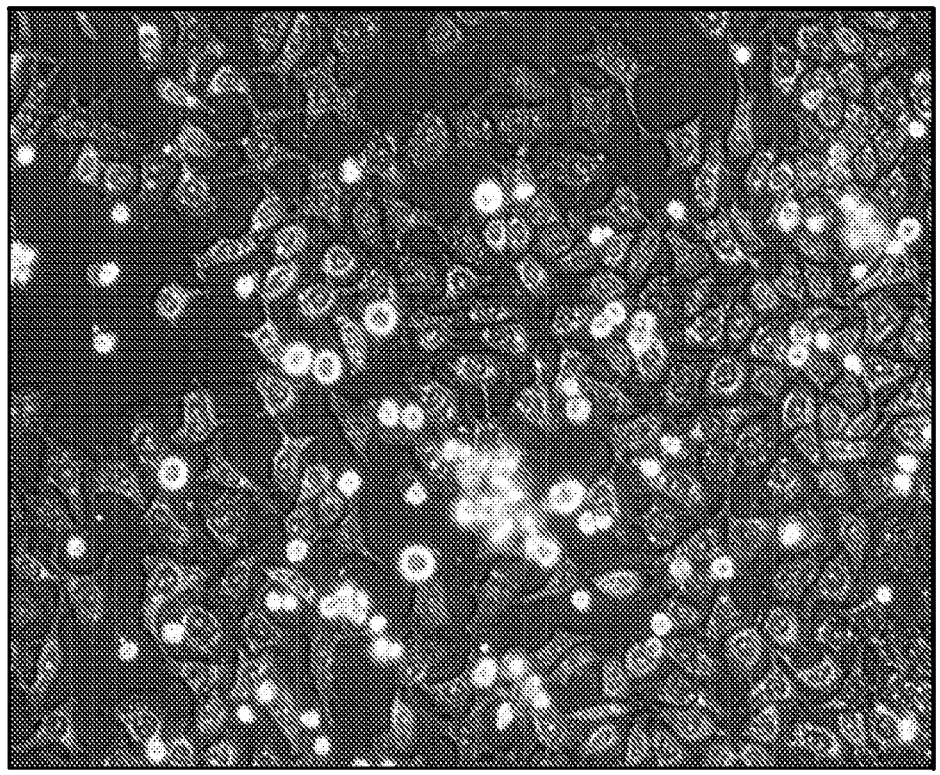
FIG. 1 is a series of photographs showing the effect of cell viability on HeLa cells treated with p600 shRNA.
Figure 1:
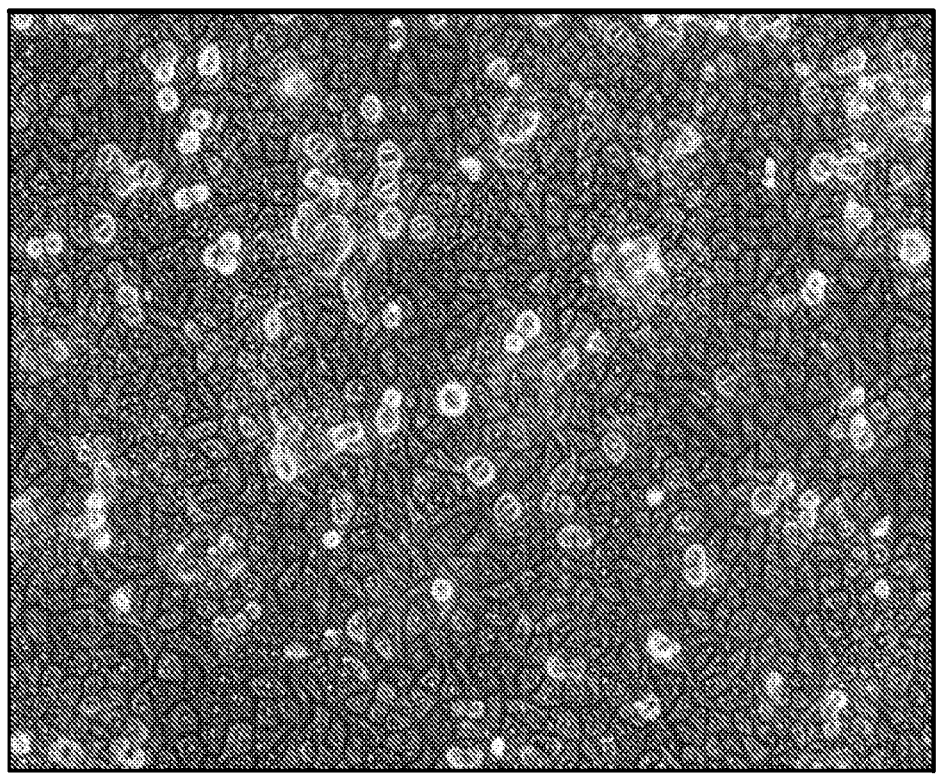
Figure 2:
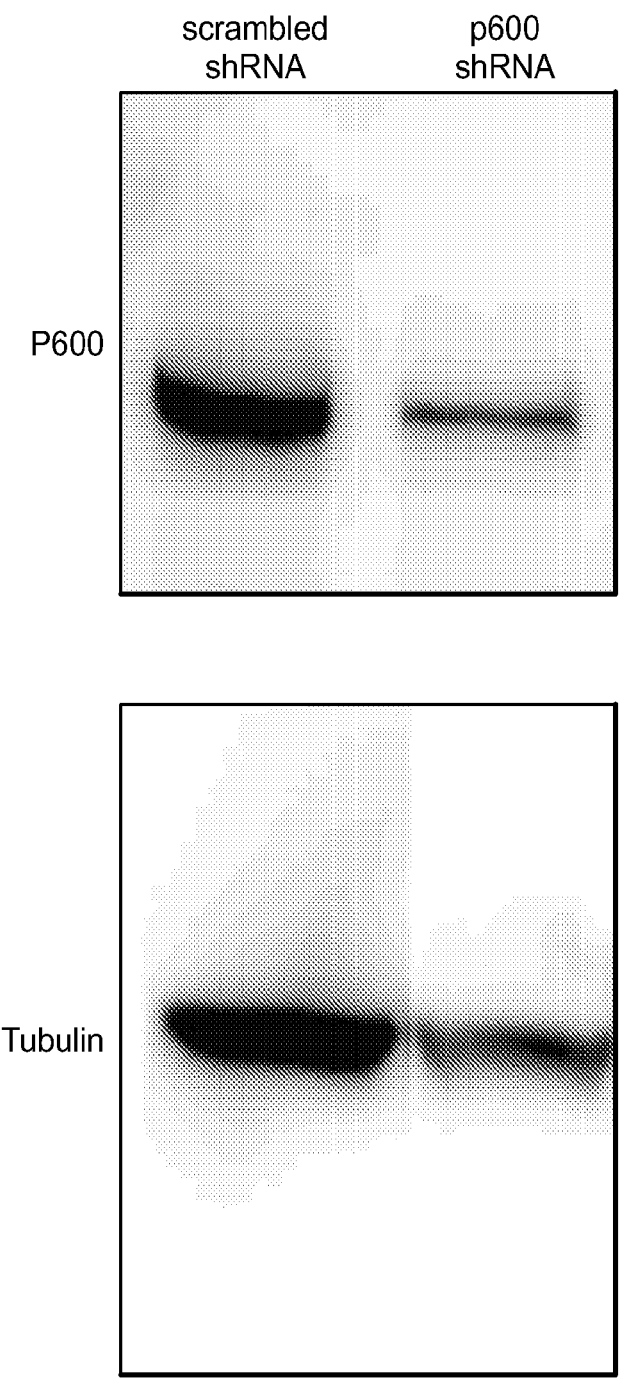
FIG. 2 is a photograph of a Western Blot showing decreased expression of p600 in HeLA cells treated with p600 shRNA
Figure 3:
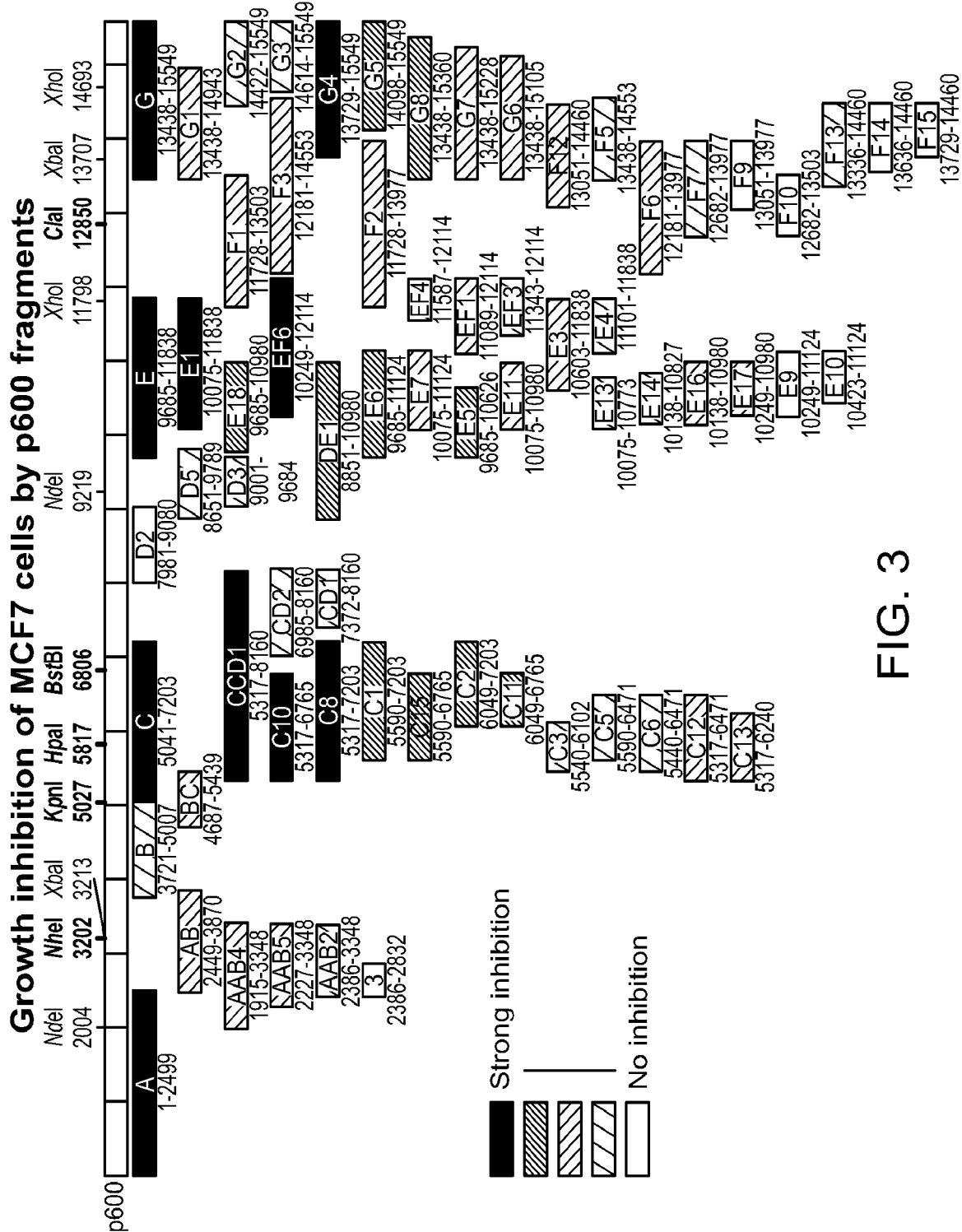
FIG. 3 is a schematic representation of the p600 produced and their effect on cell growth of HeLa cells.
Figure 4:
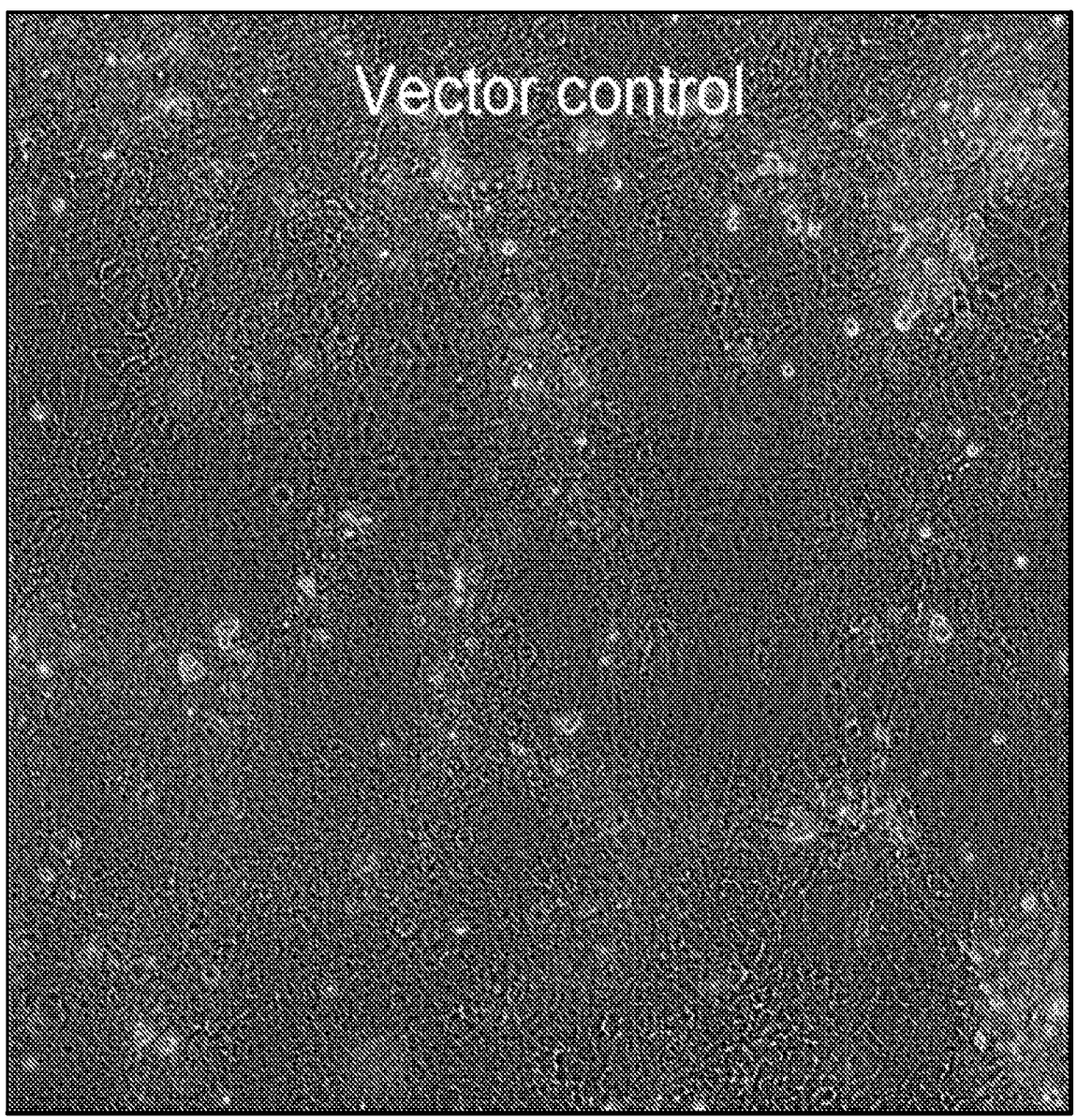
FIG. 4 is a photograph of MCF7 cells treated with a vector control
Figure 5:
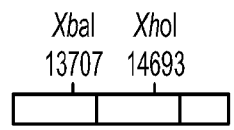
FIG. 5 is a photograph of MCF7 cells treated with p600 G7 fragment.
Figure 5:
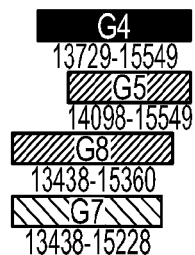
Figure 5:
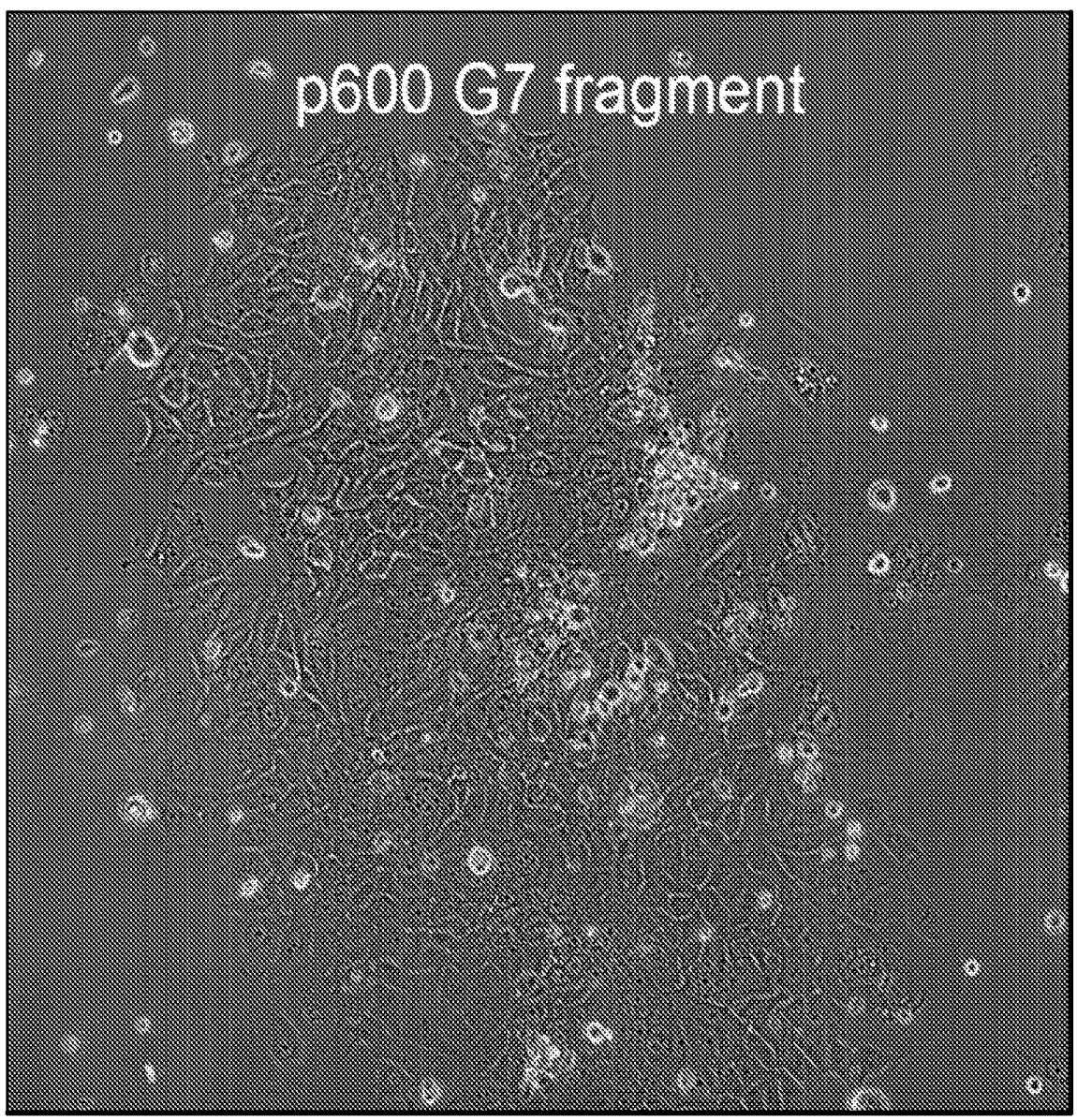
Figure 6:
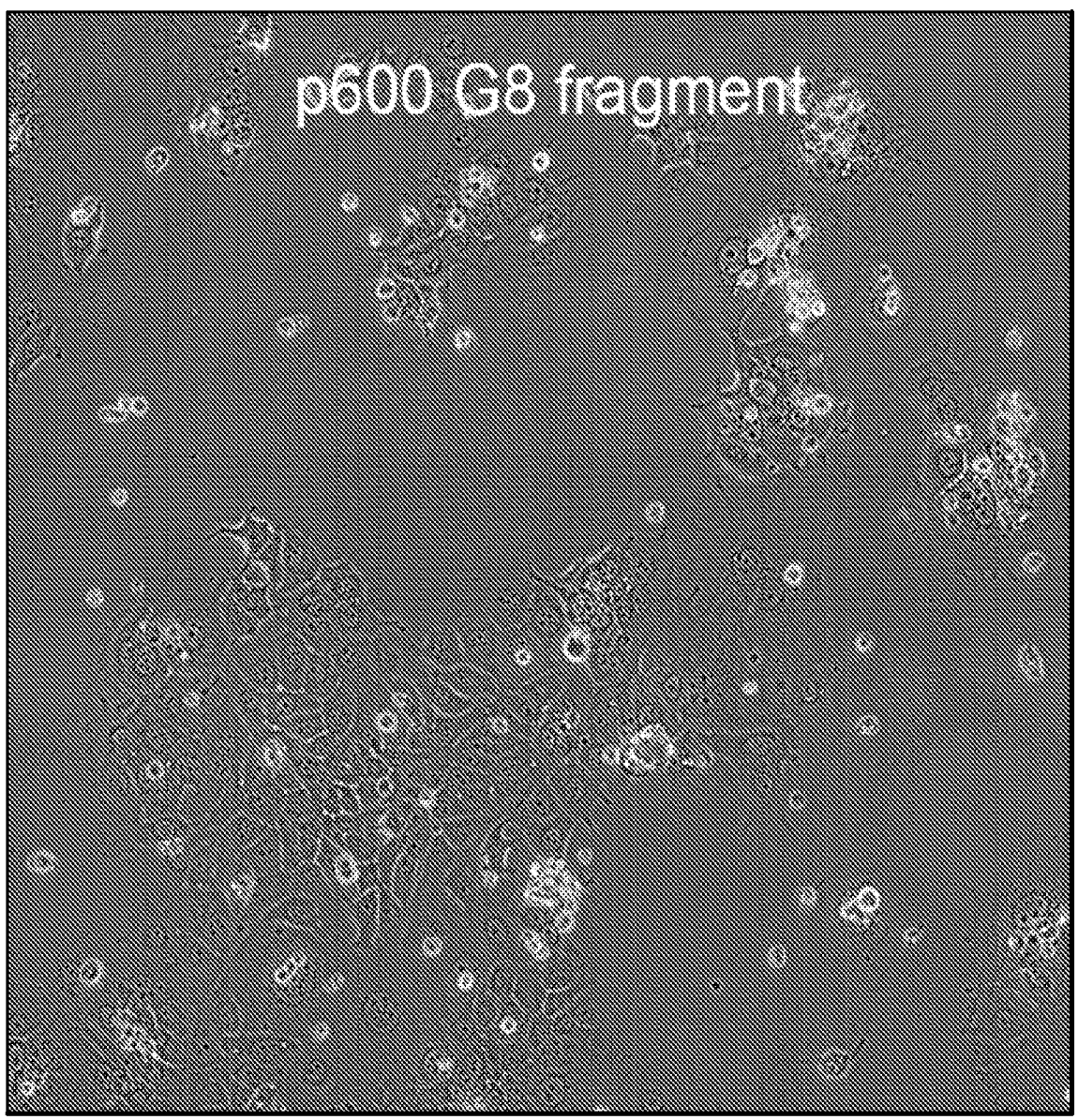
FIG. 6 is a photograph of MCF7 cells treated with p600 G8 fragment.
Figure 7:
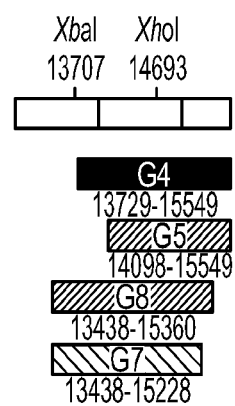
FIG. 7 is a photograph of MCF7 cells treated with p600 G5 fragment.
Figure 7:
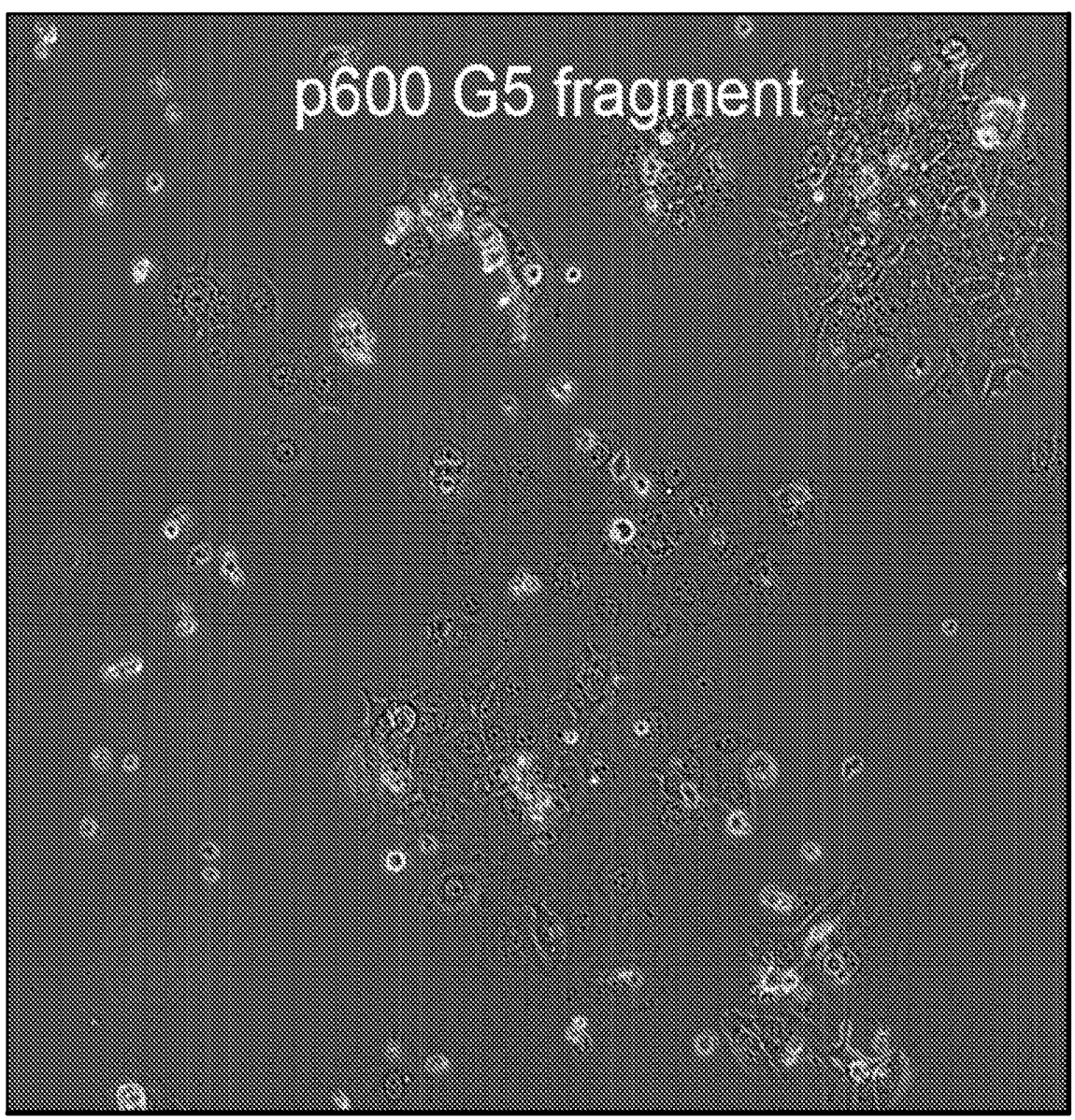
Figure 8:
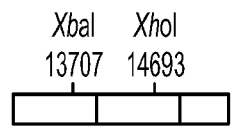
FIG. 8 is a photograph of MCF7 cells treated with p600 G4 fragment.
Figure 8:
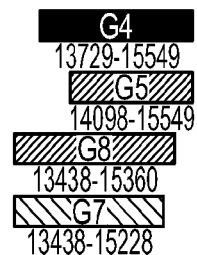
Figure 8:
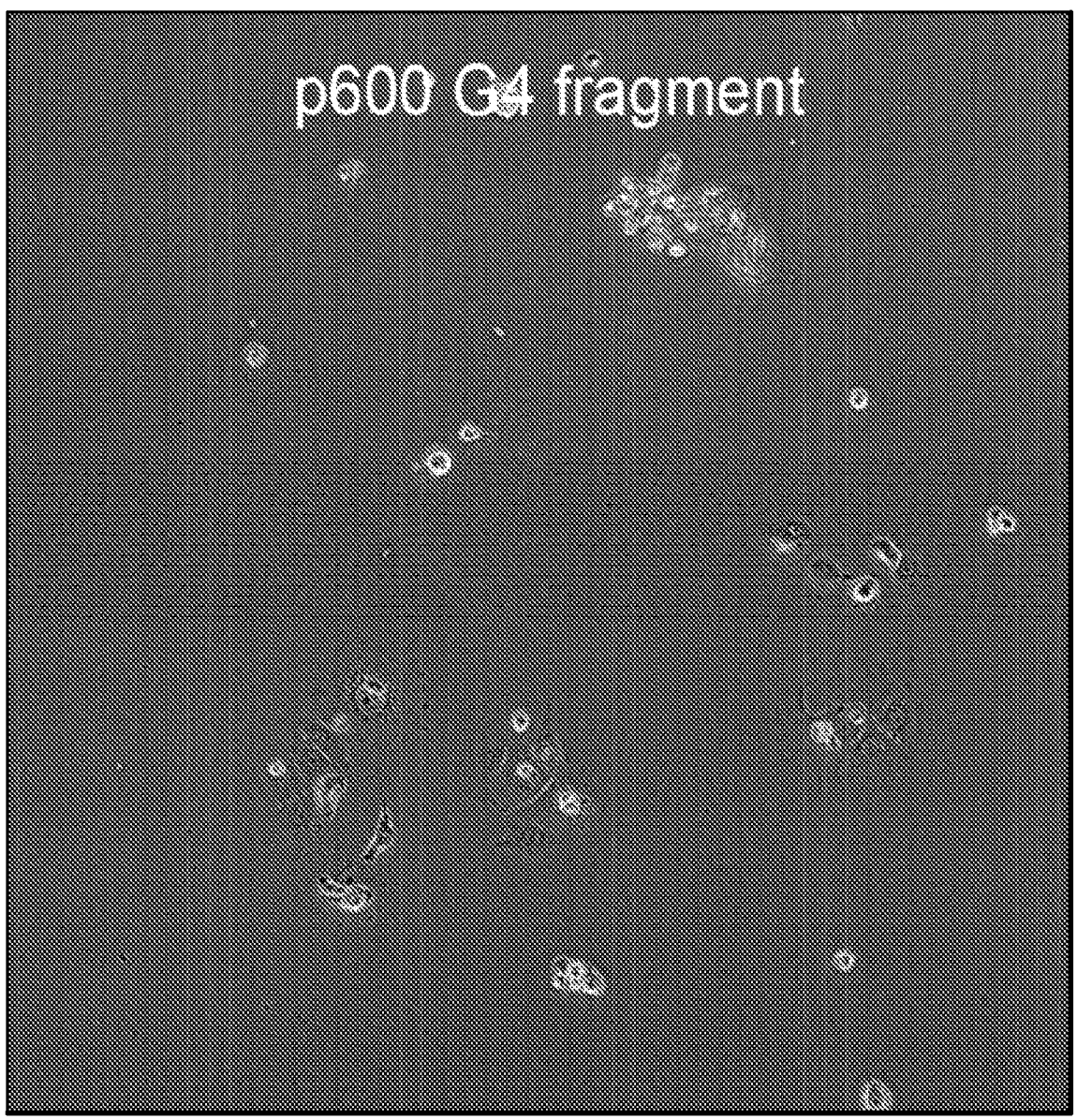
Figure 9:
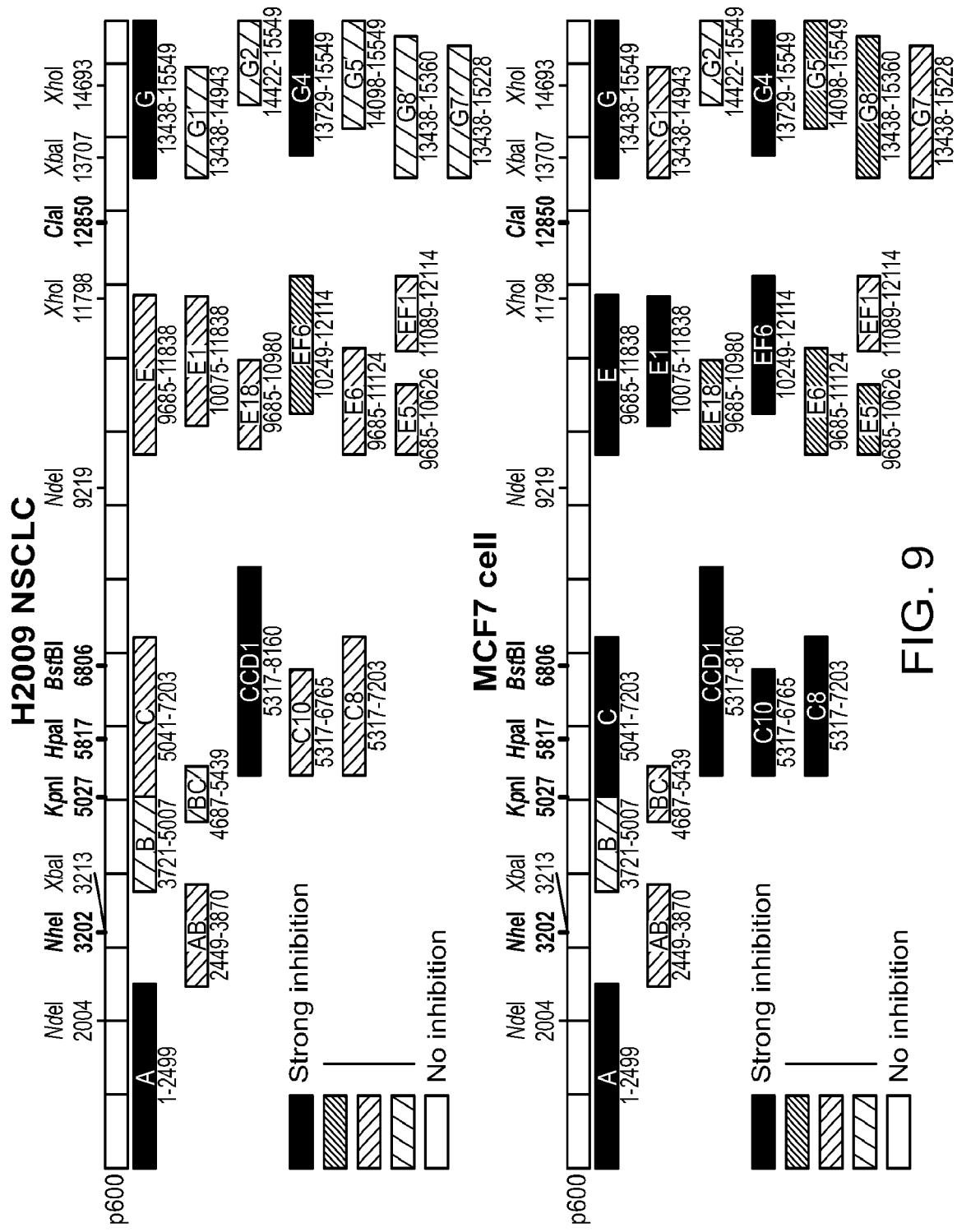
FIG. 9 is a schematic representation of the p600 produced and their effect on cell growth of H2009 NSCLC cells and MCF7 cells.
Figure 10:
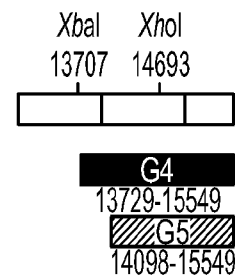
FIG. 10 is a photograph of H2009 NSCLC cells treated with a vector control.
Figure 10:
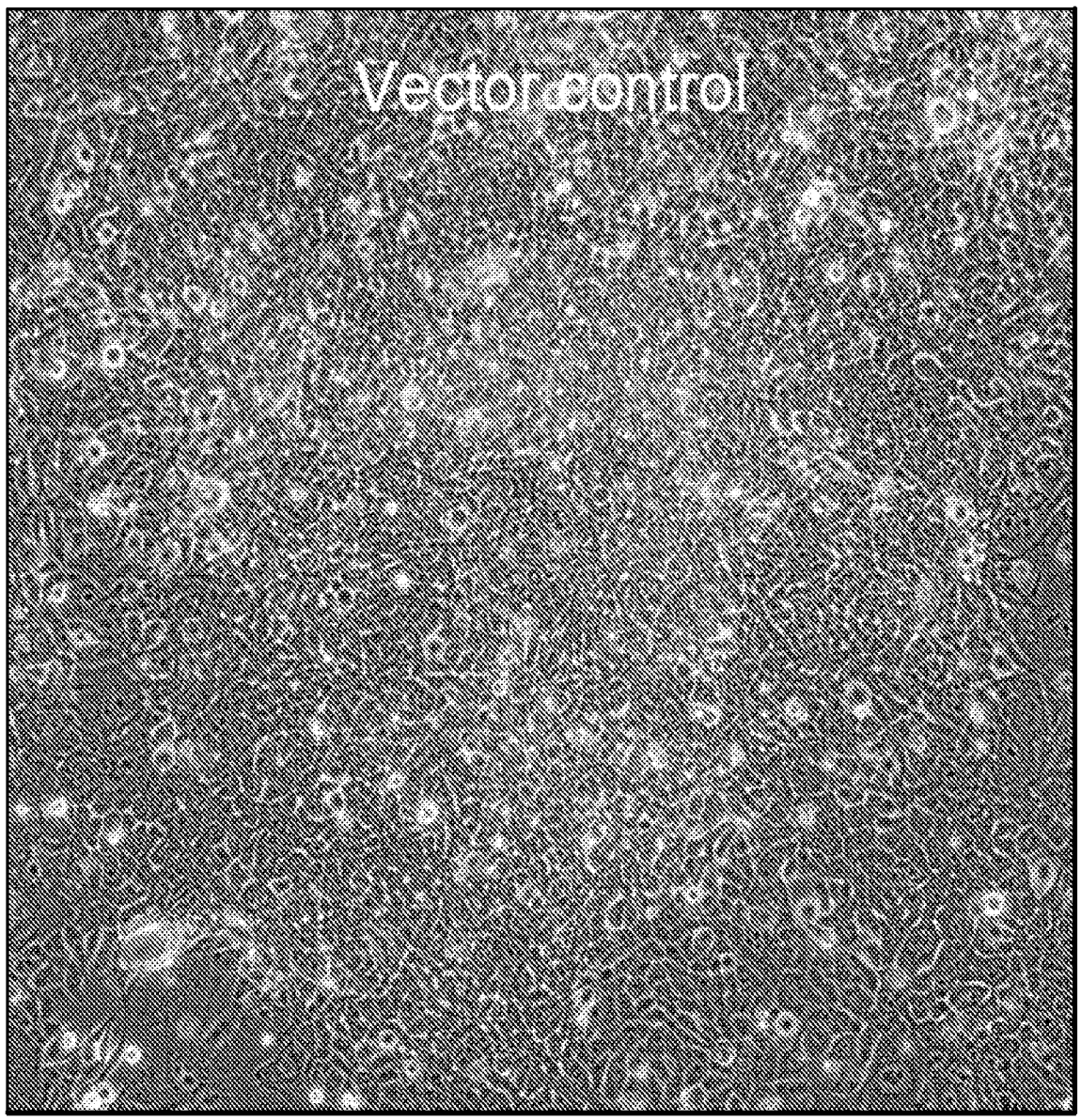
Figure 11:
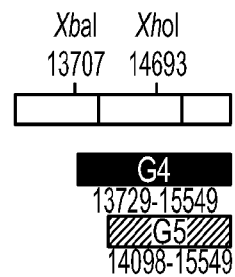
FIG. 11 is a photograph of H2009 NSCLC cells treated with p600 G5 fragment.
Figure 11:
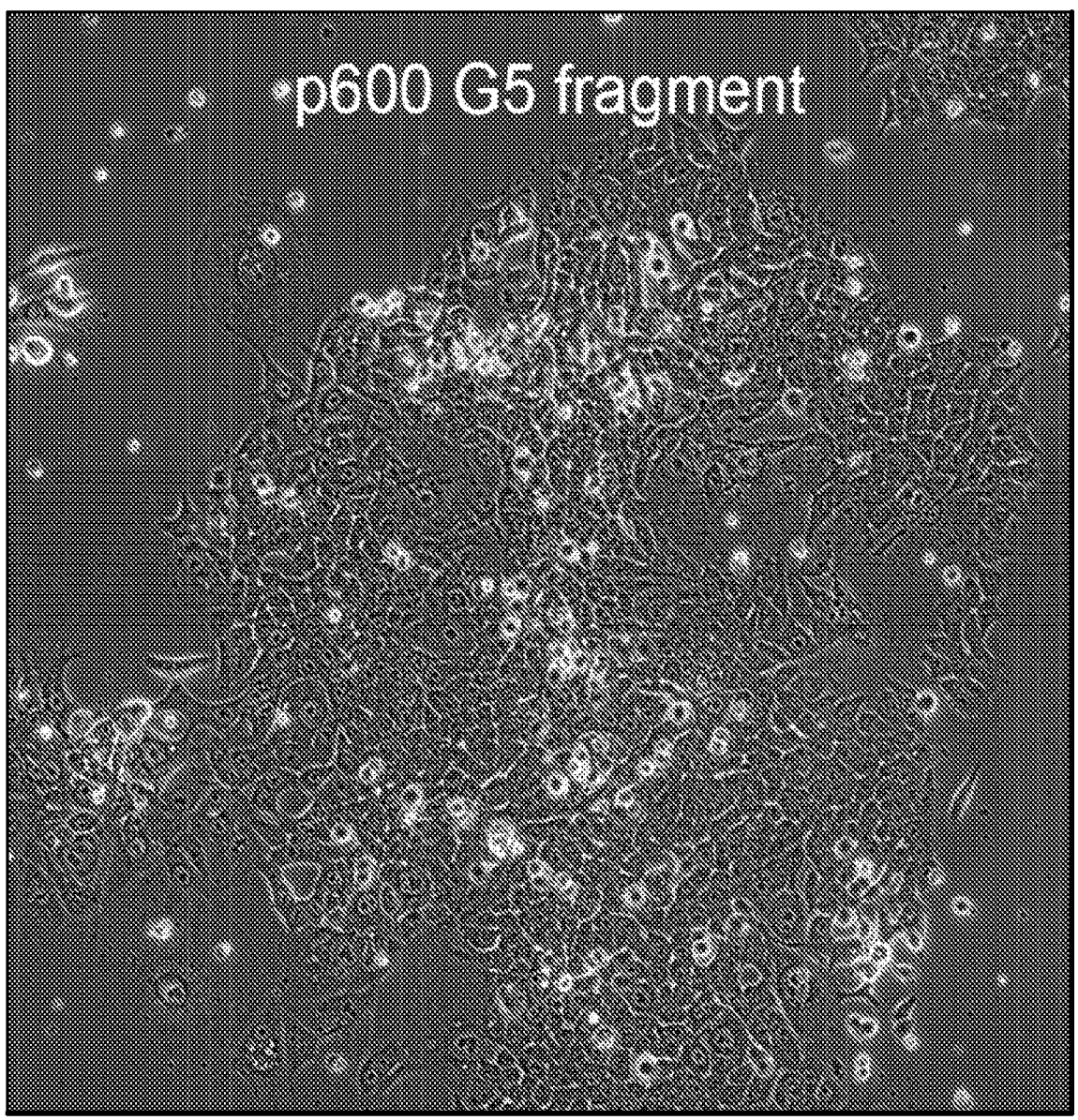
Figure 12:
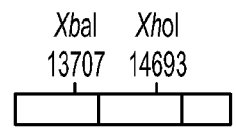
FIG. 12 is a photograph of H2009 NSCLC cells treated with p600 G4 fragment.
Figure 12:
Figure 12:
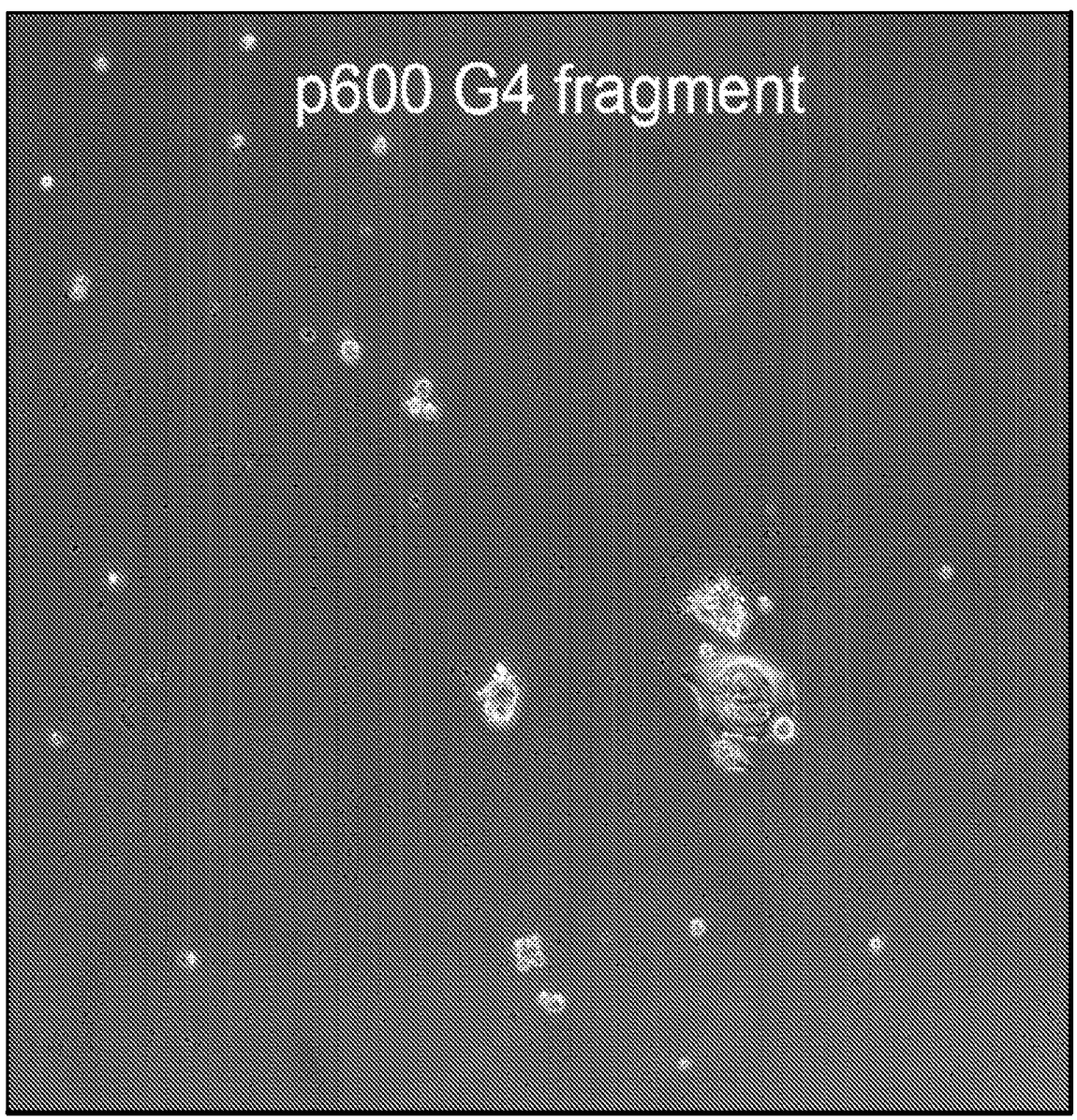
Figure 13:
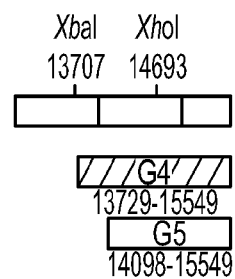
FIG. 13 is a photograph HMEC cells of treated with a vector control.
Figure 13:
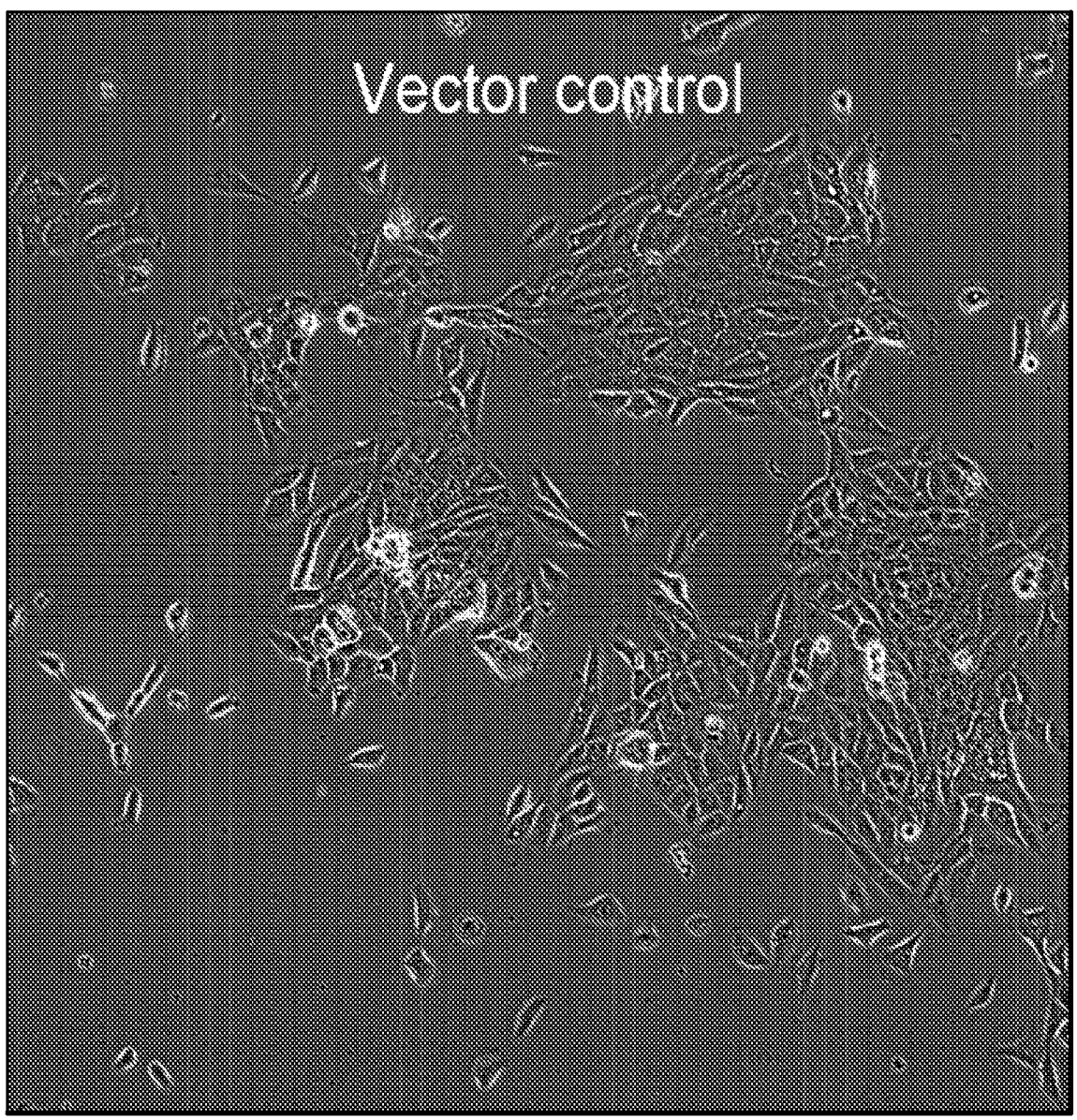
Figure 14:
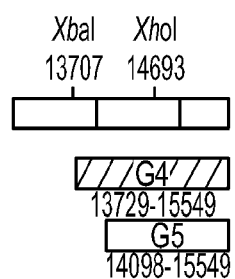
FIG. 14 is a photograph HMEC cells of treated with p600 G5 fragment.
Figure 14:
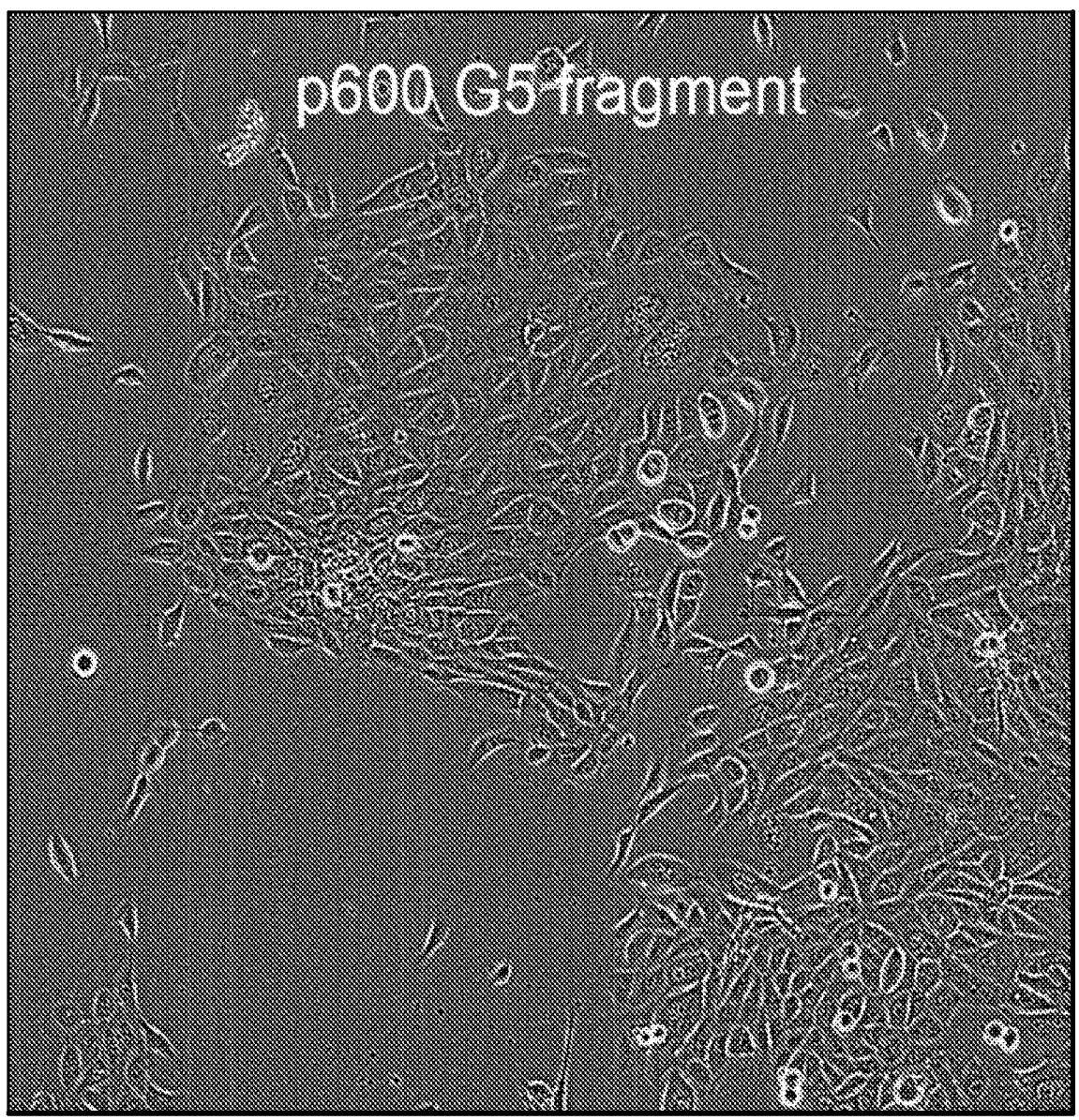
Figure 15:
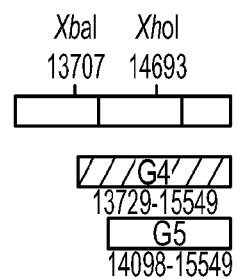
FIG. 15 is a photograph HMEC cells of treated with p600 G4 fragment.
Figure 15:
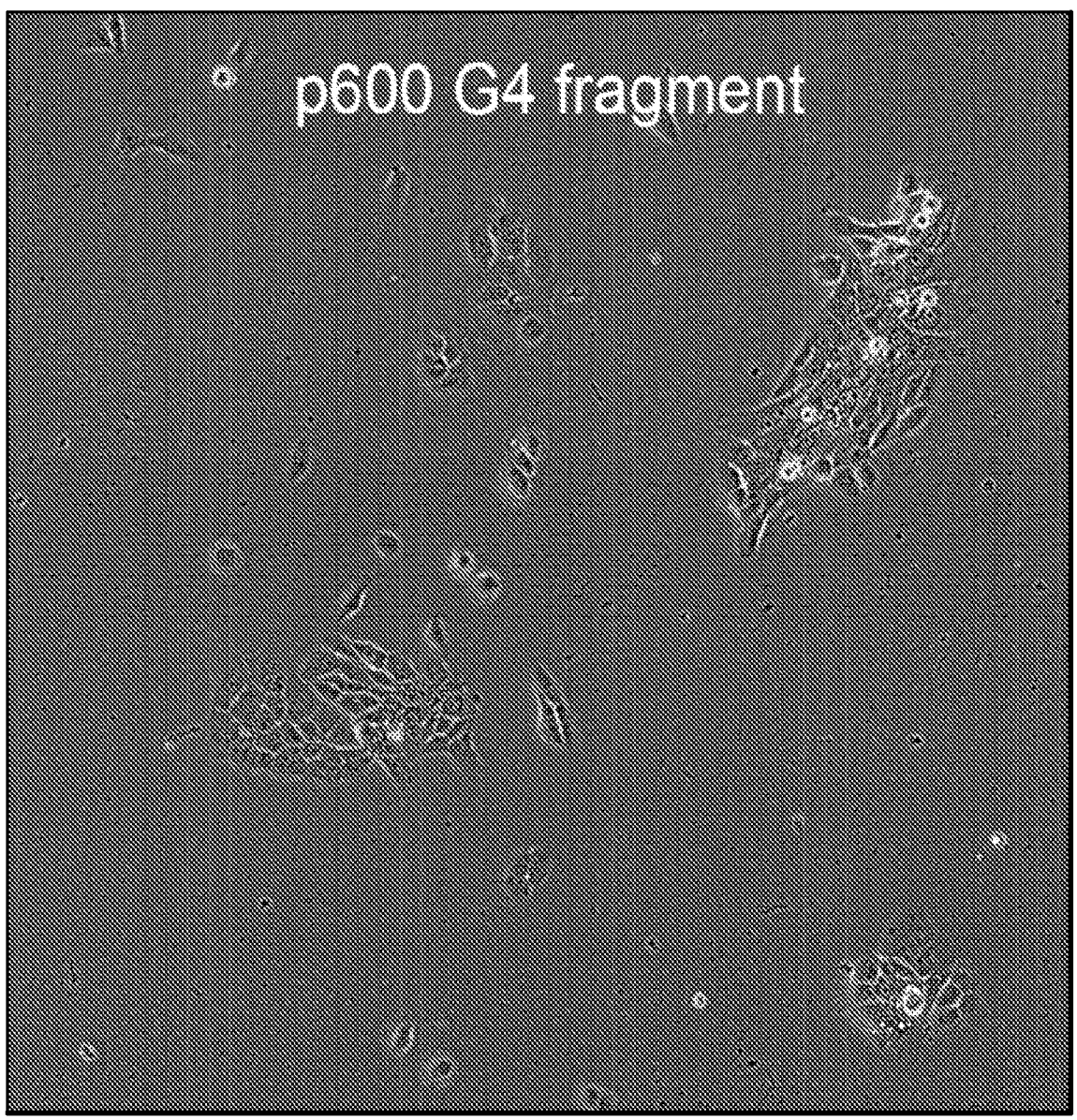

The invention is based in part upon the surprising discovery truncated forms of p600, induces cell death in various types of cancer cells. P600 is a cellular protein that is required for cell survival.

Accordingly, the invention features truncated p600 nucleic acids and polypeptides. The invention also features methods of inducing cell death and treating or alleviatiating a symptom of a cancer by contacting a cell or administering to a subject a truncated p600 nucleic acid or polypeptide.

Definitions

The term "polypeptide" refers, in one embodiment, to a protein or, in another embodiment, to a protein fragment or fragments or, in another embodiment, a string of amino acids. In one embodiment, reference to "peptide" or "polypeptide" when in reference to any polypeptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The term "DNA construct" and "vector" are used herein to mean a purified or isolated polynucleotide that has been artificially designed and which comprises at least two nucleotide sequences that are not found as contiguous nucleotide sequences in their natural environment.

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A cell in which the DNA has become integrated into the chromosome is called a "transformant". A "clone" is a population of cells derived from a single cell or common ancestor by mitosis. A "cell line" is a clone of a primary cell that is capable of stable growth in vitro for many generations (e.g., at least about 10).

The term "homology", when in reference to any nucleic acid sequence indicates a percentage of nucleotides in a candidate sequence that are identical with the nucleotides of a corresponding native nucleic acid sequence. Homology may be determined by computer algorithm for sequence alignment, by methods well described in the art. For example, computer algorithm analysis of nucleic acid or amino acid sequence homology may include the utilization of any number of software packages available, such as, for example, the BLAST, DOMAIN, BEAUTY (BLAST Enhanced Alignment Utility), GENPEPT and TREMBL packages.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological crossreactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, N.J., 1994; Sequence Analysis in Molecular Biology, von Heinje, G., Academic Press, 1987; and Sequence Analysis Primer, Gribskov, M. and Devereux, J., eds., M Stockton Press, New York, 1991).

The term "functional derivative" of a nucleic acid is used herein to mean a homolog or analog of the gene or nucleotide sequence. A functional derivative may retain at least a portion of the function of the given gene, which permits its utility in accordance with the invention. "Functional derivatives" nucleic acids and polypeptides as described herein are fragments, variants, analogs, or chemical derivatives that retain at least a portion of the apoptosis-specific activity Functional variants can also contain substitutions of similar amino acids that result in no change or an insignificant change in function. Amino acids that are essential for function can be identified by methods known in the art, such as site-directed mutagenesis or alanine-scanning mutagenesis (Cunningham et al. (1989) Science 244:1081-1085). The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al. (1992) J. Mol. Biol. 224:899-904; de Vos et al. (1992) Science 255:306-312).

A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different animal genus or species. An "analog" refers to a non-natural molecule substantially similar to or functioning in relation to the entire molecule, a variant or a fragment thereof.

Variant peptides include naturally occurring variants as well as those manufactured by methods well known in the art. Such variants can readily be identified/made using molecular techniques and the sequence information disclosed herein. Further, such variants can readily be distinguished from other proteins based on sequence and/or structural homology to the nucleic acid and polypeptides of the present invention. The degree of homology/identity present will be based primarily on whether the protein is a functional variant or non-functional variant, the amount of divergence present in the paralog family and the evolutionary distance between the orthologs.

In addition, functional variants of polypeptides can also contain substitution of similar amino acids that result in no change or an insignificant change in function. Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity or in assays.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

Thus, treating may include suppressing, inhibiting, preventing, treating, or a combination thereof. Treating refers inter alia to increasing time to sustained progression, expediting remission, inducing remission, augmenting remission, speeding recovery, increasing efficacy of or decreasing resistance to alternative therapeutics, or a combination thereof. "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

The "treatment of cancer or tumor cells", refers to an amount of peptide or nucleic acid, described throughout the specification, capable of invoking one or more of the following effects: (1) inhibition of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer to shrink or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma. Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. Examples of cancers also include metastasis from any of the cancers described herein.

A "proliferative disorder" is a disease or condition caused by cells which grow more quickly than normal cells, i.e., tumor cells. Proliferative disorders include benign tumors and malignant tumors. When classified by structure of the tumor, proliferative disorders include solid tumors and hematopoietic tumors.

The teems "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

By the term "modulate," it is meant that any of the mentioned activities, are, e.g., increased, enhanced, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

As used herein, the term "administering to a cell" (e.g., an expression vector, nucleic acid, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

Compositions for Inducing Cell Death

In one aspect the invention provides truncated p600 nucleic acids and polypeptides. The truncated p600 nucleic acids and polypeptides are capable of inducing cell death when expressed in a cell.

A p600 polypeptide and nucleic acid suitable for the production of truncated fragments of the invention is known in the art. A human p600 nucleic acid and polypeptide sequence includes SEQ ID NO: 1 and SEQ ID NO: 2 shown below.

```
P600 mRNA nucleotide sequence
                                                           (SEQ ID NO: 1)
atggcgacgagcggcggcgaagaggcggcggcagcggctccggcgccggggaccccggcaacggggcgga cacgaccccgggctggaggtggctgtgcggccctgctgtccgcgtcctactccgccttcgagatgaagg agttgccgcagctggtggcctcagtcatcgagagtgaatcagaaatcctgcaccatgagaagcagtacgag ccattctactcatcttttgttgcactttccacacactatattacaacagtttgcagtctcattccccggaa ccaacttcagtcagtggcagcagcctgtaaagttctaattgagttttctctcctgcgtctggagaatccag atgaggcttgtgctgtgtcccagaaacacttgattctcctaatcaagggcctgtgcactggctgtagccga ctagatagaactgaaattatcacatttacagcaatgatgaaatccgccaagctgccccaaacagtgaagac
```

-continued

```
actttcagacgtggaagatcagaaagagctggcctcaccagtaagccctgagttgaggcaaaaggaggtac
agatgaattttttgaaccagctgacctcagttttttaaccctagaactgtagcatcacaacctatcagtaca
cagactctggtggaaggagaaaatgatgagcagtcatctacagatcaagcctcagctatcaaaaccaagaa
tgtgttcatagctcagaacgtggctagtcttcaagagcttggtggctcggagaagctactgcgtgtatgtt
tgaacctgccatatttcctacgctatatcaatcggttccaagatgcagttttagctaattccttcttcata
atgcctgcaacagtagcagatgccactgctgttcgtaatggctttcattcattggtgattgatgtaactat
ggcattggatacccttctctacctgtgttggaacctctcaatccttctcgtctacaagatgtgacagtcc
tcagcctaagttgtctgtatgcaggtgtgagtgtggcaacgtgcatggccatcctccatgtgggtagtgcc
cagcaagtgcggacagggtccacgagctccaaagaagatgactatgaaagtgacgcagctacaattgtcca
gaaatgtctcgaaatctatgacatgattggacaagcaatcagcagttctcgcccgggctggtggtgagcact
atcagaatttccaattgctgggtgcttggtgcttgttaaacagccttttcctcatactgaacctcagtcct
actgcgttggctgataaggggaaagagaaggacccactggctgccctccgagtcagagacatcctttctcg
tactaaagagggagtgggctcccctaaactggggcctggaaaagggcatcagggatttggggtactctcag
taatattggcaaaccatgccatcaaactgctaacgtctctctttcaagacctacaagtggaggcccttcac
aagggttgggagacagatggcccccctgcagccttgagcattatggcccagagcacctccatacagaggat
tcaacggctgattgactctgtcccactgatgaacctgctcttgacgttactttcaacttcctacagaaagg
catgtgtcctgcagcggcagaggaaggctccatgagcagcgatgccagcgcctccaccgactccaatact
tactatgaggacgatttcagtagcacggaggaggacagcagccaagacgatgacagtgagcctatttggg
gcaatggtttgaggagactatttctcccagtaaagagaaagcagcacctccgcctcctcccccacctcctc
cactggaaagctctcctcgggttaaaagcccagtaagcaggcccctggtgagaagggcaacattctggcg
agtcgcaaagatcctgagttgttcttaggtctggcttccaacatttttgaacttcatcacctcttccatgct
gaactctcggaacaattttatccgaaactatctgagtgtatctctttcagaacaccatatggccaccctag
ccagtatcatcaaggaggtggacaaagatggactcaagggttcatcagatgaagagtttgctgcagctctc
tatcacttcaaccactcactggtaacctctgaccttcagtcacctaacctgcagaacacactgttgcagca
gctaggagtggctcctttttctgagggcccttggcccttgtacattcaccctcaaagcctctctgtgctttt
cacgcctcctgctcatctggcaacataaagccagtgctcaaggtgaccctgacgtcccagaatgccttaaa
gtttgggacaggttttttgtctacaatgaagcagaatgccctgcaaggtgtggtgcccagtgagacagagga
tctgaatgtagaacacctgcagatgctcctcctcattttccacaatttcaccgagacaggccggcgggcca
tattgtcgcttttttgtccagatcatccaggagttgagcgtcaacatggatgctcagatgcgcttcgtgccg
cttatcttggctcgcctccttctcatctttgattatctgcttcatcagtactccaaagcccctgtgtatct
atttgagcaggtacagcataacctgctaagtcctcccttttgggtgggcaagtggatcccaggacagcaaca
gccgccgggcaaccactcctctctatcatggattcaaagaagtagaagaaaactggtctaagcatttctca
tcagatgctgtcccacaccccagattctactgtgtcctgtccccagaagcctcagaggatgatttgaaccg
acttgattctgtggcatgtgacgtcctttttctccaagcttgtcaagtatgatgagctttatgctgcactga
cagccctgcttgcagctgggtcccagcttgatacagttaggagaaaggaaaacaagaatgtaacagccttg
gaggcctgtgcccttcaatattacttcttgatactgtggaggatcctaggaattttaccaccatcaaagac
ttacattaaccagctatccatgaactcacctgagatgagcgaatgtgacatcttgcacactctgcgatggt
cttctcggctccggatcagctcctatgtcaactggataaaggatcacctatcaaacagggaatgaaggct
gagcatgctagctcgcttctagaactggcatccaccactaagtgtagctcagtgaaatatgatgttgaaat
agtagaggaatacttcgctcgacagatctcatccttctgtagtatcgactgtaccaccatcttgcagctgc
atgaaattcccagtctgcagtccatctacacccttgatgccgcgatctcaaaggtccaggtctctttggat
```

-continued

```
gagcatttttctaagatggctgctgagactgatcctcataagtcgtctgagattaccaagaacctacttcc agccacgctgcaactcattgacacctatgcatcgttcaccagagcctatttgctgcaaaactttaatgaag agggaacaactgagaaaccttccaaggagaaactgcaaggctttgctgctgttttggctattggctctagc aggtgcaaggcaaatactctgggtccgacactggttcagaatttgccatcgtcagtgcagactgtgtgtga gtcctggaacaacatcaataccaatgaatttcccaatattggatcctggcgcaatgcctttgccaatgaca ccatcccttcagagagttatattagtgcagtgcaggctgcacacctggggactctctgtagccaaagtctg cccctggctgcttccctgaagcatacccctcctctcactggtcaggttgactggagatcttattgtttggtc agatgagatgaacccaccacaggtaattcggacactgctacctcttcttttggaatcaagcactgagagtg ttgccgagatcagtagcaactccctggaacgcatcttgggccctgctgagtctgatgagttcttggctcgt gtttatgagaagctgatcactggttgttacaacattctggccaatcatgcagatcctaacagtggactgga tgaatccatcctggaggaatgtctccagtacttggaaaagcagctggaaagtagccaggctcgtaaagcta tggaggagttttctctgacagtggagaacttgtacagatcatgatggcaacagccaatgagaacctctct gctaaattctgtaaccgagttttgaaattcttcaccaaactcttccagctgactgagaagagccctaaccc gagcctgttgcatctctgtggctccctggcacaactggcctgtgtggaacctgtgcgcctgcaggcctggc tcacccgcatgactacatcgcccccaaaagattctgatcagctggatgtaattcaggagaaccggcagctg ctgcagttactgaccacatacattgttcgggaaaacagccaagttggggaaggtgtgtgtgctgttcttct gggcaccctgactcccatggcaacagagatgctggccaacggtgatgggactggcttccctgaacttatgg ttgtgatggccactctggccagtgcaggtcaaggtgctggtcaccttcagcttcataatgctgctgtggat tggctgagcagatgcaagaaatacctgtcacagaagaatgtagttgaaaaactgaatgccaatgtaatgca tggaaagcatgtgatgatcttggagtgcacatgccatatcatgtcttacttggctgatgtcacgaatgccc tgagccagagtaatggtcaaggcccaagtcatctctcagtggatggggaagagcgggccattgaagtagac tcagactgggtggaggagttggcggtggaagaggaagattcccaggctgaggattcagatgaagattctct ttgcaataaactctgcacttttacgatcacacagaaagaattcatgaaccagcattggtaccactgtcaca cctgtaaaatggtggatggcgtgggtgtctgcacagtgtgtgctaaggtgtgccacaaggatcatgagatt tcctatgccaagtatggatccttcttctgtgactgtggagccaaggaagatggcagctgtttggctctggt gaagagaactcctagcagtggcatgagctctaccatgaaggagtcggcatttcagagtgaacccaggattt cagagagtctagtgcgtcatgccagcacctcctcgccagctgacaaagccaaggttaccatcagtgatgga aaggttgctgacgaagagaagcccaagaagagcagcctctgccgcacagtagagggctgccgggaggaatt acagaaccaggccaatttctccttcgctcctctcgtgttagacatgcttaatttccttatggatgccattc agaccaacttccagcaagcttcagccgtcgggagcagcagccgtgctcagcaagccctcagtgagctacac actgtggagaaggcagtggagatgacagaccagctgatggttcccaccttagggtcccaggaaggtgccctt tgagaatgtgcggatgaattacagtggagaccagggccagaccatccggcagctgatcagtgctcatgtgc tcaggcgggtggctatgtgtgtgctctcctctccccatgggcgccaacatttggctgtcagccatgag aagggcaagatcaccgttctgcagctctctgcactcctgaagcaagcagattccagcaaaaggaagttaac tctgacccgcttggcttctgccccagttcctttactgtgttgagcctcacaggaaatccctgcaaggaag actacttggcggtttgtgggctaaaggactgtcatgtgctcacctttagtagctcaggctctgtttcggat cacttggttttgcaccctcagttggcaacggggaacttcatcatcaaagccgtgtggttacctggttcaca gaccgagttatcaattgtcaccgcagactttgttaagatttatgacctgtgtgttgatgccttgagtccaa ccttctattttctcctgccaagctcaaagataagagatgttaccttccttttcaatgaggagggaaagaac atcattgttataatgtcttcggctgggtacatctatactcagcttatggaagaggccagcagtgcccagca
```

-continued

```
gggacccttctatgtcactaatgtgttggaaatcaatcatgaggacctgaaggacagtaacagccaggtgg
cgggcggtggtgtgtccgtgtactactcccacgtgttgcagatgttgttcttcagctattgtcaaggcaaa
tcattcgcagccaccatcagcaggacaaccctggaggtgttgcaactcttccccatcaacatcaaaagttc
caatggtggcagtaagacttctcctgctctttgccagtggtctgaggtgatgaaccaccctggcttggtgt
gctgtgtccagcaaactacaggggtgccgctggtagttatggtgaaaccagacacttttcttatccaggag
attaagactcttcctgctaaagcgaagatccaagacatggttgctattaggcacacggcctgcaatgagca
gcagcggacaacaatgattctgctgtgtgaggatggcagcctgcgcatttacatggccaacgtggagaaca
cctcctactggctgcagccatccctgcagcccagcagtgtcatcagcatcatgaagcctgttcgaaagcgc
aaaacagctacaatcacaacccgcacgtctagccaggtgactttccccattgacttttttgaacacaacca
gcagctgacagatgtggagtttggtggtaacgacctcctacaggtctataatgcacaacagataaaacacc
ggctgaattccactggcatgtatgtggccaacaccaagcccggaggcttcaccattgagattagtaacaac
aatagcactatggtgatgacaggcatgcggatccagattgggactcaagcaatagaacgggcccgtcata
tatcgagatcttcggcagaactatgcagctcaacctgagtcgctcacgctggtttgacttccccttcacca
gagaagaagccctgcaggctgataagaagctgaacctcttcattggggcctcggtggaaccagcaggtgtc
accatgatagatgctgtaaaaatttatggcaagactaaggagcagtttggctggcctgatgagcccccaga
agaattcccttctgcctctgtcagcaacatctgcccttcaaatctgaaccagagcaacggcactggagata
gcgactcagctgcccccactacgaccagtggaactgtcctggagaggctggttgtgagttctttagaagcc
ctggaaagctgctttgccgttggcccaatcatcgagaaggagagaaacaagaatgctgctcaggagctggc
cactttgctgttgtccctgccagcacctgccagtgtccagcagcagtccaagagccttctggccagcctgc
acaccagccgctcggcctaccacagccacaaggatcaggccttgctgagcaaagctgtgcagtgtctcaac
acatctagcaaagagggcaaggatttggaccctgaggtgttccagaggctagtgatcacagctcgctccat
tgccatcatgcgccccaacaaccttgtccactttacggagtcaaagctgccccagatggaaacagaaggaa
tggatgaagggaaggaaccgcagaagcagttggaaggagattgctgtagtttcatcacccagcttgtgaac
cacttctggaaactccatgcatccaaacccaagaatgccttcttggcacctgcctgccttccaggactaac
tcatattgaagctactgtcaatgctctggtggacatcatccatggctactgtacctgtgagctggattgta
ttaacacagcatccaagatctacatgcagatgctcttgtgtcctgatcctgctgtgagcttctcttgtaaa
caagctctaattcgagtcctaaggcccaggaacaaacggagacatgtgactttaccctcttcccctcgaag
caacactccaatgggagacaaggatgatgatgacgatgatgatgcagatgagaaaatgcagtcatcaggga
tcccgaatggtggtcacatccgtcaggaaagccaggaacagagtgaggtggaccatggagattttgagatg
gtgtctgagtcgatggtcctggagacagctgaaaatgtcaacaatggcaaccctctcccctggaggccct
gctggcaggcgcagagggcttccccccatgctggacatcccacctgatgcagatgacgagaccatggttg
aactagccattgccctgagcctgcagcaggaccaacaaggcagcagcagcagtgccctgggcctgcagagc
ctgggactgtccggccaggcacccagctcttcctctctggacgcaggaaccctctctgacaccacagcatc
agctccagcctcagacgacgagggcagtacagcagcgacagatggttctacccttcggacctctcctgctg
accacggtggtagtgtgggctcggagagcgggggcagtgcagtggactcagtggctggcgagcacagtgta
tctggccggagcagtgcttatggcgatgctacagctgaggggcatccggctggaccaggaagtgtcagctc
aagcactggagccatcagcaccaccactgggcaccaggagggagatggctccgagggagaagggagaaggag
aaactgaaggagatgtccacactagcaacaggctgcacatggtccgtctaatgctgttggagagattactg
cagaccctgcctcaattacgaaacgttggcggtgtccgggccatcccatacatgcaggtcattctaatgct
cactacagatctggatggagaagatgagaaagacaaggggggccctagacaacctgctctcccagcttattg
ctgagttgggtatggataaaaaaggatgtctccaagaagaatgagcgcagcgccctgaatgaagtccatctg
```

-continued

```
gtagtaatgagactcctgagtgtcttcatgtcccgcaccaaatctggatccaagtcttccatatgtgagtc atcttccctcatctccagtgccacagcagcagctctactgagctctggggctgtggactactgcctgcacg tgctcaaatcactgctggaatattggaagagccaacagaatgacgaggagcctgtggctaccagccagttg ctgaaaccacatactacctcctccccacctgacatgagcccattctttctccgccagtatgtgaagggtca tgctgctgatgtgtttgaggcctatactcagcttctaacagaaatggtactgaggcttccttaccaaatca aaaagattactgacaccaattctcgaatcccacctcctgtctttgaccactcgtggttttactttctctcc gagtacctcatgatccagcagactccatttgtgcgccgtcaagtccgcaaacttctgctcttcatctgtgg atccaaagagaagtaccgccagctccgggatttgcacaccctggactctcacgtgcgtgggatcaagaagc tgctagaagagcaggggatattcctccgggcaagtgtggttacagccagctcaggctccgccttgcaatat gacacactcatcagcctgatggagcacctgaaagcctgtgcagagattgccgcccagcgaaccatcaactg gcagaaattctgcatcaaagatgactccgtcctgtacttcctcctccaagtcagtttccttgtggatgagg gcgtgtccccagtgctgctgcaactgctctcctgtgctctgtgcggcagcaaggtgctcgctgcactggca gcctcttcgggatcctccagtgcttcttcctcctcagccctgtggctgccagttctggacaagccacaac acagtccaagtcttccactaaaaagagcaagaaagaagaaaaagaaaaggagaaagatggtgagacctctg gcagccaggaggaccagctgtgcacagctctggtgaaccagctgaacaaatttgccgataaggaaaccctg atccagttcctgcgttgtttcctgttagagtccaattcttcctcggtgcgctggcaggcccactgtctgac actgcacatctacagaaattccagcaaatctcaacaggagctcctgctagatctgatgtggtccatctggc cagaactcccagcctatggtcgtaaggctgcccagtttgtggacctactaggatatttctccctgaaaact ccacaaacagagaagaagttgaaggagtattcacagaaggctgtggagattctgcggactcaaaaccatat tcttaccaaccaccccaactcgaacatttataacactttgtctggcttagtggagtttgatggctattacc tggagagcgatccctgcctggtgtgtaataacccggaagtaccgttctgttatatcaagctgtcttccatt aaagtggacacgcggtacaccaccacccagcaggttgtgaagctcattggcagtcacaccatcagcaaagt gacagtgaaaatcggggatctgaaacggaccaagatggtgcggaccatcaacctgtattataacaaccgaa ccgtgcaggccatagtggagttgaaaaacaagccagctcgctggcacaaagccaagaaggttcagctgacc cctggacagacagaggtgaagattgacctgccgttgcccattgtggcctccaatctgatgattgagtttgc agacttctatgaaaactaccaggcctccacagagaccctgcagtgccctcgctgtagtgcctcggtccctg ccaacccaggagtctgtggcaactgtggagagaatgtgtaccagtgtcacaaatgcagatccatcaactac gatgaaaaggatcccttcctctgcaatgcctgtggcttctgtaaatatgcccgcttcgacttcatgctcta tgccaagccttgctgtgcagtggatcccattgagaatgaagaagaccggaagaaggctgtatccaacatca atacacttttggacaaagctgatcgagtgtatcatcagctgatgggacaccggccacagctggagaacctg ctctgcaaagtgaatgaggcagctccagaaaagccacaggatgactcaggaacagcaggggcatcagctc cacttctgccagtgtgaatcgttacatcctgcagttggctcaggagtattgtggagactgcaagaactctt ttgatgaactctccaaaatcatccagaaagtctttgcttcgcgcaaagagttgttggaatatgacctacag cagagggaagcagccactaaatcatcccggacctccgtgcagcccacattcactgccagccagtaccgtgc cttatccgtcctgggctgtggccacacatcctccaccaagtgctatggctgcgcctcggctgtcacagaac attgtatcacactacttcgggccctggccaccaacccagccttgaggcacatccttgtctcccagggcctt atccgggagctcttttgattataatcttcgccgaggggctgcggccatgcgggaggagtccgccagctcat gtgcctcctaactcgagacaacccagaagccacccaacagatgaatgacctgattattggcaaggtctcca cagccctgaagagccactgggccaaccccgatctggcaagtagcctgcagtatgaaatgctgctgctgacg gattctatctccaaggaggacagctgctgggagctccggttacgctgtgctctcagccttttcctcatggc
```

-continued

```
tgtgaacattaagactcctgtggtggttgaaaacattaccctcatgtgcctgaggatcttgcagaagctga taaaaccacctgctcccactagcaagaagaacaaggatgtccccgtcgaggccctccaccacggtgaagcca tactgcaatgagatccatgcccaggctcaactgtggctcaagagagaccccaaggcatcctatgatgcctg gaagaagtgtcttcctatcagagggatagatggcaatgggaaagcccccagcaaatcagagctccgccatc tctatttgactgagaagtatgtgtggaggtggaaacagttcctgagtcgtcggggaagaggacctccccc ttggatctcaaactggggcataacaactggctgcgacaagtgcttttcactccagcaacgcaggccgcacg gcaggcagcctgtaccattgtggaagctctagccaccattcccagccgcaagcagcaggtcctggacctgc ttaccagttacctggatgagctgagcatagctggggagtgtgcagctgagtacctggctctctaccagaag ctcatcacttctgcgcactggaaagtctacttggcagctcggggagtcctaccctatgtgggcaacctcat caccaaggaaatagctcgtctgctggccctggaggaggctaccctgagtaccgatctgcagcagggttatg cccttaaaagtctcacaggcctttctctcctccttgttgaggtggaatccatcaaaagacattttaaaagt cgcttggtgggtactgtgctgaatggatacctgtgcttgcggaagctggtggtgcagaggaccaagctgat cgatgagacgcaggacatgctgctggagatgctggaggacatgaccacaggtacagaatcagaaaccaagg ccttcatggctgtgtgcattgagacagccaagcgctacaatctggatgactaccggaccccggtgttcatc ttcgagaggctctgcagcatcatttatcctgaggagaatgaagtcactgagttctttgtgaccctggagaa ggatccccaacaagaagacttcttacagggcaggatgcctgggaacccgtatagcagcaatgagccaggca tcgggccgctgatgagggatataaagaacaagatttgccaggactgtgacttagtggccctcctggaagat gacagtggcatggagcttctagtgaacaataaaatcattagtttggaccttcctgtggctgaagtttacaa gaaagtctggtgtaccacgaatgagggagagcccatgaggattgtttatcgtatgcggggctgctgggcg atgccacagaggagttcattgagtccctggactctactacagatgaagaagaagatgaagaagaagtgtat aaaatggctggtgtgatggcccagtgtggggggcctggaatgcatgcttaacagactcgcagggatcagaga tttcaagcagggacgccaccttctaacagtgctactgaaattgttcagttactgcgtgaaggtgaaagtca accggcagcaactggtcaaactggaaatgaacaccttgaacgtcatgctggggaccctaaacctggcccctt gtagctgaacaagaaagcaaggacagtgggggtgcagctgtggctgagcaggtgcttagcatcatggagat cattctagatgagtccaatgctgagcccctgagtgaggacaagggcaacctcctcctgacaggtgacaagg atcaactggtgatgctcttggaccagatcaacagcacctttgttcgctccaaccccagtgtgctccagggc ctgcttcgcatcatcccgtaccttccttttggagaggtggagaaaatgcagatcttggtggagcgattcaa accatactgcaactttgataaatatgatgaagatcacagtggtgatgataaagtcttcctggactgcttct gtaaaatagctgctggcatcaagaacaacagcaatgggcaccagctgaaggatctgattctccagaagggg atcacccagaatgcacttgactacatgaaaaagcacatccctagcgccaagaatttggatgccgacatctg gaaaaagttttttgtctcgcccagccttgccatttatcctaaggctgcttcggggcctggccatccagcacc ctggcacccaggttctgattggaactgattccatcccgaacctgcataagctggagcaggtgtccagtgat gagggcattgggaccttggcagagaacctgctggaagccctgcgggaacaccctgacgtaaacaagaagat tgacgcagcccgcagggagacccgggcagagaagaaacgcatggccatggcaatgaggcagaaggccctgg gcaccctgggcatgacgacaaatgaaaagggccaggtcgtgaccaagacagcactcctgaagcagatggaa gagctgatcgaggagcctggcctcacgtgctgcatctgcaggagggatacaagttccagcccacaaaggt cctgggcatttataccttcacgaagcgggtagccttggaggagatggagaataagcccggaaacagcagg gctacagcaccgtgtcccacttcaacattgtgcactacgactgccatctggctgccgtcaggttggctcga ggccgggaagagtgggagagtgccgccctgcagaatgccaacaccaagtgcaacgggctccttccggtctg gggacctcatgtccctgaatcagcttttgccacttgcttggcaagacacaacacttacctccaggaatgta caggccagcgggagcccacgtatcagctcaacatccatgacatcaaactgctcttcctgcgcttcgccatg
```

-continued

```
gagcagtcgttcagcgcagacactggcggggcggccgggagagcaacatccacctgatcccgtacatcat tcacactgtgctttacgtcctgaacacaacccgagcaacttcccgagaagagaagaacctccaaggctttc tggaacagcccaaggagaagtgggtggagagtgcctttgaagtggacgggccctactatttcacagtcttg gcccttcacatcctgcccctgagcagtggagagccacacgtgtggaaatcttgcggaggctgttggtgac ctcgcaggctcgggcagtggctccaggtggagccaccaggctgacagataaggcagtgaaggactattccg cttaccgttcttcccttctcttttgggccctcgtcgatctcatttacaacatgtttaagaaggtgcctacc agtaacacagagggaggctggtcctgctctctcgctgagtacatccgccacaacgacatgcccatctacga agctgccgacaaagccctgaaaaccttccaggaggagttcatgccagtggagaccttctcagagttcctcg atgtggccggtcttttatcagaaatcaccgatccagagagcttcctgaaggacctgttgaactcagtcccc tga
```

P600 mRNA amino acid sequence (SEQ ID NO: 2)

```
MATSGGEEAAAAAPAPGTPATGADTTPGWEVAVRPLLSASYSAFEMKELPQLVASVIESESEILHHEKQYE

PFYSSFVALSTHYITTVCSLIPRNQLQSVAAACKVLIEFSLLRLENPDEACAVSQKHLILLIKGLCTGCSR

LDRTEIITFTAMMKSAKLPQTVKTLSDVEDQKELASPVSPELRQKEVQMNFLNQLTSVFNPRTVASQPIST

QTLVEGENDEQSSTDQASAIKTKNVFIAQNVASLQELGGSEKLLRVCLNLPYFLRYINRFQDAVLANSFFI

MPATVADATATONGFHSLVIDVTMALDTLSLPVLEPLNPSRLQDVTVLSLSCLYAGVSVATCMAILHVGSA

QQVRTGSTSSKEDDYESDAATIVQKCLEIYDMIGQAISSSRRAGGEHYQNFQLLGAWCLLNSLFLILNLSP

TALADKGKEKDPLAALRVRDILSRTKEGVGSPKLGPGKGHQGFGVLSVILANHAIKLLTSLFQDLQVEALH

KGWETDGPPAALSIMAQSTSIQRIQRLIDSVPLMNLLLTLLSTSYRKACVLQRQRKGSMSSDASASTDSNT

YYEDDFSSTEEDSSQDDDSEPILGQWFEETISPSKEKAAPPPPPPPPLESSPRVKSPSKQAPGEKGNILA

SRKDPELFLGLASNILNFITSSMLNSRNNFIRNYLSVSLSEHHMATLASIIKEVDKDGLKGSSDEEFAAAL

YHFNHSLVTSDLQSPNLQNTLLQQLGVAPFSEGPWPLYIHPQSLSVLSRLLLIWQHKASAQGDPDVPECLK

VWDRFLSTMKQNALQGVVPSETEDLNVEHLQMLLLIFHNFTETGRRAILSLFVQIIQELSVNMDAQMRFVP

LILARLLLIFDYLLHQYSKAPVYLFEQVQHNLLSPPFGWASGSQDSNSRRATTPLYHGFKEVEENWSKHFS

SDAVPHPRFYCVLSPEASEDDLNRLDSVACDVLFSKLVKYDELYAALTALLAAGSQLDTVRRKENKNVTAL

EACALQYYFLILWRILGILPPSKTYINQLSMNSPEMSECDILHTLRWSSRLRISSYVNWIKDHLIKQGMKA

EHASSLLELASTTKCSSVKYDVEIVEEYFARQISSFCSIDCTTILQLHEIPSLQSIYTLDAAISKVQVSLD

EHFSKMAAETDPHKSSEITKNLLPATLQLIDTYASFTRAYLLQNFNEEGTTEKPSKEKLQGFAAVLAIGSS

RCKANTLGPTLVQNLPSSVQTVCESWNNINTNEFPNIGSWRNAFANDTIPSESYISAVQAAHLGTLCSQSL

PLAASLKHTLLSLVRLTGDLIVWSDEMNPPQVIRTLLPLLLESSTESVAEISSNSLERILGPAESDEFLAR

VYEKLITGCYNILANHADPNSGLDESILEECLQYLEKQLESSQARKAMEEFFSDSGELVQIMMATANENLS

AKFCNRVLKFFTKLFQLTEKSPNPSLLHLCGSLAQLACVEPVRLQAWLTRMTTSPPKDSDQLDVIQENRQL

LQLLTTYIVRENSQVGEGVCAVLLGTLTPMATEMLANGDGTGFPELMVVMATLASAGQGAGHLQLHNAAVD

WLSRCKKYLSQKNVVEKLNANVMHGKHVMILECTCHIMSYLADVTNALSQSNGQGPSHLSVDGEERAIEVD

SDWVEELAVEEEDSQAEDSDEDSLCNKLCTFTITQKEFMNQHWYHCHTCKMVDGVGVCTVCAKVCHKDHEI

SYAKYGSFFCDCGAKEDGSCLALVKRTPSSGMSSTMKESAFQSEPRISESLVRHASTSSPADKAKVTISDG

KVADEEKPKKSSLCRTVEGCREELQNQANFSFAPLVLDMLNFLMDAIQTNFQQASAVGGSSSRAQQALSELH

TVEKAVEMTDQLMVPTLGSQEGAFENVRMNYSGDQGQTIRQLISAHVLRRVAMCVLSSPHGRRQHLAVSHE

KGKITVLQLSALLKQADSSKRKLTLTRLASAPVPFTVLSLTGNPCKEDYLAVCGLKDCHVLTFSSSGSVSD

HLVLHPQLATGNFIIKAVWLPGSQTELSIVTADFVKIYDLCVDALSPTFYFLLPSSKIRDVTFLFNEEGKN
```

-continued

```
IIVIMSSAGYIYTQLMEEASSAQQGPFYVTNVLEINHEDLKDSNSQVAGGGVSVYYSHVLQMLFFSYCQGK
SFAATISRTTLEVLQLFPINIKSSNGGSKTSPALCQWSEVMNHPGLVCCVQQTTGVPLVVMVKPDTFLIQE
IKTLPAKAKIQDMVAIRHTACNEQQRTTMILLCEDGSLRIYMANVENTSYWLQPSLQPSSVISIMKPVRKR
KTATITTRTSSQVTFPIDFFEHNQQLTDVEFGGNDLLQVYNAQQIKHRLNSTGMYVANTKPGGFTIEISNN
NSTMVMTGMRIQIGTQAIERAPSYIEIFGRTMQLNLSRSRWFDFPFTREEALQADKKLNLFIGASVEPAGV
TMIDAVKIYGKTKEQFGWPDEPPEEFPSASVSNICPSNLNQSNGTGDSDSAAPTTTSGTVLERLVVSSLEA
LESCFAVGPIIEKERNKNAAQELATLLLSLPAPASVQQQSKSLLASLHTSRSAYHSHKDQALLSKAVQCLN
TSSKEGKDLDPEVFQRLVITARSIAIMRPNNLVHFTESKLPQMETEGMDEGKEPQKQLEGDCCSFITQLVN
HFWKLHASKPKNAFLAPACLPGLTHIEATVNALVDIIHGYCTCELDCINTASKIYMQMLLCPDPAVSFSCK
QALIRVLRPRNKRRHVTLPSSPRSNTPMGDKDDDDDDADEKMQSSGIPNGGHIRQESQEQSEVDHGDFEM
VSESMVLETAENVNNGNPSPLEALLAGAEGFPPMLDIPPDADDETMVELAIALSLQQDQQGSSSSALGLQS
LGLSGQAPSSSSLDAGTLSDTTASAPASDDEGSTAATDGSTLRTSPADHGGSVGSESGGSAVDSVAGEHSV
SGRSSAYGDATAEGHPAGPGSVSSSTGAISTTTGHQEGDGSEGEGEGETEGDVHTSNRLHMVRLMLLERLL
QTLPQLRNVGGVRAIPYMQVILMLTTDLDGEDEKDKGALDNLLSQLIAELGMDKKDVSKKNERSALNEVHL
VVMRLLSVFMSRTKSGSKSSICESSSLISSATAAALLSSGAVDYCLHVLKSLLEYWKSQQNDEEPVATSQL
LKPHTTSSPPDMSPFFLRQYVKGHAADVFEAYTQLLTEMVLRLPYQIKKITDTNSRIPPPVFDHSWFYFLS
EYLMIQQTPFVRRQVRKLLLFICGSKEKYRQLRDLHTLDSHVRGIKKLLEEQGIFLRASVVTASSGSALQY
DTLISLMEHLKACAEIAAQRTINWQKFCIKDDSVLYFLLQVSFLVDEGVSPVLLQLLSCALCGSKVLAALA
ASSGSSSASSSSAPVAASSGQATTQSKSSTKKSKKEEKEKEKDGETSGSQEDQLCTALVNQLNKFADKETL
IQFLRCFLLESNSSSVRWQAHCLTLHIYRNSSKSQQELLLDLMWSIWPELPAYGRKAAQFVDLLGYFSLKT
PQTEKKLKEYSQKAVEILRTQNHILTNHPNSNIYNTLSGLVEFDGYYLESDPCLVCNNPEVPFCYIKLSSI
KVDTRYTTTQQVVKLIGSHTISKVTVKIGDLKRTKMVRTINLYYNNRTVQAIVELKNKPARWHKAKKVQLT
PGQTEVKIDLPLPIVASNLMIEFADFYENYQASTETLQCPRCSASVPANPGVCGNCGENVYQCHKCRSINY
DEKDPFLCNACGFCKYARFDFMLYAKPCCAVDPIENEEDRKKAVSNINTLLDKADRVYHQLMGHRPQLENL
LCKVNEAAPEKPQDDSGTAGGISSTSASVNRYILQLAQEYCGDCKNSFDELSKIIQKVFASRKELLEYDLQ
QREAATKSSRTSVQPTFTASQYRALSVLGCGHTSSTKCYGCASAVTEHCITLLRALATNPALRHILVSQGL
IRELFDYNLRRGAAAMREEVRQLMCLLTRDNPEATQQMNDLIIGKVSTALKSHWANPDLASSLQYEMLLLT
DSISKEDSCWELRLRCALSLFLMAVNIKTPVVVENITLMCLRILQKLIKPPAPTSKKNKDVPVEALTTVKP
YCNEIHAQAQLWLKRDPKASYDAWKKCLPIRGIDGNGKAPSKSELRHLYLTEKYVWRWKQFLSRRGKRTSP
LDLKLGHNNWLRQVLFTPATQAARQAACTIVEALATIPSRKQQVLDLLTSYLDELSIAGECAAEYLALYQK
LITSAHWKVYLAARGVLPYVGNLITKEIARLLALEEATLSTDLQQGYALKSLTGLLSSFVEVESIKRHFKS
RLVGTVLNGYLCLRKLVVQRTKLIDETQDMLLEMLEDMTTGTESETKAFMAVCIETAKRYNLDDYRTPVFI
FERLCSIIYPEENEVTEFFVTLEKDPQQEDFLQGRMPGNPYSSNEPGIGPLMRDIKNKICQDCDLVALLED
DSGMELLVNNKIISLDLPVAEVYKKVWCTTNEGEPMRIVYRMRGLLGDATEEFIESLDSTTDEEEDEEEVY
KMAGVMAQCGGLECMLNRLAGIRDFKQGRHLLTVLLKLFSYCVKVKVNRQQLVKLEMNTLNVMLGTLNLAL
VAEQESKDSGGAAVAEQVLSIMEIILDESNAEPLSEDKGNLLLTGDKDQLVMLLDQINSTFVRSNPSVLQG
LLRIIPYLSFGEVEKMQILVERFKPYCNFDKYDEDHSGDDKVFLDCFCKIAAGIKNNSNGHQLKDLILQKG
ITQNALDYMKKHIPSAKNLDADIWKKFLSRPALPFILRLLRGLAIQHPGTQVLIGTDSIPNLHKLEQVSSD
EGIGTLAENLLEALREHPDVNKKIDAARRETRAEKKRMAMAMRQKALGTLGMTTNEKGQVVTKTALLKQME
ELIEEPGLTCCICREGYKFQPTKVLGIYTFTKRVALEEMENKPRKQQGYSTVSHFNIVHYDCHLAAVRLAR
GREEWESAALQNANTKCNGLLPVWGPHVPESAFATCLARHNTYLQECTGQREPTYQLNIHDIKLLFLRFAM
```

EQSFSADTGGGGRESNIHLIPYIIHTVLYVLNTTRATSREEKNLQGFLEQPKEKWVESAFEVDGPYYFTVL

ALHILPPEQWRATRVEILRRLLVTSQARAVAPGGATRLTDKAVKDYSAYRSSLLFWALVDLIYNMFKKVPT

SNTEGGWSCSLAEYIRHNDMPIYEAADKALKTFQEEEMPVETESEFLDVAGLLSEITDPESFLKDLLNSVP

No particular length is implied by the term "truncated polypeptide or nucleic acid." In some embodiments, the truncated nucleic acid is less than 15,552 nucleotides in length, e.g., less than or equal to 15,000, 14,000, 13,000, 12,000, 11,000, 10,000, 9,000, 8,000, 7,000, 5,000, 4,000, 3,500, 3,250, 3,000, 2,900, 2,800, 2,800, 2,700, 2,600, 2,500, 2,400, 2,300, 2,300, 2,200, 2,100, 2,000, 1,900, 1,800, 1,700, 1,600, 1,500, 1,400, 1,300, 1,200, 1,100, 1,000, 900, 800, 700, 600, 500, 400, 300, 200, 100, or 50 nucleotides in length. In some embodiments the truncated nucleic acid is less than 15,552 nucleotides in length but greater than 50. Preferably, the truncated nucleic acid between 400-3000 nucleotides in length. More preferably the truncated nucleic acid between 717-2844 nucleotides in length.

In some aspects, truncated nucleic acid is 50, 75, 100, 200, 300, 400, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, nucleotides in length. In specific embodiments the truncated nucleic acid contains nucleotides 1-2499 of SEQ ID NO: 1; 5041-7203 of SEQ ID NO: 1; 5317-6765 of SEQ ID NO: 1; 5317-7203 of SEQ ID NO: 1; 5317-8160 of SEQ ID NO: 1; 9685-11838 of SEQ ID NO: 1; 10075-11838 of SEQ ID NO: 1; 10249-12114 of SEQ ID NO: 1; 13438-15549 of SEQ ID NO: 1; or 13729-155549 of SEQ ID NO: 1; 5590-7203 of SEQ ID NO: 1; 6049-6765 of SEQ ID NO: 1; 5590-6765 of SEQ ID NO: 1; 6049-7203 of SEQ ID NO: 1; 8851-10980 of SEQ ID NO: 1; 9685-10980 of SEQ ID NO: 1; 9685-10626 of SEQ ID NO: 1; 9685-11124 of SEQ ID NO: 1; 14098-15549 of SEQ ID NO: 1; 13438-15360 of SEQ ID NO: 1; 1915-3348 of SEQ ID NO: 1; 2227-3348 of SEQ ID NO: 1; 2449-3870 of SEQ ID NO: 1; 4687-5439 of SEQ ID NO: 1; 5317-6471 of SEQ ID NO: 1 5317-6240 of SEQ ID NO: 1; 10075-10980 of SEQ ID NO: 1; 10138-10980 of SEQ ID NO: 1; 10249-10980 of SEQ ID NO: 1; 10603-11838 of SEQ ID NO: 1; 11089-12114 of SEQ ID NO: 1; 11728-13503 of SEQ ID NO: 1; 13051-14460 of SEQ ID NO: 1; 11728-13977 of SEQ ID NO: 1; 12181-14553 of SEQ ID NO: 1; 12181-13977 of SEQ ID NO: 1; 13438-14943 of SEQ ID NO: 1; 13438-15105 of SEQ ID NO: 1; or 13438-15228 of SEQ ID NO: 1.

In some embodiments, the truncated polypeptide is less than 5,183 amino acids in length, e.g., less than or equal to 5,000, 4,000, 3,500, 3,250, 3,000, 2,900, 2,800, 2,800, 2,700, 2,600, 2,500, 2,400, 2,300, 2,300, 2,200, 2,100, 2,000, 1,900, 1,800, 1,700, 1,600, 1,500, 1,400, 1,300, 1,200, 1,100, 1,000, 900, 800, 700, 600, 500, 400, 300, 200, 100, or 50 amino acids in length. In some embodiments the truncated polypeptide is less than 5,183 amino acids in length but greater than 50. Preferably, the truncated polypeptide is between 100-1000 amino acids in length. More preferably the truncated polypeptide between 239-948 amino acids in length.

In some aspects, truncated polypeptide is 50, 75, 100, 200, 300, 400, 500, 600, 700, 800, 900, 1,000, 1,100, amino acids in length.

Exemplary truncated nucleic acids and polypeptides are summarized in Table 1.

TABLE 1

| Fragment | Category | Start (nt) | End (nt) | Nucleotide Size (bp) | Nucleotide SEQ ID NO | Peptide size (aa) | Peptide SEQ ID NO |
|---|---|---|---|---|---|---|---|
| A | 1 | 1 | 2499 | 2499 | 3 | 833 | 4 |
| C | 1 | 5041 | 7203 | 2163 | 5 | 721 | 6 |
| C10 | 1 | 5317 | 6765 | 1449 | 7 | 483 | 8 |
| C8 | 1 | 5317 | 7203 | 1887 | 9 | 629 | 10 |
| CCD1 | 1 | 5317 | 8160 | 2844 | 11 | 948 | 12 |
| E | 1 | 9685 | 11838 | 2154 | 13 | 718 | 14 |
| E1 | 1 | 10075 | 11838 | 1764 | 15 | 588 | 16 |
| EF6 | 1 | 10249 | 12114 | 1866 | 17 | 622 | 18 |
| G | 1 | 13438 | 15549 | 2112 | 19 | 704 | 20 |
| G4 | 1 | 13729 | 15549 | 1821 | 21 | 607 | 22 |
| C1 | 2 | 5590 | 7203 | 1614 | 23 | 538 | 24 |
| C11 | 2 | 6049 | 6765 | 717 | 25 | 239 | 26 |
| C15 | 2 | 5590 | 6765 | 1176 | 27 | 392 | 28 |
| C2 | 2 | 6049 | 7203 | 1155 | 29 | 385 | 30 |
| DE1 | 2 | 8851 | 10980 | 2130 | 31 | 710 | 32 |
| E18 | 2 | 9685 | 10980 | 1296 | 33 | 432 | 34 |
| E5 | 2 | 9685 | 10626 | 942 | 35 | 314 | 36 |
| E6 | 2 | 9685 | 11124 | 1440 | 37 | 480 | 38 |
| G5 | 2 | 14098 | 15549 | 1452 | 39 | 484 | 40 |
| G8 | 2 | 13438 | 15360 | 1923 | 41 | 641 | 42 |
| AAB4 | 3 | 1915 | 3348 | 1434 | 43 | 478 | 44 |
| AAB5 | 3 | 2227 | 3348 | 1122 | 45 | 374 | 46 |
| AB | 3 | 2449 | 3870 | 1422 | 47 | 474 | 48 |
| BC | 3 | 4687 | 5439 | 753 | 49 | 251 | 50 |
| C12 | 3 | 5317 | 6471 | 1155 | 51 | 385 | 52 |
| C13 | 3 | 5317 | 6240 | 924 | 53 | 308 | 54 |
| E11 | 3 | 10075 | 10980 | 906 | 55 | 302 | 56 |
| E16 | 3 | 10138 | 10980 | 843 | 57 | 281 | 58 |
| E17 | 3 | 10249 | 10980 | 732 | 59 | 244 | 60 |
| E3 | 3 | 10603 | 11838 | 1236 | 61 | 412 | 62 |
| EF1 | 3 | 11089 | 12114 | 1026 | 63 | 342 | 64 |
| F1 | 3 | 11728 | 13503 | 1776 | 65 | 592 | 66 |
| F12 | 3 | 13051 | 14460 | 1410 | 67 | 470 | 68 |
| F2 | 3 | 11728 | 13977 | 2250 | 69 | 750 | 70 |
| F3 | 3 | 12181 | 14553 | 2373 | 71 | 791 | 72 |
| F6 | 3 | 12181 | 13977 | 1797 | 73 | 599 | 74 |
| G1 | 3 | 13438 | 14943 | 1506 | 75 | 502 | 76 |
| G6 | 3 | 13438 | 15105 | 1668 | 77 | 556 | 78 |
| G7 | 3 | 13438 | 15228 | 1791 | 79 | 597 | 80 |

Fragment A nucleotide sequence (SEQ ID NO: 3)

atggcgacgagcggcggcgaagaggcggcggcagcggctccggcgccggggaccccggcaacgggggcgga cacgacccgggctggaggtggctgtgcggccctgctgtccgcgtcctactccgccttcgagatgaagg agttgccgcagctggtggcctcagtcatcgagagtgaatcagaaatcctgcaccatgagaagcagtacgag ccattctactcatcttttgttgcactttccacacactatattacaacagtttgcagtctcattccccggaa

```
ccaacttcagtcagtggcagcagcctgtaaagttctaattgagttttctctcctgcgtctggagaatccag atgaggcttgtgctgtgtcccagaaacacttgattctcctaatcaagggcctgtgcactggctgtagccga ctagatagaactgaaattatcacatttacagcaatgatgaaatccgccaagctgccccaaacagtgaagac actttcagacgtggaagatcagaaagagctggcctcaccagtaagccctgagttgaggcaaaaggaggtac agatgaattttttgaaccagctgacctcagttttttaaccctagaactgtagcatcacaacctatcagtaca cagactctggtggaaggagaaaatgatgagcagtcatctacagatcaagcctcagctatcaaaaccaagaa tgtgttcatagctcagaacgtggctagtcttcaagagcttggtggctcggagaagctactgcgtgtatgtt tgaacctgccatatttcctacgctatatcaatcggttccaagatgcagttttagctaattccttcttcata atgcctgcaacagtagcagatgccactgctgttcgtaatggctttcattcattggtgattgatgtaactat ggcattggataccctttctctacctgtgttggaacctctcaatccttctcgtctacaagatgtgacagtcc tcagcctaagttgtctgtatgcaggtgtgagtgtggcaacgtgcatggccatcctccatgtgggtagtgcc cagcaagtgcggacagggtccacgagctccaaagaagatgactatgaaagtgacgcagctacaattgtcca gaaatgtctcgaaatctatgacatgattggacaagcaatcagcagttctcgccgggctggtggtgagcact atcagaatttccaattgctgggtgcttggtgcttgttaaacagccttttcctcatactgaacctcagtcct actgcgttggctgataaggggaaagagaaggacccactggctgccctccgagtcagagacatcctttctcg tactaaagagggagtgggctcccctaaactggggcctggaaaagggcatcagggatttggggtactctcag taatattggcaaaccatgccatcaaactgctaacgtctctctttcaagacctacaagtggaggcccttcac aagggttgggagacagatggcccccctgcagccttgagcattatggcccagagcacctccatacagaggat tcaacggctgattgactctgtcccactgatgaacctgctcttgacgttactttcaacttcctacagaaagg catgtgtcctgcagcggcagaggaagggctccatgagcagcgatgccagcgcctccaccgactccaatact tactatgaggacgatttcagtagcacggaggaggacagcagccaagacgatgacagtgagcctatttttggg gcaatggtttgaggagactatttctcccagtaaagagaaagcagcacctccgcctcctcccccacctcctc cactggaaagctctcctcggttaaaagcccagtaagcaggcccctggtgagaagggcaacattctggcg agtcgcaaagatcctgagttgttcttaggtctggcttccaacattttgaacttcatcacctcttccatgct gaactctcggaacaattttatccgaaactatctgagtgtatctctttcagaacaccatatggccaccctag ccagtatcatcaaggaggtggacaaagatggactcaagggttcatcagatgaagagtttgctgcagctctc tatcacttcaaccactcactggtaacctctgaccttcagtcacctaacctgcagaacacactgttgcagca gctaggagtggctccttttctgagggcccttggcccttgtacattcaccctcaaagcctctctgtgctttt cacgcctcctgctcatctggcaacataaagccagtgctcaaggtgaccctgacgtcccagaatgccttaaa gtttgggacaggttttgtctacaatgaagcagaatgccctgcaaggtgtggtgcccagtgagacagagga tctgaatgtagaacacctgcagatgctcctcctcattttccacaatttcaccgagacaggccggcgggcca tattgtcgctttt
```

Fragment A amino acid sequence (SEQ ID NO: 4)

MATSGGEEAAAAAPAPGTPATGADTTPGWEVAVRPLLSASYSAFEMKELPQLVASVIESESEILHHEKQYE

PFYSSFVALSTHYITTVCSLIPRNQLQSVAAACKVLIEFSLLRLENPDEACAVSQKHLILLIKGLCTGCSR

LDRTEIITFTAMMKSAKLPQTVKTLSDVEDQKELASPVSPELRQKEVQMNFLNQLTSVFNPRTVASQPIST

QTLVEGENDEQSSTDQASAIKTKNVFIAQNVASLQELGGSEKLLRVCLNLPYFLRYINRFQDAVLANSFFI

MPATVADATAVRNGFHSLVIDVTMALDTLSLPVLEPLNPSRLQDVTVLSLSCLYAGVSVATCMAILHVGSA

QQVRTGSTSSKEDDYESDAATIVQKCLEIYDMIGQAISSRRAGGEHYQNFQLLGAWCLLNSLFLILNLSP

TALADKGKEKDPLAALRVRDILSRTKEGVGSPKLGPGKGHQGFGVLSVILANHAIKLLTSLFQDLQVEALH

KGWETDGPPAALSIMAQSTSIQRIQRLIDSVPLMNLLLTLLSTSYRKACVLQRQRKGSMSSDASASTDSNT

YYEDDFSSTEEDSSQDDDSEPILGQWFEETISPSKEKAAPPPPPPPPPLESSPRVKSPSKQAPGEKGNILA

SRKDPELFLGLASNILNFITSSMLNSRNNFIRNYLSVSLSEHHMATLASIIKEVDKDGLKGSSDEEFAAAL

YHFNHSLVTSDLQSPNLQNTLLQQLGVAPFSEGPWPLYIHPQSLSVLSRLLLIWQHKASAQGDPDVPECLK

VWDRFLSTMKQNALQGVVPSETEDLNVEHLQMLLLIFHNFTETGRRAILSLF

Fragment C nucleotide sequence
(SEQ ID NO: 5)
ACCTGTAAAATGGTGGATGGCGTGGGTGTCTGCACAGTGTGTGCTAAGGTGTGCCACAAGGATCATGAGAT

TTCCTATGCCAAGTATGGATCCTTCTTCTGTGACTGTGGAGCCAAGGAAGATGGCAGCTGTTTGGCTCTGG

TGAAGAGAACTCCTAGCAGTGGCATGAGCTCTACCATGAAGGAGTCGGCATTTCAGAGTGAACCCAGGATT

TCAGAGAGTCTAGTGCGTCATGCCAGCACCTCCTCGCCAGCTGACAAAGCCAAGGTTACCATCAGTGATGG

AAAGGTTGCTGACGAAGAGAAGCCCAAGAAGAGCAGCCTCTGCCGCACAGTAGAGGGCTGCCGGGAGGAAT

TACAGAACCAGGCCAATTTCTCCTTCGCTCCTCTCGTGTTAGACATGCTTAATTTCCTTATGGATGCCATT

CAGACCAACTTCCAGCAAGCTTCAGCCGTCGGGAGCAGCAGCCGTGCTCAGCAAGCCCTCAGTGAGCTACA

CACTGTGGAGAAGGCAGTGGAGATGACAGACCAGCTGATGGTTCCCACCTTAGGGTCCCAGGAAGGTGCCT

TTGAGAATGTGCGGATGAATTACAGTGGAGACCAGGGCCAGACCATCCGGCAGCTGATCAGTGCTCATGTG

CTCAGGCGGGTGGCTATGTGTGTGCTCTCCTCTCCCATGGGCGCCGCCAACATTTGGCTGTCAGCCATGA

GAAGGGCAAGATCACCGTTCTGCAGCTCTCTGCACTCCTGAAGCAAGCAGATTCCAGCAAAAGGAAGTTAA

CTCTGACCCGCTTGGCTTCTGCCCCAGTTCCTTTTACTGTGTTGAGCCTCACAGGAAATCCCTGCAAGGAA

GACTACTTGGCGGTTTGTGGGCTAAAGGACTGTCATGTGCTCACCTTTAGTAGCTCAGGCTCTGTTTCGGA

TCACTTGGTTTTGCACCCTCAGTTGGCAACGGGGAACTTCATCATCAAAGCCGTGTGGTTACCTGGTTCAC

AGACCGAGTTATCAATTGTCACCGCAGACTTTGTTAAGATTTATGACCTGTGTGTTGATGCCTTGAGTCCA

ACCTTCTATTTTCTCCTGCCAAGCTCAAAGATAAGAGATGTTACCTTCCTTTTCAATGAGGAGGGAAAGAA

CATCATTGTTATAATGTCTTCGGCTGGGTACATCTATACTCAGCTTATGGAAGAGGCCAGCAGTGCCCAGC

AGGGACCCTTCTATGTCACTAATGTGTTGGAAATCAATCATGAGGACCTGAAGGACAGTAACAGCCAGGTG

GCGGGCGGTGGTGTGTCCGTGTACTACTCCCACGTGTTGCAGATGTTGTTCTTCAGCTATTGTCAAGGCAA

ATCATTCGCAGCCACCATCAGCAGGACAACCCTGGAGGTGTTGCAACTCTTCCCCATCAACATCAAAGTT

CCAATGGTGGCAGTAAGACTTCTCCTGCTCTTTGCCAGTGGTCTGAGGTGATGAACCACCCTGGCTTGGTG

TGCTGTGTCCAGCAAACTACAGGGGTGCCGCTGGTAGTTATGGTGAAACCAGACACTTTTCTTATCCAGGA

GATTAAGACTCTTCCTGCTAAAGCGAAGATCCAAGACATGGTTGCTATTAGGCACACGGCCTGCAATGAGC

AGCAGCGGACAACAATGATTCTGCTGTGTGAGGATGGCAGCCTGCGCATTTACATGGCCAACGTGGAGAAC

ACCTCCTACTGGCTGCAGCCATCCCTGCAGCCCAGCAGTGTCATCAGCATCATGAAGCCTGTTCGAAAGCG

CAAAACAGCTACAATCACAACCCGCACGTCTAGCCAGGTGACTTTCCCCATTGACTTTTTTGAACACAACC

AGCAGCTGACAGATGTGGAGTTTGGTGGTAACGACCTCCTACAGGTCTATAATGCACAACAGATAAAACAC

CGGCTGAATTCCACTGGCATGTATGTGGCCAACACCAAGCCCGGAGGCTTCACCATTGAGATTAGTAACAA

CAATAGCACTATGGTGATGACAGGCATGCGGATCCAGATTGGGACTCAAGCAATAGAACGGGCCCCGTCAT

ATATCGAGATCTTCGGCAGAACTATGCAGCTCAACCTGAGTCGCTCACGCTGGTTTGACTTCCCCTTCACC

AGAGAAGAAGCCCTGCAGGCTGATAAGAAGCTG

Fragment C amino acid sequence
(SEQ ID NO: 6)
TCKMVDGVGVCTVCAKVCHKDHEISYAKYGSFFCDCGAKEDGSCLALVKRTPSSGMSSTMKESAFQSEPRI

SESLVRHASTSSPADKAKVTISDGKVADEEKPKKSSLCRTVEGCREELQNQANFSFAPLVLDMLNFLMDAI

QTNFQQASAVGSSSRAQQALSELHTVEKAVEMTDQLMVPTLGSQEGAFENVRMNYSGDQGQTIRQLISAHV

-continued

LRRVAMCVLSSPHGRRQHLAVSHEKGKITVLQLSALLKQADSSKRKLTLTRLASAPVPFTVLSLTGNPCKE

DYLAVCGLKDCHVLTFSSSGSVSDHLVLHPQLATGNFIIKAVWLPGSQTELSIVTADFVKIYDLCVDALSP

TFYFLLPSSKIRDVTFLFNEEGKNIIVIMSSAGYIYTQLMEEASSAQQGPFYVTNVLEINHEDLKDSNSQV

AGGGVSVYYSHVLQMLFFSYCQGKSFAATISRTTLEVLQLFPINIKSSNGGSKTSPALCQWSEVMNHPGLV

CCVQQTTGVPLVVMVKPDTFLIQEIKTLPAKAKIQDMVAIRHTACNEQQRTTMILLCEDGSLRIYMANVEN

TSYWLQPSLQPSSVISIMKPVRKRKTATITTRTSSQVTFPIDFFEHNQQLTDVEFGGNDLLQVYNAQQIKH

RLNSTGMYVANTKPGGFTIEISNNNSTMVMTGMRIQIGTQAIERAPSYIEIFGRTMQLNLSRSRWFDFPFT

REEALQADKKL

Fragment C10 nucleotide sequence
(SEQ ID NO: 7)
agtgatggaaaggttgctgacgaagagaagcccaagaagagcagcctctgccgcacagtagagggctgccg ggaggaattacagaaccaggccaatttctccttcgctcctctcgtgttagacatgcttaatttccttatgg atgccattcagaccaacttccagcaagcttcagccgtcgggagcagcagccgtgctcagcaagccctcagt gagctacacactgtggagaaggcagtggagatgacagaccagctgatggttcccaccttagggtcccagga aggtgcctttgagaatgtgcggatgaattacagtggagaccagggccagaccatccggcagctgatcagtg ctcatgtgctcaggcgggtggctatgtgtgtgctctcctctcccatgggcgccgccaacatttggctgtc agccatgagaagggcaagatcaccgttctgcagctctctgcactcctgaagcaagcagattccagcaaaag gaagttaactctgacccgcttggcttctgccccagttccttttactgtgttgagcctcacaggaaatccct gcaaggaagactacttggcggtttgtgggctaaaggactgtcatgtgctcacctttagtagctcaggctct gtttcggatcacttggttttgcaccctcagttggcaacggggaacttcatcatcaaagccgtgtggttacc tggttcacagaccgagttatcaattgtcaccgcagactttgttaagatttatgacctgtgtgttgatgcct tgagtccaaccttctattttctcctgccaagctcaaagataagagatgttaccttccttttcaatgaggag ggaaagaacatcattgttataatgtcttcggctgggtacatctatactcagcttatggaagaggccagcag tgcccagcagggacccttctatgtcactaatgtgttggaaatcaatcatgaggacctgaaggacagtaaca gccaggtggcgggcggtggtgtgtccgtgtactactcccacgtgttgcagatgttgttcttcagctattgt caaggcaaatcattcgcagccaccatcagcaggacaaccctggaggtgttgcaactcttccccatcaacat caaaagttccaatggtggcagtaagacttctcctgctctttgccagtggtctgaggtgatgaaccaccctg gcttggtgtgctgtgtccagcaaactacaggggtgccgctggtagttatggtgaaaccagacacttttctt atccaggagattaagactcttcctgctaaagcgaagatccaagacatggttgctattaggcacacggcctg caatgagcagcagcggacaacaatgattctgctgtgtgaggatggcagcctgcgcatttacatggccaacg tggagaacacctcctactggctgcagcca Fragment C10 amino acid sequence
(SEQ ID NO: 8)
SDGKVADEEKPKKSSLCRTVEGCREELQNQANFSFAPLVLDMLNFLMDAIQTNFQQASAVGSSSRAQQALS

ELHTVEKAVEMTDQLMVPTLGSQEGAFENVRMNYSGDQGQTIRQLISAHVLRRVAMCVLSSPHGRRQHLAV

SHEKGKITVLQLSALLKQADSSKRKLTLTRLASAPVPFTVLSLTGNPCKEDYLAVCGLKDCHVLTFSSSGS

VSDHLVLHPQLATGNFIIKAVWLPGSQTELSIVTADFVKIYDLCVDALSPTFYFLLPSSKIRDVTFLFNEE

GKNIIVIMSSAGYIYTQLMEEASSAQQGPFYVTNVLEINHEDLKDSNSQVAGGGVSVYYSHVLQMLFFSYC

QGKSFAATISRTTLEVLQLFPINIKSSNGGSKTSPALCQWSEVMNHPGLVCCVQQTTGVPLVVMVKPDTFL

IQEIKTLPAKAKIQDMVAIRHTACNEQQRTTMILLCEDGSLRIYMANVENTSYWLQP

Fragment C8 nucleotide sequence (SEQ ID NO: 9)

agtgatggaaaggttgctgacgaagagaagcccaagaagagcagcctctgccgcacagtagagggctgccg ggaggaattacagaaccaggccaatttctccttcgctcctctcgtgttagacatgcttaatttccttatgg atgccattcagaccaacttccagcaagcttcagccgtcgggagcagcagccgtgctcagcaagccctcagt gagctacacactgtggagaaggcagtggagatgacagaccagctgatggttcccaccttagggtcccagga aggtgcctttgagaatgtgcggatgaattacagtggagaccagggccagaccatccggcagctgatcagtg ctcatgtgctcaggcgggtggctatgtgtgtgctctcctctcccatgggcgccgccaacatttggctgtc agccatgagaagggcaagatcaccgttctgcagctctctgcactcctgaagcaagcagattccagcaaaag gaagttaactctgacccgcttggcttctgccccagttccttttactgtgttgagcctcacaggaaatccct gcaaggaagactacttggcggtttgtgggctaaaggactgtcatgtgctcacctttagtagctcaggctct gtttcggatcacttggttttgcaccctcagttggcaacggggaacttcatcatcaaagccgtgtggttacc tggttcacagaccgagttatcaattgtcaccgcagactttgttaagatttatgacctgtgtgttgatgcct tgagtccaaccttctatttctcctgccaagctcaaagataagagatgttaccttccttttcaatgaggag ggaaagaacatcattgttataatgtcttcggctgggtacatctatactcagcttatggaagaggccagcag tgcccagcagggacccttctatgtcactaatgtgttggaaatcaatcatgaggacctgaaggacagtaaca gccaggtggcgggcggtggtgtgtccgtgtactactcccacgtgttgcagatgttgttcttcagctattgt caaggcaaatcattcgcagccaccatcagcaggacaaccctggaggtgttgcaactcttccccatcaacat caaaagttccaatggtggcagtaagacttctcctgctctttgccagtggtctgaggtgatgaaccaccctg gcttggtgtgctgtgtccagcaaactacaggggtgccgctggtagttatggtgaaaccagacacttttctt atccaggagattaagactcttcctgctaaagcgaagatccaagacatggttgctattaggcacacggcctg caatgagcagcagcggacaacaatgattctgctgtgtgaggatggcagcctgcgcatttacatggccaacg tggagaacacctcctactggctgcagccatccctgcagcccagcagtgtcatcagcatcatgaagcctgtt cgaaagcgcaaaacagctacaatcacaacccgcacgtctagccaggtgactttccccattgacttttttga acacaaccagcagctgacagatgtggagtttggtggtaacgacctcctacaggtctataatgcacaacaga taaaacaccggctgaattccactggcatgtatgtggccaacaccaagcccggaggcttcaccattgagatt agtaacaacaatagcactatggtgatgacaggcatgcggatccagattgggactcaagcaatagaacgggc cccgtcatatatcgagatcttcggcagaactatgcagctcaacctgagtcgctcacgctggtttgacttcc ccttcaccagagaagaagccctgcaggctgataagaagctg Fragment C8 amino acid sequence (SEQ ID NO: 10)

SDGKVADEEKPKKSSLCRTVEGCREELQNQANFSPAPLVLDMLNFLMDAIQTNFQQASAVGSSSRAQQALS

ELHTVEKAVEMTDQLMVPTLGSQEGAFENVRMNYSGDQGQTIRQLISAHVLRRVAMCVLSSPHGRRQHLAV

SHEKGKITVLQLSALLKQADSSKRKLTLTRLASAPVPFTVLSLTGNPCKEDYLAVCGLKDCHVLTFSSSGS

VSDHLVLHPQLATGNFIIKAVWLPGSQTELSIVTADFVKIYDLCVDALSPTFYFLLPSSKIRDVTFLFNEE

GKNIIVIMSSAGYIYTQLMEEASSAQQGPFYVTNVLEINHEDLKDSNSQVAGGGVSVYYSHVLQMLFFSYC

QGKSFAATISRTTLEVLQLFPINIKSSNGGSKTSPALCQWSEVMNHPGLVCCVQQTTGVPLVVMVKPDTFL

IQEIKTLPAKAKIQDMVAIRHTACNEQQRTTMILLCEDGSLRIYMANVENTSYWLQPSLQPSSVISIMKPV

RKRKTATITTRTSSQVTFPIDFFEHNQQLTDVEFGGNDLLQVYNAQQIKHRLNSTGMYVANTKPGGFTIEI

SNNNSTMVMTGMRIQIGTQAIERAPSYIEIFGRTMQLNLSRSRWFDFPFTREEALQADKKL

Fragment CCD1 nucleotide sequence (SEQ ID NO: 11)

agtgatggaaaggttgctgacgaagagaagcccaagaagagcagcctctgccgcacagtagagggctgccg ggaggaattacagaaccaggccaatttctccttcgctcctctcgtgttagacatgcttaatttccttatgg atgccattcagaccaacttccagcaagcttcagccgtcgggagcagcagccgtgctcagcaagccctcagt gagctacacactgtggagaaggcagtggagatgacagaccagctgatggttcccaccttagggtcccagga aggtgcctttgagaatgtgcggatgaattacagtggagaccagggccagaccatccggcagctgatcagtg ctcatgtgctcaggcgggtggctatgtgtgtgctctcctctccccatgggcgccgccaacatttggctgtc agccatgagaagggcaagatcaccgttctgcagctctctgcactcctgaagcaagcagattccagcaaaag gaagttaactctgacccgcttggcttctgccccagttccttttactgtgttgagcctcacaggaaatccct gcaaggaagactacttggcggtttgtgggctaaaggactgtcatgtgctcacctttagtagctcaggctct gtttcggatcacttggttttgcaccctcagttggcaacggggaacttcatcatcaaagccgtgtggttacc tggttcacagaccgagttatcaattgtcaccgcagactttgttaagatttatgacctgtgtgttgatgcct tgagtccaaccttctattttctcctgccaagctcaaagataagagatgttaccttccttttcaatgaggag ggaaagaacatcattgttataatgtcttcggctgggtacatctatactcagcttatggaagaggccagcag tgcccagcagggacccttctatgtcactaatgtgttggaaatcaatcatgaggacctgaaggacagtaaca gccaggtggcgggcggtggtgtgtccgtgtactactcccacgtgttgcagatgttgttcttcagctattgt caaggcaaatcattcgcagccaccatcagcaggacaaccctggaggtgttgcaactcttccccatcaacat caaaagttccaatggtggcagtaagacttctcctgctctttgccagtggtctgaggtgatgaaccaccctg gcttggtgtgctgtgtccagcaaactacaggggtgccgctggtagttatggtgaaaccagacacttttctt atccaggagattaagactcttcctgctaaagcgaagatccaagacatggttgctataggcacacggcctg caatgagcagcagcggacaacaatgattctgctgtgtgaggatggcagcctgcgcatttacatggccaacg tggagaacacctcctactggctgcagccatccctgcagcccagcagtgtcatcagcatcatgaagcctgtt cgaaagcgcaaaacagctacaatcacaacccgcacgtctagccaggtgactttccccattgacttttttga acacaaccagcagctgacagatgtggagtttggtggtaacgacctcctacaggtctataatgcacaacaga taaaacaccggctgaattccactggcatgtatgtggccaacaccaagcccggaggcttcaccattgagatt agtaacaacaatagcactatggtgatgacaggcatgcggatccagattgggactcaagcaatagaacgggc cccgtcatatatcgagatcttcggcagaactatgcagctcaacctgagtcgctcacgctggtttgacttcc ccttcaccagagaagaagccctgcaggctgataagaagctgaacctcttcattggggcctcggtggaacca gcaggtgtcaccatgatagatgctgtaaaaatttatggcaagactaaggagcagtttggctggcctgatga gcccccagaagaattcccttctgcctctgtcagcaacatctgcccttcaaatctgaaccagagcaacggca ctggagatagcgactcagctgcccccactacgaccagtgaactgtcctggagaggctggttgtgagttct ttagaagccctggaaagctgctttgccgttggcccaatcatcgagaaggagagaaacaagaatgctgctca ggagctggccactttgctgttgtccctgccagcacctgccagtgtccagcagcagtccaagagccttctgg ccagcctgcacaccagccgctcggcctaccacagccacaaggatcaggccttgctgagcaaagctgtgcag tgtctcaacacatctagcaaagagggcaaggatttggaccctgaggtgttccagaggctagtgatcacagc tcgctccattgccatcatgcgccccaacaaccttgtccactttacggagtcaaagctgccccagatggaaa cagaaggaatggatgaagggaaggaaccgcagaagcagttggaaggagattgctgtagtttcatcacccag cttgtgaaccacttctggaaactccatgcatccaaacccaagaatgccttcttggcacctgcctgccttcc aggactaactcatattgaagctactgtcaatgctctggtggacatcatccatggctactgtacctgtgagc tggattgtattaacacagcatccaagatctacatgcagatgctcttgtgtcctgatcctgctgtgagcttc -continued tcttgtaaacaagctctaattcgagtcctaaggcccaggaacaaacggagacatgtgactttaccctcttc
ccct Fragment CCD1 amino acid sequence (SEQ ID NO: 12)

SDGKVADEEKPKKSSLCRTVEGCREELQNQANFSFAPLVLDMLNFLMDAIQTNFQQASAVGSSSRAQQALS

ELHTVEKAVEMTDQLMVPTLGSQEGAFENVRMNYSGDQGQTIRQLISAHVLRRVAMCVLSSPHGRRQHLAV

SHEKGKITVLQLSALLKQADSSKRKLTLTRLASAPVPFTVLSLTGNPCKEDYLAVCGLKDCHVLTFSSSGS

VSDHLVLHPQLATGNFIIKAVWLPGSQTELSIVTADFVKIYDLCVDALSPTFYFLLPSSKIRDVTFLFNEE

GKNIIVIMSSAGYIYTQLMEEASSAQQGPFYVTNVLEINHEDLKDSNSQVAGGGVSVYYSHVLQMLFFSYC

QGKSFAATISRTTLEVLQLFPINIKSSNGGSKTSPALCQWSEVMNHPGLVCCVQQTTGVPLVVMVKPDTFL

IQEIKTLPAKAKIQDMVAIRHTACNEQQATTMILLCEDGSLRIYMANVENTSYWLQPSLQPSSVISIMKPV

RKRKTATITTRTSSQVTFPIDFFEHNQQLTDVEFGGNDLLQVYNAQQIKHRLNSTGMYVANTKPGGFTIEI

SNNNSTMVMTGMRIQIGTQAIERAPSYIEIFGRTMQLNLSRSRWFDFPFTREEALQADKKLNLFIGASVEP

AGVTMIDAVKIYGKTKEQFGWPDEPPEEFPSASVSNICPSNLNQSNGTGDSDSAAPTTTSGTVLERLVVSS

LEALESCFAVGPIIEKERNKNAAQELATLLLSLPAPASVQQQSKSLLASLHTSRSAYHSHKDQALLSKAVQ

CLNTSSKEGKDLDPEVFQRLVITARSIAIMRPNNLVHFTESKLPQMETEGMDEGKEPQKQLEGDCCSFITQ

LVNHFWKLHASKPKNAFLAPACLPGLTHIEATVNALVDIIHGYCTCELDCINTASKIYMQMLLCPDPAVSF

SCKQALIRVLRPRNKRRHVTLPSSP

Fragment E nucleotide sequence (SEQ ID NO: 13)

GATTTGCACACCCTGGACTCTCACGTGCGTGGGATCAAGAAGCTGCTAGAAGAGCAGGGGATATTCCTCCG

GGCAAGTGTGGTTACAGCCAGCTCAGGCTCCGCCTTGCAATATGACACACTCATCAGCCTGATGGAGCACC

TGAAAGCCTGTGCAGAGATTGCCGCCCAGCGAACCATCAACTGGCAGAAATTCTGCATCAAAGATGACTCC

GTCCTGTACTTCCTCCTCCAAGTCAGTTTCCTTGTGGATGAGGGCGTGTCCCCAGTGCTGCTGCAACTGCT

CTCCTGTGCTCTGTGCGGCAGCAAGGTGCTCGCTGCACTGGCAGCCTCTTCGGGATCCTCCAGTGCTTCTT

CCTCCTCAGCCCCTGTGGCTGCCAGTTCTGGACAAGCCACAACACAGTCCAAGTCTTCCACTAAAAAGAGC

AAGAAAGAAGAAAAAGAAAGGAGAAAGATGGTGAGACCTCTGGCAGCCAGGAGGACCAGCTGTGCACAGC

TCTGGTGAACCAGCTGAACAAATTTGCCGATAAGGAAACCCTGATCCAGTTCCTGCGTTGTTTCCTGTTAG

AGTCCAATTCTTCCTCGGTGCGCTGGCAGGCCCACTGTCTGACACTGCACATCTACAGAAATTCCAGCAAA

TCTCAACAGGAGCTCCTGCTAGATCTGATGTGGTCCATCTGGCCAGAACTCCCAGCCTATGGTCGTAAGGC

TGCCCAGTTTGTGGACCTACTAGGATATTTCTCCCTGAAAACTCCACAAACAGAAGAAGTTGAAGGAGT

ATTCACAGAAGGCTGTGGAGATTCTGCGGACTCAAAACCATATTCTTACCAACCACCCCAACTCGAACATT

TATAACACTTTGTCTGGCTTAGTGGAGTTTGATGGCTATTACCTGGAGAGCGATCCCTGCCTGGTGTGTAA

TAACCCGGAAGTACCGTTCTGTTATATCAAGCTGTCTTCCATTAAAGTGGACACGCGGTACACCACCACCC

AGCAGGTTGTGAAGCTCATTGGCAGTCACACCATCAGCAAAGTGACAGTGAAAATCGGGGATCTGAAACGG

ACCAAGATGGTGCGGACCATCAACCTGTATTATAACAACCGAACCGTGCAGGCCATCGTGGAGTTGAAAAA

CAAGCCAGCTCGCTGGCACAAAGCCAAGAAGGTTCAGCTGACCCCTGGACAGACAGAGGTGAAGATTGACC

TGCCGTTGCCCATTGTGGCCTCCAATCTGATGATTGAGTTTGCAGACTTCTATGAAAACTACCAGGCCTCC

ACAGAGACCCTGCAGTGCCCTCGCTGTAGTGCCTCGGTCCCTGCCAACCCAGGAGTCTGTGGCAACTGTGG

AGAGAATGTGTACCAGTGTCACAAATGCAGATCCATCAACTACGATGAAAAGGATCCCTTCCTCTGCAATG

CCTGTGGCTTCTGTAAATATGCCCGCTTCGACTTCATGCTCTATGCCAAGCCTTGCTGTGCAGTGGATCCC

ATTGAGAATGAAGAAGACCGGAAGAAGGCTGTATCCAACATCAATACACTTTTGGACAAAGCTGATCGAGT

GTATCATCAGCTGATGGGACACCGGCCACAGCTGGAGAACCTGCTCTGCAAAGTGAATGAGGCAGCTCCAG

```
AAAAGCCACAGGATGACTCAGGAACAGCAGGGGGCATCAGCTCCACTTCTGCCAGTGTGAATCGTTACATC
CTGCAGTTGGCTCAGGAGTATTGTGGAGACTGCAAGAACTCTTTTGATGAACTCTCCAAAATCATCCAGAA
AGTCTTTGCTTCGCGCAAAGAGTTGTTGGAATATGACCTACAGCAGAGGGAAGCAGCCACTAAATCATCCC
GGACCTCCGTGCAGCCCACATTCACTGCCAGCCAGTACCGTGCCTTATCCGTCCTGGGCTGTGGCCACACA
TCCTCCACCAAGTGCTATGGCTGCGCCTCGGCTGTCACAGAACATTGTATCACACTACTTCGGGCCCTGGC
CACCAACCCAGCCTTGAGGCACATCCTTGTCTCCCAGGGCCTTATCCGGGAGCTCTTTGATTATAATCTTC
GCCGAGGGGCTGCGGCCATGCGGGAGGAGGTCCGCCAGCTCATGTGCCTCCTAACTCGAGACAACCCAGAA
GCCACCCAACAGATGAATGACCTG
```

Fragment E amino acid sequence
(SEQ ID NO: 14)
```
DLHTLDSHVRGIKKLLEEQGIFLRASVVTASSGSALQYDTLISLMEHLKACAEIAAQRTINWQKFCIKDDS
VLYFLLQVSFLVDEGVSPVLLQLLSCALCGSKVLAALAASSGSSSASSSSAPVAASSGQATTQSKSSTKKS
KKEEKEKEKDGETSGSQEDQLCTALVNQLNKFADKETLIQFLRCFLLESNSSSVRWQAHCLTLHIYRNSSK
SQQELLLDLMWSIWPELPAYGRKAAQFVDLLGYFSLKTPQTEKKLKEYSQKAVEILRTQNHILTNHPNSNI
YNTLSGLVEFDGYYLESDPCLVCNNPEVPFCYIKLSSIKVDTRYTTTQQVVKLIGSHTISKVTVKIGDLKR
TKMVRTINLYYNNRTVQAIVELKNKPARWHKAKKVQLTPGQTEVKIDLPLPIVASNLMIEFADEYENYQAS
TETLQCPRCSASVPANPGVCGNCGENVYQCHKCRSINYDEKDPFLCNACGFCKYARFDFMLYAKPCCAVDP
IENEEDRKKAVSNINTLLDKADRVYHQLMGHRPQLENLLCKVNEAAPEKPQDDSGTAGGISSTSASVNRYI
LQLAQEYCGDCKNSFDELSKIIQKVFASRKELLEYDLQQREAATKSSRTSVQPTFTASQYRALSVLGCGHT
SSTKCYGCASAVTEHCITLLRALATNPALRHILVSQGLIRELFDYNLRRGAAAMREEVRQLMCLLTRDNPE
ATQQMNDL
```

Fragment E1 nucleotide sequence
(SEQ ID NO: 15)
```
gccacaacacagtccaagtcttccactaaaaagagcaagaaagaagaaaaagaaaaggagaaagatggtga
gacctctggcagccaggaggaccagctgtgcacagctctggtgaaccagctgaacaaatttgccgataagg
aaaccctgatccagttcctgcgttgtttcctgttagagtccaattcttcctcggtgcgctggcaggcccac
tgtctgacactgcacatctacagaaattccagcaaatctcaacaggagctcctgctagatctgatggtgtc
catctggccagaactcccagcctatggtcgtaaggctgcccagtttgtggacctactaggatatttctccc
tgaaaactccacaaacagagaagaagttgaaggagtattcacagaaggctgtggagattctgcggactcaa
aaccatattcttaccaaccaccccaactcgaacatttataacactttgtctggcttagtggagtttgatgg
ctattacctggagagcgatccctgcctggtgtgtaataacccggaagtaccgttctgttatatcaagctgt
cttccattaaagtggacacgcggtacaccaccacccagcaggttgtgaagctcattggcagtcacaccatc
agcaaagtgacagtgaaaatcggggatctgaaacggaccaagatggtgcggaccatcaacctgtattataa
caaccgaaccgtgcaggccatcgtggagttgaaaaacaagccagctcgctggcacaaagccaagaaggttc
agctgacccctggacagacagaggtgaagattgacctgccgttgcccattgtggcctccaatctgatgatt
gagtttgcagacttctatgaaaactaccaggcctccacagagaccctgcagtgccctcgctgtagtgcctc
ggtccctgccaacccaggagtctgtggcaactgtggagagaatgtgtaccagtgtcacaaatgcagatcca
tcaactacgatgaaaaggatccctctctgcaatgcctgtggcttctgtaaatatgcccgcttcgacttc
atgctctatgccaagccttgctgtgcagtggatcccattgagaatgaagaagaccggaagaaggctgtatc
caacatcaatacacttttggacaaagctgatcgagtgtatcatcagctgatgggacaccggccacagctgg
agaacctgctctgcaaagtgaatgaggcagctccagaaaagccacaggatgactcaggaacagcaggggc
atcagctccacttctgccagtgtgaatcgttacatcctgcagttggctcaggagtattgtggagactgcaa
```

-continued gaactcttttgatgaactctccaaaatcatccagaaagtctttgcttcgcgcaaagagttgttggaatatg acctacagcagagggaagcagccactaaatcatcccggacctccgtgcagcccacattcactgccagccag taccgtgccttatccgtcctgggctgtggccacacatcctccaccaagtgctatggctgcgcctcggctgt cacagaacattgtatcacactacttcgggccctggccaccaacccagccttgaggcacatccttgtctccc agggccttatccgggagctctttgattataatcttcgccgaggggctgcggccatgcgggaggaggtccgc cagctcatgtgcctcctaactcgagacaacccagaagccacccaacagatgaatgacctg Fragment E1 amino acid sequence (SEQ ID NO: 16)
ATTQSKSSTKKSKKEEKEKEKDGETSGSQEDQLCTALVNQLNKFADKETLIQFLRCFLLESNSSSVRWQAH

CLTLHIYRNSSKSQQELLLDLMWSIWPELPAYGRKAAQFVDLLGYFSLKTPQTEKKLKEYSQKAVEILRTQ

NHILTNHPNSNIYNTLSGLVEFDGYYLESDPCLVCNNPEVPFCYIKLSSIKVDTRYTTTQQVVKLIGSHTI

SKVTVKIGDLKRTKMVRTINLYYNNRTVQAIVELKNKPARWHKAKKVQLTPGQTEVKIDLPLPIVASNLMI

EFADFYENYQASTETLQCPRCSASVPANPGVCGNCGENVYQCHKCRSINYDEKDPFLCNACGFCKYARFDF

MLYAKPCCAVDPIENEEDRKKAVSNINTLLDKADRVYHQLMGHRPQLENLLCKVNEAAPEKPQDDSGTAGG

ISSTSASVNRYILQLAQEYCGDCKNSFDELSKIIQKVFASRKELLEYDLQQREAATKSSRTSVQPTFTASQ

YRALSVLGCGHTSSTKCYGCASAVTEHCITLLRALATNPALRHILVSQGLIRELFDYNLRRGAAAMREEVR

QLMCLLTRDNPEATQQMNDL

Fragment EF6 nucleotide sequence (SEQ ID NO: 17)
TTAGAGTCCAATTCTTCCTCGGTGCGCTGGCAGGCCCACTGTCTGACACTGCACATCTACAGAAATTCCAG

CAAATCTCAACAGGAGCTCCTGCTAGATCTGATGTGGTCCATCTGGCCAGAACTCCCAGCCTATGGTCGTA

AGGCTGCCCAGTTTGTGGACCTACTAGGATATTTCTCCCTGAAAACTCCACAAACAGAGAAGAAGTTGAAG

GAGTATTCACAGAAGGCTGTGGAGATTCTGCGGACTCAAAACCATATTCTTACCAACCACCCCAACTCGAA

CATTTATAACACTTTGTCTGGCTTAGTGGAGTTTGATGGCTATTACCTGGAGAGCGATCCCTGCCTGGTGT

GTAATAACCCGGAAGTACCGTTCTGTTATATCAAGCTGTCTTCCATTAAAGTGGACACGCGGTACACCACC

ACCCAGCAGGTTGTGAAGCTCATTGGCAGTCACACCATCAGCAAAGTGACAGTGAAAATCGGGGATCTGAA

ACGGACCAAGATGGTGCGGACCATCAACCTGTATTATAACAACCGAACCGTGCAGGCCATCGTGGAGTTGA

AAAACAAGCCAGCTCGCTGGCACAAAGCCAAGAAGGTTCAGCTGACCCCTGGACAGACAGAGGTGAAGATT

GACCTGCCGTTGCCCATTGTGGCCTCCAATCTGATGATTGAGTTTGCAGACTTCTATGAAAACTACCAGGC

CTCCACAGAGACCCTGCAGTGCCCTCGCTGTAGTGCCTCGGTCCCTGCCAACCCAGGAGTCTGTGGCAACT

GTGGAGAGAATGTGTACCAGTGTCACAAATGCAGATCCATCAACTACGATGAAAAGGATCCCTTCCTCTGC

AATGCCTGTGGCTTCTGTAAATATGCCCGCTTCGACTTCATGCTCTATGCCAAGCCTTGCTGTGCAGTGGA

TCCCATTGAGAATGAAGAAGACCGGAAGAAGGCTGTATCCAACATCAATACACTTTTGGACAAAGCTGATC

GAGTGTATCATCAGCTGATGGGACACCGGCCACAGCTGGAGAACCTGCTCTGCAAAGTGAATGAGGCAGCT

CCAGAAAAGCCACAGGATGACTCAGGAACAGCAGGGGGCATCAGCTCCACTTCTGCCAGTGTGAATCGTTA

CATCCTGCAGTTGGCTCAGGAGTATTGTGGAGACTGCAAGAACTCTTTTGATGAACTCTCCAAAATCATCC

AGAAAGTCTTTGCTTCGCGCAAAGAGTTGTTGGAATATGACCTACAGCAGAGGGAAGCAGCCACTAAATCA

TCCCGGACCTCCGTGCAGCCCACATTCACTGCCAGCCAGTACCGTGCCTTATCCGTCCTGGGCTGTGGCCA

CACATCCTCCACCAAGTGCTATGGCTGCGCCTCGGCTGTCACAGAACATTGTATCACACTACTTCGGGCCC

TGGCCACCAACCCAGCCTTGAGGCACATCCTTGTCTCCCAGGGCCTTATCCGGGAGCTCTTTGATTATAAT

CTTCGCCGAGGGGCTGCGGCCATGCGGGAGGAGGTCCGCCAGCTCATGTGCCTCCTAACTCGAGACAACCC

AGAAGCCACCCAACAGATGAATGACCTGATTATTGGCAAGGTCTCCACAGCCCTGAAGAGCCACTGGGCCA

ACCCCGATCTGGCAAGTAGCCTGCAGTATGAAATGCTGCTGCTGACGGATTCTATCTCCAAGGAGGACAGC

-continued

```
TGCTGGGAGCTCCGGTTACGCTGTGCTCTCAGCCTTTTCCTCATGGCTGTGAACATTAAGACTCCTGTGGT

GGTTGAAAACATTACCCTCATGTGCCTGAGGATCTTGCAGAAGCTGATAAAACCACCTGCTCCCACTAGCA

AGAAGAACAAGGATGTCCCC
```

Fragment EF6 amino acid sequence
(SEQ ID NO: 18)

```
LESNSSSVRWQAHCLTLHIYRNSSKSQQELLLDLMWSIWPELPAYGRKAAQFVDLLGYFSLKTPQTEKKLK

EYSQKAVEILRTQNHILTNHPNSNIYNTLSGLVEFDGYYLESDPCLVCNNPEVPFCYIKLSSIKVDTRYTT

TQQVVKLIGSHTISKVTVKIGDLKRTKMVRTINLYYNNRTVQAIVELKNKPARWHKAKKVQLTPGQTEVKI

DLPLPIVASNLMIEFADFYENYQASTETLQCPRCSASVPANPGVCGNCGENVYQCHKCRSINYDEKDPFLC

NACGFCKYARFDFMLYAKPCCAVDPIENEEDRKKAVSNINTLLDKADRVYHQLMGHRPQLENLLCKVNEAA

PEKPQDDSGTAGGISSTSASVNRYILQLAQEYCGDCKNSFDELSKIIQKVFASRKELLEYDLQQREAATKS

SRTSVQPTFTASQYRALSVLGCGHTSSTKCYGCASAVTEHCITLLRALATNPALRHILVSQGLIRELFDYN

LRRGAAAMREEVRQLMCLLTRDNPEATQQMNDLIIGKVSTALKSHWANPDLASSLQYEMLLLTDSISKEDS

CWELRLRCALSLFLMAVNIKTPVVVENITLMCLRILQKLIKPPAPTSKKNKDVP
```

Fragment G nucleotide sequence
(SEQ ID NO: 19)

```
gcccagtgtgggggcctggaatgcatgcttaacagactcgcagggatcagagatttcaagcagggacgcca ccttctaacagtgctactgaaattgttcagttactgcgtgaaggtgaaagtcaaccggcagcaactggtca aactggaaatgaacaccttgaacgtcatgctggggaccctaaacctggcccttgtagctgaacaagaaagc aaggacagtgggggtgcagctgtggctgagcaggtgcttagcatcatggagatcattctagatgagtccaa tgctgagcccctgagtgaggacaagggcaacctcctcctgacaggtgacaaggatcaactggtgatgctct tggaccagatcaacagcacctttgttcgctccaaccccagtgtgctccagggcctgcttcgcatcatcccg tacctttcctttggagaggtggagaaaatgcagatcttggtggagcgattcaaaccatactgcaactttga taaatatgatgaagatcacagtggtgatgataaagtcttcctggactgcttctgtaaaatagctgctggca tcaagaacaacagcaatgggcaccagctgaaggatctgattctccagaagggatcacccagaatgcactt gactacatgaaaaagcacatccctagcgccaagaatttggatgccgacatctggaaaaagttttttgtctcg cccagccttgccatttatcctaaggctgcttcggggcctggccatccagcaccctggcacccaggttctga ttggaactgattccatcccgaacctgcataagctggagcaggtgtccagtgatgagggcattgggaccttg gcagagaacctgctggaagccctgcgggaacaccctgacgtaaacaagaagattgacgcagcccgcaggga gacccgggcagagaagaaacgcatggccatggcaatgaggcagaaggccctgggcaccctgggcatgacga caaatgaaaagggccaggtcgtgaccaagacagcactcctgaagcagatggaagagctgatcgaggagcct ggcctcacgtgctgcatctgcagggagggatacaagttccagcccacaaaggtcctgggcatttataccctt cacgaagcgggtagccttggaggagatggagaataagccccggaaacagcagggctacagcaccgtgtccc acttcaacattgtgcactacgactgccatctggctgccgtcaggttggctcgaggccgggaagagtgggag agtgccgccctgcagaatgccaacaccaagtgcaacgggctccttccggtctggggacctcatgtccctga atcagcttttgccacttgcttggcaagacacaacacttacctccaggaatgtacaggccagcgggagccca cgtatcagctcaacatccatgacatcaaactgctcttcctgcgcttcgccatggagcagtcgttcagcgca gacactggcggggggcggccgggagagcaacatccacctgatcccgtacatcattcacactgtgctttacgt cctgaacacaacccgagcaacttcccgagaagagaagaacctccaaggctttctggaacagcccaaggaga agtgggtggagagtgcctttgaagtggacgggccctactatttcacagtcttggcccttcacatcctgccc cctgagcagtggagagccacacgtgtggaaatcttgcggaggctgttggtgacctcgcaggctcgggcagt ggctccaggtggagccaccaggctgacagataaggcagtgaaggactattccgcttaccgttcttcccttc
```

-continued

```
tcttttgggccctcgtcgatctcatttacaacatgtttaagaaggtgcctaccagtaacacagagggaggc tggtcctgctctctcgctgagtacatccgccacaacgacatgcccatctacgaagctgccgacaaagccct gaaaaccttccaggaggagttcatgccagtggagaccttctcagagttcctcgatgtggccggtcttttat cagaaatcaccgatccagagagcttcctgaaggacctgttgaactcagtcccc
```

Fragment G amino acid sequence (SEQ ID NO: 20)

AQCGGLECMLNRLAGIRDFKQGRHLLTVLLKLFSYCVKVKVNRQQLVKLEMNTLNVMLGTLNLALVAEQES

KDSGGAAVAEQVLSIMEIILDESNAEPLSEDKGNLLLTGDKDQLVMLLDQINSTFVRSNPSVLQGLLRIIP

YLSFGEVEKMQILVERFKPYCNFDKYDEDHSGDDKVFLDCFCKIAAGIKNNSNGHQLKDLILQKGITQNAL

DYMKKHIPSAKNLDADIWKKFLSRPALPFILRLLRGLAIQHPGTQVLIGTDSIPNLHKLEQVSSDEGIGTL

AENLLEALREHPDVNKKIDAARRETRAEKKRMAMAMRQKALGTLGMTTNEKGQVVTKTALLKQMEELIEEP

GLTCCICREGYKFQPTKVLGIYTFTKRVALEEMENKPRKQQGYSTVSHFNIVHYDCHLAAVRLARGREEWE

SAALQNANTKCNGLLPVWGPHVPESAFATCLARHNTYLQECTGQREPTYQLNIHDIKLLFLRFAMEQSFSA

DTGGGGRESNIHLIPYIIHTVLYVLNTTRATSREEKNLQGFLEQPKEKWVESAFEVDGPYYFTVLALHILP

PEQWRATRVEILRRLLVTSQARAVAPGGATRLTDKAVKDYSAYRSSLLFWALVDLIYNMFKKVPTSNTEGG

WSCSLAEYIRHNDMPIYEAADKALKTFQEEFMPVETFSEFLDVAGLLSEITDPESFLKDLLNSVP

Fragment G4 nucleotide sequence (SEQ ID NO: 21)

```
CCCCTGAGTGAGGACAAGGGCAACCTCCTCCTGACAGGTGACAAGGATCAACTGGTGATGCTCTTGGACCA

GATCAACAGCACCTTTGTTCGCTCCAACCCCAGTGTGCTCCAGGGCCTGCTTCGCATCATCCCGTACCTTT

CCTTTGGAGAGGTGGAGAAAATGCAGATCTTGGTGGAGCGATTCAAACCATACTGCAACTTTGATAAATAT

GATGAAGATCACAGTGGTGATGATAAAGTCTTCCTGGACTGCTTCTGTAAAATAGCTGCTGGCATCAAGAA

CAACAGCAATGGGCACCAGCTGAAGGATCTGATTCTCCAGAAGGGGATCACCCAGAATGCACTTGACTACA

TGAAAAAGCACATCCCTAGCGCCAAGAATTTGGATGCCGACATCTGGAAAAAGTTTTTGTCTCGCCCAGCC

TTGCCATTTATCCTAAGGCTGCTTCGGGGCCTGGCCATCCAGCACCCTGGCACCCAGGTTCTGATTGGAAC

TGATTCCATCCCGAACCTGCATAAGCTGGAGCAGGTGTCCAGTGATGAGGGCATTGGGACCTTGGCAGAGA

ACCTGCTGGAAGCCCTGCGGGAACACCCTGACGTAAACAAGAAGATTGACGCAGCCCGCAGGGAGACCCGG

GCAGAGAAGAAACGCATGGCCATGGCAATGAGGCAGAAGGCCCTGGGCACCCTGGGCATGACGACAAATGA

AAAGGGCCAGGTCGTGACCAAGACAGCACTCCTGAAGCAGATGGAAGAGCTGATCGAGGAGCCTGGCCTCA

CGTGCTGCATCTGCAGGGAGGGATACAAGTTCCAGCCCACAAAGGTCCTGGGCATTTATACCTTCACGAAG

CGGGTAGCCTTGGAGGAGATGGAGAATAAGCCCCGGAAACAGCAGGGCTACAGCACCGTGTCCCACTTCAA

CATTGTGCACTACGACTGCCATCTGGCTGCCGTCAGGTTGGCTCGAGGCCGGGAAGAGTGGGAGAGTGCCG

CCCTGCAGAATGCCAACACCAAGTGCAACGGGCTCCTTCCGGTCTGGGGACCTCATGTCCCTGAATCAGCT

TTTGCCACTTGCTTGGCAAGACACAACACTTACCTCCAGGAATGTACAGGCCAGCGGGAGCCCACGTATCA

GCTCAACATCCATGACATCAAACTGCTCTTCCTGCGCTTCGCCATGGAGCAGTCGTTCAGCGCAGACACTG

GCGGGGGCGGCCGGGAGAGCAACATCCACCTGATCCCGTACATCATTCACACTGTGCTTTACGTCCTGAAC

ACAACCCGAGCAACTTCCCGAGAAGAGAAGAACCTCCAAGGCTTTCTGGAACAGCCCAAGGAGAAGTGGGT

GGAGAGTGCCTTTGAAGTGGACGGGCCCTACTATTTCACAGTCTTGGCCCTTCACATCCTGCCCCCTGAGC

AGTGGAGAGCCACACGTGTGGAAATCTTGCGGAGGCTGTTGGTGACCTCGCAGGCTCGGGCAGTGGCTCCA

GGTGGAGCCACCAGGCTGACAGATAAGGCAGTGAAGGACTATTCCGCTTACCGTTCTTCCCTTCTCTTTTG

GGCCCTCGTCGATCTCATTTACAACATGTTTAAGAAGGTGCCTACCAGTAACACAGAGGGAGGCTGGTCCT

GCTCTCTCGCTGAGTACATCCGCCACAACGACATGCCCATCTACGAAGCTGCCGACAAAGCCCTGAAAACC
```

-continued

```
TTCCAGGAGGAGTTCATGCCAGTGGAGACCTTCTCAGAGTTCCTCGATGTGGCCGGTCTTTTATCAGAAAT

CACCGATCCAGAGAGCTTCCTGAAGGACCTGTTGAACTCAGTCCCC
```

Fragment G4 amino acid sequence (SEQ ID NO: 22)

```
PLSEDKGNLLLTGDKDQLVMLLDQINSTFVRSNPSVLQGLLRIIPYLSFGEVEKMQILVERFKPYCNFDKY

DEDHSGDDKVFLDCFCKIAAGIKNNSNGHQLKDLILQKGITQNALDYMKKHIPSAKNLDADIWKKFLSRPA

LPFILRLLRGLAIQHPGTQVLIGTDSIPNLHKLEQVSSDEGIGTLAENLLEALREHPDVNKKIDAARRETR

AEKKRMAMAMRQKALGTLGMTTNEKGQVVTKTALLKQMEELIEEPGLTCCICREGYKFQPTKVLGIYTFTK

RVALEEMENKPRKQQGYSTVSHFNIVHYDCHLAAVRLARGREEWESAALQNANTKCNGLLPVWGPHVPESA

FATCLARHNTYLQECTGQREPTYQLNIHDIKLLFLRFAMEQSFSADTGGGGRESNIHLIPYIIHTVLYVLN

TTRATSREEKNLQGFLEQPKEKWVESAFEVDGPYYFTVLALHILPPEQWRATRVEILRRLLVTSQARAVAP

GGATRLTDKAVKDYSAYRSSLLFWALVDLIYNMFKKVPTSNTEGGWSCSLAEYIRHNDMPIYEAADKALKT

FQEEFMPVETFSEFLDVAGLLSEITDPESFLICDLLNSVP
```

Fragment C1 nucleotide sequence (SEQ ID NO: 23)

```
gggtcccaggaaggtgcctttgagaatgtgcggatgaattacagtggagaccagggccagaccatccggca gctgatcagtgctcatgtgctcaggcgggtggctatgtgtgtgctctcctctcccatgggcgccgccaac atttggctgtcagccatgagaagggcaagatcaccgttctgcagctctctgcactcctgaagcaagcagat tccagcaaaaggaagttaactctgacccgcttggcttctgccccagttccttttactgtgttgagcctcac aggaaatccctgcaaggaagactacttggcggtttgtgggctaaaggactgtcatgtgctcaccttagta gctcaggctctgtttcggatcacttggttttgcaccctcagttggcaacggggaacttcatcatcaaagcc gtgtggttacctggttcacagaccgagttatcaattgtcaccgcagactttgttaagatttatgacctgtg tgttgatgccttgagtccaaccttctattttctcctgccaagctcaaagataagagatgttaccttcctttt tcaatgaggagggaaagaacatcattgttataatgtcttcggctgggtacatctatactcagcttatggaa gaggccagcagtgcccagcagggaccccttctatgtcactaatgtgttggaaatcaatcatgaggacctgaa ggacagtaacagccaggtggcgggcggtggtgtgtccgtgtactactcccacgtgttgcagatgttgttct tcagctattgtcaaggcaaatcattcgcagccaccatcagcaggacaaccctggaggtgttgcaactcttc cccatcaacatcaaaagttccaatggtggcagtaagacttctcctgctcttttgccagtggtctgaggtgat gaaccaccctggcttggtgtgctgtgtccagcaaactacaggggtgccgctggtagttatggtgaaaccag acacttttcttatccaggagattaagactcttcctgctaaagcgaagatccaagacatggttgctattagg cacacgcctgcaatgagcagcagcggacaacaatgattctgctgtgtgaggatggcagcctgcgcattta catggccaacgtggagaacacctcctactggctgcagccatccctgcagcccagcagtgtcatcagcatca tgaagcctgttcgaaagcgcaaaacagctacaatcacaacccgcacgtctagccaggtgactttccccatt gacttttttgaacacaaccagcagctgacagatgtggagtttggtggtaacgacctcctacaggtctataa tgcacaacagataaaacaccggctgaattccactggcatgtatgtggccaacaccaagcccggaggcttca ccattgagattagtaacaacaatagcactatggtgatgacaggcatgcggatccagattgggactcaagca atagaacgggccccgtcatatatcgagatcttcggcagaactatgcagctcaacctgagtcgctcacgctg gtttgacttccccttcaccagagaagaagccctgcaggctgataagaagctg
```

Fragment C1 amino acid sequence (SEQ ID NO: 24)

```
GSQEGAFENVRMNYSGDQGQTIRQLISAHVLRRVAMCVLSSPHGRRQHLAVSHEKGKITVLQLSALLKQAD

SSKRKLTLTRLASAPVPFTVLSLTGNPCKEDYLAVCGLKDCHVLTFSSSGSVSDHLVLHPQLATGNFIIKA

VWLPGSQTELSIVTADFVKIYDLCVDALSPTFYFLLPSSKIRDVTFLFNEEGKNIIVIMSSAGYIYTQLME
```

-continued

EASSAQQGPFYVTNVLEINHEDLKDSNSQVAGGGVSVYYSHVLQMLFFSYCQGKSFAATISRTTLEVLQLF
PINIKSSNGGSKTSPALCQWSEVMNHPGLVCCVQQTTGVPLVVMVKPDTFLIQEIKTLPAKAKIQDMVAIR
HTACNEQQRTTMILLCEDGSLRIYMANVENTSYWLQPSLQPSSVISIMKPVRKRKTATITTRTSSQVTFPI
DFFEHNQQLTDVEFGGNDLLQVYNAQQIKHRLNSTGMYVANTKPGGFTIEISNNNSTMVMTGMRIQIGTQA
IERAPSYIEIFGRTMQLNLSRSRWFDFPFTREEALQADKKL

Fragment C11 nucleotide sequence
(SEQ ID NO: 25)
attgtcaccgcagactttgttaagatttatgacctgtgtgttgatgccttgagtccaaccttctattttct
cctgccaagctcaaagataagagatgttaccttccttttcaatgaggagggaaagaacatcattgttataa
tgtcttcggctgggtacatctatactcagcttatggaagaggccagcagtgcccagcagggacccttctat
gtcactaatgtgttggaaatcaatcatgaggacctgaaggacagtaacagccaggtggcggggcggtggtgt
gtccgtgtactactcccacgtgttgcagatgttgttcttcagctattgtcaaggcaaatcattcgcagcca
ccatcagcaggacaaccctggaggtgttgcaactcttccccatcaacatcaaaagttccaatggtggcagt
aagacttctcctgctctttgccagtggtctgaggtgatgaaccaccctggcttggtgtgctgtgtccagca
aactacaggggtgccgctggtagttatggtgaaaccagacacttttcttatccaggagattaagactcttc
ctgctaaagcgaagatccaagacatggttgctattaggcacacgcctgcaatgagcagcagcggacaaca
atgattctgctgtgtgaggatggcagcctgcgcatttacatggccaacgtggagaacacctcctactggct
gcagcca Fragment C11 amino acid sequence
(SEQ ID NO: 26)
IVTADFVKIYDLCVDALSPTFYFLLPSSKIRDVTFLENEEGKNIIVIMSSAGYIYTQLMEEASSAQQGPFY
VTNVLEINHEDLKDSNSQVAGGGVSVYYSHVLQMLFFSYCQGKSFAATISRTTLEVLQLFPINIKSSNGGS
KTSPALCQWSEVMNHPGLVCCVQQTTGVPLVVMVKPDTFLIQEIKTLPAKAKIQDMVAIRHTACNEQQRTT
MILLCEDGSLRIYMANVENTSYWLQP Fragment C15 nucleotide sequence
(SEQ ID NO: 27)
gggtcccaggaaggtgcctttgagaatgtgcggatgaattacagtggagaccagggccagaccatccggca
gctgatcagtgctcatgtgctcaggcgggtggctatgtgtgtgctctcctctccccatgggcgccgccaac
atttggctgtcagccatgagaagggcaagatcaccgttctgcagctctctgcactcctgaagcaagcagat
tccagcaaaaggaagttaactctgacccgcttggcttctgccccagttccttttactgtgttgagcctcac
aggaaatccctgcaaggaagactacttggcggtttgtgggctaaaggactgtcatgtgctcaccttagta
gctcaggctctgtttcggatcacttggttttgcaccctcagttggcaacggggaacttcatcatcaaagcc
gtgtggttacctggttcacagaccgagttatcaattgtcaccgcagactttgttaagatttatgacctgtg
tgttgatgccttgagtccaaccttctattttctcctgccaagctcaaagataagagatgttaccttccttt
tcaatgaggagggaaagaacatcattgttataatgtcttcggctgggtacatctatactcagcttatggaa
gaggccagcagtgcccagcagggacccttctatgtcactaatgtgttggaaatcaatcatgaggacctgaa
ggacagtaacagccaggtggcggggcggtggtgtgtccgtgtactactcccacgtgttgcagatgttgttct
tcagctattgtcaaggcaaatcattcgcagccaccatcagcaggacaaccctggaggtgttgcaactcttc
cccatcaacatcaaaagttccaatggtggcagtaagacttctcctgctctttgccagtggtctgaggtgat
gaaccaccctggcttggtgtgctgtgtccagcaaactacaggggtgccgctggtagttatggtgaaaccag
acacttttcttatccaggagattaagactcttcctgctaaagcgaagatccaagacatggttgctattagg
cacacgcctgcaatgagcagcagcggacaacaatgattctgctgtgtgaggatggcagcctgcgcattta
catggccaacgtggagaacacctcctactggctgcagcca -continued Fragment C15 amino acid sequence
(SEQ ID NO: 28)
GSQEGAFENVRMNYSGDQGQTIRQLISAHVLRRVAMCVLSSPHGRRQHLAVSHEKGKITVLQLSALLKQAD

SSKRKLTLTRLASAPVPFTVLSLTGNPCKEDYLAVCGLKDCHVLTFSSSGSVSDHLVLHPQLATGNFIIKA

VWLPGSQTELSIVTADFVKIYDLCVDALSPTFYFLLPSSKIRDVTFLFNEEGKNIIVIMSSAGYIYTQLME

EASSAQQGPFYVTNVLEINHEDLKDSNSQVAGGGVSVYYSHVLQMLFFSYCQGKSFAATISRTTLEVLQLF

PINIKSSNGGSKTSPALCQWSEVMNHPGLVCCVQQTTGVPLVVMVKPDTFLIQEIKTLPAKAKIQDMVAIR

HTACNEQQRTTMILLCEDGSLRIYMANVENTSYWLQP

Fragment C2 nucleotide sequence
(SCQ ID NO: 29)
attgtcaccgcagactttgttaagatttatgacctgtgtgttgatgccttgagtccaaccttctattttct cctgccaagctcaaagataagagatgttaccttccttttcaatgaggagggaaagaacatcattgttataa tgtcttcggctgggtacatctatactcagcttatggaagaggccagcagtgcccagcagggacccttctat gtcactaatgtgttggaaatcaatcatgaggacctgaaggacagtaacagccaggtggcgggcggtggtgt gtccgtgtactactcccacgtgttgcagatgttgttcttcagctattgtcaaggcaaatcattcgcagcca ccatcagcaggacaaccctggaggtgttgcaactcttccccatcaacatcaaaagttccaatggtggcagt aagacttctcctgctctttgccagtggtctgaggtgatgaaccaccctggcttggtgtgctgtgtccagca aactacaggggtgccgctggtagttatggtgaaaccagacacttttcttatccaggagattaagactcttc ctgctaaagcgaagatccaagacatggttgctattaggcacacggcctgcaatgagcagcagcggacaaca atgattctgctgtgtgaggatggcagcctgcgcatttacatggccaacgtggagaacacctcctactggct gcagccatccctgcagcccagcagtgtcatcagcatcatgaagcctgttcgaaagcgcaaaacagctacaa tcacaacccgcacgtctagccaggtgactttccccattgacttttttgaacacaaccagcagctgacagat gtggagtttggtggtaacgacctcctacaggtctataatgcacaacagataaaacaccggctgaattccac tggcatgtatgtggccaacaccaagcccggaggcttcaccattgagattagtaacaacaatagcactatgg tgatgacaggcatgcggatccagattgggactcaagcaatagaacgggcccccgtcatatatcgagatcttc ggcagaactatgcagctcaacctgagtcgctcacgctggtttgacttccccttcaccagagaagaagccct gcaggctgataagaagctg Fragment C2 amino acid sequence
(SEQ ID NO: 30)
IVTADFVKIYDLCVDALSPTFYFLLPSSKIRDVTFLFNEEGKNIIVIMSSAGYIYTQLMEEASSAQQGPFY

VTNVLEINHEDLKDSNSQVAGGGVSVYYSHVLQMLFFSYCQGKSFAATISRTTLEVLQLFPINIKSSNGGS

KTSPALCQWSEVMNHPGLVCCVQQTTGVPLVVMVKPDTFLIQEIKTLPAKAKIQDMVAIRHTACNEQQRTT

MILLCEDGSLRIYMANVENTSYWLQPSLQPSSVISIMKPVRKRKTATITTRTSSQVTFPIDFFEHNQQLTD

VEFGGNDLLQVYNAQQIKHRLNSTGMYVANTKPGGFTIEISNNNSTMVMTGMRIQIGTQAIERAPSYIEIF

GRTMQLNLSRSRWFDFPFTREEALQADKKL

Fragment DE1 nucleotide sequence
(SEQ ID NO: 31)
GGCTCCGAGGGAGAAGGAGAAGGAGAAACTGAAGGAGATGTCCACACTAGCAACAGGCTGCACATGGTCCG

TCTAATGCTGTTGGAGAGATTACTGCAGACCCTGCCTCAATTACGAAACGTTGGCGGTGTCCGGGCCATCC

CATACATGCAGGTCATTCTAATGCTCACTACAGATCTGGATGGAGAAGATGAGAAAGACAAGGGGGCCCTA

GACAACCTGCTCTCCCAGCTTATTGCTGAGTTGGGTATGGATAAAAAGGATGTCTCCAAGAAGAATGAGCG

CAGCGCCCTGAATGAAGTCCATCTGGTAGTAATGAGACTCCTGAGTGTCTTCATGTCCCGCACCAAATCTG

GATCCAAGTCTTCCATATGTGAGTCATCTTCCCTCATCTCCAGTGCCACAGCAGCAGCTCTACTGAGCTCT

GGGGCTGTGGACTACTGCCTGCACGTGCTCAAATCACTGCTGGAATATTGGAAGAGCCAACAGAATGACGA

-continued

```
GGAGCCTGTGGCTACCAGCCAGTTGCTGAAACCACATACTACCTCCTCCCCACCTGACATGAGCCCATTCT

TTCTCCGCCAGTATGTGAAGGGTCATGCTGCTGATGTGTTTGAGGCCTATACTCAGCTTCTAACAGAAATG

GTACTGAGGCTTCCTTACCAAATCAAAAAGATTACTGACACCAATTCTCGAATCCCACCTCCTGTCTTTGA

CCACTCGTGGTTTTACTTTCTCTCCGAGTACCTCATGATCCAGCAGACTCCATTTGTGCGCCGTCAAGTCC

GCAAACTTCTGCTCTTCATCTGTGGATCCAAAGAGAAGTACCGCCAGCTCCGGGATTTGCACACCCTGGAC

TCTCACGTGCGTGGGATCAAGAAGCTGCTAGAAGAGCAGGGGATATTCCTCCGGGCAAGTGTGGTTACAGC

CAGCTCAGGCTCCGCCTTGCAATATGACACACTCATCAGCCTGATGGAGCACCTGAAAGCCTGTGCAGAGA

TTGCCGCCCAGCGAACCATCAACTGGCAGAAATTCTGCATCAAAGATGACTCCGTCCTGTACTTCCTCCTC

CAAGTCAGTTTCCTTGTGGATGAGGGCGTGTCCCCAGTGCTGCTGCAACTGCTCTCCTGTGCTCTGTGCGG

CAGCAAGGTGCTCGCTGCACTGGCAGCCTCTTCGGGATCCTCCAGTGCTTCTTCCTCCTCAGCCCCTGTGG

CTGCCAGTTCTGGACAAGCCACAACACAGTCCAAGTCTTCCACTAAAAAGAGCAAGAAAGAAGAAAAAGAA

AAGGAGAAAGATGGTGAGACCTCTGGCAGCCAGGAGGACCAGCTGTGCACAGCTCTGGTGAACCAGCTGAA

CAAATTTGCCGATAAGGAAACCCTGATCCAGTTCCTGCGTTGTTTCCTGTTAGAGTCCAATTCTTCCTCGG

TGCGCTGGCAGGCCCACTGTCTGACACTGCACATCTACAGAAATTCCAGCAAATCTCAACAGGAGCTCCTG

CTAGATCTGATGTGGTCCATCTGGCCAGAACTCCCAGCCTATGGTCGTAAGGCTGCCCAGTTTGTGGACCT

ACTAGGATATTTCTCCCTGAAAACTCCACAAACAGAGAAGAAGTTGAAGGAGTATTCACAGAAGGCTGTGG

AGATTCTGCGGACTCAAAACCATATTCTTACCAACCACCCCAACTCGAACATTTATAACACTTTGTCTGGC

TTAGTGGAGTTTGATGGCTATTACCTGGAGAGCGATCCTGCCTGGTGTGTAATAACCCGGAAGTACCGTT

CTGTTATATCAAGCTGTCTTCCATTAAAGTGGACACGCGGTACACCACCACCCAGCAGGTTGTGAAGCTCA

TTGGCAGTCACACCATCAGCAAAGTGACAGTGAAAATCGGGGATCTGAAACGGACCAAGATGGTGCGGACC

ATCAACCTGTATTATAACAACCGAACCGTGCAGGCCATCGTGGAGTTGAAAAACAAGCCAGCTCGCTGGCA

CAAAGCCAAGAAGGTTCAGCTGACCCCTGGACAGACAGAGGTGAAGATTGACCTGCCGTTGCCCATTGTGG

CCTCCAATCTGATGATTGAGTTTGCAGACTTCTATGAAAACTACCAGGCCTCCACAGAGACCCTGCAGTGC
```

Fragment DE1 amino acid sequence
(SEQ ID NO: 32)

GSEGEGEGETEGDVHTSNRLHMVRLMLLERLLQTLPQLRNVGGVRAIPYMQVILMLTTDLDGEDEKDKGAL
DNLLSQLIAELGMDKKDVSKKNERSALNEVHLVVMRLLSVFMSRTKSGSKSSICESSSLISSATAAALLSS
GAVDYCLHVLKSLLEYWKSQQNDEEPVATSQLLKPHTTSSPPDMSPFFLRQYVKGHAADVFEAYTQLLTEM
VLRLPYQIKKITDTNSRIPPPVFDHSWFYFLSEYLMIQQTPFVRRQVRKLLLFICGSKEKYRQLRDLHTLD
SHVRGIKKLLEEQGIFLRASVVTASSGSALQYDTLISLMEHLKACAEIAAQRTINWQKFCIKDDSVLYFLL
QVSFLVDEGVSPVLLQLLSCALCGSKVLAALAASSGSSSASSSSAPVAASSGQATTQSKSSTKKSKKEEKE
KEKDGETSGSQEDQLCTALVNQLNKFADKETLIQFLRCFLLESNSSSVRWQAHCLTLHIYRNSSKSQQELL
LDLMWSIWPELPAYGRKAAQFVDLLGYFSLKTPQTEKKLKEYSQKAVEILRTQNHILTNHPNSNIYNTLSG
LVEFDGYYLESDPCLVCNNPEVPFCYIKLSSIKVDTRYTTTQQVVKLIGSHTISKVTVKIGDLKRTKMVRT
INLYYNNRTVQAIVELKNKPARWHKAKKVQLTPGQTEVKIDLPLPIVASNLMIEFADFYENYQASTETLQC

Fragment E18 nucleotide sequence
(SEQ ID NO: 33)

```
gatttgcacaccctggactctcacgtgcgtgggatcaagaagctgctagaagagcaggggatattcctccg ggcaagtgtggttacagccagctcaggctccgccttgcaatatgacacactcatcagcctgatggagcacc tgaaagcctgtgcagagattgccgcccagcgaaccatcaactggcagaaattctgcatcaaagatgactcc gtcctgtacttcctcctccaagtcagtttccttgtggatgagggcgtgtccccagtgctgctgcaactgct ctcctgtgctctgtgcggcagcaaggtgctcgctgcactggcagcctcttcgggatcctccagtgcttctt cctcctcagcccctgtggctgccagttctggacaagccacaacacagtccaagtcttccactaaaaagagc
```

-continued

```
aagaaagaagaaaaagaaaaggagaaagatggtgagacctctggcagccaggaggaccagctgtgcacagc tctggtgaaccagctgaacaaatttgccgataaggaaaccctgatccagttcctgcgttgtttcctgttag agtccaattcttcctcggtgcgctggcaggccactgtctgacactgcacatctacagaaattccagcaaa tctcaacaggagctcctgctagatctgatgtggtccatctggccagaactcccagcctatggtcgtaaggc tgcccagtttgtggacctactaggatatttctccctgaaaactccacaaacagagaagaagttgaaggagt attcacagaaggctgtggagattctgcggactcaaaaccatattcttaccaaccaccccaactcgaacatt tataacactttgtctggcttagtggagtttgatggctattacctggagagcgatccctgcctggtgtgtaa taacccggaagtaccgttctgttatatcaagctgtcttccattaaagtggacacgcggtacaccaccaccc agcaggttgtgaagctcattggcagtcacaccatcagcaaagtgacagtgaaaatcggggatctgaaacgg accaagatggtgcggaccatcaacctgtattataacaaccgaaccgtgcaggccatcgtggagttgaaaaa caagccagctcgctggcacaaagccaagaaggttcagctgacccctggacagacagaggtgaagattgacc tgccgttgcccattgtggcctccaatctgatgattgagtttgcagacttctatgaaaactaccaggcctcc acagagaccctgcagtgc
```

Fragment E18 amino acid sequence
(SEQ ID NO: 34)

```
DLHTLDSHVRGIKKLLEEQGIFLRASVVTASSGSALQYDTLISLMEHLKACAEIAAQRTINWQKFCIKDDS

VLYFLLQVSFLVDEGVSPVLLQLLSCALCGSKVLAALAASSGSSSASSSSAPVAASSGQATTQSKSSTKKS

KKEEKEKEKDGETSGSQEDQLCTALVNQLNKFADKETLIQFLRCFLLESNSSSVRWQAHCLTLHIYRNSSK

SQQELLLDLMWSIWPELPAYGRKAAQFVDLLGYFSLKTPQTEKKLKEYSQKAVEILRTQNHILTNHPNSNI

YNTLSGLVEFDGYYLESDPCLVCNNPEVPFCYIKLSSIKVDTRYTTTQQVVKLIGSHTISKVTVKIGDLKR

TKMVRTINLYYNNRTVQAIVELKNKPARWHKAKKVQLTPGQTEVKIDLPLPIVASNLMIEFADFYENYQAS

TETLQC
```

Fragment E5 nucleotide sequence
(SEQ ID NO: 35)

```
gatttgcacaccctggactctcacgtgcgtgggatcaagaagctgctagaagagcagggatattcctccg ggcaagtgtggttacagccagctcaggctccgccttgcaatatgacacactcatcagcctgatggagcacc tgaaagcctgtgcagagattgccgcccagcgaaccatcaactggcagaaattctgcatcaaagatgactcc gtcctgtacttcctcctccaagtcagtttccttgtggatgagggcgtgtccccagtgctgctgcaactgct ctcctgtgctctgtgcggcagcaaggtgctcgctgcactggcagcctcttcgggatcctccagtgcttctt cctcctcagcccctgtggctgccagttctggacaagccacaacacagtccaagtcttccactaaaaagagc aagaaagaagaaaaagaaaaggagaaagatggtgagacctctggcagccaggaggaccagctgtgcacagc tctggtgaaccagctgaacaaatttgccgataaggaaaccctgatccagttcctgcgttgtttcctgttag agtccaattcttcctcggtgcgctggcaggccactgtctgacactgcacatctacagaaattccagcaaa tctcaacaggagctcctgctagatctgatgtggtccatctggccagaactcccagcctatggtcgtaaggc tgcccagtttgtggacctactaggatatttctccctgaaaactccacaaacagagaagaagttgaaggagt attcacagaaggctgtggagattctgcggactcaaaaccatattcttaccaaccaccccaactcgaacatt tataacactttgtctggcttagtggagtttgatggctattacctggagagcgatccctgcctggtgtgtaa taacccggaagtaccgttc
```

Fragment E5 amino acid sequence
(SEQ ID NO: 36)

```
DLHTLDSHVRGIKKLLEEQGIFLRASVVTASSGSALQYDTLISLMEHLKACAEIAAQRTINWQKFCIKDDS

VLYFLLQVSFLVDEGVSPVLLQLLSCALCGSKVLAALAASSGSSSASSSSAPVAASSGQATTQSKSSTKKS

KKEEKEKEKDGETSGSQEDQLCTALVNQLNKFADKETLIQFLRCFLLESNSSSVRWQAHCLTLHIYRNSSK
```

-continued

SQQELLLDLMWSIWPELPAYGRKAAQFVDLLGYFSLKTPQTEKKLKEYSQKAVEILRTQNHILTNHPNSNI

YNTLSGLVEFDGYYLESDPCLVCNNPEVPF

Fragment E6 nucleotide sequence (SEQ ID NO: 37)

gatttgcacaccctggactctcacgtgcgtgggatcaagaagctgctagaagagcagggggatattcctccg ggcaagtgtggttacagccagctcaggctccgccttgcaatatgacacactcatcagcctgatggagcacc tgaaagcctgtgcagagattgccgcccagcgaaccatcaactggcagaaattctgcatcaaagatgactcc gtcctgtacttcctcctccaagtcagtttccttgtggatgagggcgtgtccccagtgctgctgcaactgct ctcctgtgctctgtgcggcagcaaggtgctcgctgcactggcagcctcttcgggatcctccagtgcttctt cctcctcagccctgtggctgccagttctggacaagccacaacacagtccaagtcttccactaaaaagagc aagaaagaagaaaaagaaaaggagaaagatggtgagacctctggcagccaggaggaccagctgtgcacagc tctggtgaaccagctgaacaaatttgccgataaggaaaccctgatccagttcctgcgttgtttcctgttag agtccaattcttcctcggtgcgctggcaggcccactgtctgacactgcacatctacagaaattccagcaaa tctcaacaggagctcctgctagatctgatgtggtccatctggccagaactcccagcctatggtcgtaaggc tgcccagtttgtggacctactaggatatttctccctgaaaactccacaaacagagaagaagttgaaggagt attcacagaaggctgtggagattctgcggactcaaaaccatattcttaccaaccaccccaactgaacatt tataacactttgtctggcttagtggagtttgatggctattacctggagagcgatccctgcctggtgtgtaa taacccggaagtaccgttctgttatatcaagctgtcttccattaaagtggacacgcggtacaccaccaccc agcaggttgtgaagctcattggcagtcacaccatcagcaaagtgacagtgaaaatcggggatctgaaacgg accaagatggtgcggaccatcaacctgtattataacaaccgaaccgtgcaggccatcgtggagttgaaaaa caagccagctcgctggcacaaagccaagaaggttcagctgacccctggacagacagaggtgaagattgacc tgccgttgcccattgtggcctccaatctgatgattgagtctgcagacttctatgaaaactaccaggcctcc acagagaccctgcagtgccctcgctgtagtgcctcggtccctgccaacccaggagtctgtggcaactgtgg agagaatgtgtaccagtgtcacaaatgcagatccatcaactacgatgaaaaggatcccttcctctgcaatg cctgtggcttctgtaaatat Fragment E6 amino acid sequence (SEQ ID NO: 38)

DLHTLDSHVRGIKKLLEEQGIFLRASVVTASSGSALQYDTLISLMEHLKACAEIAAQRTINWQKFCIKDDS

VLYFLLQVSFLVDEGVSPVLLQLLSCALCGSKVLAALAASSGSSSASSSSAPVAASSGQATTQSKSSTKKS

KKEEKEKEKDGETSGSQEDQLCTALVNQLNKFADKETLIQFLRCFLLESNSSSVRWQAHCLTLHIYRNSSK

SQQELLLDLMWSIWPELPAYGRKAAQFVDLLGYFSLKTPQTEKKLKEYSQKAVEILRTQNHILTNHPNSNI

YNTLSGLVEFDGYYLESDPCLVCNNPEVPFCYIKLSSIKVDTRYTTTQQVVKLIGSHTISKVTVKIGDLKR

TKMVRTINLYYNNRTVQAIVELKNKPARWHKAKKVQLTPGQTEVKIDLPLPIVASNLMIEFADFYENYQAS

TETLQCPRCSASVPANPGVCGNCGENVYQCHKCRSINYDEKDPFLCNACGFCKY

Fragment G5 nucleotide sequence (SEQ ID NO: 39)

cctagcgccaagaatttggatgccgacatctggaaaaagttttttgtctcgcccagccttgccatttatcct aaggctgcttcggggcctggccatccagcaccctggcacccaggttctgattggaactgattccatcccga acctgcataagctggagcaggtgtccagtgatgagggcattgggaccttggcagagaacctgctggaagcc ctgcgggaacaccctgacgtaaacaagaagattgacgcagcccgcagggagacccgggcagagaagaaacg catggccatggcaatgaggcagaaggccctgggcaccctgggcatgacgacaaatgaaaagggccaggtcg tgaccaagacagcactcctgaagcagatggaagagctgatcgaggagcctggcctcacgtgctgcatctgc agggagggatacaagttccagcccacaaaggtcctgggcatttataccttcacgaagcgggtagccttgga ggagatggagaataagcccccggaaacagcagggctacagcaccgtgtcccacttcaacattgtgcactacg -continued actgccatctggctgccgtcaggttggctcgaggccgggaagagtgggagagtgccgccctgcagaatgcc aacaccaagtgcaacgggctccttccggtctggggacctcatgtccctgaatcagcttttgccacttgctt ggcaagacacaacacttacctccaggaatgtacaggccagcgggagcccacgtatcagctcaacatccatg acatcaaactgctcttcctgcgcttcgccatggagcagtcgttcagcgcagacactggcgggggcggccgg gagagcaacatccacctgatcccgtacatcattcacactgtgctttacgtcctgaacacaacccgagcaac ttcccgagaagagaagaacctccaaggctttctggaacagcccaaggagaagtgggtggagagtgccttty aagtggacgggccctactatttcacagtcttggcccttcacatcctgccccctgagcagtggagagccaca cgtgtggaaatcttgcggaggctgttggtgacctcgcaggctcgggcagtggctccaggtggagccaccag gctgacagataaggcagtgaaggactattccgcttaccgttcttcccttctcttttgggccctcgtcgatc tcatttacaacatgtttaagaaggtgcctaccagtaacacagagggaggctggtcctgctctctcgctgag tacatccgccacaacgacatgcccatctacgaagctgccgacaaagccctgaaaaccttccaggaggagtt catgccagtggagaccttctcagagttcctcgatgtggccggtcttttatcagaaataccgatccagaga gcttcctgaaggacctgttgaactcagtcccc Fragment G5 amino acid sequence
(SEQ ID NO: 40)
PSAKNLDADIWKKFLSRPALPFILRLLRGLAIQHPGTQVLIGTDSIPNLHKLEQVSSDEGIGTLAENLLEA

LREHPDVNKKIDAARRETRAEKKRMAMAMRQKALGTLGMTTNEKGQVVTKTALLKQMEELIEEPGLTCCIC

REGYKFQPTKVLGIYTFTKRVALEEMENKPRKQQGYSTVSHFNIVHYDCHLAAVRLARGREEWESAALQNA

NTKCNGLLPVWGPHVPESAFATCLARHNTYLQECTGQREPTYQLNIHDIKLLFLRFAMEQSFSADTGGGGR

ESNIHLIPYIIHTVLYVLNTTRATSREEKNLQGFLEQPKEKWVESAFEVDGPYYFTVLALHILPPEQWRAT

RVEILRRLLVTSQARAVAPGGATRLTDKAVKDYSAYRSSLLFWALVDLIYNMFKKVPTSNTEGGWSCSLAE

YIRHNDMPIYEAADKALKTFQEEFMPVETFSEFLDVAGLLSEITDPESFLKDLLNSVP

Fragment G8 nucleotide sequence
(SEQ ID NO: 41)
gcccagtgtgggggcctggaatgcatgcttaacagactcgcagggatcagagatttcaagcagggacgcca ccttctaacagtgctactgaaattgttcagttactgcgtgaaggtgaaagtcaaccggcagcaactggtca aactggaaatgaacaccttgaacgtcatgctggggaccctaaacctggcccttgtagctgaacaagaaagc aaggacagtgggggtgcagctgtggctgagcaggtgcttagcatcatggagatcattctagatgagtccaa tgctgagcccctgagtgaggacaagggcaacctcctcctgacaggtgacaaggatcaactggtgatgctct ggaccagatcaacagcacctttgttcgctccaaccccagtgtgctccagggcctgcttcgcatcatcccg tacctttcctttggagaggtggagaaaatgcagatcttggtggagcgattcaaaccatactgcaactttga taaatatgatgaagatcacagtggtgatgataaagtcttcctggactgcttctgtaaaatagctgctggca tcaagaacaacagcaatgggcaccagctgaaggatctgattctccagaagggatcacccagaatgcactt gactacatgaaaaagcacatccctagcgccaagaatttggatgccgacatctggaaaaagttttgtctcg cccagccttgccatttatcctaaggctgcttcggggcctggccatccagcaccctggcacccaggttctga ttggaactgattccatcccgaacctgcataagctggagcaggtgtccagtgatgagggcattgggacctyg gcagagaacctgctggaagccctgcgggaacaccctgacgtaaacaagaagattgacgcagcccgcaggga gacccgggcagagaagaaacgcatggccatggcaatgaggcagaaggccctgggcaccctgggcatgacga caaatgaaaagggccaggtcgtgaccaagacagcactcctgaagcagatggaagagctgatcgaggagcct ggcctcacgtgctgcatctgcagggagggatacaagttccagcccacaaaggtcctgggcatttatacctt cacgaagcgggtagccttggaggagatggagaataagccccggaaacagcagggctacagcaccgtgtccc acttcaacattgtgcactacgactgccatctggctgccgtcaggttggctcgaggccgggaagagtgggag

```
agtgccgccctgcagaatgccaacaccaagtgcaacgggctccttccggtctggggacctcatgtccctga atcagcttttgccacttgcttggcaagacacaacacttacctccaggaatgtacaggccagcgggagccca cgtatcagctcaacatccatgacatcaaactgctcttcctgcgcttcgccatggagcagtcgttcagcgca gacactggcgggggcggccgggagagcaacatccacctgatcccgtacatcattcacactgtgctttacgt cctgaacacaacccgagcaacttcccgagaagagaagaacctccaaggctttctggaacagcccaaggaga agtgggtggagagtgcctttgaagtggacgggccctactatttcacagtcttggcccttcacatcctgccc cctgagcagtggagagccacacgtgtggaaatcttgcggaggctgttggtgacctcgcaggctcgggcagt ggctccaggtggagccaccaggctgacagataaggcagtgaaggactattccgcttaccgttcttcccttc tcttttgggccctcgtcgatctcatttacaacatgtttaagaaggtgcctaccagtaacacagagggaggc tggtcc
```

Fragment G8 amino acid sequence
(SEQ ID NO: 42)

```
AQCGGLECMLNRLAGIRDFKQGRHLLTVLLKLFSYCVKVKVNRQQLVKLEMNTLNVMLGTLNLALVAEQES

KDSGGAAVAEQVLSIMEIILDESNAEPLSEDKGNLLLTGDKDQLVMLLDQINSTFVRSNPSVLQGLLRIIP

YLSFGEVEKMQILVERFKPYCNFDKYDEDHSGDDKVFLDCFCKIAAGIKNNSNGHQLKDLILQKGITQNAL

DYMKKHIPSAKNLDADIWKKFLSRPALPFILRLLRGLAIQHPGTQVLIGTDSIPNLHKLEQVSSDEGIGTL

AENLLEALREHPDVNKKIDAARRETRAEKKRMAMAMRQKALGTLGMTTNEKGQVVTKTALLKQMEELIEEP

GLTCCICREGYKFQPTKVLGIYTFTKRVALEEMENKPRKQQGYSTVSHFNIVHYDCHLAAVRLARGREEWE

SAALQNANTKCNGLLPVWGPHVPESAFATCLARHNTYLQECTGQREPTYQLNIHDIKLLFLRFAMEQSFSA

DTGGGGRESNIHLIPYIIHTVLYVLNTTRATSREEKNLQGFLEQPKEKWVESAFEVDGPYYFTVLALHILP

PEQWRATRVEILRRLLVTSQARAVAPGGATRLTDKAVKDYSAYRSSLLFWALVDLIYNMFKKVPTSNTEGG

WS
```

Fragment AAB4 nucleotide sequence
(SEQ ID NO: 43)

```
gcgagtcgcaaagatcctgagttgttcttaggtctggcttccaacatttttgaacttcatcacctcttccat gctgaactctcggaacaattttatccgaaactatctgagtgtatctctttcagaacaccatatggccaccc tagccagtatcatcaaggaggtggacaaagatggactcaaggggttcatcagatgaagagtttgctgcagct ctctatcacttcaaccactcactggtaacctctgaccttcagtcacctaacctgcagaacacactgttgca gcagctaggagtggctccttttttctgagggcccttggcccttgtacattcaccctcaaagcctctctgtgc tttcacgcctcctgctcatctggcaacataaagccagtgctcaaggtgaccctgacgtcccagaatgcctt aaagtttgggacaggttttttgtctacaatgaagcagaatgccctgcaaggtgtggtgcccagtgagacaga ggatctgaatgtagaacacctgcagatgctcctcctcatttttccacaatttcaccgagacaggccggcggg ccatattgtcgcttttttgtccagatcatccaggagttgagcgtcaacatggatgctcagatgcgcttcgtg ccgcttatcttggctcgcctccttctcatctttgattatctgcttcatcagtactccaaagcccctgtgta tctatttgagcaggtacagcataacctgctaagtcctcccttttgggtgggcaagtggatcccaggacagca acagccgccgggcaaccactcctctctatcatggattcaaagaagtagaagaaaactggtctaagcatttc tcatcagatgctgtcccacaccccagattctactgtgtcctgtcccagaagcctcagaggatgatttgaa ccgacttgattctgtggcatgtgacgtcctttttctccaagcttgtcaagtatgatgagctttatgctgcac tgacagccctgcttgcagctgggtcccagcttgatacagttaggagaaaggaaaacaagaatgtaacagcc ttggaggcctgtgcccttcaatattacttcttgatactgtggaggatcctaggaattttaccaccatcaaa gacttacattaaccagctatccatgaactcacctgagatgagcgaatgtgacatcttgcacactctgcgat ggtcttctcggctccggatcagctcctatgtcaactggataaaggatcacccttatcaaacagggaatgaag gctgagcatgctagctcgcttctagaactggcatccaccactaagtgtagctcagtgaaatatgatgttga
```

-continued aatagtagaggaatacttcgctcgacagatctcatccttctgtagtatcgactgtaccaccatcttgcagc tgcatgaaattccc Fragment AAB4 amino acid sequence
(SEQ ID NO: 44)
ASRKDPELFLGLASNILNFITSSMLNSRNNFIRNYLSVSLSEHHMATLASIIKEVDKDGLKGSSDEEFAAA

LYHFNHSLVTSDLQSPNLQNTLLQQLGVAPFSEGPWPLYIHPQSLSVLSRLLLIWQHKASAQGDPDVPECL

KVWDRFLSTMKQNALQGVVPSETEDLNVEHLQMLLLIFHNFTETGRRAILSLFVQIIQELSVNMDAQMRFV

PLILARLLLIFDYLLHQYSKAPVYLFEQVQHNLLSPPFGWASGSQDSNSRRATTPLYHGFKEVEENWSKHF

SSDAVPHPRFYCVLSPEASEDDLNRLDSVACDVLFSKLVKYDELYAALTALLAAGSQLDTVRRKENKNVTA

LEACALQYYFLILWRILGILPPSKTYINQLSMNSPEMSECDILHTLRWSSRLRISSYVNWIKDHLIKQGMK

AEHASSLLELASTTKCSSVKYDVEIVEEYFARQISSFCSIDCTTILQLHEIP

Fragment AAB5 nucleotide sequence
(SEQ ID NO: 45)
ggcccttggcccttgtacattcaccctcaaagcctctctgtgctttcacgcctcctgctcatctggcaaca taaagccagtgctcaaggtgaccctgacgtcccagaatgccttaaagtttgggacaggttttttgtctacaa tgaagcagaatgccctgcaaggtgtggtgcccagtgagacagaggatctgaatgtagaacacctgcagatg ctcctcctcatttcccacaatttcaccgagacaggccggcgggccatattgtcgcttttttgtccagatcat ccaggagttgagcgtcaacatggatgctcagatgcgcttcgtgccgcttatcttggctcgcctccttctca tctttgattatctgcttcatcagtactccaaagcccctgtgtatctatttgagcaggtacagcataacctg ctaagtcctcccttttgggtgggcaagtggatcccaggacagcaacagccgccgggcaaccactcctctcta tcatggattcaaagaagtagaagaaaactggtctaagcatttctcatcagatgctgtcccacaccccagat tctactgtgtcctgtcccagaagcctcagaggatgatttgaaccgacttgattctgtggcatgtgacgtc cttttctccaagcttgtcaagtatgatgagctttatgctgcactgacagccctgcttgcagctgggtccca gcttgatacagttaggagaaaggaaaacaagaatgtaacagccttggaggcctgtgcccttcaatattact tcttgatactgtggaggatcctaggaattttaccaccatcaaagacttacattaaccagctatccatgaac tcacctgagatgagcgaatgtgacatcttgcacactctgcgatggtcttctcggctccggatcagctccta tgtcaactggataaaggatcaccttatcaaacagggaatgaaggctgagcatgctagctcgcttctagaac tggcatccaccactaagtgtagctcagtgaaatatgatgttgaaatagtagaggaatacttcgctcgacag atctcatccttctgtagtatcgactgtaccaccatcttgcagctgcatgaaattccc Fragment AAB5 amino acid sequence
(SEQ ID NO: 46)
GPWPLYIHPQSLSVLSRLLLIWQHKASAQGDPDVPECLKVWDRELSTMKQNALQGVVPSETEDLNVEHLQM

LLLIFHNFTETGRRAILSLFVQIIQELSVNMDAQMREVPLILARLLLIFDYLLHQYSKAPVYLFEQVQHNL

LSPPFGWASGSQDSNSRRATTPLYHGEKEVEENWSKHESSDAVPHPREYCVLSPEASEDDLNRLDSVACDV

LFSKLVKYDELYAALTALLAAGSQLDTVRRKENKNVTALEACALQYYFLILWRILGILPPSKTYINQLSMN

SPEMSECDILHTLRWSSRLRISSYVNWIKDHLIKQGMKAEHASSLLELASTTKCSSVKYDVEIVEEYFARQ

ISSFCSIDCTTILQLHEIP

Fragment AB nucleotide sequence
(SEQ ID NO: 47)
attttccacaatttcaccgagacaggccggcgggccatattgtcgcttttttgtccagatcatccaggagtt gagcgtcaacatggatgctcagatgcgcttcgtgccgcttatcttggctcgcctccttctcatctttgatt atctgcttcatcagtactccaaagcccctgtgtatctatttgagcaggtacagcataacctgctaagtcct cccttgggtgggcaagtggatcccaggacagcaacagccgccgggcaaccactcctctctatcatggatt caaagaagtagaagaaaactggtctaagcatttctcatcagatgctgtcccacaccccagattctactgtg -continued

```
tcctgtccccagaagcctcagaggatgatttgaaccgacttgattctgtggcatgtgacgtccttttctcc aagcttgtcaagtatgatgagctttatgctgcactgacagccctgcttgcagctgggtcccagcttgatac agttaggagaaaggaaaacaagaatgtaacagccttggaggcctgtgcccttcaatattacttcttgatac tgtggaggatcctaggaattttaccaccatcaaagacttacattaaccagctatccatgaactcacctgag atgagcgaatgtgacatcttgcacactctgcgatggtcttctcggctccggatcagctcctatgtcaactg gataaaggatcaccttatcaaacagggaatgaaggctgagcatgctagctcgcttctagaactggcatcca ccactaagtgtagctcagtgaaatatgatgttgaaatagtagaggaatacttcgctcgacagatctcatcc ttctgtagtatcgactgtaccaccatcttgcagctgcatgaaattcccagtctgcagtccatctacaccct tgatgccgcgatctcaaaggtccaggtctctttggatgagcattttctaagatggctgctgagactgatc ctcataagtcgtctgagattaccaagaacctacttccagccacgctgcaactcattgacacctatgcatcg ttcaccagagcctatttgctgcaaaactttaatgaagagggaacaactgagaaaccttccaaggagaaact gcaaggctttgctgctgtttggctattggctctagcaggtgcaaggcaaatactctgggtccgacactgg ttcagaatttgccatcgtcagtgcagactgtgtgtgagtcctggaacaacatcaataccaatgaatttccc aatattggatcctggcgcaatgcctttgccaatgacaccatcccttcagagagttatattagtgcagtgca ggctgcacacctggggactctctgtagccaaagtctgcccctggctgcttccctgaagcatacccctcctct ca
```

Fragment AB amino acid sequence
(SEQ ID NO: 48)
IFHNFTETGRRAILSLFVQIIQELSVNMDAQMRFVPLILARLLLIFDYLLHQYSKAPVYLFEQVQHNLLSP
PFGWASGSQDSNSRRATTPLYHGEKEVEENWSKHFSSDAVPHPREYCVLSPEASEDDLNRLDSVACDVLFS
KLVKYDELYAALTALLAAGSQLDTVRRKENKNVTALEACALQYYFLILWRILGILPPSKTYINQLSMNSPE
MSECDILHTLRWSSRLRISSYVNWIKDHLIKQGMKAEHASSLLELASTTKCSSVKYDVEIVEEYFARQISS
FCSIDCTTILQLHEIPSLQSIYTLDAAISKVQVSLDEHFSKMAAETDPHKSSEITKNLLPATLQLIDTYAS
FTRAYLLQNFNEEGTTEKPSKEKLQGFAAVLAIGSSRCKANTLGPTLVQNLPSSVQTVCESWNNINTNEFP
NIGSWRNAFANDTIPSESYISAVQAAHLGTLCSQSLPLAASLKHTLLS Fragment BC nucleotide sequence
(SEQ ID NO: 49)
```
tggctgagcagatgcaagaaatacctgtcacagaagaatgtagttgaaaaactgaatgccaatgtaatgca tggaaagcatgtgatgatcttggagtgcacatgccatatcatgtcttacttggctgatgtcacgaatgccc tgagccagagtaatggtcaaggcccaagtcatctctcagtggatggggaagagcgggccattgaagtagac tcagactgggtggaggagttggcgtggaagaggaagattcccaggctgaggattcagatgaagattctct ttgcaataaactctgcacttttacgatcacacagaaagaattcatgaaccagcattggtaccactgtcaca cctgtaaaatggtggatggcgtgggtgtctgcacagtgtgtgctaaggtgtgccacaaggatcatgagatt tcctatgccaagtatggatccttcttctgtgactgtggagccaaggaagatggcagctgtttggctctggt gaagagaactcctagcagtggcatgagctctaccatgaaggagtcggcatttcagagtgaacccaggattt cagagagtctagtgcgtcatgccagcacctcctcgccagctgacaaagccaaggttaccatcagtgatgga aaggttgctgacgaagagaagcccaagaagagcagcctctgccgcacagtagagggctgccgggaggaatt acagaaccaggccaatttctccttcgctcctctcgtgttagac
```

Fragment BC amino acid sequence
(SEQ ID NO: 50)
WLSRCKKYLSQKNVVEKLNANVMHGKHVMILECTCHIMSYLADVTNALSQSNGQGPSHLSVDGEERAIEVD
SDWVEELAVEEEDSQAEDSDEDSLCNKLCTFTITQKEFMNQHWYHCHTCKMVDGVGVCTVCAKVCHKDHEI
SYAKYGSFECDCGAKEDGSCLALVKRTPSSGMSSTMKESAFQSEPRISESLVRHASTSSPADKAKVTISDG
KVADEEKPKKSSLCRTVEGCREELQNQANFSFAPLVLD -continued Fragment C12 nucleotide sequence (SEQ ID NO: 51)

agtgatggaaaggttgctgacgaagagaagcccaagaagagcagcctctgccgcacagtagagggctgccg ggaggaattacagaaccaggccaatttctccttcgctcctctcgtgttagacatgcttaatttccttatgg atgccattcagaccaaCttccagcaagcttcagccgtcgggagcagcagccgtgctcagcaagccctcagt gagctacacactgtggagaaggcagtggagatgacagaccagctgatggttcccaccttagggtcccagga aggtgcctttgagaatgtgcggatgaattacagtggagaccagggccagaccatccggcagctgatcagtg ctcatgtgctcaggcgggtggctatgtgtgtgctctcctctccccatgggcgccgccaacatttggctgtc agccatgagaagggcaagatcaccgttctgcagctctctgcactcctgaagcaagcagattccagcaaaag gaagttaactctgacccgcttggcttctgccccagttccttttactgtgttgagcctcacaggaaatccct gcaaggaagactacttggcggtttgtgggctaaaggactgtcatgtgctcacctttagtagctcaggctct gtttcggatcacttggttttgcaccctcagttggcaacggggaacttcatcatcaaagccgtgtggttacc tggttcacagaccgagttatcaattgtcaccgcagactttgttaagatttatgacctgtgtgttgatgcct tgagtccaaccttctattttctcctgccaagctcaaagataagagatgttaccttccttttcaatgaggag ggaaagaacatcattgttataatgtcttcggctgggtacatctatactcagcttatggaagaggccagcag tgcccagcagggacccttctatgtcactaatgtgttggaaatcaatcatgaggacctgaaggacagtaaca gccaggtggcgggcggtggtgtgtccgtgtactactcccacgtgttgcagatgttgttcttcagctattgt caaggcaaatcattcgcagccaccatcagcaggacaaccctggaggtgttgcaactcttccccatcaacat caaaagttccaatggtggc Fragment C12 amino acid sequence (SEQ ID NO: 52)

SDGKVADEEKPKKSSLCRTVEGCREELQNQANFSFAPLVLDMLNFLMDAIQTNFQQASAVGSSSRAQQALS

ELHTVEKAVEMTDQLMVPTLGSQEGAFENVRMNYSGDQGQTIRQLISAHVLRRVAMCVLSSPHGRRQHLAV

SHEKGKITVLQLSALLKQADSSKRKLTLTRLASAPVPFTVLSLTGNPCKEDYLAVCGLKDCHVLTFSSSGS

VSDHLVLHPQLATGNFIIKAVWLPGSQTELSIVTADFVKIYDLCVDALSPTFYFLLPSSKIRDVTFLFNEE

GKNIIVIMSSAGYIYTQLMEEASSAQQGPFYVTNVLEINHEDLKDSNSQVAGGGVSVYYSHVLQMLFFSYC

QGKSFAATISRTTLEVLQLFPINIKSSNGG

Fragment C13 nucleotide sequence (SEQ ID NO: 53)

agtgatggaaaggttgctgacgaagagaagcccaagaagagcagcctctgccgcacagtagagggctgccg ggaggaattacagaaccaggccaatttctccttcgctcctctcgtgttagacatgcttaatttccttatgg atgccattcagaccaacttccagcaagcttcagccgtcgggagcagcagccgtgctcagcaagccctcagt gagctacacactgtggagaaggcagtggagatgacagaccagctgatggttcccaccttagggtcccagga aggtgcctttgagaatgtgcggatgaattacagtggagaccagggccagaccatccggcagctgatcagtg ctcatgtgctcaggcgggtggctatgtgtgtgctctcctctccccatgggcgccgccaacatttggctgtc agccatgagaagggcaagatcaccgttctgcagctctctgcactcctgaagcaagcagattccagcaaaag gaagttaactctgacccgcttggcttctgccccagttccttttactgtgttgagcctcacaggaaatccct gcaaggaagactacttggcggtttgtgggctaaaggactgtcatgtgctcacctttagtagctcaggctct gtttcggatcacttggttttgcaccctcagttggcaacggggaacttcatcatcaaagccgtgtggttacc tggttcacagaccgagttatcaattgtcaccgcagactttgttaagatttatgacctgtgtgttgatgcct tgagtccaaccttctattttctcctgccaagctcaaagataagagatgttaccttccttttcaatgaggag ggaaagaacatcattgttataatgtcttcggctgggtacatctatactcagcttatggaagaggccagcag t -continued Fragment C13 amino acid sequence (SEQ ID NO: 54)

SDGKVADEEKPKKSSLCRTVEGCREELQNQANFSFAPLVLDMLNFLMDAIQTNFQQASAVGSSSRAQQALS

ELHTVEKAVEMTDQLMVPTLGSQEGAFENVRMNYSGDQGQTIRQLISAHVLRRVAMCVLSSPHGRRQHLAV

SHEKGKITVLQLSALLKQADSSKRKLTLTRLASAPVPFTVLSLTGNPCKEDYLAVCGLKDCHVLTFSSSGS

VSDHLVLHPQLATGNFIIKAVWLPGSQTELSIVTADFVKIYDLCVDALSPTFYFLLPSSKIRDVTFLFNEE

GKNIIVIMSSAGYIYTQLMEEASS

Fragment E11 nucleotide sequence (SEQ ID NO: 55)

gccacaacacagtccaagtcttccactaaaaagagcaagaaagaagaaaaagaaaaggagaaagatggtga gacctctggcagccaggaggaccagctgtgcacagctctggtgaaccagctgaacaaatttgccgataagg aaaccctgatccagttcctgcgttgtttcctgttagagtccaattcttcctcggtgcgctggcaggcccac tgtctgacactgcacatctacagaaattccagcaaatctcaacaggagctcctgctagatctgatgtggtc catctggccagaactcccagcctatggtcgtaaggctgcccagtttgtggacctactaggatatttctccc tgaaaactccacaaacagagaagaagttgaaggagtattcacagaaggctgtggagattctgcggactcaa aaccatattcttaccaacaccccaactcgaacatttataacactttgtctggcttagtggagtttgatgg ctattacctggagagcgatccctgcctggtgtgtaataacccggaagtaccgttctgttatatcaagctgt cttccattaaagtggacacgcggtacaccaccacccagcaggttgtgaagctcattggcagtcacaccatc agcaaagtgacagtgaaaatcggggatctgaaacggaccaagatggtgcggaccatcaacctgtattataa caaccgaaccgtgcaggccatcgtggagttgaaaaacaagccagctcgctggcacaaagccaagaaggttc agctgacccctggacagacagaggtgaagattgacctgccgttgcccattgtggcctccaatctgatgatt gagtttgcagacttctatgaaaactaccaggcctccacagagaccctgcagtgc Fragment E11 amino acid sequence (SEQ ID NO: 56)

ATTQSKSSTKKSKKEEKEKEKDGETSGSQEDQLCTALVNQLNKFADKETLIQFLRCELLESNSSSVRWQAH

CLTLHIYRNSSKSQQELLLDLMWSIWPELPAYGRKAAQFVDLLGYFSLKTPQTEKKLKEYSQKAVEILRTQ

NHILTNHPNSNIYNTLSGLVEEDGYYLESDPCLVCNNPEVPFCYIKLSSIKVDTRYTTTQQVVKLIGSHTI

SKVTVKIGDLKRTKMVRTINLYYNNRTVQAIVELKNKPARWHKAKKVQLTPGQTEVKIDLPLPIVASNLMI

EFADFYENYQASTETLQC

Fragment E16 nucleotide sequence (SEQ ID NO: 57)

gatggtgagacctctggcagccaggaggaccagctgtgcacagctctggtgaaccagctgaacaaatttgc cgataaggaaaccctgatccagttcctgcgttgtttcctgttagagtccaattcttcctcggtgcgctggc aggcccactgtctgacactgcacatctacagaaattccagcaaatctcaacaggagctcctgctagatctg atgtggtccatctggccagaactcccagcctatggtcgtaaggctgcccagtttgtggacctactaggata tttctccctgaaaactccacaaacagagaagaagttgaaggagtattcacagaaggctgtggagattctgc ggactcaaaaccatattcttaccaacaccccaactcgaacatttataacactttgtctggcttagtggag tttgatggctattacctggagagcgatccctgcctggtgtgtaataacccggaagtaccgttctgttatat caagctgtcttccattaaagtggacacgcggtacaccaccacccagcaggttgtgaagctcattggcagtc acaccatcagcaaagtgacagtgaaaatcggggatctgaaacggaccaagatggtgcggaccatcaacctg tattataacaaccgaaccgtgcaggccatcgtggagttgaaaaacaagccagctcgctggcacaaagccaa gaaggttcagctgacccctggacagacagaggtgaagattgacctgccgttgcccattgtggcctccaatc tgatgattgagtttgcagacttctatgaaaactaccaggcctccacagagaccctgcagtgc Fragment E16 amino acid sequence
(SEQ ID NO: 58)
DGETSGSQEDQLCTALVNQLNKFADKETLIQFLRCFLLESNSSSVRWQAHCLTLHIYRNSSKSQQELLLDL

MWSIWPELPAYGRKAAQFVDLLGYFSLKTPQTEKKLKEYSQKAVEILRTQNHILTNHPNSNIYNTLSGLVE

FDGYYLESDPCLVCNNPEVPFCYIKLSSIKVDTRYTTTQQVVKLIGSHTISKVTVKIGDLKRTKMVRTINL

YYNNRTVQAIVELKNKPARWHKAKKVQLTPGQTEVKIDLPLPIVASNLMIEFADFYENYQASTETLQC

Fragment E17 nucleotide sequence
(SEQ ID NO: 59)
ttagagtccaattcttcctcggtgcgctggcaggcccactgtctgacactgcacatctacagaaattccag caaatctcaacaggagctcctgctagatctgatgtggtccatctggccagaactcccagcctatggtcgta aggctgcccagtttgtggacctactaggatatttctccctgaaaactccacaaacagagaagaagttgaag gagtattcacagaaggctgtggagattctgcggactcaaaaccatattcttaccaacaccccaactcgaa catttataacactttgtctggcttagtggagtttgatggctattacctggagagcgatccctgcctggtgt gtaataacccggaagtaccgttctgttatatcaagctgtcttccattaaagtggacacgcggtacaccacc acccagcaggttgtgaagctcattggcagtcacaccatcagcaaagtgacagtgaaaatcggggatctgaa acggaccaagatggtgcggaccatcaacctgtattataacaaccgaaccgtgcaggccatcgtggagttga aaaacaagccagctcgctggcacaaagccaagaaggttcagctgacccctggacagacagaggtgaagatt gacctgccgttgcccattgtggcctccaatctgatgattgagtttgcagacttctatgaaaactaccaggc ctccacagagaccctgcagtgc Fragment E17 amino acid sequence
(SEQ ID NO: 60)
LESNSSSVRWQAHCLTLHIYRNSSKSQQELLLDLMWSIWPELPAYGRKAAQFVDLLGYFSLKTPQTEKKLK

EYSQKAVEILRTQNHILTNHPNSNIYNTLSGLVEFDGYYLESDPCLVCNNPEVPFCYIKLSSIKVDTRYTT

TQQVVKLIGSHTISKVTVKIGDLKRTKMVRTINLYYNNRTVQAIVELKNKPARWHKAKKVQLTPGQTEVKI

DLPLPIVASNLMIEFADFYENYQASTETLQC

Fragment E3 nucleotide sequence
(SEQ ID NO: 61)
tgtaataacccggaagtaccgttctgttatatcaagctgtcttccattaaagtggacacgcggtacaccac cacccagcaggttgtgaagctcattggcagtcacaccatcagcaaagtgacagtgaaaatcggggatctga aacggaccaagatggtgcggaccatcaacctgtattataacaaccgaaccgtgcaggccatcgtggagttg aaaaacaagccagctcgctggcacaaagccaagaaggttcagctgacccctggacagacagaggtgaagat tgacctgccgttgcccattgtggcctccaatctgatgattgagtttgcagacttctatgaaaactaccagg cctccacagagaccctgcagtgccctcgctgtagtgcctcggtccctgccaacccaggagtctgtggcaac tgtgagagaatgtgtaccagtgtcacaaatgcagatccatcaactacgatgaaaaggatcccttcctctg caatgcctgtggcttctgtaaatatgcccgcttcgacttcatgctctatgccaagccttgctgtgcagtgg atcccattgagaatgaagaagaccggaagaaggctgtatccaacatcaatacattttggacaaagctgat cgagtgtatcatcagctgatgggacaccggccacagctggagaacctgctctgcaaagtgaatgaggcagc tccagaaaagccacaggatgactcaggaacagcagggggcatcagctccacttctgccagtgtgaatcgtt acatcctgcagttggctcaggagtattgtggagactgcaagaactcttttgatgaactctccaaaatcatc cagaaagtctttgcttcgcgcaaagagttgttggaatatgacctacagcagagggaagcagccactaaatc atcccgacctccgtgcagcccacattcactgccagccagtaccgtgccttatccgtcctgggctgtggcc acacatcctccaccaagtgctatggctgcgcctcggctgtcacagaacattgtatcacactacttcgggcc ctggccaccaacccagccttgaggcacatccttgtctcccagggccttatccgggagctcttttgattataa

```
tcttcgccgaggggctgcggccatgcgggaggaggtccgccagctcatgtgcctcctaactcgagacaacc cagaagccacccaacagatgaatgacctg
```

Fragment E3 amino acid sequence (SEQ ID NO: 62)

```
CNNPEVPFCYIKLSSIKVDTRYTTTQQVVKLIGSHTISKVTVKIGDLKRTKMVRTINLYYNNRTVQAIVEL

KNKPARWHKAKKVQLTPGQTEVKIDLPLPIVASNLMIEFADFYENYQASTETLQCPRCSASVPANPGVCGN

CGENVYQCHKCRSINYDEKDPFLCNACGFCKYARFDFMLYAKPCCAVDPIENEEDRKKAVSNINTLLDKAD

RVYHQLMGHRPQLENLLCKVNEAAPEKPQDDSGTAGGISSTSASVNRYILQLAQEYCGDCKNSFDELSKII

QKVFASRKELLEYDLQQREAATKSSRTSVQPTFTASQYRALSVLGCGHTSSTKCYGCASAVTEHCITLLRA

LATNPALRHILVSQGLIRELFDYNLRRGAAAMREEVRQLMCLLTRDNPEATQQMNDL
```

Fragment EF1 nucleotide sequence (SEQ ID NO: 63)

```
cccttcctctgcaatgcctgtggcttctgtaaatatgcccgcttcgacttcatgctctatgccaagccttg ctgtgcagtggatcccattgagaatgaagaagaccggaagaaggctgtatccaacatcaatacacttttgg acaaagctgatcgagtgtatcatcagctgatgggacaccggccacagctggagaacctgctctgcaaagtg aatgaggcagctccagaaaagccacaggatgactcaggaacagcaggggcatcagctccacttctgccag tgtgaatcgttacatcctgcagttggctcaggagtattgtggagactgcaagaactcttttgatgaactct ccaaaatcatccagaaagtctttgcttcgcgcaaagagttgttggaatatgacctacagcagagggaagca gccactaaatcatcccggacctccgtgcagcccacattcactgccagccagtaccgtgccttatccgtcct gggctgtggccacacatcctccaccaagtgctatggctgcgcctcggctgtcacagaacattgtatcacac tactcggggccctggccaccaacccagccttgaggcacatccttgtctcccagggccttatccgggagctc tttgattataatcttcgccgaggggctgcggccatgcgggaggaggtccgccagctcatgtgcctcctaac tcgagacaacccagaagccacccaacagatgaatgacctgattattggcaaggtctccacagccctgaaga gccactgggccaaccccgatctggcaagtagcctgcagtatgaaatgctgctgctgacggattctatctcc aaggaggacagctgctgggagctccggttacgctgtgctctcagccttttcctcatggctgtgaacattaa gactcctgtggtggttgaaaacattaccctcatgtgcctgaggatcttgcagaagctgataaaaccacctg ctcccactagcaagaagaacaaggatgtcccc
```

Fragment EF1 amino acid sequence (SEQ ID NO: 64)

```
PFLCNACGFCKYARFDFMLYAKPCCAVDPIENEEDRKKAVSNINTLLDKADRVYHQLMGHRPQLENLLCKV

NEAAPEKPQDDSGTAGGISSTSASVNRYILQLAQEYCGDCKNSFDELSKIIQKVFASRKELLEYDLQQREA

ATKSSRTSVQPTFTASQYRALSVLGCGHTSSTKCYGCASAVTEHCITLLRALATNPALRHILVSQGLIREL

FDYNLRRGAAAMREEVRQLMCLLTRDNPEATQQMNDLIIGKVSTALKSHWANPDLASSLQYEMLLLTDSIS

KEDSCWELRLRCALSLFLMAVNIKTPVVVENITLMCLRILQKLIKPPAPTSKKNKDVP
```

Fragment F1 nucleotide sequence (SEQ ID NO: 65)

```
tttgattataatcttcgccgaggggctgcggccatgcgggaggaggtccgccagctcatgtgcctcctaac tcgagacaacccagaagccacccaacagatgaatgacctgattattggcaaggtctccacagccctgaaga gccactgggccaaccccgatctggcaagtagcctgcagtatgaaatgctgctgctgacggacccctacctcc aaggaggacagctgctgggagctccggttacgctgtgctctcagccttttcctcatggctgtgaacattaa gactcctgtggtggttgaaaacattaccctcatgtgcctgaggatcttgcagaagctgataaaaccacctg ctcccactagcaagaagaacaaggatgtcccgtcgaggccctcaccacggtgaagccatactgcaatgag atccatgccccaggctcaactgtggctcaagagagaccccaaggcatcctatgatgcctggaagaagtgtct tcctatcagagggatagatggcaatgggaaagcccccagcaaatcagagctccgccatctctatttgactg
```

-continued agaagtatgtgtggaggtggaaacagttcctgagtcgtcgggggaagaggacctcccccttggatctcaaa ctggggcataacaactggctgcgacaagtgcttttcactccagcaacgcaggccgcacggcaggcagcctg taccattgtggaagctctagccaccattcccagccgcaagcagcaggtcctggacctgcttaccagttacc tggatgagctgagcatagctggggagtgtgcagctgagtacctggctctctaccagaagctcatcacttct gcgcactggaaagtctacttggcagctcggggagtcctaccctatgtgggcaacctcatcaccaaggaaat agctcgtctgctggccctggaggaggctaccctgagtaccgatctgcagcagggttatgcccttaaaagtc tcacaggccttctctcctcctttgttgaggtggaatccatcaaaagacattttaaaagtcgcttggtgggt actgtgctgaatggatacctgtgcttgcggaagctggtggtgcagaggaccaagctgatcgatgagacgca ggacatgctgctggagatgctggaggacatgaccacaggtacagaatcagaaaccaaggccttcatggctg tgtgcattgagacagccaagcgctacaatctggatgactaccggaccccggtgttcatcttcgagaggctc tgcagcatcatttatcctgaggagaatgaagtcactgagttctttgtgaccctggagaaggatccccaaca agaagacttcttacagggcaggatgcctgggaacccgtatagcagcaatgagccaggcatcgggccgctga tgagggatataaagaacaagatttgccaggactgtgacttagtggccctcctggaagatgacagtggcatg gagcttctagtgaacaataaaatcattagtttggaccttcctgtggctgaagtttacaagaaagtctggtg taccacgaatgagggagagcccatgaggattgtttatcgtatgcgggggctgctgggcgatgccacagagg agttcattgagtccctggactctactacagatgaagaagaagatgaagaagaagtgtataaaatggctggt gtgatggcccagtgtgggggcctggaatgcatgcttaacagactcgcagggatcagagatttcaagcaggg a Fragment F1 amino acid sequence (SEQ ID NO: 66)

FDYNLRRGAAAMREEVRQLMCLLTRDNPEATQQMNDLIIGKVSTALKSHWANPDLASSLQYEMLLLTDSIS

KEDSCWELRLRCALSLFLMAVNIKTPVVVENITLMCLRILQKLIKPPAPTSKKNKDVPVEALTTVKPYCNE

IHAQAQLWLKRDPKASYDAWKKCLPIRGIDGNGKAPSKSELRHLYLTEKYVWRWKQFLSRRGKRTSPLDLK

LGHNNWLRQVLFTPATQAARQAACTIVEAIATIPSRKQQVLDLLTSYLDELSIAGECAAEYLALYQKLITS

AHWKVYLAARGVLPYVGNLITKEIARLLALEEATLSTDLQQGYALKSLTGLLSSFVEVESIKRHFKSRLVG

TVLNGYLCLRKLVVQRTKLIDETQDMLLEMLEDMTTGTESETKAFMAVCIETAKRYNLDDYRTPVFIFERL

CSIIYPEENEVTEFFVTLEKDPQQEDFLQGRMPGNPYSSNEPGIGPLMRDIKNKICQDCDLVALLEDDSGM

ELLVNNKIISLDLPVAEVYKKVWCTTNEGEPMRIVYRMRGLLGDATEEFIESLDSTTDEEEDEEEVYKMAG

VMAQCGGLECMLNRLAGIRDFKQG

Fragment F12 nucleotide sequence (SEQ ID NO: 67)

gtgaccctggagaaggatccccaacaagaagacttcttacagggcaggatgcctgggaacccgtatagcag caatgagccaggcatcgggccgctgatgagggatataaagaacaagatttgccaggactgtgacttagtgg ccctcctggaagatgacagtggcatggagcttctagtgaacaataaaatcattagtttggaccttcctgtg gctgaagtttacaagaaagtctggtgtaccacgaatgagggagagcccatgaggattgtttatcgtatgcg ggggctgctgggcgatgccacagaggagttcattgagtccctggactctactacagatgaagaagaagatg aagaagaagtgtataaaatggctggtgtgatggcccagtgtgggggcctggaatgcatgcttaacagactc gcagggatcagagatttcaagcagggacgccaccttctaacagtgctactgaaattgttcagttactgcgc gaaggtgaaagtcaaccggcagcaactggtcaaactggaaatgaacaccttgaacgtcatgctggggaccc taaacctggcccttgtagctgaacaagaaagcaaggacagtgggggtgcagctgtggctgagcaggtgctt agcatcatggagatcattctagatgagtccaatgctgagcccctgagtgaggacaagggcaacctcctcct gacaggtgacaaggatcaactggtgatgctcttggaccagatcaacagcaccttgttcgctccaacccca gtgtgctccagggcctgcttcgcatcatcccgtaccttttcctttggagaggtggagaaaatgcagatcttg -continued

```
gtggagcgattcaaaccatactgcaactttgataaatatgatgaagatcacagtggtgatgataaagtctt cctggactgcttctgtaaaatagctgctggcatcaagaacaacagcaatgggcaccagctgaaggatctga ttctccagaaggggatcacccagaatgcacttgactacatgaaaaagcacatccctagcgccaagaatttg gatgccgacatctggaaaaagttttgtctcgcccagccttgccatttatcctaaggctgcttcggggcct ggccatccagcaccctggcacccaggttctgattggaactgattccatcccgaacctgcataagctggagc aggtgtccagtgatgagggcattgggacctggcagagaacctgctggaagccctgcgggaacaccctgac gtaaacaagaagattgacgcagcccgcagggagacccgggcagagaagaaacgcatggccatggcaatgag gcagaaggccctgggcaccctgggcatgacgacaaatgaaaagggccaggtcgtgaccaag
```

Fragment F12 amino acid sequence
(SEQ ID NO: 68)

VTLEKDPQQEDFLQGRMPGNPYSSNEPGIGPLMRDIKNKICQDCDLVALLEDDSGMELLVNNKIISLDLPV
AEVYKKVWCTTNEGEPMRIVYRMRGLLGDATEEFIESLDSTTDEEEDEEEVYKMAGVMAQCGGLECMLNRL
AGIRDFKQGRHLLTVLLKLESYCVKVKVNRQQLVKLEMNTLNVMLGTLNLALVAEQESKDSGGAAVAEQVL
SIMEIILDESNAEPLSEDKGNLLLTGDKDQLVMLLDQINSTFVRSNPSVLQGLLRIIPYLSFGEVEKMQIL
VERFKPYCNFDKYDEDHSGDDKVFLDCFCKIAAGIKNNSNGHQLKDLILQKGITQNALDYMKKHIPSAKNL
DADIWKKFLSRPALPFILRLLRGLAIQHPGTQVLIGTDSIPNLHKLEQVSSDEGIGTLAENLLEALREHPD
VNKKIDAARRETRAEKKRMAMAMRQKALGTLGMTTNEKGQVVTK

Fragment F2 nucleotide sequence
(SEQ ID NO: 69)

```
tttgattataatcttcgccgagggggctgcggccatgcgggaggaggtccgccagctcatgtgcctcctaac tcgagacaacccagaagccaccccaacagatgaatgacctgattattggcaaggtctccacagccctgaaga gccactgggccaaccccgatctggcaagtagcctgcagtatgaaatgctgctgctgacggattctatctcc aaggaggacagctgctgggagctccggttacgctgtgctctcagccttttcctcatggctgtgaacattaa gactcctgtggtggttgaaaacattaccctcatgtgcctgaggatcttgcagaagctgataaaaccacctg ctcccactagcaagaagaacaaggatgtcccgtcgaggccctcaccacggtgaagccatactgcaatgag atccatgcccaggctcaactgtggctcaagagagaccccaaggcatcctatgatgcctggaagaagtgtct tcctatcagagggatagatggcaatgggaaagcccccagcaaatcagagctccgccatctctatttgactg agaagtatgtgtggaggtggaaacagttcctgagtcgtcggggggaagaggacctcccccttggatctcaaa ctggggcataacaactggctgcgacaagtgcttttcactccagcaacgcaggccgcacggcaggcagcctg taccattgtggaagctctagccaccattcccagccgcaagcagcaggtcctggacctgcttaccagttacc tggatgagctgagcatagctggggagtgtgcagctgagtacctggctctctaccagaagctcatcacttct gcgcactggaaagtctacttggcagctcggggagtcctaccctatgtgggcaacctcatcaccaaggaaat agctcgtctgctggccctggaggaggctaccctgagtaccgatctgcagcagggttatgcccttaaaagtc tcacaggccttctctcctcctttgttgaggtggaatccatcaaaagacattttaaaagtcgcttggtgggt actgtgctgaatggatacctgtgcttgcggaagctggtggtgcagaggaccaagctgatcgatgagacgca ggacatgctgctggagatgctggaggacatgaccacaggtacagaatcagaaaccaaggccttcatggctg tgtgcattgagacagccaagcgctacaatctggatgactaccggaccccggtgttcatcttcgagaggctc tgcagcatcatttatcctgaggagaatgaagtcactgagttctttgtgaccctggagaaggatccccaaca agaagacttcttacagggcaggatgcctgggaacccgtatagcagcaatgagccaggcatcgggccgctga tgagggatataaagaacaagatttgccaggactgtgacttagtggccctcctggaagatgacagtggcatg gagcttctagtgaacaataaaatcattagtttggaccttcctgtggctgaagtttacaagaaagtctggtg taccacgaatgagggagagcccatgaggattgtttatcgtatgcgggggctgctgggcgatgccacagagg
```

-continued

```
agttcattgagtccctggactctactacagatgaagaagaagatgaagaagaagtgtataaaatggctggt gtgatggcccagtgtgggggcctggaatgcatgcttaacagactcgcagggatcagagatttcaagcaggg acgccaccttctaacagtgctactgaaattgttcagttactgcgtgaaggtgaaagtcaaccggcagcaac tggtcaaactggaaatgaaacccttgaacgtcatgctggggaccctaaacctggcccttgtagctgaacaa gaaagcaaggacagtgggggtgcagctgtggctgagcaggtgcttagcatcatggagatcattctagatga gtccaatgctgagcccctgagtgaggacaagggcaacctcctcctgacaggtgacaaggatcaactggtga tgctcttggaccagatcaacagcacctttgttcgctccaaccccagtgtgctccagggcctgcttcgcatc atcccgtacctttcctttggagaggtggagaaaatgcagatcttggtggagcgattcaaaccatactgcaa ctttgataaatatgatgaagatcacagtggtgatgataaagtcttcctg
```

Fragment F2 amino acid sequence
(SEQ ID NO: 70)

FDYNLRRGAAAMREEVRQLMCLLTRDNPEATQQMNDLIIGKVSTALKSHWANPDLASSLQYEMLLLTDSIS

KEDSCWELRLRCALSLFLMAVNIKTPVVVENITLMCLRILQKLIKPPAPTSKKNKDVPVEALTTVKPYCNE

IHAQAQLWLKRDPKASYDAWKKCLPIRGIDGNGKAPSKSELRHLYLTEKYVWRWKQFLSRRGKRTSPLDLK

LGHNNWLRQVLFTPATQAARQAACTIVEALATIPSRKQQVLDLLTSYLDELSIAGECAAEYLALYQKLITS

AHWKVYLAARGVLPYVGNLITKEIARLLALEEATLSTDLQQGYALKSLTGLLSSFVEVESIKRHFKSRLVG

TVLNGYLCLRKLVVQRTKLIDETQDMLLEMLEDMTTGTESETKAFMAVCIETAKRYNLDDYRTPVFIFERL

CSIIYPEENEVTEFFVTLEKDPQQEDFLQGRMPGNPYSSNEPGIGPLMRDIKNKICQDCDLVALLEDDSGM

ELLVNNKIISLDLPVAEVYKKVWCTTNEGEPMRIVYRMRGLLGDATEEFIESLDSTTDEEEDEEEVYKMAG

VMAQCGGLECMLNRLAGIRDFKQGRHLLTVLLKLFSYCVKVKVNRQQLVKLEMNTLNVMLGTLNLALVAEQ

ESKDSGGAAVAEQVLSIMEIILDESNAEPLSEDKGNLLLTGDKDQLVMLLDQINSTFVRSNPSVLQGLLRI

IPYLSFGEVEKMQILVERFKPYCNFDKYDEDHSGDDKVFL

Fragment F3 nucleotide sequence
(SEQ ID NO: 71)

```
aagagagaccccaaggcatcctatgatgcctggaagaagtgtcttcctatcagagggatagatggcaatgg gaaagcccccagcaaatcagagctccgccatctctatttgactgagaagtatgtgtggaggtggaaacagt tcctgagtcgtcgggggaagaggacctccccttggatctcaaactgggcataacaactggctgcgacaa gtgcttttcactccagcaacgcaggccgcacggcaggcagcctgtaccattgtggaagctctagccaccat tcccagccgcaagcagcaggtcctggacctgcttaccagttacctggatgagctgagcatagctggggagt gtgcagctgagtacctggctctctaccagaagctcatcacttctgcgcactggaaagtctacttggcagct cggggagtcccaccctatgtgggcaacctcatcaccaaggaaatagctcgtctgctggccctggaggaggc tacccctgagtaccgatctgcagcagggttatgcccttaaaagtctcacaggccttctctcctcctttgttg aggtggaatccatcaaaagacatttttaaaagtcgcttggtgggtactgtgctgaatggatacctgtgcttg cggaagctggtggtgcagaggaccaagctgatcgatgagacgcaggacatgctgctggagatgctggagga catgaccacaggtacagaatcagaaaccaaggccttcatggctgtgtgcattgagacagccaagcgctaca atctggatgactaccggaccccggtgttcatcttcgagaggctctgcagcatcatttatcctgaggagaat gaagtcactgagttctttgtgaccctggagaaggatccccaacaagaagacttcttacagggcaggatgcc tgggaacccgtatagcagcaatgagccaggcatcgggccgctgatgagggatataaagaacaagatttgcc aggactgtgacttagtggcccctcctggaagatgacagtggcatggagcttctagtgaacaataaaatcatt agtttggaccttcctgtggctgaagtttacaagaaagtctggtgtaccacgaatgagggagagcccatgag gattgtttatcgtatgcgggggctgctggcgatgccacagaggagttcattgagtccctggactctacta cagatgaagaagaagatgaagaagaagtgtataaaatggctggtgtgatggcccagtgtgggggcctggaa tgcatgcttaacagactcgcagggatcagagatttcaagcagggacgccaccttctaacagtgctactgaa
```

-continued

```
attgttcagttactgcgtgaaggtgaaagtcaaccggcagcaactggtcaaactggaaatgaacaccttga acgtcatgctggggaccctaaacctggcccttgtagctgaacaagaaagcaaggacagtgggggtgcagct gtggctgagcaggtgcttagcatcatggagatcattctagatgagtccaatgctgagcccctgagtgagga caagggcaacctcctcctgacaggtgacaaggatcaactggtgatgctcttggaccagatcaacagcacct tgttcgctccaaccccagtgtgctccagggcctgcttcgcatcatcccgtacctttcctttggagaggtg gagaaaatgcagatcttggtggagcgattcaaaccatactgcaactttgataaatatgatgaagatcacag tggtgatgataaagtcttcctggactgcttctgcaaaatagctgctggcatcaagaacaacagcaatgggc accagctgaaggatctgattctccagaaggggatcacccagaatgcacttgactacatgaaaaagcacatc cctagcgccaagaatttggatgccgacatctggaaaaagttttgtctcgcccagccttgccatttatcct aaggctgcttcggggcctggccatccagcaccctggcacccaggttctgattggaactgattccatcccga acctgcataagctggagcaggtgtccagtgatgagggcattgggaccttggcagagaacctgctggaagcc ctgcgggaacaccctgacgtaaacaagaagattgacgcagcccgcagggagacccgggcagagaagaaacg catggccatggcaatgaggcagaaggccctgggcaccctgggcatgacgacaaatgaaaagggccaggtcg tgaccaagacagcactcctgaagcagatggaagagctgatcgaggagcctggcctcacgtgctgcatctgc agggagggatacaagttccagcccacaaag
```

Fragment F3 amino acid sequence
(SEQ ID NO: 72)
```
KRDPKASYDAWKKCLPIRGIDGNGKAPSKSELRHLYLTEKYVWRWKQFLSRRGKRTSPLDLKLGHNNWLRQ

VLFTPATQAARQAACTIVEALATIPSRKQQVLDLLTSYLDELSIAGECAAEYLALYQKLITSAHWKVYLAA

RGVLPYVGNLITKEIARLLALEEATLSTDLQQGYALKSLTGLLSSFVEVESIKRHFKSRLVGTVLNGYLCL

RKLVVQRTKLIDETQDMLLEMLEDMTTGTESETKAFMAVCIETAKRYNLDDYRTPVFIFERLCSIIYPEEN

EVTEFFVTLEKDPQQEDFLQGRMPGNPYSSNEPGIGPLMRDIKNKICQDCDLVALLEDDSGMELLVNNKII

SLDLPVAEVYKKVWCTTNEGEPMRIVYRMRGLLGDATEEFIESLDSTTDEEEDEEEVYKMAGVMAQCGGLE

CMLNRLAGIRDFKQGRHLLTVLLKLFSYCVKVKVNRQQLVKLEMNTLNVMLGTLNLALVAEQESKDSGGAA

VAEQVLSIMEIILDESNAEPLSEDKGNLLLTGDKDQLVMLLDQINSTFVRSNPSVLQGLLRIIPYLSFGEV

EKMQILVERFKPYCNFDKYDEDHSGDDKVFLDCFCKIAAGIKNNSNGHQLKDLILQKGITQNALDYMKKHI

PSAKNLDADIWKKFLSRPALPFILRLLRGLAIQHPGTQVLIGTDSIPNLHKLEQVSSDEGIGTLAENLLEA

LREHPDVNKKIDAARRETRAEKKRMAMAMRQKALGTLGMTTNEKGQVVTKTALLKQMEELIEEPGLTCCIC

REGYKFQPTK
```

Fragment F6 nucleotide sequence
(SEQ ID NO: 73)
```
aagagagaccccaaggcatcctatgatgcctggaagaagtgtcttcctatcagagggatagatggcaatgg gaaagcccccagcaaatcagagctccgccatctctatttgactgagaagtatgtgtggaggtggaaacagt tcctgagtcgtcggggaagaggacctcccccttggatctcaaactggggcataacaactggctgcgacaa gtgcttttcactccagcaacgcaggccgcacggcaggcagcctgtaccattgtgaagctctagccaccat tcccagccgcaagcagcaggtcctggacctgcttaccagttacctggatgagctgagcatagctggggagt gtgcagctgagtacctggctctctaccagaagctcatcacttctgcgcactggaaagtctacttggcagct cggggagtcctaccctatgtgggcaacctcatcaccaaggaaatagctcgtctgctggccctggaggaggc taccctgagtaccgatctgcagcagggttatgcccttaaaagtctcacaggccttctctcctccttttgttg aggtggaatccatcaaaagacattttaaaagtcgcttggtgggtactgtgctgaatggatacctgtgcttg cggaagctggtggtgcagaggaccaagctgatcgatgagacgcaggacatgctgctggagatgctggagga catgaccacaggtacagaatcagaaaccaaggccttcatggctgtgtgcattgagacagccaagcgctaca
```

-continued

```
atctggatgactaccggaccccggtgttcatcttcgagaggctctgcagcatcatttatcctgaggagaat gaagtcactgagttctttgtgaccctggagaaggatccccaacaagaagacttcttacagggcaggatgcc tgggaacccgtatagcagcaatgagccaggcatcgggccgctgatgagggatataaagaacaagatttgcc aggactgtgacttagtggccctcctggaagatgacagtggcatggagcttctagtgaacaataaaatcatt agtttggaccttcctgtggctgaagtttacaagaaagtctggtgtaccacgaatgagggagagcccatgag gattgtttatcgtatgcggggcgctgctgggcgatgccacagaggagttcattgagtccctggactctacta cagatgaagaagaagatgaagaagaagtgtataaaatggctggtgtgatggcccagtgtgggggcctggaa tgcatgcttaacagactcgcagggatcagagatttcaagcagggacgccaccttctaacagtgctactgaa attgttcagttactgcgtgaaggtgaaagtcaaccggcagcaactggtcaaactggaaatgaacaccttga acgtcatgctggggaccctaaacctggcccttgtagctgaacaagaaagcaaggacagtgggggtgcagct gtggctgagcaggtgcttagcatcatggagatcattctagatgagtccaatgctgagcccctgagtgagga caagggcaacctcctcctgacaggtgacaaggatcaactggtgatgctcttggaccagatcaacagcacct ttgttcgctccaaccccagtgtgctccagggcctgcttcgcatcatcccgtacctttcctttggagaggtg gagaaaatgcagatcttggtggagcgattcaaaccatactgcaactttgataaatatgatgaagatcacag tggtgatgataaagtcttcctg
```

Fragment F6 amino acid sequence
(SEQ ID NO: 74)

KRDPKASYDAWKKCLPIRGIDGNGKAPSKSELRHLYLTEKYVRWKQFLSRRGKRTSPLDLKLGHNNWLRQ

VLFTPATQAARQAACTIVEALATIPSRKQQVLDLLTSYLDELSIAGECAAEYLALYQKLITSAHWKVYLAA

RGVLPYVGNLITKEIARLLALEEATLSTDLQQGYALKSLTGLLSSFVEVESIKRHFKSRLVGTVLNGYLCL

RKLVVQRTKLIDETQDMLLEMLEDMTTGTESETKAFMAVCIETAKRYNLDDYRTPVFIFERLCSIIYPEEN

EVTEFFVTLEKDPQQEDFLQGRMPGNPYSSNEPGIGPLMRDIKNKICQDCDLVALLEDDSGMELLVNNKII

SLDLPVAEVYKKVWCTTNEGEPMRIVYRMRGLLGDATEEFIESLDSTTDEEEDEEEVYKMAGVMAQCGGLE

CMLNRLAGIRDFKQGRHLLTVLLKLFSYCVKVKVNRQQLVKLEMNTLNVMLGTLNLALVAEQESKDSGGAA

VAEQVLSIMEIILDESNAEPLSEDKGNLLLTGDKDQLVMLLDQINSTFVRSNPSVLQGLLRIIPYLSFGEV

EKMQILVERFKPYCNFDKYDEDHSGDDKVFL

Fragment G1 nucleotide sequence
(SEQ ID NO: 75)

```
gcccagtgtgggggcctggaatgcatgcttaacagactcgcagggatcagagatttcaagcagggacgcca ccttctaacagtgctactgaaattgttcagttactgcgtgaaggtgaaagtcaaccggcagcaactggtca aactggaaatgaacaccttgaacgtcatgctggggaccctaaacctggcccttgtagctgaacaagaaagc aaggacagtgggggtgcagctgtggctgagcaggtgcttagcatcatggagatcattctagatgagtccaa tgctgagcccctgagtgaggacaagggcaacctcctcctgacaggtgacaaggatcaactggtgatgctct tggaccagatcaacagcacctttgttcgctccaaccccagtgtgctccagggcctgcttcgcatcatcccg tacctttcctttggagaggtggagaaaatgcagatcttggtggagcgattcaaaccatactgcaactttga taaatatgatgaagatcacagtggtgatgataaagtcttcctggactgcttctgtaaaatagctgctggca tcaagaacaacagcaatgggcaccagctgaaggatctgattctccagaagggatcacccagaatgcactt gactacatgaaaaagcacatccctagcgccaagaatttggatgccgacatctggaaaaagttttttgtctcg cccagccttgccatttatcctaaggctgcttcggggcctggccatccagcaccctggcacccaggttctga ttggaactgattccatcccgaacctgcataagctggagcaggtgtccagtgatgagggcattgggaccttg gcagagaacctgctggaagccctgcgggaacaccctgacgtaaacaagaagattgacgcagcccgcaggga gacccgggcagagaagaaacgcatggccatggcaatgaggcagaaggccctgggcaccctgggcatgacga caaatgaaaagggccaggtcgtgaccaagacagcactcctgaagcagatggaagagctgatcgaggagcct
```

-continued

```
ggcctcacgtgctgcatctgcagggagggatacaagttccagcccacaaaggtcctgggcatttatacctt cacgaagcgggtagccttggaggagatggagaataagccccggaaacagcagggctacagcaccgtgtccc acttcaacattgtgcactacgactgccatctggctgccgtcaggttggctcgaggccgggaagagtgggag agtgccgccctgcagaatgccaacaccaagtgcaacgggctccttccggtctggggacctcatgtccctga atcagcttttgccacttgcttggcaagacacaacacttacctccaggaatgtacaggccagcgggagccca cgtatcagctcaacatccatgacatcaaactgctcttcctgcgcttcgccatggagcagtcgttcagcgca gacactggcgggggc
```

Fragment G1 amino acid sequence
(SEQ ID NO: 76)

```
AQCGGLECMLNRLAGIRDFKQGRHLLTVLLKLFSYCVKVKVNRQQLVKLEMNTLNVMLGTLNLALVAEQES

KDSGGAAVAEQVLSIMEIILDESNAEPLSEDKGNLLLTGDKDQLVMLLDQINSTFVRSNPSVLQGLLRIIP

YLSFGEVEKMQILVERFKPYCNFDKYDEDHSGDDKVFLDCFCKIAAGIKNNSNGHQLKDLILQKGITQNAL

DYMKKHIPSAKNLDADIWKKFLSRPALPFILRLLRGLAIQHPGTQVLIGTDSIPNLHKLEQVSSDEGIGTL

AENLLEALREHPDVNKKIDAARRETRAEKKRMAMAMRQKALGTLGMTTNEKGQVVTKTALLKQMEELIEEP

GLTCCICREGYKFQPTKVLGIYTFTKRVALEEMENKPRKQQGYSTVSHFNIVHYDCHLAAVRLARGREEWE

SAALQNANTKCNGLLPVWGPHVPESAFATCLARHNTYLQECTGQREPTYQLNIHDIKLLFLRFAMEQSFSA

DTGGG
```

Fragment G6 nucleotide sequence
(SEQ ID NO: 77)

```
gcccagtgtgggggcctggaatgcatgcttaacagactcgcagggatcagagatttcaagcagggacgcca ccttctaacagtgctactgaaattgttcagttactgcgtgaaggtgaaagtcaaccggcagcaactggtca aactggaaatgaacaccttgaacgtcatgctggggaccctaaacctggcccttgtagctgaacaagaaagc aaggacagtgggggtgcagctgtggctgagcaggtgcttagcatcatggagatcattctagatgagtccaa tgctgagcccctgagtgaggacaagggcaacctcctcctgacaggtgacaaggatcaactggtgatgctct tggaccagatcaacagcacctttgttcgctccaaccccagtgtgctccagggcctgcttcgcatcatcccg tacctttcctttggagaggtggagaaaatgcagatcttggtggagcgattcaaaccatactgcaactttga taaatatgatgaagatcacagtggtgatgataaagtcttcctggactgcttctgtaaaatagctgctggca tcaagaacaacagcaatgggcaccagctgaaggatctgattctccagaaggggatcacccagaatgcactt gactacatgaaaaagcacatccctagcgccaagaatttggatgccgacatctggaaaaagttttttgtctcg cccagccttgccatttatcctaaggctgcttcggggcctggccatccagcaccctggcacccaggttctga ttggaactgattccatcccgaacctgcataagctggagcaggtgtccagtgatgagggcattgggaccttg gcagagaacctgctggaagccctgcgggaacaccctgacgtaaacaagaagattgacgcagcccgcaggga gacccgggcagagaagaaacgcatggccatggcaatgaggcagaaggccctgggcaccctgggcatgacga caaatgaaaagggccaggtcgtgaccaagacagcactcctgaagcagatggaagagctgatcgaggagcct ggcctcacgtgctgcatctgcagggagggatacaagttccagcccacaaaggtcctgggcatttatacctt cacgaagcgggtagccttggaggagatggagaataagccccggaaacagcagggctacagcaccgtgtccc acttcaacattgtgcactacgactgccatctggctgccgtcaggttggctcgaggccgggaagagtgggag agtgccgccctgcagaatgccaacaccaagtgcaacgggctccttccggtctggggacctcatgtccctga atcagcttttgccacttgcttggcaagacacaacacttacctccaggaatgtacaggccagcgggagccca cgtatcagctcaacatccatgacatcaaactgctcttcctgcgcttcgccatggagcagtcgttcagcgca gacactggcgggggcggccgggagagcaadatccacctgatcccgtacatcattcacactgtgctttacgt
```

-continued

```
cctgaacacaacccgagcaacttcccgagaagagaagaacctccaaggctttctggaacagcccaaggaga agtgggtggagagtgcctttgaagtggacgggccc
```

Fragment G6 amino acid sequence
(SEQ ID NO: 78)

```
AQCGGLECMLNRLAGIRDFKQGRHLLTVLLKLFSYCVKVKVNRQQLVKLEMNTLNVMLGTLNLALVAEQES

KDSGGAAVAEQVLSIMEIILDESNAEPLSEDKGNLLLTGDKDQLVMLLDQINSTFVRSNPSVLQGLLRIIP

YLSFGEVEKMQILVERFKPYCNFDKYDEDHSGDDKVFLDCFCKIAAGIKNNSNGHQLKDLILQKGITQNAL

DYMKKHIPSAKNLDADIWKKFLSRPALPFILRLLRGLAIQHPGTQVLIGTDSIPNLHKLEQVSSDEGIGTL

AENLLEALREHPDVNKKIDAARRETRAEKKRMAMAMRQKALGTLGMTTNEKGQVVTKTALLKQMEELIEEP

GLTCCICREGYKFQPTKVLGIYTFTKRVALEEMENKPRKQQGYSTVSHFNIVHYDCHLAAVRLARGREEWE

SAALQNANTKCNGLLPVWGPHVPESAFATCLARHNTYLQECTGQREPTYQLNIHDIKLLFLRFAMEQSFSA

DTGGGGRESNIHLIPYIIHTVLYVLNTTRATSREEKNLQGFLEQPKEKWVESAFEVDGP
```

Fragment G7 nucleotide sequence
(SEQ ID NO: 79)

```
gcccagtgtgggggcctggaatgcatgcttaacagactcgcagggatcagagatttcaagcagggacgcca ccttctaacagtgctactgaaattgttcagttactgcgtgaaggtgaaagtcaaccggcagcaactggtca aactggaaatgaacaccttgaacgtcatgctggggaccctaaacctggcccttgtagctgaacaagaaagc aaggacagtgggggtgcagctgtggctgagcaggtgcttagcatcatggagatcattctagatgagtccaa tgctgagcccctgagtgaggacaagggcaacctcctcctgacaggtgacaaggatcaactggtgatgctct tggaccagatcaacagcacctttgttcgctccaaccccagtgtgctccagggcctgcttcgcatcatcccg tacctttcctttggagaggtggagaaaatgcagatcttggtggagcgattcaaaccatactgcaactttga taaatatgatgaagatcacagtggtgatgataaagtcttcctggactgcttctgtaaaatagctgctggca tcaagaacaacagcaatgggcaccagctgaaggatctgattctccagaaggggatcacccagaatgcactt gactacatgaaaaagcacatccctagcgccaagaatttggatgccgacatctggaaaaagttttttgtctcg cccagccttgccatttatcctaaggctgcttcggggcctggccatccagcaccctggcacccaggttctga ttggaactgattccatcccgaacctgcataagctggagcaggtgtccagtgatgagggcattgggacctttg gcagagaacctgctggaagccctgcgggaacaccctgacgtaaacaagaagattgacgcagcccgcaggga gacccgggcagagaagaaacgcatggccatggcaatgaggcagaaggccctgggcaccctgggcatgacga caaatgaaaagggccaggtcgtgaccaagacagcactcctgaagcagatggaagagctgatcgaggagcct ggcctcacgtgctgcatctgcaggagggatacaagttccagcccacaaaggtcctgggcatttatacctt cacgaagcgggtagccttggaggagatggagaataagcccggaaacagcagggctacagcaccgtgtccc acttcaacattgtgcactacgactgccatctggctgccgtcaggttggctcgaggccgggaagagtgggag agtgccgccctgcagaatgccaacaccaagtgcaacgggctccttccggtctggggacctcatgtccctga atcagcttttgccacttgcttggcaagacacaacacttacctccaggaatgtacaggccagcgggagccca cgtatcagctcaacatccatgacatcaaactgctcttcctgcgcttcgccatggagcagtcgttcagcgca gacactggcgggggcggccgggagagcaacatccacctgatcccgtacatcattcacactgtgctttacgt cctgaacacaacccgagcaacttcccgagaagagaagaacctccaaggctttctggaacagcccaaggaga agtgggtggagagtgcctttgaagtggacgggcccactatttcacagtcttggcccttcacatcctgccc cctgagcagtggagagccacacgtgtggaaatcttgcggaggctgttggtgacctcgcaggctcgggcagt ggctccaggtggagcc
```

```
Fragment G7 amino acid sequence
                                                          (SEQ ID NO: 80)
AQCGGLECMLNRLAGIRDFKQGRHLLTVLLKLFSYCVKVKVNRQQLVKLEMNTLNVMLGTLNLALVAEQES

KDSGGAAVAEQVLSIMEIILDESNAEPLSEDKGNLLLTGDKDQLVMLLDQINSTFVRSNPSVLQGLLRIIP

YLSFGEVEKMQILVERFKPYCNFDKYDEDHSGDDKVFLDCFCKIAAGIKNNSNGHQLKDLILQKGITQNAL

DYMKKHIPSAKNLDADIWKKFLSRPALPFILRLLRGLAIQHPGTQVLIGTDSIPNLHKLEQVSSDEGIGTL

AENLLEALREHPDVNKKIDAARRETRAEKKRMAMAMRQKALGTLGMTTNEKGQVVTKTALLKQMEELIEEP

GLTCCICREGYKFQPTKVLGIYTFTKRVALEEMENKPRKQQGYSTVSHFNIVHYDCHLAAVRLARGREEWE

SAALQNANTKCNGLLPVWGPHVPESAFATCLARHNTYLQECTGQREPTYQLNIHDIKLLFLRFAMEQSFSA

DTGGGGRESNIHLIPYIIHTVLYVLNTTRATSREEKNLQGFLEQPKEKWVESAFEVDGPYYFTVLALHILP

PEQWRATRVEILRRLLVTSQARAVAPGGA
```

The nucleic acids of the present invention can be DNA, RNA, DNA/RNA duplexes, protein-nucleic acid (PNA), or derivatives thereof. As used herein, a nucleic acid or polypeptide is said to be "isolated" or "purified" when it is substantially free of cellular material or free of chemical precursors or other chemicals. It should be appreciated that the term isolated or purified does not refer to a library-type preparation containing a myriad of other sequence fragments. The nucleic acid or polypeptide of the present invention can be purified to homogeneity or other degrees of purity. The level of purification will be based on the intended use. The critical feature is that the preparation allows for the desired function of the nucleic acid or polypeptide, even if in the presence of considerable amounts of other components.

The truncated polypeptide can be purified from cells that naturally express it, purified from cells that have been altered to express it (recombinant), or synthesized using known protein synthesis methods. For example recombinant production of proteins involves cloning a nucleic acid molecule encoding the polypeptide into an expression vector. The expression vector is introduced into a host cell and the protein is expressed in the host cell. The protein can then be isolated from the cells by any appropriate purification scheme using standard protein purification techniques.

The truncated peptides may be obtained or produced by methods well-known in the art, e.g. chemical synthesis. For example, a peptide corresponding to a portion of a truncated peptide including a desired region or domain, or that mediates the desired activity in vitro, e.g., apoptosis, may be synthesized by use of a peptide synthesizer.

The truncated peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed, and the term "D-retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Therapeutic Methods

The growth of cells is inhibited, e.g. reduced by contacting a cell with a composition a truncated p600 nucleic acid or polypeptide. By inhibition of cell growth is meant the cell proliferates at a lower rate or has decreased viability compared to a cell not exposed to the composition. Cell growth is measured by methods know in the art such as, the MTT cell proliferation assay or measurement of total GFP from GFP expressing cell lines.

Tissues and cells may be in direct contact with compounds and compositions of the invention, or exposed indirectly, through methods well described in the art. Alternatively, the compounds and compositions of the invention are administered systemically.

Alternatively, contacting a cell may include any route of administration to a subject, for example, oral or parenteral administration of a polypeptide, peptide, nucleic acid, vector or composition of this invention to a subject, wherein administration results in in vivo cellular exposure to these materials, within specific sites within a body.

The cell is a tumor cell such as a carcinoma, adenocarcinoma, blastoma, leukemia, myeloma, or sarcoma. In particular, the cancer is melanoma, colon cancer, lung cancer, brain cancer, hematologic cancers or thyroid cancer The methods are useful to alleviate the symptoms and/or treat of a variety of cancers. Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficaciousness is determined in association with any known method for diagnosing or treating the particular tumor type.

Pharmaceutical Compositions

The truncated p600 nucleic acids and polypeptides, (also referred to herein as "active compounds") of the invention, and derivatives, fragments, analogs and homologs thereof, can be incorporated into pharmaceutical compositions suitable for administration. Such compositions typically comprise the peptide or mimetic, and a pharmaceutically acceptable carrier.

The truncated p600 nucleic acids and polypeptides may be administered either as a monotherapy or as a combination therapy with other pharmaceutical agents. For example, they may be administered together with other pharmaceutical agents suitable for the treatment or prevention of cell proliferative disorders such as cancer.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In certain embodiments, liposomes, nanocapsules, microparticles, lipid particles, vesicles, and the like, are used for the administration of the truncated p600 nucleic acids and polypeptides of the present invention. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

As described herein, the present invention also provides an active compound that is a nucleic acid and a vector comprising a nucleic acid either of which can be in a pharmaceutically acceptable carrier. Such nucleic acids and vectors can be used in gene therapy protocols to treat a subject in accordance with the methods of the invention.

The nucleic acid can be administered to the cell in a virus, which can be, for example, adenovirus, retrovirus and adeno-associated virus. Alternatively, the nucleic acid of this invention can be administered to the cell in a liposome. The cell of the subject can be either in vivo or ex vivo. Also, the cell of the subject can be any cell which can take up and express exogenous nucleic acid If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject. Delivery by transfection and by liposome injections may be achieved using methods, which are well known in the art.

For in vivo methods, compounds can be administered to the subject in a pharmaceutically acceptable carrier as described herein.

In the methods described herein which include the administration and uptake of exogenous DNA into the cells of a subject (i.e., gene transduction or transfection), the nucleic acids can be in the form of naked DNA or the nucleic acids can be in a vector for delivering the nucleic acids to the cells for expression of the nucleic acid. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Vector delivery can also be via a viral system, such as a retroviral vector system which can package a recombinant retroviral genome. The recombinant retrovirus can then be used to infect and thereby deliver to the infected cells nucleic acid. The exact method of introducing the exogenous nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

Various adenoviruses may be used in the compositions and methods described herein. For example, a nucleic acid can be inserted within the genome of adenovirus type 5. Similarly, other types of adenovirus may be used such as type 1, type 2, etc. Furthermore, it is contemplated that a recombinant nucleic acid comprising an adenoviral nucleic acid from one type adenovirus can be packaged using capsid proteins from a different type adenovirus.

The adenovirus of the present invention is preferably rendered replication deficient, depending upon the specific application of the compounds and methods described herein. Methods of rendering an adenovirus replication deficient are well known in the art. For example, mutations such as point mutations, deletions, insertions and combinations thereof, can be directed toward a specific adenoviral gene or genes, such as the E1 gene. For a specific example of the generation of a replication deficient adenovirus for use in gene therapy, see WO 94/28938 (Adenovirus Vectors for Gene Therapy Sponsorship) which is incorporated herein in its entirety.

In the present invention, the nucleic acid encoding the active compound can be inserted within an adenoviral genome and the fusion protein encoding sequence can be positioned such that an adenovirus promoter is operatively linked to the active compound nucleic acid insert such that the adenoviral promoter can then direct transcription of the nucleic acid, or the active compound insert may contain its own adenoviral promoter. Similarly, the active compound insert may be positioned such that the nucleic acid encoding the active compound may use other adenoviral regulatory regions or sites such as splice junctions and polyadenylation signals and/or sites. Alternatively, the nucleic acid encoding the active compound may contain a different enhancer/promoter (e.g., CMV or RSV-LTR enhancer/promoter sequences) or other regulatory sequences, such as splice sites and polyadenylation sequences, such that the nucleic acid encoding the active compound may contain those sequences necessary for expression of the active compound and not partially or totally require these regulatory regions and/or sites of the adenovirus genome. These regulatory sites may also be derived from another source, such as a virus other than adenovirus. For example, a polyadenylation signal from SV40 or BGH may be used rather than an adenovirus, a human, or a murine polyadenylation signal. The active compound nucleic acid insert may, alternatively, contain some sequences necessary for expression of the nucleic acid encoding the active compound and derive other sequences necessary for the expression of the active compound nucleic acid from the adenovirus genome, or even from the host in which the recombinant adenovirus is introduced.

As another example, for administration of nucleic acid encoding the active compound to an individual in an AAV vector, the AAV particle can be directly injected intravenously. The AAV has a broad host range, so the vector can be used to transduce any of several cell types, but preferably cells in those organs that are well perfused with blood vessels. To more specifically administer the vector, the AAV particle can be directly injected into a target organ, such as muscle, liver or kidney. Furthermore, the vector can be administered intraarterially, directly into a body cavity, such as intraperitoneally, or directly into the central nervous system (CNS).

An AAV vector can also be administered in gene therapy procedures in various other formulations in which the vector plasmid is administered after incorporation into other delivery systems such as liposomes or systems designed to target cells by receptor-mediated or other endocytosis procedures. The AAV vector can also be incorporated into an adenovirus, retrovirus or other virus which can be used as the delivery vehicle.

As described above, the nucleic acid or vector can be administered in vivo in a pharmaceutically acceptable carrier.

The mode of administration of the nucleic acid or vector can vary predictably according to the disease being treated and the tissue being targeted. For example, for administration of the nucleic acid or vector in a liposome, catheterization of an artery upstream from the target organ is a preferred mode of delivery, because it avoids significant clearance of the liposome by the lung and liver.

The nucleic acid or vector may be administered orally as described herein for oral administration, parenterally (e.g., intravenously), by intramuscular injection, by intraperitoneal injection, transdermally, extracorporeally, topically or the like, although intravenous administration is typically preferred. The exact amount of the nucleic acid or vector required will vary from subject to subject, depending on the species, age, weight and general condition of the subject, the severity of the disorder being treated, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein.

Parenteral administration of the nucleic acid or vector of the present invention, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety.

Any of the therapeutic methods described to above may be applied to any suitable subject including, for example, mammals such as dogs, cats, cows, horses, rabbits, monkeys, and most preferably, humans.

The pharmaceutical compositions can be included in a container, pack, or dispenser together with instructions for administration.

I claim:

1. A p600 deoxyribonucleic acid (DNA) fragment consisting of a DNA sequence selected from the group consisting of SEQ ID NO: 7, 9, 11, 13, 15, 17, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 wherein the p600 DNA fragment encodes a polypeptide that when expressed in a cell induces cell death.

2. The p600 DNA fragment of claim 1, wherein the p600 DNA fragment is SEQ ID NO: 21.

3. The DNA fragment of claim 1, wherein the DNA fragment is in a vector.

4. A composition comprising the p600 DNA fragment of claim 1 and a pharmaceutically acceptable carrier.

5. A nanoparticle or nanosphere comprising a p600 DNA fragment consisting of a DNA sequence selected from the group consisting of SEQ ID NO: 3, 5, 7, 9, 11, 13 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79, wherein the DNA fragment encodes a polypeptide that when expressed in a cell induces cell death.

6. A p600 DNA fragment selected from the group consisting of a p600 DNA sequence comprising SEQ ID NO: 7 that is less than 1,500 nucleotides in length, a p600 DNA sequence comprising SEQ ID NO: 9 that is less than 2,000 nucleotides in length, a p600 DNA sequence comprising SEQ ID NO: 11 that is less than 2,900 nucleotides in length, a p600 DNA sequence comprising SEQ ID NO: 13 that is less than 2,200 nucleotides in length, a p600 DNA sequence comprising SEQ ID NO: 15 that is less than 1,800 nucleotides in length, a p600 DNA sequence comprising SEQ ID NO: 17 that is less than 1,900 nucleotides in length, a p600 DNA sequence comprising of SEQ ID NO: 21 that is less than 1,900 nucleotides in length, a p600 DNA sequence comprising of SEQ ID NO: 23 that is less than 1,700 nucleotides in length, a p600 DNA sequence comprising of SEQ ID NO: 25 that is less than 800 nucleotides in length, a p600 DNA sequence comprising of SEQ ID NO: 27 that is less than 1,200 nucleotides in length, a p600 DNA sequence comprising of SEQ ID NO: 29 that is less than 1,200 nucleotides in length, a p600 DNA sequence comprising of SEQ ID NO: 31 that is less than 2,200 nucleotides in length, a p600 DNA sequence comprising of SEQ ID NO: 33 that is less than 1,300 nucleotides in length, a p600 DNA sequence comprising of SEQ ID NO: 35 that is less than 1,000 nucleotides in length, a p600 DNA sequence comprising of SEQ ID NO: 37 that is less than 1,500 nucleotides in length, a p600 DNA sequence comprising of SEQ ID NO: 39 that is less than 1,500 nucleotides in length, a p600 DNA sequence comprising of SEQ ID NO: 41 that is less than 2,000 nucleotides in length, a p600 DNA sequence comprising of SEQ ID NO: 43 that is less than 1,500 nucleotides in length, a p600 DNA sequence comprising of SEQ ID NO: 45 that is less than 1,200 nucleotides in length, a p600 DNA sequence comprising of SEQ ID NO: 47 that is less than 1,500 nucleotides in length, a p600 DNA sequence comprising of SEQ ID NO: 49 that is less than 800 nucleotides in length, a p600 DNA sequence comprising of SEQ ID NO: 51 that is less than 1,200 nucleotides in length, a p600 DNA sequence comprising of SEQ ID NO: 53 that is less than 1,000 nucleotides in length, a p600 DNA sequence comprising of SEQ ID NO: 55 that is less than 1,000 nucleotides in length, a p600 DNA sequence comprising of SEQ ID NO: 57 that is less than 900 nucleotides in length, a p600 DNA sequence comprising of SEQ ID NO: 59 that is less than 800 nucleotides in length, a p600 DNA sequence comprising of SEQ ID NO: 61 that is less than 1,300 nucleotides in length, a p600 DNA sequence comprising of SEQ ID NO: 63 that is less than 1,100 nucleotides in length, a p600 DNA sequence comprising of SEQ ID NO: 65 that is less than 1,800 nucleotides in length, a p600 DNA sequence comprising of SEQ ID NO: 67 that is less than 1,500 nucleotides in length, a p600 DNA sequence comprising of SEQ ID NO: 69 that is less than 2,300 nucleotides in length, a p600 DNA sequence comprising of SEQ ID NO: 71 that is less than 2,400 nucleotides in length, a p600 DNA sequence comprising of SEQ ID NO: 73 that is less than 1,800 nucleotides in length, a p600 DNA sequence comprising of SEQ ID NO: 75 that is less than 1,600 nucleotides in length, a p600 DNA sequence comprising of SEQ ID NO: 77 that is less than 1,700 nucleotides in length, and a p600 DNA sequence comprising of SEQ ID NO: 79 that is less than 1,800 nucleotides in length, wherein the p600 DNA fragment encodes a polypeptide that when expressed in a cell induces cell death.

7. The p600 DNA fragment of claim 6, wherein the DNA fragment is in a vector.

8. A composition comprising the p600 DNA fragment of claim 6 and a pharmaceutically acceptable carrier.

9. A nanoparticle or nanosphere comprising a p600 DNA fragment selected from the group consisting of a p600 DNA sequence comprising SEQ ID NO: 3 that is less than 2,600 nucleotides in length, a p600 DNA sequence comprising SEQ ID NO: 5 that is less than 2,200 nucleotides in length, a p600 DNA sequence comprising SEQ ID NO: 7 that is less than 1,500 nucleotides in length, a p600 DNA sequence comprising SEQ ID NO: 9 that is less than 2,000 nucleotides in length, a p600 DNA sequence comprising SEQ ID NO: 11 that is less than 2,900 nucleotides in length, a p600 DNA sequence comprising SEQ ID NO: 13 that is less than 2,200 nucleotides in length, a p600 DNA sequence comprising SEQ ID NO: 15 that is less than 1,800 nucleotides in length, a p600 DNA sequence comprising SEQ ID NO: 17 that is less than 1,900 nucleotides in length, a p600 DNA sequence comprising SEQ ID NO: 19 that is less than 2,200 nucleotides in length, and a p600 DNA sequence comprising SEQ ID NO: 21 that is less than 1,900 nucleotides in length, a p600 DNA sequence comprising of SEQ ID NO: 23 that is less than 1,700 nucleotides in length, a p600 DNA sequence comprising of SEQ ID NO: 25 that is less than 800 nucleotides in length, a p600 DNA sequence comprising of SEQ ID NO: 27 that is less than 1,200 nucleotides in length, a p600 DNA sequence comprising of SEQ ID NO: 29 that is less than 1,200 nucleotides in length, a p600 DNA sequence comprising of SEQ ID NO: 31 that is less than 2,200 nucleotides in length, a p600 DNA sequence comprising of SEQ ID NO: 33 that is less than 1,300 nucleotides in length, a p600 DNA sequence comprising of SEQ ID NO: 35 that is less than 1,000 nucleotides in length, a p600 DNA sequence comprising of SEQ ID NO: 37 that is less than 1,500 nucleotides in length, a p600 DNA sequence comprising of SEQ ID NO: 39 that is less than 1,500 nucleotides in length, a p600 DNA sequence comprising of SEQ ID NO: 41 that is less than 2,000 nucleotides in length, a p600 DNA sequence comprising of SEQ ID NO: 43 that is less than 1,500 nucleotides in length, a p600 DNA sequence comprising of SEQ ID NO: 45 that is less than 1,200 nucleotides in length, a p600 DNA sequence comprising of SEQ ID NO: 47 that is less than 1,500 nucleotides in length, a p600 DNA sequence comprising of SEQ ID NO: 49 that is less than 800 nucleotides in length, a p600 DNA sequence comprising of SEQ ID NO: 51 that is less than 1,200 nucleotides in length, a p600 DNA sequence comprising of SEQ ID NO: 53 that is less than 1,000 nucleotides in length, a p600 DNA sequence comprising of SEQ ID NO: 55 that is less than 1,000 nucleotides in length, a p600 DNA sequence comprising of SEQ ID NO: 57 that is less than 900 nucleotides in length, a p600 DNA sequence comprising of SEQ ID NO: 59 that is less than 800 nucleotides in length, a p600 DNA sequence comprising of SEQ ID NO: 61 that is less than 1,300 nucleotides in length, a p600 DNA sequence comprising of SEQ ID NO: 63 that is less than 1,100 nucleotides in length, a p600 DNA sequence comprising of SEQ ID NO: 65 that is less than 1,800 nucleotides in length, a p600 DNA sequence comprising of SEQ ID NO: 67 that is less than 1,500 nucleotides in length, a p600 DNA sequence comprising of SEQ ID NO: 69 that is less than 2,300 nucleotides in length, a p600 DNA sequence comprising of SEQ ID NO: 71 that is less than 2,400 nucleotides in length, a p600 DNA sequence comprising of SEQ ID NO: 73 that is less than 1,800 nucleotides in length, a p600 DNA sequence comprising of SEQ ID NO: 75 that is less than 1,600 nucleotides in length, a p600 DNA sequence comprising of SEQ ID NO: 77 that is less than 1,700 nucleotides in length, and a p600 DNA sequence comprising of SEQ ID NO: 79 that is less than 1,800 nucleotides in length, wherein the p600 DNA fragment encodes a polypeptide that when expressed in a cell induces cell death.

* * * * *

SEQUENCE LISTING

```
<160> NUMBER OF SEQ ID NOS: 80

<210> SEQ ID NO 1
<211> LENGTH: 15552
<212> TYPE: DNA
<213> ORGANISM: Homo sapiens

<400> SEQUENCE: 1
atggcgacga gcggcggcga agaggcggcg gcagcggctc cggcgccggg gaccccggca        60 acggggggcgg acacgacccc gggctgggag gtggctgtgc ggccccctgct gtccgcgtcc       120 tactccgcct tcgagatgaa ggagttgccg cagctggtgg cctcagtcat cgagagtgaa       180
tcagaaatcc tgcaccatga gaagcagtac gagccattct actcatcttt tgttgcactt       240
tccacacact atattacaac agtttgcagt ctcattcccc ggaaccaact tcagtcagtg       300
gcagcagcct gtaaagttct aattgagttt tctctcctgc gtctggagaa tccagatgag       360
gcttgtgctg tgtcccagaa acacttgatt ctcctaatca agggcctgtg cactggctgt       420
agccgactag atagaactga aattatcaca tttacagcaa tgatgaaatc cgccaagctg       480
ccccaaacag tgaagacact ttcagacgtg gaagatcaga aagagctggc ctcaccagta       540
agccctgagt tgaggcaaaa ggaggtacag atgaattttt tgaaccagct gacctcagtt       600
tttaacccta gaactgtagc atcacaacct atcagtacac agactctggt ggaaggagaa       660
aatgatgagc agtcatctac agatcaagcc tcagctatca aaaccaagaa tgtgttcata       720
gctcagaacg tggctagtct tcaagagctt ggtggctcgg agaagctact gcgtgtatgt       780
ttgaacctgc catatttcct acgctatatc aatcggttcc aagatgcagt tttagctaat       840
tccttcttca taatgcctgc aacagtagca gatgccactg ctgttcgtaa tggctttcat       900
tcattggtga ttgatgtaac tatggcattg gatacccttt ctctacctgt gttggaacct       960
ctcaatcctt ctcgtctaca agatgtgaca gtcctcagcc taagttgtct gtatgcaggt      1020
gtgagtgtgg caacgtgcat ggccatcctc catgtgggta gtgcccagca agtgcggaca      1080
```

```
gggtccacga gctccaaaga agatgactat gaaagtgacg cagctacaat tgtccagaaa    1140
tgtctcgaaa tctatgacat gattggacaa gcaatcagca gttctcgccg ggctggtggt    1200
gagcactatc agaatttcca attgctgggt gcttggtgct tgttaaacag ccttttcctc    1260
atactgaacc tcagtcctac tgcgttggct gataagggga aagagaagga cccactggct    1320
gccctccgag tcagagacat ccttttctcg actaaagagg gagtgggctc ccctaaactg    1380
gggcctggaa aagggcatca gggatttggg gtactctcag taatattggc aaaccatgcc    1440
atcaaactgc taacgtctct ctttcaagac ctacaagtgg aggcccttca caagggttgg    1500
gagacagatg gccccctgc agccttgagc attatggccc agagcacctc catacagagg    1560
attcaacggc tgattgactc tgtcccactg atgaacctgc tcttgacgtt actttcaact    1620
tcctacagaa aggcatgtgt cctgcagcgg cagaggaagg gctccatgag cagcgatgcc    1680
agcgcctcca ccgactccaa tacttactat gaggacgatt tcagtagcac ggaggaggac    1740
agcagccaag acgatgacag tgagcctatt ttggggcaat ggtttgagga gactatttct    1800
cccagtaaag agaaagcagc acctccgcct cctcccccac ctcctccact ggaaagctct    1860
cctcgggtta aaagcccag taagcaggcc cctggtgaga agggcaacat tctggcgagt    1920
cgcaaagatc ctgagttgtt cttaggtctg gcttccaaca ttttgaactt catcacctct    1980
tccatgctga actctcggaa caattttatc cgaaactatc tgagtgtatc tctttcagaa    2040
caccatatgg ccaccctagc cagtatcatc aaggaggtgg acaaagatgg actcaagggt    2100
tcatcagatg aagagtttgc tgcagctctc tatcacttca accactcact ggtaacctct    2160
gaccttcagt cacctaacct gcagaacaca ctgttcagc agctaggagt ggctcctttt    2220
tctgagggcc cttggccctt gtacattcac cctcaaagcc tctctgtgct ttcacgcctc    2280
ctgctcatct ggcaacataa agccagtgct caaggtgacc ctgacgtccc agaatgcctt    2340
aaagtttggg acaggttttt gtctacaatg aagcagaatg ccctgcaagg tgtggtgccc    2400
agtgagacag aggatctgaa tgtagaacac ctgcagatgc tcctcctcat tttccacaat    2460
ttcaccgaga caggccggcg ggccatattg tcgcttttg tccagatcat ccaggagttg    2520
agcgtcaaca tggatgctca gatgcgcttc gtgccgctta tcttggctcg cctccttctc    2580
atctttgatt atctgcttca tcagtactcc aaagcccctg tgtatctatt tgagcaggta    2640
cagcataacc tgctaagtcc tccctttggg tgggcaagtg atcccagga cagcaacagc    2700 cgccgggcaa ccactcctct ctatcatgga ttcaaagaag tagaagaaaa ctggtctaag    2760
catttctcat cagatgctgt cccacacccc agattctact gtgtcctgtc cccagaagcc    2820
tcagaggatg atttgaaccg acttgattct gtggcatgtg acgtcctttt ctccaagctt    2880
gtcaagtatg atgagcttta tgctgcactg acagccctgc ttgcagctgg gtcccagctt    2940
gatacagtta ggagaaagga aaacaagaat gtaacagcct ggaggcctg tgcccttcaa    3000 tattacttct tgatactgtg gaggatccta ggaattttac caccatcaaa gacttacatt    3060
aaccagctat ccatgaactc acctgagatg agcgaatgtg acatcttgca cactctgcga    3120
tggtcttctc ggctccggat cagctcctat gtcaactgga taaaggatca ccttatcaaa    3180
cagggaatga aggctgagca tgctagctcg cttctagaac tggcatccac cactaagtgt    3240
agctcagtga aatatgatgt tgaaatagta gaggaatact cgctcgaca gatctcatcc    3300 ttctgtagta tcgactgtac caccatcttg cagctgcatg aaattcccag tctgcagtcc    3360
atctacaccc ttgatgccgc gatctcaaag gtccaggtct ctttggatga gcattttct    3420 aagatggctg ctgagactga tcctcataag tcgtctgaga ttaccaagaa cctacttcca    3480
```

```
gccacgctgc aactcattga cacctatgca tcgttcacca gagcctattt gctgcaaaac   3540
tttaatgaag agggaacaac tgagaaacct tccaaggaga aactgcaagg ctttgctgct   3600
gttttggcta ttggctctag caggtgcaag gcaaatactc tgggtccgac actggttcag   3660
aatttgccat cgtcagtgca gactgtgtgt gagtcctgga caacatcaa taccaatgaa    3720 tttcccaata ttggatcctg gcgcaatgcc tttgccaatg acaccatccc ttcagagagt   3780
tatattagtg cagtgcaggc tgcacacctg gggactctct gtagccaaag tctgcccctg   3840
gctgcttccc tgaagcatac cctcctctca ctggtcaggt tgactggaga tcttattgtt   3900
tggtcagatg agatgaaccc accacaggta attcggacac tgctacctct tcttttggaa   3960
tcaagcactg agagtgttgc cgagatcagt agcaactccc tggaacgcat cttgggccct   4020
gctgagtctg atgagttctt ggctcgtgtt tatgagaagc tgatcactgg ttgttacaac   4080
attctggcca atcatgcaga tcctaacagt ggactggatg aatccatcct ggaggaatgt   4140
ctccagtact tggaaaagca gctggaaagt agccaggctc gtaaagctat ggaggagttt   4200
ttctctgaca gtggagaact tgtacagatc atgatggcaa cagccaatga gaacctctct   4260
gctaaattct gtaaccgagt tttgaaattc ttcaccaaac tcttccagct gactgagaag   4320
agccctaacc cgagcctgtt gcatctctgt ggctccctgg cacaactggc ctgtgtggaa   4380
cctgtgcgcc tgcaggcctg gctcacccgc atgactacat cgcccccaaa agattctgat   4440
cagctggatg taattcagga gaaccggcag ctgctgcagt tactgaccac atacattgtt   4500
cgggaaaaca gccaagttgg ggaaggtgtg tgtgctgttc ttctgggcac cctgactccc   4560
atggcaacag agatgctggc caacggtgat gggactggct cccctgaact tatggttgtg   4620
atggccactc tggccagtgc aggtcaaggt gctggtcacc ttcagcttca taatgctgct   4680
gtggattggc tgagcagatg caagaaatac ctgtcacaga gaatgtagt tgaaaaactg    4740 aatgccaatg taatgcatgg aaagcatgtg atgatcttgg agtgcacatg ccatatcatg   4800
tcttacttgg ctgatgtcac gaatgccctg agccagagta atggtcaagg cccaagtcat   4860
ctctcagtgg atggggaaga gcgggccatt gaagtagact cagactgggt ggaggagttg   4920
gcggtggaag aggaagattc ccaggctgag gattcagatg aagattctct ttgcaataaa   4980
ctctgcactt ttacgatcac acagaaagaa ttcatgaacc agcattggta ccactgtcac   5040
acctgtaaaa tggtggatgg cgtgggtgtc tgcacagtgt gtgctaaggt gtgccacaag   5100
gatcatgaga tttcctatgc caagtatgga tccttcttct gtgactgtgg agccaaggaa   5160
gatggcagct gtttggctct ggtgaagaga actcctagca gtggcatgag ctctaccatg   5220
aaggagtcgg catttcagag tgaacccagg atttcagaga gtctagtgcg tcatgccagc   5280
acctcctcgc cagctgacaa agccaaggtt accatcagtg atgaaaggt tgctgacgaa    5340 gagaagccca gaagagcag cctctgccgc acagtagagg gctgccggga ggaattacag    5400
aaccaggcca atttctcctt cgctcctctc gtgttagaca tgcttaattt ccttatggat   5460
gccattcaga ccaacttcca gcaagcttca gccgtcggga gcagcagccg tgctcagcaa   5520
gccctcagtg agctacacac tgtggagaag gcagtggaga tgacagacca gctgatggtt   5580
cccaccttag ggtcccagga aggtgccttt gagaatgtgc ggatgaatta cagtggagac   5640
cagggccaga ccatccggca gctgatcagt gctcatgtgc tcaggcgggt ggctatgtgt   5700
gtgctctcct ctccccatgg gcgccgccaa catttggctg tcagccatga aagggcaag    5760 atcaccgttc tgcagctctc tgcactcctg aagcaagcag attccagcaa aaggaagtta   5820
```

```
actctgaccc gcttggcttc tgccccagtt ccttttactg tgttgagcct cacaggaaat    5880
ccctgcaagg aagactactt ggcggtttgt gggctaaagg actgtcatgt gctcacctt     5940 agtagctcag gctctgtttc ggatcacttg gttttgcacc ctcagttggc aacggggaac    6000
ttcatcatca aagccgtgtg gttacctggt tcacagaccg agttatcaat tgtcaccgca    6060
gactttgtta agatttatga cctgtgtgtt gatgccttga gtccaacctt ctattttctc    6120
ctgccaagct caaagataag agatgttacc ttccttttca atgaggaggg aaagaacatc    6180
attgttataa tgtcttcggc tgggtacatc tatactcagc ttatggaaga ggccagcagt    6240
gcccagcagg gacccttcta tgtcactaat gtgttggaaa tcaatcatga ggacctgaag    6300
gacagtaaca gccaggtggc gggcggtggt gtgtccgtgt actactccca cgtgttgcag    6360
atgttgttct tcagctattg tcaaggcaaa tcattcgcag ccaccatcag caggacaacc    6420
ctggaggtgt tgcaactctt ccccatcaac atcaaaagtt ccaatggtgg cagtaagact    6480
tctcctgctc tttgccagtg gtctgaggtg atgaaccacc ctggcttggt gtgctgtgtc    6540
cagcaaacta caggggtgcc gctggtagtt atggtgaaac cagacacttt tcttatccag    6600
gagattaaga ctcttcctgc taaagcgaag atccaagaca tggttgctat taggcacacg    6660
gcctgcaatg agcagcagcg gacaacaatg attctgctgt gtgaggatgg cagcctgcgc    6720
atttacatgg ccaacgtgga gaacacctcc tactggctgc agccatccct gcagcccagc    6780
agtgtcatca gcatcatgaa gcctgttcga aagcgcaaaa cagctacaat cacaacccgc    6840
acgtctagcc aggtgacttt ccccattgac ttttttgaac acaaccagca gctgacagat    6900
gtggagtttg gtgtaacga cctcctacag gtctataatg cacaacagat aaaacaccgg    6960
ctgaattcca ctggcatgta tgtggccaac accaagcccg gaggcttcac cattgagatt    7020
agtaacaaca atagcactat ggtgatgaca ggcatgcgga tccagattgg gactcaagca    7080
atagaacggg ccccgtcata tatcgagatc ttcggcagaa ctatgcagct caacctgagt    7140
cgctcacgct ggtttgactt ccccttcacc agagaagaag ccctgcaggc tgataagaag    7200
ctgaacctct tcattggggc ctcggtggaa ccagcaggtg tcaccatgat agatgctgta    7260
aaaatttatg gcaagactaa ggagcagttt ggctggcctg atgagccccc agaagaattc    7320
ccttctgcct ctgtcagcaa catctgccct tcaaatctga accagagcaa cggcactgga    7380
gatagcgact cagctgcccc cactacgacc agtggaactg tcctggagag gctggttgtg    7440
agttctttag aagccctgga aagctgcttt gccgttggcc caatcatcga aaggagaga     7500 aacaagaatg ctgctcagga gctggccact ttgctgttgt ccctgccagc acctgccagt    7560
gtccagcagc agtccaagag ccttctggcc agcctgcaca ccagccgctc ggcctaccac    7620
agccacaagg atcaggcctt gctgagcaaa gctgtgcagt gtctcaacac atctagcaaa    7680
gagggcaagg atttggaccc tgaggtgttc cagaggctag tgatcacagc tcgctccatt    7740
gccatcatgc gccccaacaa ccttgtccac tttacggagt caaagctgcc ccagatggaa    7800
acagaaggaa tggatgaagg gaaggaaccg cagaagcagt tggaaggaga ttgctgtagt    7860
ttcatcaccc agcttgtgaa ccacttctgg aaactccatg catccaaacc caagaatgcc    7920
ttcttggcac ctgcctgcct tccaggacta actcatattg aagctactgt caatgctctg    7980
gtggacatca tccatggcta ctgtacctgt gagctggatt gtattaacac agcatccaag    8040
atctacatgc agatgctctt gtgtcctgat cctgctgtga gcttctcttg taaacaagct    8100
ctaattcgag tcctaaggcc caggaacaaa cggagacatg tgactttacc ctcttcccct    8160
cgaagcaaca ctccaatggg agacaaggat gatgatgacg atgatgatgc agatgagaaa    8220
```

```
atgcagtcat cagggatccc gaatggtggt cacatccgtc aggaaagcca ggaacagagt    8280
gaggtggacc atggagattt tgagatggtg tctgagtcga tggtcctgga gacagctgaa    8340
aatgtcaaca atgcaacccc ctctcccctg gaggccctgc tggcaggcgc agagggcttc    8400 cccccatgc tggacatccc acctgatgca gatgacgaga ccatggttga actagccatt    8460
gccctgagcc tgcagcagga ccaacaaggc agcagcagca gtgccctggg cctgcagagc    8520
ctgggactgt ccggccaggc acccagctct tcctctctgg acgcaggaac cctctctgac    8580
accacagcat cagctccagc ctcagacgac gagggcagta cagcagcgac agatggttct    8640
acccttcgga cctctcctgc tgaccacggt ggtagtgtgg gctcgagag cgggggcagt     8700 gcagtggact cagtggctgg cgagcacagt gtatctggcc ggagcagtgc ttatggcgat    8760
gctacagctg aggggcatcc ggctggacca ggaagtgtca gctcaagcac tggagccatc    8820
agcaccacca ctgggcacca ggagggagat ggctccgagg agaaggaga aggagaaact     8880 gaaggagatg tccacactag caacaggctg cacatggtcc gtctaatgct gttggagaga    8940
ttactgcaga ccctgcctca attacgaaac gttggcggtg tccgggccat cccatacatg    9000
caggtcattc taatgctcac tacagatctg gatggagaag atgagaaaga caagggggcc    9060
ctagacaacc tgctctccca gcttattgct gagttgggta tggataaaaa ggatgtctcc    9120
aagaagaatg agcgcagcgc cctgaatgaa gtccatctgg tagtaatgag actcctgagt    9180
gtcttcatgt cccgcaccaa atctggatcc aagtcttcca tatgtgagtc atcttccctc    9240
atctccagtg ccacagcagc agctctactg agctctgggg ctgtggacta ctgcctgcac    9300
gtgctcaaat cactgctgga atattggaag agccaacaga atgacgagga gcctgtggct    9360
accagccagt tgctgaaacc acatactacc tcctccccac ctgacatgag cccattcttt    9420
ctccgccagt atgtgaaggg tcatgctgct gatgtgtttg aggcctatac tcagcttcta    9480
acagaaatgg tactgaggct tccttaccaa atcaaaaaga ttactgacac caattctcga    9540
atcccacctc ctgtctttga ccactcgtgg ttttactttc tctccgagta cctcatgatc    9600
cagcagactc catttgtgcg ccgtcaagtc cgcaaacttc tgctcttcat ctgtggatcc    9660
aaagagaagt accgccagct ccgggatttg cacaccctgg actctcacgt gcgtgggatc    9720
aagaagctgc tagaagagca ggggatattc ctccgggcaa gtgtggttac agccagctca    9780
ggctccgcct tgcaatatga cacactcatc agcctgatgg agcacctgaa agcctgtgca    9840
gagattgccg cccagcgaac catcaactgg cagaaattct gcatcaaaga tgactccgtc    9900
ctgtacttcc tcctccaagt cagtttcctt gtggatgagg gcgtgtcccc agtgctgctg    9960
caactgctct cctgtgctct gtgcggcagc aaggtgctcg ctgcactggc agcctcttcg    10020
ggatcctcca gtgcttcttc ctcctcagcc cctgtggctg ccagttctgg acaagccaca    10080
acacagtcca gtcttccac taaaaagagc aagaagaag aaaaagaaaa ggagaaagat     10140
ggtgagacct ctggcagcca ggaggaccag ctgtgcacag ctctggtgaa ccagctgaac    10200
aaatttgccg ataaggaaac cctgatccag ttcctgcgtt gtttcctgtt agagtccaat    10260
tcttcctcgg tgcgctggca ggcccactgt ctgacactgc acatctacag aaattccagc    10320
aaatctcaac aggagctcct gctagatctg atgtggtcca tctggccaga actcccagcc    10380
tatggtcgta aggctgccca gtttgtggac ctactaggat attctccct gaaaactcca     10440 caaacagaga agaagttgaa ggagtattca cagaaggctg tggagattct gcggactcaa    10500
aaccatattc ttaccaacca ccccaactcg aacatttata acactttgtc tggcttagtg    10560
```

```
gagtttgatg gctattacct ggagagcgat ccctgcctgg tgtgtaataa cccggaagta   10620
ccgttctgtt atatcaagct gtcttccatt aaagtggaca cgcggtacac caccacccag   10680
caggttgtga agctcattgg cagtcacacc atcagcaaag tgacagtgaa aatcggggat   10740
ctgaaacgga ccaagatggt gcggaccatc aacctgtatt ataacaaccg aaccgtgcag   10800
gccatcgtgg agttgaaaaa caagccagct cgctggcaca aagccaagaa ggttcagctg   10860
acccctggac agacagaggt gaagattgac ctgccgttgc ccattgtggc tccaatctg   10920
atgattgagt ttgcagactt ctatgaaaac taccaggcct ccacagagac cctgcagtgc   10980
cctcgctgta gtgcctcggt ccctgccaac ccaggagtct gtggcaactg tggagagaat   11040
gtgtaccagt gtcacaaatg cagatccatc aactacgatg aaaaggatcc cttcctctgc   11100
aatgcctgtg gcttctgtaa atatgcccgc ttcgacttca tgctctatgc caagccttgc   11160
tgtgcagtgg atcccattga gaatgaagaa gaccggaaga aggctgtatc caacatcaat   11220
acacttttgg acaaagctga tcgagtgtat catcagctga tgggacaccg gccacagctg   11280
gagaacctgc tctgcaaagt gaatgaggca gctccagaaa agccacagga tgactcagga   11340
acagcagggg gcatcagctc cacttctgcc agtgtgaatc gttacatcct gcagttggct   11400
caggagtatt gtggagactg caagaactct tttgatgaac tctccaaaat catccagaaa   11460
gtctttgctt cgcgcaaaga gttgttggaa tatgacctac agcagaggga agcagccact   11520
aaatcatccc ggacctccgt gcagcccaca ttcactgcca gccagtaccg tgccttatcc   11580
gtcctgggct gtggccacac atcctccacc aagtgctatg gctgcgcctc ggctgtcaca   11640
gaacattgta tcacactact tcgggccctg gccaccaacc cagccttgag gcacatcctt   11700
gtctcccagg gccttatccg ggagctcttt gattataatc ttcgccgagg ggctgcggcc   11760
atgcgggagg aggtccgcca gctcatgtgc ctcctaactc gagacaaccc agaagccacc   11820
caacagatga atgacctgat tattggcaag gtctccacag ccctgaagag ccactgggcc   11880
aaccccgatc tggcaagtag cctgcagtat gaaatgctgc tgctgacgga ttctatctcc   11940
aaggaggaca gctgctggga gctccggtta cgctgtgctc tcagccttt cctcatggct   12000
gtgaacatta agactcctgt ggtggttgaa aacattaccc tcatgtgcct gaggatcttg   12060
cagaagctga taaaaccacc tgctcccact agcaagaaga caaggatgt ccccgtcgag   12120
gccctcacca cggtgaagcc atactgcaat gagatccatg cccaggctca actgtggctc   12180
aagagagacc ccaaggcatc ctatgatgcc tggaagaagt gtcttcctat cagagggata   12240
gatggcaatg ggaaagcccc cagcaaatca gagctccgcc atctctattt gactgagaag   12300
tatgtgtgga ggtggaaaca gttcctgagt cgtcgggga agaggacctc cccccttggat   12360
ctcaaactgg ggcataacaa ctggctgcga caagtgcttt tcactccagc aacgcaggcc   12420
gcacggcagg cagcctgtac cattgtggaa gctctagcca ccattccag ccgcaagcag   12480
caggtcctgg acctgcttac cagttacctg gatgagctga gcatagctgg ggagtgtgca   12540
gctgagtacc tggctctcta ccagaagctc atcacttctg cgcactggaa agtctacttg   12600
gcagctcggg gagtcctacc ctatgtgggc aacctcatca ccaaggaaat agctcgtctg   12660
ctggcccctgg aggaggctac cctgagtacc gatctgcagc agggttatgc ccttaaaagt   12720
ctcacaggcc ttctctcctc ctttgttgag gtggaatcca tcaaaagaca ttttaaaagt   12780
cgcttggtgg gtactgtgct gaatggatac ctgtgcttgc ggaagctggt ggtgcagagg   12840
accaagctga tcgatgagac gcaggacatg ctgctggaga tgctggagga catgaccaca   12900
ggtacagaat cagaaaccaa ggccttcatg gctgtgtgca ttgagacagc caagcgctac   12960
```

-continued

```
aatctggatg actaccggac cccggtgttc atcttcgaga ggctctgcag catcatttat   13020
cctgaggaga atgaagtcac tgagttcttt gtgaccctgg agaaggatcc ccaacaagaa   13080
gacttcttac agggcaggat gcctgggaac ccgtatagca gcaatgagcc aggcatcggg   13140
ccgctgatga gggatataaa gaacaagatt tgccaggact gtgacttagt ggccctcctg   13200
gaagatgaca gtggcatgga gcttctagtg aacaataaaa tcattagttt ggaccttcct   13260
gtggctgaag tttacaagaa agtctggtgt accacgaatg agggagagcc catgaggatt   13320
gtttatcgta tgcgggggct gctgggcgat gccacagagg agttcattga gtccctggac   13380
tctactacag atgaagaaga agatgaagaa gaagtgtata aaatggctgg tgtgatggcc   13440
cagtgtgggg gcctggaatg catgcttaac agactcgcag ggatcagaga tttcaagcag   13500
ggacgccacc ttctaacagt gctactgaaa ttgttcagtt actgcgtgaa ggtgaaagtc   13560
aaccggcagc aactggtcaa actggaaatg aacaccttga acgtcatgct ggggacccta   13620
aacctggccc ttgtagctga acaagaaagc aaggacagtg ggggtgcagc tgtggctgag   13680
caggtgctta gcatcatgga gatcattcta gatgagtcca atgctgagcc cctgagtgag   13740
gacaagggca acctcctcct gacaggtgac aaggatcaac tggtgatgct cttggaccag   13800
atcaacagca cctttgttcg ctccaaccccc agtgtgctcc agggcctgct tcgcatcatc   13860
ccgtaccttt cctttggaga ggtggagaaa atgcagatct tggtggagcg attcaaacca   13920
tactgcaact ttgataaata tgatgaagat cacagtggtg atgataaagt cttcctggac   13980
tgcttctgta aaatagctgc tggcatcaag aacaacagca atgggcacca gctgaaggat   14040
ctgattctcc agaaggggat cacccagaat gcacttgact acatgaaaaa gcacatccct   14100
agcgccaaga atttggatgc cgacatctgg aaaaagtttt tgtctcgccc agccttgcca   14160
tttatcctaa ggctgcttcg gggcctggcc atccagcacc ctggcaccca ggttctgatt   14220
ggaactgatt ccatcccgaa cctgcataag ctggagcagg tgtccagtga tgagggcatt   14280
gggaccttgg cagagaacct gctggaagcc ctgcgggaac accctgacgt aaacaagaag   14340
attgacgcag cccgcaggga gacccgggca gagaagaaac gcatggccat ggcaatgagg   14400
cagaaggccc tgggcaccct gggcatgacg acaaatgaaa agggccaggt cgtgaccaag   14460
acagcactcc tgaagcagat ggaagagctg atcgaggagc ctggcctcac gtgctgcatc   14520
tgcagggagg gatacaagtt ccagcccaca aaggtcctgg gcatttatac cttcacgaag   14580
cgggtagcct tggaggagat ggagaataag ccccggaaac agcagggcta cagcaccgtg   14640
tcccacttca acattgtgca ctacgactgc catctggctg ccgtcaggtt ggctcgaggc   14700
cgggaagagt gggagagtgc cgccctgcag aatgccaaca ccaagtgcaa cgggctcctt   14760
ccggtctggg gacctcatgt ccctgaatca gcttttgcca cttgcttggc aagacacaac   14820
acttacctcc aggaatgtac aggccagcgg gagcccacgt atcagctcaa catccatgac   14880
atcaaactgc tcttcctgcg cttcgccatg gagcagtcgt tcagcgcaga cactggcggg   14940
ggcggccggg agagcaacat ccacctgatc ccgtacatca ttcacactgt gctttacgtc   15000
ctgaacacaa cccgagcaac ttcccgagaa gagaagaacc tccaaggctt tctggaacag   15060
cccaaggaga agtgggtgga gagtgccttt gaagtggacg ggccctacta tttcacagtc   15120
ttggcccttc acatcctgcc ccctgagcag tggagagcca cacgtgtgga aatcttgcgg   15180
aggctgttgg tgacctcgca ggctcgggca gtggctccag gtggagccac caggctgaca   15240
gataaggcag tgaaggacta ttccgcttac cgttcttccc ttctcttttg ggccctcgtc   15300
```

```
gatctcattt acaacatgtt taagaaggtg cctaccagta acacagaggg aggctggtcc   15360
tgctctctcg ctgagtacat ccgccacaac gacatgccca tctacgaagc tgccgacaaa   15420
gccctgaaaa ccttccagga ggagttcatg ccagtggaga ccttctcaga gttcctcgat   15480
gtggccggtc ttttatcaga aatcaccgat ccagagagct tcctgaagga cctgttgaac   15540
tcagtcccct ga                                                       15552
```

<210> SEQ ID NO 2
<211> LENGTH: 5183
<212> TYPE: PRT
<213> ORGANISM: Homo sapiens

<400> SEQUENCE: 2

```
Met Ala Thr Ser Gly Gly Glu Ala Ala Ala Ala Pro Ala Pro
1               5                   10                  15

Gly Thr Pro Ala Thr Gly Ala Asp Thr Thr Pro Gly Trp Glu Val Ala
                20                  25                  30

Val Arg Pro Leu Leu Ser Ala Ser Tyr Ser Ala Phe Glu Met Lys Glu
            35                  40                  45

Leu Pro Gln Leu Val Ala Ser Val Ile Glu Ser Glu Ser Glu Ile Leu
        50                  55                  60

His His Glu Lys Gln Tyr Glu Pro Phe Tyr Ser Ser Phe Val Ala Leu
65                  70                  75                  80

Ser Thr His Tyr Ile Thr Thr Val Cys Ser Leu Ile Pro Arg Asn Gln
                85                  90                  95

Leu Gln Ser Val Ala Ala Cys Lys Val Leu Ile Glu Phe Ser Leu
            100                 105                 110

Leu Arg Leu Glu Asn Pro Asp Glu Ala Cys Ala Val Ser Gln Lys His
        115                 120                 125

Leu Ile Leu Leu Ile Lys Gly Leu Cys Thr Gly Cys Ser Arg Leu Asp
130                 135                 140

Arg Thr Glu Ile Ile Thr Phe Thr Ala Met Met Lys Ser Ala Lys Leu
145                 150                 155                 160

Pro Gln Thr Val Lys Thr Leu Ser Asp Val Glu Asp Gln Lys Glu Leu
                165                 170                 175

Ala Ser Pro Val Ser Pro Glu Leu Arg Gln Lys Glu Val Gln Met Asn
            180                 185                 190

Phe Leu Asn Gln Leu Thr Ser Val Phe Asn Pro Arg Thr Val Ala Ser
        195                 200                 205

Gln Pro Ile Ser Thr Gln Thr Leu Val Glu Gly Glu Asn Asp Glu Gln
    210                 215                 220

Ser Ser Thr Asp Gln Ala Ser Ala Ile Lys Thr Lys Asn Val Phe Ile
225                 230                 235                 240

Ala Gln Asn Val Ala Ser Leu Gln Glu Leu Gly Gly Ser Glu Lys Leu
                245                 250                 255

Leu Arg Val Cys Leu Asn Leu Pro Tyr Phe Leu Arg Tyr Ile Asn Arg
            260                 265                 270

Phe Gln Asp Ala Val Leu Ala Asn Ser Phe Phe Ile Met Pro Ala Thr
        275                 280                 285

Val Ala Asp Ala Thr Ala Val Arg Asn Gly Phe His Ser Leu Val Ile
    290                 295                 300

Asp Val Thr Met Ala Leu Asp Thr Leu Ser Leu Pro Val Leu Glu Pro
305                 310                 315                 320

Leu Asn Pro Ser Arg Leu Gln Asp Val Thr Val Leu Ser Leu Ser Cys
```

```
                    325                 330                 335
Leu Tyr Ala Gly Val Ser Val Ala Thr Cys Met Ala Ile Leu His Val
                340                 345                 350
Gly Ser Ala Gln Gln Val Arg Thr Gly Ser Thr Ser Lys Glu Asp
                355                 360                 365
Asp Tyr Glu Ser Asp Ala Ala Thr Ile Val Gln Lys Cys Leu Glu Ile
    370                 375                 380
Tyr Asp Met Ile Gly Gln Ala Ile Ser Ser Arg Arg Ala Gly Gly
385                 390                 395                 400
Glu His Tyr Gln Asn Phe Gln Leu Leu Gly Ala Trp Cys Leu Asn
                405                 410                 415
Ser Leu Phe Leu Ile Leu Asn Leu Ser Pro Thr Ala Leu Ala Asp Lys
                420                 425                 430
Gly Lys Glu Lys Asp Pro Leu Ala Ala Leu Arg Val Arg Asp Ile Leu
                435                 440                 445
Ser Arg Thr Lys Glu Gly Val Gly Ser Pro Lys Leu Gly Pro Gly Lys
                450                 455                 460
Gly His Gln Gly Phe Gly Val Leu Ser Val Ile Leu Ala Asn His Ala
465                 470                 475                 480
Ile Lys Leu Leu Thr Ser Leu Phe Gln Asp Leu Gln Val Glu Ala Leu
                485                 490                 495
His Lys Gly Trp Glu Thr Asp Gly Pro Pro Ala Ala Leu Ser Ile Met
                500                 505                 510
Ala Gln Ser Thr Ser Ile Gln Arg Ile Gln Arg Leu Ile Asp Ser Val
                515                 520                 525
Pro Leu Met Asn Leu Leu Leu Thr Leu Leu Ser Thr Ser Tyr Arg Lys
                530                 535                 540
Ala Cys Val Leu Gln Arg Gln Arg Lys Gly Ser Met Ser Ser Asp Ala
545                 550                 555                 560
Ser Ala Ser Thr Asp Ser Asn Thr Tyr Tyr Glu Asp Asp Phe Ser Ser
                565                 570                 575
Thr Glu Glu Asp Ser Ser Gln Asp Asp Asp Ser Glu Pro Ile Leu Gly
                580                 585                 590
Gln Trp Phe Glu Glu Thr Ile Ser Pro Ser Lys Glu Lys Ala Ala Pro
                595                 600                 605
Pro Pro Pro Pro Pro Pro Pro Leu Glu Ser Pro Arg Val Lys
                610                 615                 620
Ser Pro Ser Lys Gln Ala Pro Gly Glu Lys Gly Asn Ile Leu Ala Ser
625                 630                 635                 640
Arg Lys Asp Pro Glu Leu Phe Leu Gly Leu Ala Ser Asn Ile Leu Asn
                645                 650                 655
Phe Ile Thr Ser Ser Met Leu Asn Ser Arg Asn Asn Phe Ile Arg Asn
                660                 665                 670
Tyr Leu Ser Val Ser Leu Ser Glu His His Met Ala Thr Leu Ala Ser
                675                 680                 685
Ile Ile Lys Glu Val Asp Lys Asp Gly Leu Lys Gly Ser Ser Asp Glu
                690                 695                 700
Glu Phe Ala Ala Ala Leu Tyr His Phe Asn His Ser Leu Val Thr Ser
705                 710                 715                 720
Asp Leu Gln Ser Pro Asn Leu Gln Asn Thr Leu Leu Gln Gln Leu Gly
                725                 730                 735
Val Ala Pro Phe Ser Glu Gly Pro Trp Pro Leu Tyr Ile His Pro Gln
                740                 745                 750
```

```
Ser Leu Ser Val Leu Ser Arg Leu Leu Leu Ile Trp Gln His Lys Ala
        755                 760                 765

Ser Ala Gln Gly Asp Pro Asp Val Pro Glu Cys Leu Lys Val Trp Asp
    770                 775                 780

Arg Phe Leu Ser Thr Met Lys Gln Asn Ala Leu Gln Gly Val Val Pro
785                 790                 795                 800

Ser Glu Thr Glu Asp Leu Asn Val His Leu Gln Met Leu Leu Leu
                805                 810                 815

Ile Phe His Asn Phe Thr Glu Thr Gly Arg Arg Ala Ile Leu Ser Leu
                820                 825                 830

Phe Val Gln Ile Ile Gln Glu Leu Ser Val Asn Met Asp Ala Gln Met
                835                 840                 845

Arg Phe Val Pro Leu Ile Leu Ala Arg Leu Leu Leu Ile Phe Asp Tyr
    850                 855                 860

Leu Leu His Gln Tyr Ser Lys Ala Pro Val Tyr Leu Phe Glu Gln Val
865                 870                 875                 880

Gln His Asn Leu Leu Ser Pro Pro Phe Gly Trp Ala Ser Gly Ser Gln
                885                 890                 895

Asp Ser Asn Ser Arg Arg Ala Thr Thr Pro Leu Tyr His Gly Phe Lys
                900                 905                 910

Glu Val Glu Glu Asn Trp Ser Lys His Phe Ser Ser Asp Ala Val Pro
                915                 920                 925

His Pro Arg Phe Tyr Cys Val Leu Ser Pro Glu Ala Ser Glu Asp Asp
                930                 935                 940

Leu Asn Arg Leu Asp Ser Val Ala Cys Asp Val Leu Phe Ser Lys Leu
945                 950                 955                 960

Val Lys Tyr Asp Glu Leu Tyr Ala Ala Leu Thr Ala Leu Leu Ala Ala
                965                 970                 975

Gly Ser Gln Leu Asp Thr Val Arg Arg Lys Glu Asn Lys Asn Val Thr
                980                 985                 990

Ala Leu Glu Ala Cys Ala Leu Gln Tyr Tyr Phe Leu Ile Leu Trp Arg
        995                 1000                1005

Ile Leu Gly Ile Leu Pro Pro Ser Lys Thr Tyr Ile Asn Gln Leu
    1010                1015                1020

Ser Met Asn Ser Pro Glu Met Ser Glu Cys Asp Ile Leu His Thr
    1025                1030                1035

Leu Arg Trp Ser Ser Arg Leu Arg Ile Ser Ser Tyr Val Asn Trp
    1040                1045                1050

Ile Lys Asp His Leu Ile Lys Gln Gly Met Lys Ala Glu His Ala
    1055                1060                1065

Ser Ser Leu Leu Glu Leu Ala Ser Thr Thr Lys Cys Ser Ser Val
    1070                1075                1080

Lys Tyr Asp Val Glu Ile Val Glu Glu Tyr Phe Ala Arg Gln Ile
    1085                1090                1095

Ser Ser Phe Cys Ser Ile Asp Cys Thr Thr Ile Leu Gln Leu His
    1100                1105                1110

Glu Ile Pro Ser Leu Gln Ser Ile Tyr Thr Leu Asp Ala Ala Ile
    1115                1120                1125

Ser Lys Val Gln Val Ser Leu Asp Glu His Phe Ser Lys Met Ala
    1130                1135                1140

Ala Glu Thr Asp Pro His Lys Ser Ser Glu Ile Thr Lys Asn Leu
    1145                1150                1155
```

```
Leu Pro Ala Thr Leu Gln Leu Ile Asp Thr Tyr Ala Ser Phe Thr
    1160             1165             1170

Arg Ala Tyr Leu Leu Gln Asn Phe Asn Glu Glu Gly Thr Thr Glu
    1175             1180             1185

Lys Pro Ser Lys Glu Lys Leu Gln Gly Phe Ala Ala Val Leu Ala
    1190             1195             1200

Ile Gly Ser Ser Arg Cys Lys Ala Asn Thr Leu Gly Pro Thr Leu
    1205             1210             1215

Val Gln Asn Leu Pro Ser Ser Val Gln Thr Val Cys Glu Ser Trp
    1220             1225             1230

Asn Asn Ile Asn Thr Asn Glu Phe Pro Asn Ile Gly Ser Trp Arg
    1235             1240             1245

Asn Ala Phe Ala Asn Asp Thr Ile Pro Ser Glu Ser Tyr Ile Ser
    1250             1255             1260

Ala Val Gln Ala Ala His Leu Gly Thr Leu Cys Ser Gln Ser Leu
    1265             1270             1275

Pro Leu Ala Ala Ser Leu Lys His Thr Leu Leu Ser Leu Val Arg
    1280             1285             1290

Leu Thr Gly Asp Leu Ile Val Trp Ser Asp Glu Met Asn Pro Pro
    1295             1300             1305

Gln Val Ile Arg Thr Leu Leu Pro Leu Leu Glu Ser Ser Thr
    1310             1315             1320

Glu Ser Val Ala Glu Ile Ser Ser Asn Ser Leu Glu Arg Ile Leu
    1325             1330             1335

Gly Pro Ala Glu Ser Asp Glu Phe Leu Ala Arg Val Tyr Glu Lys
    1340             1345             1350

Leu Ile Thr Gly Cys Tyr Asn Ile Leu Ala Asn His Ala Asp Pro
    1355             1360             1365

Asn Ser Gly Leu Asp Glu Ser Ile Leu Glu Glu Cys Leu Gln Tyr
    1370             1375             1380

Leu Glu Lys Gln Leu Glu Ser Ser Gln Ala Arg Lys Ala Met Glu
    1385             1390             1395

Glu Phe Phe Ser Asp Ser Gly Glu Leu Val Gln Ile Met Met Ala
    1400             1405             1410

Thr Ala Asn Glu Asn Leu Ser Ala Lys Phe Cys Asn Arg Val Leu
    1415             1420             1425

Lys Phe Phe Thr Lys Leu Phe Gln Leu Thr Glu Lys Ser Pro Asn
    1430             1435             1440

Pro Ser Leu Leu His Leu Cys Gly Ser Leu Ala Gln Leu Ala Cys
    1445             1450             1455

Val Glu Pro Val Arg Leu Gln Ala Trp Leu Thr Arg Met Thr Thr
    1460             1465             1470

Ser Pro Pro Lys Asp Ser Asp Gln Leu Asp Val Ile Gln Glu Asn
    1475             1480             1485

Arg Gln Leu Leu Gln Leu Leu Thr Thr Tyr Ile Val Arg Glu Asn
    1490             1495             1500

Ser Gln Val Gly Glu Gly Val Cys Ala Val Leu Leu Gly Thr Leu
    1505             1510             1515

Thr Pro Met Ala Thr Glu Met Leu Ala Asn Gly Asp Gly Thr Gly
    1520             1525             1530

Phe Pro Glu Leu Met Val Val Met Ala Thr Leu Ala Ser Ala Gly
    1535             1540             1545

Gln Gly Ala Gly His Leu Gln Leu His Asn Ala Ala Val Asp Trp
```

-continued

|  |  | 1550 |  |  | 1555 |  |  | 1560 |  |  |
|---|---|---|---|---|---|---|---|---|---|---|

Leu Ser Arg Cys Lys Lys Tyr Leu Ser Gln Lys Asn Val Val Glu
1565                1570                1575

Lys Leu Asn Ala Asn Val Met His Gly Lys His Val Met Ile Leu
          1580                1585                1590

Glu Cys Thr Cys His Ile Met Ser Tyr Leu Ala Asp Val Thr Asn
     1595                1600                1605

Ala Leu Ser Gln Ser Asn Gly Gln Gly Pro Ser His Leu Ser Val
1610                1615                1620

Asp Gly Glu Glu Arg Ala Ile Glu Val Asp Ser Asp Trp Val Glu
     1625                1630                1635

Glu Leu Ala Val Glu Glu Glu Asp Ser Gln Ala Glu Asp Ser Asp
          1640                1645                1650

Glu Asp Ser Leu Cys Asn Lys Leu Cys Thr Phe Thr Ile Thr Gln
     1655                1660                1665

Lys Glu Phe Met Asn Gln His Trp Tyr His Cys His Thr Cys Lys
     1670                1675                1680

Met Val Asp Gly Val Gly Val Cys Thr Val Cys Ala Lys Val Cys
     1685                1690                1695

His Lys Asp His Glu Ile Ser Tyr Ala Lys Tyr Gly Ser Phe Phe
1700                1705                1710

Cys Asp Cys Gly Ala Lys Glu Asp Gly Ser Cys Leu Ala Leu Val
     1715                1720                1725

Lys Arg Thr Pro Ser Ser Gly Met Ser Ser Thr Met Lys Glu Ser
     1730                1735                1740

Ala Phe Gln Ser Glu Pro Arg Ile Ser Glu Ser Leu Val Arg His
     1745                1750                1755

Ala Ser Thr Ser Ser Pro Ala Asp Lys Ala Lys Val Thr Ile Ser
     1760                1765                1770

Asp Gly Lys Val Ala Asp Glu Glu Lys Pro Lys Lys Ser Ser Leu
     1775                1780                1785

Cys Arg Thr Val Glu Gly Cys Arg Glu Glu Leu Gln Asn Gln Ala
     1790                1795                1800

Asn Phe Ser Phe Ala Pro Leu Val Leu Asp Met Leu Asn Phe Leu
     1805                1810                1815

Met Asp Ala Ile Gln Thr Asn Phe Gln Gln Ala Ser Ala Val Gly
     1820                1825                1830

Ser Ser Ser Arg Ala Gln Gln Ala Leu Ser Glu Leu His Thr Val
     1835                1840                1845

Glu Lys Ala Val Glu Met Thr Asp Gln Leu Met Val Pro Thr Leu
     1850                1855                1860

Gly Ser Gln Glu Gly Ala Phe Glu Asn Val Arg Met Asn Tyr Ser
     1865                1870                1875

Gly Asp Gln Gly Gln Thr Ile Arg Gln Leu Ile Ser Ala His Val
     1880                1885                1890

Leu Arg Arg Val Ala Met Cys Val Leu Ser Ser Pro His Gly Arg
     1895                1900                1905

Arg Gln His Leu Ala Val Ser His Glu Lys Gly Lys Ile Thr Val
     1910                1915                1920

Leu Gln Leu Ser Ala Leu Leu Lys Gln Ala Asp Ser Ser Lys Arg
     1925                1930                1935

Lys Leu Thr Leu Thr Arg Leu Ala Ser Ala Pro Val Pro Phe Thr
     1940                1945                1950

```
Val Leu Ser Leu Thr Gly Asn Pro Cys Lys Glu Asp Tyr Leu Ala
    1955             1960            1965

Val Cys Gly Leu Lys Asp Cys His Val Leu Thr Phe Ser Ser Ser
    1970             1975            1980

Gly Ser Val Ser Asp His Leu Val Leu His Pro Gln Leu Ala Thr
    1985             1990            1995

Gly Asn Phe Ile Ile Lys Ala Val Trp Leu Pro Gly Ser Gln Thr
    2000             2005            2010

Glu Leu Ser Ile Val Thr Ala Asp Phe Val Lys Ile Tyr Asp Leu
    2015             2020            2025

Cys Val Asp Ala Leu Ser Pro Thr Phe Tyr Phe Leu Leu Pro Ser
    2030             2035            2040

Ser Lys Ile Arg Asp Val Thr Phe Leu Phe Asn Glu Glu Gly Lys
    2045             2050            2055

Asn Ile Ile Val Ile Met Ser Ser Ala Gly Tyr Ile Tyr Thr Gln
    2060             2065            2070

Leu Met Glu Glu Ala Ser Ser Ala Gln Gln Gly Pro Phe Tyr Val
    2075             2080            2085

Thr Asn Val Leu Glu Ile Asn His Glu Asp Leu Lys Asp Ser Asn
    2090             2095            2100

Ser Gln Val Ala Gly Gly Gly Val Ser Val Tyr Tyr Ser His Val
    2105             2110            2115

Leu Gln Met Leu Phe Phe Ser Tyr Cys Gln Gly Lys Ser Phe Ala
    2120             2125            2130

Ala Thr Ile Ser Arg Thr Thr Leu Glu Val Leu Gln Leu Phe Pro
    2135             2140            2145

Ile Asn Ile Lys Ser Ser Asn Gly Gly Ser Lys Thr Ser Pro Ala
    2150             2155            2160

Leu Cys Gln Trp Ser Glu Val Met Asn His Pro Gly Leu Val Cys
    2165             2170            2175

Cys Val Gln Gln Thr Thr Gly Val Pro Leu Val Val Met Val Lys
    2180             2185            2190

Pro Asp Thr Phe Leu Ile Gln Glu Ile Lys Thr Leu Pro Ala Lys
    2195             2200            2205

Ala Lys Ile Gln Asp Met Val Ala Ile Arg His Thr Ala Cys Asn
    2210             2215            2220

Glu Gln Gln Arg Thr Thr Met Ile Leu Leu Cys Glu Asp Gly Ser
    2225             2230            2235

Leu Arg Ile Tyr Met Ala Asn Val Glu Asn Thr Ser Tyr Trp Leu
    2240             2245            2250

Gln Pro Ser Leu Gln Pro Ser Ser Val Ile Ser Ile Met Lys Pro
    2255             2260            2265

Val Arg Lys Arg Lys Thr Ala Thr Ile Thr Thr Arg Thr Ser Ser
    2270             2275            2280

Gln Val Thr Phe Pro Ile Asp Phe Phe Glu His Asn Gln Gln Leu
    2285             2290            2295

Thr Asp Val Glu Phe Gly Gly Asn Asp Leu Leu Gln Val Tyr Asn
    2300             2305            2310

Ala Gln Gln Ile Lys His Arg Leu Asn Ser Thr Gly Met Tyr Val
    2315             2320            2325

Ala Asn Thr Lys Pro Gly Gly Phe Thr Ile Glu Ile Ser Asn Asn
    2330             2335            2340
```

```
Asn Ser Thr Met Val Met Thr Gly Met Arg Ile Gln Ile Gly Thr
2345                2350                2355

Gln Ala Ile Glu Arg Ala Pro Ser Tyr Ile Glu Ile Phe Gly Arg
2360                2365                2370

Thr Met Gln Leu Asn Leu Ser Arg Ser Arg Trp Phe Asp Phe Pro
2375                2380                2385

Phe Thr Arg Glu Glu Ala Leu Gln Ala Asp Lys Lys Leu Asn Leu
2390                2395                2400

Phe Ile Gly Ala Ser Val Glu Pro Ala Gly Val Thr Met Ile Asp
2405                2410                2415

Ala Val Lys Ile Tyr Gly Lys Thr Lys Glu Gln Phe Gly Trp Pro
2420                2425                2430

Asp Glu Pro Pro Glu Glu Phe Pro Ser Ala Ser Val Ser Asn Ile
2435                2440                2445

Cys Pro Ser Asn Leu Asn Gln Ser Asn Gly Thr Gly Asp Ser Asp
2450                2455                2460

Ser Ala Ala Pro Thr Thr Thr Ser Gly Thr Val Leu Glu Arg Leu
2465                2470                2475

Val Val Ser Ser Leu Glu Ala Leu Glu Ser Cys Phe Ala Val Gly
2480                2485                2490

Pro Ile Ile Glu Lys Glu Arg Asn Lys Asn Ala Ala Gln Glu Leu
2495                2500                2505

Ala Thr Leu Leu Leu Ser Leu Pro Ala Pro Ala Ser Val Gln Gln
2510                2515                2520

Gln Ser Lys Ser Leu Leu Ala Ser Leu His Thr Ser Arg Ser Ala
2525                2530                2535

Tyr His Ser His Lys Asp Gln Ala Leu Leu Ser Lys Ala Val Gln
2540                2545                2550

Cys Leu Asn Thr Ser Ser Lys Glu Gly Lys Asp Leu Asp Pro Glu
2555                2560                2565

Val Phe Gln Arg Leu Val Ile Thr Ala Arg Ser Ile Ala Ile Met
2570                2575                2580

Arg Pro Asn Asn Leu Val His Phe Thr Glu Ser Lys Leu Pro Gln
2585                2590                2595

Met Glu Thr Glu Gly Met Asp Glu Gly Lys Glu Pro Gln Lys Gln
2600                2605                2610

Leu Glu Gly Asp Cys Cys Ser Phe Ile Thr Gln Leu Val Asn His
2615                2620                2625

Phe Trp Lys Leu His Ala Ser Lys Pro Lys Asn Ala Phe Leu Ala
2630                2635                2640

Pro Ala Cys Leu Pro Gly Leu Thr His Ile Glu Ala Thr Val Asn
2645                2650                2655

Ala Leu Val Asp Ile Ile His Gly Tyr Cys Thr Cys Glu Leu Asp
2660                2665                2670

Cys Ile Asn Thr Ala Ser Lys Ile Tyr Met Gln Met Leu Leu Cys
2675                2680                2685

Pro Asp Pro Ala Val Ser Phe Ser Cys Lys Gln Ala Leu Ile Arg
2690                2695                2700

Val Leu Arg Pro Arg Asn Lys Arg Arg His Val Thr Leu Pro Ser
2705                2710                2715

Ser Pro Arg Ser Asn Thr Pro Met Gly Asp Lys Asp Asp Asp
2720                2725                2730

Asp Asp Asp Ala Asp Glu Lys Met Gln Ser Ser Gly Ile Pro Asn
```

```
                2735                2740                2745
Gly Gly His Ile Arg Gln Glu Ser Gln Glu Ser Glu Val Asp
    2750                2755                2760
His Gly Asp Phe Glu Met Val Ser Glu Ser Met Val Leu Glu Thr
    2765                2770                2775
Ala Glu Asn Val Asn Asn Gly Asn Pro Ser Pro Leu Glu Ala Leu
    2780                2785                2790
Leu Ala Gly Ala Glu Gly Phe Pro Pro Met Leu Asp Ile Pro Pro
    2795                2800                2805
Asp Ala Asp Asp Glu Thr Met Val Glu Leu Ala Ile Ala Leu Ser
    2810                2815                2820
Leu Gln Gln Asp Gln Gln Gly Ser Ser Ser Ser Ala Leu Gly Leu
    2825                2830                2835
Gln Ser Leu Gly Leu Ser Gly Gln Ala Pro Ser Ser Ser Ser Leu
    2840                2845                2850
Asp Ala Gly Thr Leu Ser Asp Thr Thr Ala Ser Ala Pro Ala Ser
    2855                2860                2865
Asp Asp Glu Gly Ser Thr Ala Ala Thr Asp Gly Ser Thr Leu Arg
    2870                2875                2880
Thr Ser Pro Ala Asp His Gly Gly Ser Val Gly Ser Glu Ser Gly
    2885                2890                2895
Gly Ser Ala Val Asp Ser Val Ala Gly Glu His Ser Val Ser Gly
    2900                2905                2910
Arg Ser Ser Ala Tyr Gly Asp Ala Thr Ala Glu Gly His Pro Ala
    2915                2920                2925
Gly Pro Gly Ser Val Ser Ser Thr Gly Ala Ile Ser Thr Thr
    2930                2935                2940
Thr Gly His Gln Glu Gly Asp Gly Ser Glu Gly Gly Glu Gly
    2945                2950                2955
Glu Thr Glu Gly Asp Val His Thr Ser Asn Arg Leu His Met Val
    2960                2965                2970
Arg Leu Met Leu Leu Glu Arg Leu Leu Gln Thr Leu Pro Gln Leu
    2975                2980                2985
Arg Asn Val Gly Gly Val Arg Ala Ile Pro Tyr Met Gln Val Ile
    2990                2995                3000
Leu Met Leu Thr Thr Asp Leu Asp Gly Glu Asp Glu Lys Asp Lys
    3005                3010                3015
Gly Ala Leu Asp Asn Leu Leu Ser Gln Leu Ile Ala Glu Leu Gly
    3020                3025                3030
Met Asp Lys Lys Asp Val Ser Lys Lys Asn Glu Arg Ser Ala Leu
    3035                3040                3045
Asn Glu Val His Leu Val Val Met Arg Leu Leu Ser Val Phe Met
    3050                3055                3060
Ser Arg Thr Lys Ser Gly Ser Lys Ser Ser Ile Cys Glu Ser Ser
    3065                3070                3075
Ser Leu Ile Ser Ser Ala Thr Ala Ala Ala Leu Leu Ser Ser Gly
    3080                3085                3090
Ala Val Asp Tyr Cys Leu His Val Leu Lys Ser Leu Leu Glu Tyr
    3095                3100                3105
Trp Lys Ser Gln Gln Asn Asp Glu Glu Pro Val Ala Thr Ser Gln
    3110                3115                3120
Leu Leu Lys Pro His Thr Thr Ser Ser Pro Pro Asp Met Ser Pro
    3125                3130                3135
```

```
Phe Phe Leu Arg Gln Tyr Val Lys Gly His Ala Ala Asp Val Phe
    3140                3145            3150
Glu Ala Tyr Thr Gln Leu Leu Thr Glu Met Val Leu Arg Leu Pro
    3155                3160            3165
Tyr Gln Ile Lys Lys Ile Thr Asp Thr Asn Ser Arg Ile Pro Pro
    3170                3175            3180
Pro Val Phe Asp His Ser Trp Phe Tyr Phe Leu Ser Glu Tyr Leu
    3185                3190            3195
Met Ile Gln Gln Thr Pro Phe Val Arg Arg Gln Val Arg Lys Leu
    3200                3205            3210
Leu Leu Phe Ile Cys Gly Ser Lys Glu Lys Tyr Arg Gln Leu Arg
    3215                3220            3225
Asp Leu His Thr Leu Asp Ser His Val Arg Gly Ile Lys Lys Leu
    3230                3235            3240
Leu Glu Glu Gln Gly Ile Phe Leu Arg Ala Ser Val Val Thr Ala
    3245                3250            3255
Ser Ser Gly Ser Ala Leu Gln Tyr Asp Thr Leu Ile Ser Leu Met
    3260                3265            3270
Glu His Leu Lys Ala Cys Ala Glu Ile Ala Ala Gln Arg Thr Ile
    3275                3280            3285
Asn Trp Gln Lys Phe Cys Ile Lys Asp Asp Ser Val Leu Tyr Phe
    3290                3295            3300
Leu Leu Gln Val Ser Phe Leu Val Asp Glu Gly Val Ser Pro Val
    3305                3310            3315
Leu Leu Gln Leu Leu Ser Cys Ala Leu Cys Gly Ser Lys Val Leu
    3320                3325            3330
Ala Ala Leu Ala Ala Ser Ser Gly Ser Ser Ser Ala Ser Ser Ser
    3335                3340            3345
Ser Ala Pro Val Ala Ala Ser Ser Gly Gln Ala Thr Thr Gln Ser
    3350                3355            3360
Lys Ser Ser Thr Lys Lys Ser Lys Lys Glu Glu Lys Glu Lys Glu
    3365                3370            3375
Lys Asp Gly Glu Thr Ser Gly Ser Gln Glu Asp Gln Leu Cys Thr
    3380                3385            3390
Ala Leu Val Asn Gln Leu Asn Lys Phe Ala Asp Lys Glu Thr Leu
    3395                3400            3405
Ile Gln Phe Leu Arg Cys Phe Leu Leu Glu Ser Asn Ser Ser Ser
    3410                3415            3420
Val Arg Trp Gln Ala His Cys Leu Thr Leu His Ile Tyr Arg Asn
    3425                3430            3435
Ser Ser Lys Ser Gln Gln Glu Leu Leu Leu Asp Leu Met Trp Ser
    3440                3445            3450
Ile Trp Pro Glu Leu Pro Ala Tyr Gly Arg Lys Ala Ala Gln Phe
    3455                3460            3465
Val Asp Leu Leu Gly Tyr Phe Ser Leu Lys Thr Pro Gln Thr Glu
    3470                3475            3480
Lys Lys Leu Lys Glu Tyr Ser Gln Lys Ala Val Glu Ile Leu Arg
    3485                3490            3495
Thr Gln Asn His Ile Leu Thr Asn His Pro Asn Ser Asn Ile Tyr
    3500                3505            3510
Asn Thr Leu Ser Gly Leu Val Glu Phe Asp Gly Tyr Tyr Leu Glu
    3515                3520            3525
```

```
Ser Asp Pro Cys Leu Val Cys   Asn Asn Pro Glu Val   Pro Phe Cys
    3530              3535                3540

Tyr Ile Lys Leu Ser Ser Ile   Lys Val Asp Thr Arg   Tyr Thr Thr
    3545              3550                3555

Thr Gln Gln Val Val Lys Leu   Ile Gly Ser His Thr   Ile Ser Lys
    3560              3565                3570

Val Thr Val Lys Ile Gly Asp   Leu Lys Arg Thr Lys   Met Val Arg
    3575              3580                3585

Thr Ile Asn Leu Tyr Tyr Asn   Asn Arg Thr Val Gln   Ala Ile Val
    3590              3595                3600

Glu Leu Lys Asn Lys Pro Ala   Arg Trp His Lys Ala   Lys Lys Val
    3605              3610                3615

Gln Leu Thr Pro Gly Gln Thr   Glu Val Lys Ile Asp   Leu Pro Leu
    3620              3625                3630

Pro Ile Val Ala Ser Asn Leu   Met Ile Glu Phe Ala   Asp Phe Tyr
    3635              3640                3645

Glu Asn Tyr Gln Ala Ser Thr   Glu Thr Leu Gln Cys   Pro Arg Cys
    3650              3655                3660

Ser Ala Ser Val Pro Ala Asn   Pro Gly Val Cys Gly   Asn Cys Gly
    3665              3670                3675

Glu Asn Val Tyr Gln Cys His   Lys Cys Arg Ser Ile   Asn Tyr Asp
    3680              3685                3690

Glu Lys Asp Pro Phe Leu Cys   Asn Ala Cys Gly Phe   Cys Lys Tyr
    3695              3700                3705

Ala Arg Phe Asp Phe Met Leu   Tyr Ala Lys Pro Cys   Cys Ala Val
    3710              3715                3720

Asp Pro Ile Glu Asn Glu Glu   Asp Arg Lys Lys Ala   Val Ser Asn
    3725              3730                3735

Ile Asn Thr Leu Leu Asp Lys   Ala Asp Arg Val Tyr   His Gln Leu
    3740              3745                3750

Met Gly His Arg Pro Gln Leu   Glu Asn Leu Leu Cys   Lys Val Asn
    3755              3760                3765

Glu Ala Ala Pro Glu Lys Pro   Gln Asp Asp Ser Gly   Thr Ala Gly
    3770              3775                3780

Gly Ile Ser Ser Thr Ser Ala   Ser Val Asn Arg Tyr   Ile Leu Gln
    3785              3790                3795

Leu Ala Gln Glu Tyr Cys Gly   Asp Cys Lys Asn Ser   Phe Asp Glu
    3800              3805                3810

Leu Ser Lys Ile Ile Gln Lys   Val Phe Ala Ser Arg   Lys Glu Leu
    3815              3820                3825

Leu Glu Tyr Asp Leu Gln Gln   Arg Glu Ala Ala Thr   Lys Ser Ser
    3830              3835                3840

Arg Thr Ser Val Gln Pro Thr   Phe Thr Ala Ser Gln   Tyr Arg Ala
    3845              3850                3855

Leu Ser Val Leu Gly Cys Gly   His Thr Ser Ser Thr   Lys Cys Tyr
    3860              3865                3870

Gly Cys Ala Ser Ala Val Thr   Glu His Cys Ile Thr   Leu Leu Arg
    3875              3880                3885

Ala Leu Ala Thr Asn Pro Ala   Leu Arg His Ile Leu   Val Ser Gln
    3890              3895                3900

Gly Leu Ile Arg Glu Leu Phe   Asp Tyr Asn Leu Arg   Arg Gly Ala
    3905              3910                3915

Ala Ala Met Arg Glu Glu Val   Arg Gln Leu Met Cys   Leu Leu Thr
```

```
                3920                3925                3930

Arg Asp Asn Pro Glu Ala Thr Gln Gln Met Asn Asp Leu Ile Ile
        3935                3940                3945

Gly Lys Val Ser Thr Ala Leu Lys Ser His Trp Ala Asn Pro Asp
        3950                3955                3960

Leu Ala Ser Ser Leu Gln Tyr Glu Met Leu Leu Leu Thr Asp Ser
        3965                3970                3975

Ile Ser Lys Glu Asp Ser Cys Trp Glu Leu Arg Leu Arg Cys Ala
        3980                3985                3990

Leu Ser Leu Phe Leu Met Ala Val Asn Ile Lys Thr Pro Val Val
        3995                4000                4005

Val Glu Asn Ile Thr Leu Met Cys Leu Arg Ile Leu Gln Lys Leu
        4010                4015                4020

Ile Lys Pro Pro Ala Pro Thr Ser Lys Lys Asn Lys Asp Val Pro
        4025                4030                4035

Val Glu Ala Leu Thr Thr Val Lys Pro Tyr Cys Asn Glu Ile His
        4040                4045                4050

Ala Gln Ala Gln Leu Trp Leu Lys Arg Asp Pro Lys Ala Ser Tyr
        4055                4060                4065

Asp Ala Trp Lys Lys Cys Leu Pro Ile Arg Gly Ile Asp Gly Asn
        4070                4075                4080

Gly Lys Ala Pro Ser Lys Ser Glu Leu Arg His Leu Tyr Leu Thr
        4085                4090                4095

Glu Lys Tyr Val Trp Arg Trp Lys Gln Phe Leu Ser Arg Arg Gly
        4100                4105                4110

Lys Arg Thr Ser Pro Leu Asp Leu Lys Leu Gly His Asn Asn Trp
        4115                4120                4125

Leu Arg Gln Val Leu Phe Thr Pro Ala Thr Gln Ala Ala Arg Gln
        4130                4135                4140

Ala Ala Cys Thr Ile Val Glu Ala Leu Ala Thr Ile Pro Ser Arg
        4145                4150                4155

Lys Gln Gln Val Leu Asp Leu Leu Thr Ser Tyr Leu Asp Glu Leu
        4160                4165                4170

Ser Ile Ala Gly Glu Cys Ala Ala Glu Tyr Leu Ala Leu Tyr Gln
        4175                4180                4185

Lys Leu Ile Thr Ser Ala His Trp Lys Val Tyr Leu Ala Ala Arg
        4190                4195                4200

Gly Val Leu Pro Tyr Val Gly Asn Leu Ile Thr Lys Glu Ile Ala
        4205                4210                4215

Arg Leu Leu Ala Leu Glu Glu Ala Thr Leu Ser Thr Asp Leu Gln
        4220                4225                4230

Gln Gly Tyr Ala Leu Lys Ser Leu Thr Gly Leu Leu Ser Ser Phe
        4235                4240                4245

Val Glu Val Glu Ser Ile Lys Arg His Phe Lys Ser Arg Leu Val
        4250                4255                4260

Gly Thr Val Leu Asn Gly Tyr Leu Cys Leu Arg Lys Leu Val Val
        4265                4270                4275

Gln Arg Thr Lys Leu Ile Asp Glu Thr Gln Asp Met Leu Leu Glu
        4280                4285                4290

Met Leu Glu Asp Met Thr Thr Gly Thr Glu Ser Glu Thr Lys Ala
        4295                4300                4305

Phe Met Ala Val Cys Ile Glu Thr Ala Lys Arg Tyr Asn Leu Asp
        4310                4315                4320
```

```
Asp Tyr Arg Thr Pro Val Phe Ile Phe Glu Arg Leu Cys Ser Ile
4325                4330                4335

Ile Tyr Pro Glu Glu Asn Glu Val Thr Glu Phe Phe Val Thr Leu
4340                4345                4350

Glu Lys Asp Pro Gln Gln Glu Asp Phe Leu Gln Gly Arg Met Pro
4355                4360                4365

Gly Asn Pro Tyr Ser Ser Asn Glu Pro Gly Ile Gly Pro Leu Met
4370                4375                4380

Arg Asp Ile Lys Asn Lys Ile Cys Gln Asp Cys Asp Leu Val Ala
4385                4390                4395

Leu Leu Glu Asp Asp Ser Gly Met Glu Leu Leu Val Asn Asn Lys
4400                4405                4410

Ile Ile Ser Leu Asp Leu Pro Val Ala Glu Val Tyr Lys Lys Val
4415                4420                4425

Trp Cys Thr Thr Asn Glu Gly Glu Pro Met Arg Ile Val Tyr Arg
4430                4435                4440

Met Arg Gly Leu Leu Gly Asp Ala Thr Glu Glu Phe Ile Glu Ser
4445                4450                4455

Leu Asp Ser Thr Thr Asp Glu Glu Glu Asp Glu Glu Val Tyr
4460                4465                4470

Lys Met Ala Gly Val Met Ala Gln Cys Gly Gly Leu Glu Cys Met
4475                4480                4485

Leu Asn Arg Leu Ala Gly Ile Arg Asp Phe Lys Gln Gly Arg His
4490                4495                4500

Leu Leu Thr Val Leu Leu Lys Leu Phe Ser Tyr Cys Val Lys Val
4505                4510                4515

Lys Val Asn Arg Gln Gln Leu Val Lys Leu Glu Met Asn Thr Leu
4520                4525                4530

Asn Val Met Leu Gly Thr Leu Asn Leu Ala Leu Val Ala Glu Gln
4535                4540                4545

Glu Ser Lys Asp Ser Gly Gly Ala Ala Val Ala Glu Gln Val Leu
4550                4555                4560

Ser Ile Met Glu Ile Ile Leu Asp Glu Ser Asn Ala Glu Pro Leu
4565                4570                4575

Ser Glu Asp Lys Gly Asn Leu Leu Leu Thr Gly Asp Lys Asp Gln
4580                4585                4590

Leu Val Met Leu Leu Asp Gln Ile Asn Ser Thr Phe Val Arg Ser
4595                4600                4605

Asn Pro Ser Val Leu Gln Gly Leu Leu Arg Ile Ile Pro Tyr Leu
4610                4615                4620

Ser Phe Gly Glu Val Glu Lys Met Gln Ile Leu Val Glu Arg Phe
4625                4630                4635

Lys Pro Tyr Cys Asn Phe Asp Lys Tyr Asp Glu Asp His Ser Gly
4640                4645                4650

Asp Asp Lys Val Phe Leu Asp Cys Phe Cys Lys Ile Ala Ala Gly
4655                4660                4665

Ile Lys Asn Asn Ser Asn Gly His Gln Leu Lys Asp Leu Ile Leu
4670                4675                4680

Gln Lys Gly Ile Thr Gln Asn Ala Leu Asp Tyr Met Lys Lys His
4685                4690                4695

Ile Pro Ser Ala Lys Asn Leu Asp Ala Asp Ile Trp Lys Lys Phe
4700                4705                4710
```

```
Leu Ser Arg Pro Ala Leu Pro Phe Ile Leu Arg Leu Arg Gly
    4715            4720                4725

Leu Ala Ile Gln His Pro Gly Thr Gln Val Leu Ile Gly Thr Asp
    4730            4735                4740

Ser Ile Pro Asn Leu His Lys Leu Glu Gln Val Ser Ser Asp Glu
    4745            4750                4755

Gly Ile Gly Thr Leu Ala Glu Asn Leu Leu Glu Ala Leu Arg Glu
    4760            4765                4770

His Pro Asp Val Asn Lys Lys Ile Asp Ala Ala Arg Arg Glu Thr
    4775            4780                4785

Arg Ala Glu Lys Lys Arg Met Ala Met Ala Met Arg Gln Lys Ala
    4790            4795                4800

Leu Gly Thr Leu Gly Met Thr Thr Asn Glu Lys Gly Gln Val Val
    4805            4810                4815

Thr Lys Thr Ala Leu Leu Lys Gln Met Glu Glu Leu Ile Glu Glu
    4820            4825                4830

Pro Gly Leu Thr Cys Cys Ile Cys Arg Glu Gly Tyr Lys Phe Gln
    4835            4840                4845

Pro Thr Lys Val Leu Gly Ile Tyr Thr Phe Thr Lys Arg Val Ala
    4850            4855                4860

Leu Glu Glu Met Glu Asn Lys Pro Arg Lys Gln Gln Gly Tyr Ser
    4865            4870                4875

Thr Val Ser His Phe Asn Ile Val His Tyr Asp Cys His Leu Ala
    4880            4885                4890

Ala Val Arg Leu Ala Arg Gly Arg Glu Glu Trp Glu Ser Ala Ala
    4895            4900                4905

Leu Gln Asn Ala Asn Thr Lys Cys Asn Gly Leu Leu Pro Val Trp
    4910            4915                4920

Gly Pro His Val Pro Glu Ser Ala Phe Ala Thr Cys Leu Ala Arg
    4925            4930                4935

His Asn Thr Tyr Leu Gln Glu Cys Thr Gly Gln Arg Glu Pro Thr
    4940            4945                4950

Tyr Gln Leu Asn Ile His Asp Ile Lys Leu Leu Phe Leu Arg Phe
    4955            4960                4965

Ala Met Glu Gln Ser Phe Ser Ala Asp Thr Gly Gly Gly Arg
    4970            4975                4980

Glu Ser Asn Ile His Leu Ile Pro Tyr Ile Ile His Thr Val Leu
    4985            4990                4995

Tyr Val Leu Asn Thr Thr Arg Ala Thr Ser Arg Glu Glu Lys Asn
    5000            5005                5010

Leu Gln Gly Phe Leu Glu Gln Pro Lys Glu Lys Trp Val Glu Ser
    5015            5020                5025

Ala Phe Glu Val Asp Gly Pro Tyr Tyr Phe Thr Val Leu Ala Leu
    5030            5035                5040

His Ile Leu Pro Pro Glu Gln Trp Arg Ala Thr Arg Val Glu Ile
    5045            5050                5055

Leu Arg Arg Leu Leu Val Thr Ser Gln Ala Arg Ala Val Ala Pro
    5060            5065                5070

Gly Gly Ala Thr Arg Leu Thr Asp Lys Ala Val Lys Asp Tyr Ser
    5075            5080                5085

Ala Tyr Arg Ser Ser Leu Leu Phe Trp Ala Leu Val Asp Leu Ile
    5090            5095                5100

Tyr Asn Met Phe Lys Lys Val Pro Thr Ser Asn Thr Glu Gly Gly
```

| | | | |
|---|---|---|---|
| | 5105 | 5110 | 5115 |

Trp Ser Cys Ser Leu Ala Glu Tyr Ile Arg His Asn Asp Met Pro
    5120                     5125                  5130

Ile Tyr Glu Ala Ala Asp Lys Ala Leu Lys Thr Phe Gln Glu Glu
    5135                     5140                  5145

Phe Met Pro Val Glu Thr Phe Ser Glu Phe Leu Asp Val Ala Gly
    5150                     5155                  5160

Leu Leu Ser Glu Ile Thr Asp Pro Glu Ser Phe Leu Lys Asp Leu
    5165                     5170                  5175

Leu Asn Ser Val Pro
    5180

<210> SEQ ID NO 3
<211> LENGTH: 2499
<212> TYPE: DNA
<213> ORGANISM: Homo sapiens

<400> SEQUENCE: 3

```
atggcgacga gcggcggcga agaggcggcg gcagcggctc cggcgccggg gaccccggca      60
acggggcgg  acacgacccc gggctgggag gtggctgtgc ggcccctgct gtccgcgtcc     120
tactccgcct tcgagatgaa ggagttgccg cagctggtgg cctcagtcat cgagagtgaa     180
tcagaaatcc tgcaccatga gaagcagtac gagccattct actcatcttt tgttgcactt     240
tccacacact atattacaac agtttgcagt ctcattcccc ggaaccaact tcagtcagtg     300
gcagcagcct gtaaagttct aattgagttt tctctcctgc gtctggagaa tccagatgag     360
gcttgtgctg tgtcccagaa acacttgatt ctcctaatca agggcctgtg cactggctgt     420
agccgactag atagaactga aattatcaca tttacagcaa tgatgaaatc cgccaagctg     480
ccccaaacag tgaagacact tcagacgtg  gaagatcaga aagagctggc ctcaccagta     540
agccctgagt tgaggcaaaa ggaggtacag atgaattttt tgaaccagct gacctcagtt     600
tttaacccta gaactgtagc atcacaacct atcagtacac agactctggt ggaaggagaa     660
aatgatgagc agtcatctac agatcaagcc tcagctatca aaaccaagaa tgtgttcata     720
gctcagaacg tggctagtct tcaagagctt ggtggctcgg agaagctact gcgtgtatgt     780
ttgaacctgc catatttcct acgctatatc aatcggttcc aagatgcagt tttagctaat     840
tccttcttca taatgcctgc aacagtagca gatgccactc tgttcgtaa  tggctttcat     900
tcattggtga ttgatgtaac tatggcattg gataccctt  ctctacctgt gttggaacct     960
ctcaatcctt ctcgtctaca agatgtgaca gtcctcagcc taagttgtct gtatgcaggt    1020
gtgagtgtgg caacgtgcat ggccatcctc catgtgggta gtgcccagca agtgcggaca    1080
gggtccacga gctccaaaga agatgactat gaaagtgacg cagctacaat tgtccagaaa    1140
tgtctcgaaa tctatgacat gattggacaa gcaatcagca gttctcgccg ggctggtggt    1200
gagcactatc agaattttca attgctgggt gcttggtgct gttaaacag  ccttttcctc    1260
atactgaacc tcagtcctac tgcgttggct gataagggga agagaagga  cccactggct    1320
gccctccgag tcagagacat cctttctcgt actaaagagg gagtgggctc ccctaaactg    1380
gggcctggaa aagggcatca gggatttggg gtactctcag taatattggc aaaccatgcc    1440
atcaaactgc taacgtctct ctttcaagac ctacaagtgg aggcccttca caagggttgg    1500
gagacagatg gccccctgc  agccttgagc attatggccc agagcacctc catacagagg    1560
attcaacggc tgattgactc tgtcccactg atgaacctgc tcttgacgtt actttcaact    1620
```

-continued

```
tcctacagaa aggcatgtgt cctgcagcgg cagaggaagg gctccatgag cagcgatgcc    1680
agcgcctcca ccgactccaa tacttactat gaggacgatt tcagtagcac ggaggaggac    1740
agcagccaag acgatgacag tgagcctatt ttggggcaat ggtttgagga gactatttct    1800
cccagtaaag agaaagcagc acctccgcct cctcccccac ctcctccact ggaaagctct    1860
cctcgggtta aaagccccag taagcaggcc cctggtgaga agggcaacat tctggcgagt    1920
cgcaaagatc ctgagttgtt cttaggtctg gcttccaaca ttttgaactt catcacctct    1980
tccatgctga actctcggaa caattttatc cgaaactatc tgagtgtatc tctttcagaa    2040
caccatatgg ccaccctagc cagtatcatc aaggaggtgg acaaagatgg actcaagggt    2100
tcatcagatg aagagtttgc tgcagctctc tatcacttca accactcact ggtaacctct    2160
gaccttcagt cacctaacct gcagaacaca ctgttgcagc agctaggagt ggctcctttt    2220
tctgagggcc cttggcccctt gtacattcac cctcaaagcc tctctgtgct tcacgcctc    2280 ctgctcatct ggcaacataa agccagtgct caaggtgacc ctgacgtccc agaatgcctt    2340
aaagtttggg acaggttttt gtctacaatg aagcagaatg ccctgcaagg tgtggtgccc    2400
agtgagacag aggatctgaa tgtagaacac ctgcagatgc tcctcctcat tttccacaat    2460
ttcaccgaga caggccggcg ggccatattg tcgctttttt                          2499
```

<210> SEQ ID NO 4
<211> LENGTH: 833
<212> TYPE: PRT
<213> ORGANISM: Homo sapiens

<400> SEQUENCE: 4

```
Met Ala Thr Ser Gly Gly Glu Glu Ala Ala Ala Ala Pro Ala
1               5                   10                  15

Gly Thr Pro Ala Thr Gly Ala Asp Thr Thr Pro Gly Trp Glu Val Ala
                20                  25                  30

Val Arg Pro Leu Leu Ser Ala Ser Tyr Ser Ala Phe Glu Met Lys Glu
            35                  40                  45

Leu Pro Gln Leu Val Ala Ser Val Ile Glu Ser Glu Ser Glu Ile Leu
        50                  55                  60

His His Glu Lys Gln Tyr Glu Pro Phe Tyr Ser Ser Phe Val Ala Leu
65                  70                  75                  80

Ser Thr His Tyr Ile Thr Thr Val Cys Ser Leu Ile Pro Arg Asn Gln
                85                  90                  95

Leu Gln Ser Val Ala Ala Ala Cys Lys Val Leu Ile Glu Phe Ser Leu
            100                 105                 110

Leu Arg Leu Glu Asn Pro Asp Glu Ala Cys Ala Val Ser Gln Lys His
        115                 120                 125

Leu Ile Leu Leu Ile Lys Gly Leu Cys Thr Gly Cys Ser Arg Leu Asp
    130                 135                 140

Arg Thr Glu Ile Ile Thr Phe Thr Ala Met Met Lys Ser Ala Lys Leu
145                 150                 155                 160

Pro Gln Thr Val Lys Thr Leu Ser Asp Val Glu Asp Gln Lys Glu Leu
                165                 170                 175

Ala Ser Pro Val Ser Pro Glu Leu Arg Gln Lys Glu Val Gln Met Asn
            180                 185                 190

Phe Leu Asn Gln Leu Thr Ser Val Phe Asn Pro Arg Thr Val Ala Ser
        195                 200                 205

Gln Pro Ile Ser Thr Gln Thr Leu Val Glu Gly Glu Asn Asp Glu Gln
    210                 215                 220
```

-continued

Ser Ser Thr Asp Gln Ala Ser Ala Ile Lys Thr Lys Asn Val Phe Ile
225                 230                 235                 240

Ala Gln Asn Val Ala Ser Leu Gln Glu Leu Gly Gly Ser Glu Lys Leu
            245                 250                 255

Leu Arg Val Cys Leu Asn Leu Pro Tyr Phe Leu Arg Tyr Ile Asn Arg
        260                 265                 270

Phe Gln Asp Ala Val Leu Ala Asn Ser Phe Phe Ile Met Pro Ala Thr
    275                 280                 285

Val Ala Asp Ala Thr Ala Val Arg Asn Gly Phe His Ser Leu Val Ile
290                 295                 300

Asp Val Thr Met Ala Leu Asp Thr Leu Ser Leu Pro Val Leu Glu Pro
305                 310                 315                 320

Leu Asn Pro Ser Arg Leu Gln Asp Val Thr Val Leu Ser Leu Ser Cys
                325                 330                 335

Leu Tyr Ala Gly Val Ser Val Ala Thr Cys Met Ala Ile Leu His Val
            340                 345                 350

Gly Ser Ala Gln Gln Val Arg Thr Gly Ser Thr Ser Ser Lys Glu Asp
        355                 360                 365

Asp Tyr Glu Ser Asp Ala Ala Thr Ile Val Gln Lys Cys Leu Glu Ile
370                 375                 380

Tyr Asp Met Ile Gly Gln Ala Ile Ser Ser Arg Arg Ala Gly Gly
385                 390                 395                 400

Glu His Tyr Gln Asn Phe Gln Leu Leu Gly Ala Trp Cys Leu Leu Asn
                405                 410                 415

Ser Leu Phe Leu Ile Leu Asn Leu Ser Pro Thr Ala Leu Ala Asp Lys
            420                 425                 430

Gly Lys Glu Lys Asp Pro Leu Ala Ala Leu Arg Val Arg Asp Ile Leu
        435                 440                 445

Ser Arg Thr Lys Glu Gly Val Gly Ser Pro Lys Leu Gly Pro Gly Lys
450                 455                 460

Gly His Gln Gly Phe Gly Val Leu Ser Val Ile Leu Ala Asn His Ala
465                 470                 475                 480

Ile Lys Leu Leu Thr Ser Leu Phe Gln Asp Leu Gln Val Glu Ala Leu
                485                 490                 495

His Lys Gly Trp Glu Thr Asp Gly Pro Pro Ala Ala Leu Ser Ile Met
            500                 505                 510

Ala Gln Ser Thr Ser Ile Gln Arg Ile Gln Arg Leu Ile Asp Ser Val
        515                 520                 525

Pro Leu Met Asn Leu Leu Thr Leu Leu Ser Thr Ser Tyr Arg Lys
530                 535                 540

Ala Cys Val Leu Gln Arg Gln Arg Lys Gly Ser Met Ser Ser Asp Ala
545                 550                 555                 560

Ser Ala Ser Thr Asp Ser Asn Thr Tyr Tyr Glu Asp Asp Phe Ser Ser
                565                 570                 575

Thr Glu Glu Asp Ser Ser Gln Asp Asp Ser Glu Pro Ile Leu Gly
            580                 585                 590

Gln Trp Phe Glu Glu Thr Ile Ser Pro Ser Lys Glu Lys Ala Ala Pro
        595                 600                 605

Pro Pro Pro Pro Pro Pro Pro Leu Glu Ser Ser Pro Arg Val Lys
                615                 620

Ser Pro Ser Lys Gln Ala Pro Gly Glu Lys Gly Asn Ile Leu Ala Ser
625                 630                 635                 640

```
Arg Lys Asp Pro Glu Leu Phe Leu Gly Leu Ala Ser Asn Ile Leu Asn
            645                 650                 655

Phe Ile Thr Ser Ser Met Leu Asn Ser Arg Asn Asn Phe Ile Arg Asn
        660                 665                 670

Tyr Leu Ser Val Ser Leu Ser Glu His His Met Ala Thr Leu Ala Ser
    675                 680                 685

Ile Ile Lys Glu Val Asp Lys Asp Gly Leu Lys Gly Ser Ser Asp Glu
690                 695                 700

Glu Phe Ala Ala Ala Leu Tyr His Phe Asn His Ser Leu Val Thr Ser
705                 710                 715                 720

Asp Leu Gln Ser Pro Asn Leu Gln Asn Thr Leu Leu Gln Gln Leu Gly
                725                 730                 735

Val Ala Pro Phe Ser Glu Gly Pro Trp Pro Leu Tyr Ile His Pro Gln
            740                 745                 750

Ser Leu Ser Val Leu Ser Arg Leu Leu Ile Trp Gln His Lys Ala
        755                 760                 765

Ser Ala Gln Gly Asp Pro Asp Val Pro Glu Cys Leu Lys Val Trp Asp
    770                 775                 780

Arg Phe Leu Ser Thr Met Lys Gln Asn Ala Leu Gln Gly Val Val Pro
785                 790                 795                 800

Ser Glu Thr Glu Asp Leu Asn Val Glu His Leu Gln Met Leu Leu Leu
                805                 810                 815

Ile Phe His Asn Phe Thr Glu Thr Gly Arg Arg Ala Ile Leu Ser Leu
            820                 825                 830

Phe

<210> SEQ ID NO 5
<211> LENGTH: 2163
<212> TYPE: DNA
<213> ORGANISM: Homo sapiens

<400> SEQUENCE: 5
acctgtaaaa tggtggatgg cgtgggtgtc tgcacagtgt gtgctaaggt gtgccacaag      60
gatcatgaga tttcctatgc caagtatgga tccttcttct gtgactgtgg agccaaggaa     120
gatggcagct gtttggctct ggtgaagaga actcctagca gtggcatgag ctctaccatg     180
aaggagtcgg catttcagag tgaacccagg atttcagaga gtctagtgcg tcatgccagc     240
acctcctcgc cagctgacaa agccaaggtt accatcagtg atggaaaggt tgctgacgaa     300
gagaagccca gaagagcagc ctctgccgcc acagtagagg gctgccggga ggaattacag     360
aaccaggcca atttctcctt cgctcctctc gtgttagaca tgcttaattt ccttatggat     420
gccattcaga ccaacttcca gcaagcttca gccgtcggga gcagcagccg tgctcagcaa     480
gccctcagtg agctacacac tgtggagaag gcagtggaga tgacagacca gctgatggtt     540
cccaccttag ggtcccagga aggtgccttt gagaatgtgc ggatgaatta cagtggagac     600
cagggccaga ccatccggca gctgatcagt gctcatgtgc tcaggcgggt ggctatgtgt     660
gtgctctcct ctccccatgg gcgccgccaa catttggctg tcagccatga aagggcaag      720
atcaccgttc tgcagctctc tgcactcctg aagcaagcag attccagcaa aggaagtta     780
actctgaccc gcttggcttc tgccccagtt ccttttactg tgttgagcct cacaggaaat     840
ccctgcaagg aagactactt ggcggtttgt gggctaaagg actgtcatgt gctcaccttt     900
agtagctcag gctctgtttc ggatcacttg gttttgcacc ctcagttggc aacggggaac     960
ttcatcatca aagccgtgtg gttacctggt tcacagaccg agttatcaat tgtcaccgca    1020
```

```
gactttgtta agatttatga cctgtgtgtt gatgccttga gtccaacctt ctattttctc    1080
ctgccaagct caaagataag agatgttacc ttccttttca atgaggaggg aaagaacatc    1140
attgttataa tgtcttcggc tgggtacatc tatactcagc ttatggaaga ggccagcagt    1200
gcccagcagg gacccttcta tgtcactaat gtgttggaaa tcaatcatga ggacctgaag    1260
gacagtaaca gccaggtggc gggcggtggt gtgtccgtgt actactccca cgtgttgcag    1320
atgttgttct tcagctattg tcaaggcaaa tcattcgcag ccaccatcag caggacaacc    1380
ctggaggtgt tgcaactctt ccccatcaac atcaaaagtt ccaatggtgg cagtaagact    1440
tctcctgctc tttgccagtg gtctgaggtg atgaaccacc ctggcttggt gtgctgtgtc    1500
cagcaaacta caggggtgcc gctggtagtt atggtgaaac cagacacttt tcttatccag    1560
gagattaaga ctcttcctgc taaagcgaag atccaagaca tggttgctat taggcacacg    1620
gcctgcaatg agcagcagcg gacaacaatg attctgctgt gtgaggatgg cagcctgcgc    1680
atttacatgg ccaacgtgga gaacacctcc tactggctgc agccatccct gcagcccagc    1740
agtgtcatca gcatcatgaa gcctgttcga aagcgcaaaa cagctacaat cacaacccgc    1800
acgtctagcc aggtgacttt ccccattgac tttttttgaac acaaccagca gctgacagat    1860
gtggagtttg gtggtaacga cctcctacag gtctataatg cacaacagat aaaacaccgg    1920
ctgaattcca ctggcatgta tgtggccaac accaagcccg gaggcttcac cattgagatt    1980
agtaacaaca atagcactat ggtgatgaca ggcatgcgga tccagattgg gactcaagca    2040
atagaacggg ccccgtcata tatcgagatc ttcggcagaa ctatgcagct caacctgagt    2100
cgctcacgct ggtttgactt ccccttcacc agagaagaag ccctgcaggc tgataagaag    2160
ctg                                                                  2163
```

<210> SEQ ID NO 6
<211> LENGTH: 721
<212> TYPE: PRT
<213> ORGANISM: Homo sapiens

<400> SEQUENCE: 6

```
Thr Cys Lys Met Val Asp Gly Val Gly Val Cys Thr Val Cys Ala Lys
1               5                   10                  15

Val Cys His Lys Asp His Glu Ile Ser Tyr Ala Lys Tyr Gly Ser Phe
            20                  25                  30

Phe Cys Asp Cys Gly Ala Lys Glu Asp Gly Ser Cys Leu Ala Leu Val
        35                  40                  45

Lys Arg Thr Pro Ser Ser Gly Met Ser Ser Thr Met Lys Glu Ser Ala
    50                  55                  60

Phe Gln Ser Glu Pro Arg Ile Ser Glu Ser Leu Val Arg His Ala Ser
65                  70                  75                  80

Thr Ser Ser Pro Ala Asp Lys Ala Lys Val Thr Ile Ser Asp Gly Lys
                85                  90                  95

Val Ala Asp Glu Glu Lys Pro Lys Lys Ser Ser Leu Cys Arg Thr Val
            100                 105                 110

Glu Gly Cys Arg Glu Glu Leu Gln Asn Gln Ala Asn Phe Ser Phe Ala
        115                 120                 125

Pro Leu Val Leu Asp Met Leu Asn Phe Leu Met Asp Ala Ile Gln Thr
    130                 135                 140

Asn Phe Gln Gln Ala Ser Ala Val Gly Ser Ser Ser Arg Ala Gln Gln
145                 150                 155                 160
```

```
Ala Leu Ser Glu Leu His Thr Val Glu Lys Ala Val Glu Met Thr Asp
            165                 170                 175

Gln Leu Met Val Pro Thr Leu Gly Ser Gln Glu Gly Ala Phe Glu Asn
        180                 185                 190

Val Arg Met Asn Tyr Ser Gly Asp Gln Gly Gln Thr Ile Arg Gln Leu
    195                 200                 205

Ile Ser Ala His Val Leu Arg Arg Val Ala Met Cys Val Leu Ser Ser
210                 215                 220

Pro His Gly Arg Arg Gln His Leu Ala Val Ser His Glu Lys Gly Lys
225                 230                 235                 240

Ile Thr Val Leu Gln Leu Ser Ala Leu Leu Lys Gln Ala Asp Ser Ser
                245                 250                 255

Lys Arg Lys Leu Thr Leu Thr Arg Leu Ala Ser Ala Pro Val Pro Phe
            260                 265                 270

Thr Val Leu Ser Leu Thr Gly Asn Pro Cys Lys Glu Asp Tyr Leu Ala
        275                 280                 285

Val Cys Gly Leu Lys Asp Cys His Val Leu Thr Phe Ser Ser Ser Gly
    290                 295                 300

Ser Val Ser Asp His Leu Val Leu His Pro Gln Leu Ala Thr Gly Asn
305                 310                 315                 320

Phe Ile Ile Lys Ala Val Trp Leu Pro Gly Ser Gln Thr Glu Leu Ser
                325                 330                 335

Ile Val Thr Ala Asp Phe Val Lys Ile Tyr Asp Leu Cys Val Asp Ala
            340                 345                 350

Leu Ser Pro Thr Phe Tyr Phe Leu Leu Pro Ser Ser Lys Ile Arg Asp
        355                 360                 365

Val Thr Phe Leu Phe Asn Glu Glu Gly Lys Asn Ile Ile Val Ile Met
    370                 375                 380

Ser Ser Ala Gly Tyr Ile Tyr Thr Gln Leu Met Glu Glu Ala Ser Ser
385                 390                 395                 400

Ala Gln Gln Gly Pro Phe Tyr Val Thr Asn Val Leu Glu Ile Asn His
                405                 410                 415

Glu Asp Leu Lys Asp Ser Asn Ser Gln Val Ala Gly Gly Val Ser
        420                 425                 430

Val Tyr Tyr Ser His Val Leu Gln Met Leu Phe Phe Ser Tyr Cys Gln
    435                 440                 445

Gly Lys Ser Phe Ala Ala Thr Ile Ser Arg Thr Thr Leu Glu Val Leu
450                 455                 460

Gln Leu Phe Pro Ile Asn Ile Lys Ser Ser Asn Gly Gly Ser Lys Thr
465                 470                 475                 480

Ser Pro Ala Leu Cys Gln Trp Ser Glu Val Met Asn His Pro Gly Leu
                485                 490                 495

Val Cys Cys Val Gln Gln Thr Thr Gly Val Pro Leu Val Val Met Val
            500                 505                 510

Lys Pro Asp Thr Phe Leu Ile Gln Glu Ile Lys Thr Leu Pro Ala Lys
        515                 520                 525

Ala Lys Ile Gln Asp Met Val Ala Ile Arg His Thr Ala Cys Asn Glu
    530                 535                 540

Gln Gln Arg Thr Thr Met Ile Leu Leu Cys Glu Asp Gly Ser Leu Arg
545                 550                 555                 560

Ile Tyr Met Ala Asn Val Glu Asn Thr Ser Tyr Trp Leu Gln Pro Ser
                565                 570                 575

Leu Gln Pro Ser Ser Val Ile Ser Ile Met Lys Pro Val Arg Lys Arg
```

|  |  |  |  |  |  |  |  |  |
|---|---|---|---|---|---|---|---|---|
| Lys | Thr | Ala | Thr | Ile | Thr | Thr | Arg | Thr | Ser | Ser | Gln | Val | Thr | Phe | Pro |
| 580 |  |  |  |  | 585 |  |  |  | 590 |  |  |  |  |  |  |

```
            580                 585                 590
Lys Thr Ala Thr Ile Thr Thr Arg Thr Ser Ser Gln Val Thr Phe Pro
            595                 600                 605
Ile Asp Phe Phe Glu His Asn Gln Gln Leu Thr Asp Val Glu Phe Gly
            610                 615                 620
Gly Asn Asp Leu Leu Gln Val Tyr Asn Ala Gln Gln Ile Lys His Arg
625                 630                 635                 640
Leu Asn Ser Thr Gly Met Tyr Val Ala Asn Thr Lys Pro Gly Gly Phe
                645                 650                 655
Thr Ile Glu Ile Ser Asn Asn Asn Ser Thr Met Val Met Thr Gly Met
                660                 665                 670
Arg Ile Gln Ile Gly Thr Gln Ala Ile Glu Arg Ala Pro Ser Tyr Ile
            675                 680                 685
Glu Ile Phe Gly Arg Thr Met Gln Leu Asn Leu Ser Arg Ser Arg Trp
        690                 695                 700
Phe Asp Phe Pro Phe Thr Arg Glu Glu Ala Leu Gln Ala Asp Lys Lys
705                 710                 715                 720
Leu
```

<210> SEQ ID NO 7
<211> LENGTH: 1449
<212> TYPE: DNA
<213> ORGANISM: Homo sapiens

<400> SEQUENCE: 7

```
agtgatggaa aggttgctga cgaagagaag cccaagaaga gcagcctctg ccgcacagta      60
gagggctgcc gggaggaatt acagaaccag gccaatttct ccttcgctcc tctcgtgtta     120
gacatgctta atttccttat ggatgccatt cagaccaact ccagcaagc ttcagccgtc      180
gggagcagca gccgtgctca gcaagccctc agtgagctac acactgtgga aaggcagtg      240
gagatgacag accagctgat ggttcccacc ttagggtccc aggaaggtgc ctttgagaat     300
gtgcggatga attacagtgg agaccagggc cagaccatcc ggcagctgat cagtgctcat     360
gtgctcaggc gggtggctat gtgtgtgctc tcctctcccc atgggcgccg ccaacatttg     420
gctgtcagcc atgagaaggg caagatcacc gttctgcagc tctctgcact cctgaagcaa     480
gcagattcca gcaaaaggaa gttaactctg acccgcttgg cttctgcccc agttcctttt     540
actgtgttga gcctcacagg aaatccctgc aaggaagact acttggcggt tgtgggcta      600
aaggactgtc atgtgctcac ctttagtagc tcaggctctg tttcggatca cttggttttg     660
caccctcagt tggcaacggg gaacttcatc atcaaagccg tgtggttacc tggttcacag     720
accgagttat caattgtcac cgcagacttt gttaagattt atgacctgtg tgttgatgcc     780
ttgagtccaa ccttctattt tctcctgcca agctcaaaga taagagatgt taccttcctt     840
ttcaatgagg agggaaagaa catcattgtt ataatgtctt cggctgggta catctatact     900
cagcttatgg aagaggccag cagtgcccag cagggaccct tctatgtcac taatgtgttg     960
gaaatcaatc atgaggacct gaaggacagt aacagccagg tggcgggcgg tggtgtgtcc    1020
gtgtactact cccacgtgtt gcagatgttg ttcttcagct attgtcaagg caaatcattc    1080
gcagccacca tcagcaggac aaccctggag gtgttgcaac tcttccccat caacatcaaa    1140
agttccaatg gtggcagtaa gacttctcct gctctttgcc agtggtctga ggtgatgaac    1200
caccctggct tggtgtgctg tgtccagcaa actacagggg tgccgctggt agttatggtg    1260
aaaccagaca cttttcttat ccaggagatt aagactcttc ctgctaaagc gaagatccaa    1320
```

```
gacatggttg ctattaggca cacggcctgc aatgagcagc agcggacaac aatgattctg   1380
ctgtgtgagg atggcagcct gcgcatttac atggccaacg tggagaacac ctcctactgg   1440
ctgcagcca                                                           1449
```

<210> SEQ ID NO 8
<211> LENGTH: 483
<212> TYPE: PRT
<213> ORGANISM: Homo sapiens

<400> SEQUENCE: 8

```
Ser Asp Gly Lys Val Ala Asp Glu Glu Lys Pro Lys Lys Ser Ser Leu
1               5                   10                  15

Cys Arg Thr Val Glu Gly Cys Arg Glu Glu Leu Gln Asn Gln Ala Asn
                20                  25                  30

Phe Ser Phe Ala Pro Leu Val Leu Asp Met Leu Asn Phe Leu Met Asp
            35                  40                  45

Ala Ile Gln Thr Asn Phe Gln Gln Ala Ser Ala Val Gly Ser Ser Ser
        50                  55                  60

Arg Ala Gln Gln Ala Leu Ser Glu Leu His Thr Val Glu Lys Ala Val
65                  70                  75                  80

Glu Met Thr Asp Gln Leu Met Val Pro Thr Leu Gly Ser Gln Glu Gly
                85                  90                  95

Ala Phe Glu Asn Val Arg Met Asn Tyr Ser Gly Asp Gln Gly Gln Thr
            100                 105                 110

Ile Arg Gln Leu Ile Ser Ala His Val Leu Arg Arg Val Ala Met Cys
        115                 120                 125

Val Leu Ser Ser Pro His Gly Arg Arg Gln His Leu Ala Val Ser His
    130                 135                 140

Glu Lys Gly Lys Ile Thr Val Leu Gln Leu Ser Ala Leu Leu Lys Gln
145                 150                 155                 160

Ala Asp Ser Ser Lys Arg Lys Leu Thr Leu Thr Arg Leu Ala Ser Ala
                165                 170                 175

Pro Val Pro Phe Thr Val Leu Ser Leu Thr Gly Asn Pro Cys Lys Glu
            180                 185                 190

Asp Tyr Leu Ala Val Cys Gly Leu Lys Asp Cys His Val Leu Thr Phe
        195                 200                 205

Ser Ser Ser Gly Ser Val Ser Asp His Leu Val Leu His Pro Gln Leu
    210                 215                 220

Ala Thr Gly Asn Phe Ile Ile Lys Ala Val Trp Leu Pro Gly Ser Gln
225                 230                 235                 240

Thr Glu Leu Ser Ile Val Thr Ala Asp Phe Val Lys Ile Tyr Asp Leu
                245                 250                 255

Cys Val Asp Ala Leu Ser Pro Thr Phe Tyr Phe Leu Leu Pro Ser Ser
            260                 265                 270

Lys Ile Arg Asp Val Thr Phe Leu Phe Asn Glu Glu Gly Lys Asn Ile
        275                 280                 285

Ile Val Ile Met Ser Ser Ala Gly Tyr Ile Tyr Thr Gln Leu Met Glu
    290                 295                 300

Glu Ala Ser Ser Ala Gln Gly Pro Phe Tyr Val Thr Asn Val Leu
305                 310                 315                 320

Glu Ile Asn His Glu Asp Leu Lys Asp Ser Asn Ser Gln Val Ala Gly
                325                 330                 335

Gly Gly Val Ser Val Tyr Tyr Ser His Val Leu Gln Met Leu Phe Phe
```

|   |   |   | 340 |   |   | 345 |   |   | 350 |   |   |
|---|---|---|---|---|---|---|---|---|---|---|---|
| Ser | Tyr | Cys | Gln | Gly | Lys | Ser | Phe | Ala | Ala | Thr | Ile | Ser | Arg | Thr | Thr |
|   |   |   | 355 |   |   |   |   |   | 360 |   |   |   | 365 |   |   |

Leu Glu Val Leu Gln Leu Phe Pro Ile Asn Ile Lys Ser Ser Asn Gly
    370             375             380

Gly Ser Lys Thr Ser Pro Ala Leu Cys Gln Trp Ser Glu Val Met Asn
385             390             395             400

His Pro Gly Leu Val Cys Cys Val Gln Gln Thr Thr Gly Val Pro Leu
            405             410             415

Val Val Met Val Lys Pro Asp Thr Phe Leu Ile Gln Glu Ile Lys Thr
        420             425             430

Leu Pro Ala Lys Ala Lys Ile Gln Asp Met Val Ala Ile Arg His Thr
        435             440             445

Ala Cys Asn Glu Gln Gln Arg Thr Thr Met Ile Leu Leu Cys Glu Asp
    450             455             460

Gly Ser Leu Arg Ile Tyr Met Ala Asn Val Glu Asn Thr Ser Tyr Trp
465             470             475             480

Leu Gln Pro

```
<210> SEQ ID NO 9
<211> LENGTH: 1887
<212> TYPE: DNA
<213> ORGANISM: Homo sapiens

<400> SEQUENCE: 9
agtgatggaa aggttgctga cgaagagaag cccaagaaga gcagcctctg ccgcacagta      60
gagggctgcc gggaggaatt acagaaccag gccaatttct ccttcgctcc tctcgtgtta     120
gacatgctta atttccttat ggatgccatt cagaccaact ccagcaagc ttcagccgtc      180
gggagcagca gccgtgctca gcaagccctc agtgagctac acactgtgga aaggcagtg     240
gagatgacag accagctgat ggttcccacc ttagggtccc aggaaggtgc ctttgagaat     300
gtgcggatga attacagtgg agaccagggc cagaccatcc ggcagctgat cagtgctcat    360
gtgctcaggc gggtggctat gtgtgtgctc tcctctcccc atgggcgccg ccaacatttg    420
gctgtcagcc atgagaaggg caagatcacc gttctgcagc tctctgcact cctgaagcaa   480
gcagattcca gcaaaaggaa gttaactctg acccgcttgg cttctgcccc agttcctttt    540
actgtgttga gcctcacagg aaatccctgc aaggaagact acttggcggt tgtgggcta    600
aaggactgtc atgtgctcac ctttagtagc tcaggctctg tttcggatca cttggttttg    660
cacccctcagt tggcaacggg gaacttcatc atcaaagccg tgtggttacc tggttcacag  720
accgagttat caattgtcac cgcagacttt gttaagattt atgacctgtg tgttgatgcc    780
ttgagtccaa ccttctattt tctcctgcca agctcaaaga taagagatgt taccttcctt   840
ttcaatgagg agggaaagaa catcattgtt ataatgtctt cggctgggta catctatact    900
cagcttatgg aagaggccag cagtgcccag cagggaccct tctatgtcac taatgtgttg    960
gaaatcaatc atgaggacct gaaggacagt aacagccagg tggcgggcgg tggtgtgtcc  1020
gtgtactact cccacgtgtt gcagatgttg ttcttcagct attgtcaagg caaatcattc   1080
gcagccacca tcagcaggac aaccctggag gtgttgcaac tcttccccat caacatcaaa   1140
agttccaatg gtggcagtaa gacttctcct gctctttgcc agtggtctga ggtgatgaac   1200
caccctggct tggtgtgctg tgtccagcaa actacagggg tgccgctggt agttatggtg   1260
aaaccagaca ctttttcttat ccaggagatt aagactcttc ctgctaaagc gaagatccaa   1320
```

-continued

```
gacatggttg ctattaggca cacggcctgc aatgagcagc agcggacaac aatgattctg    1380
ctgtgtgagg atggcagcct gcgcatttac atggccaacg tggagaacac ctcctactgg    1440
ctgcagccat ccctgcagcc cagcagtgtc atcagcatca tgaagcctgt tcgaaagcgc    1500
aaaacagcta caatcacaac ccgcacgtct agccaggtga cttttcccat tgactttttt    1560
gaacacaacc agcagctgac agatgtggag tttggtggta acgacctcct acaggtctat    1620
aatgcacaac agataaaaca ccggctgaat tccactggca tgtatgtggc caacaccaag    1680
cccggaggct tcaccattga gattagtaac aacaatagca ctatggtgat gacaggcatg    1740
cggatccaga ttgggactca agcaatagaa cgggccccgt catatatcga gatcttcggc    1800
agaactatgc agctcaacct gagtcgctca cgctggtttg acttccccctt caccagagaa    1860 gaagccctgc aggctgataa gaagctg                                        1887
```

<210> SEQ ID NO 10
<211> LENGTH: 629
<212> TYPE: PRT
<213> ORGANISM: Homo sapiens

<400> SEQUENCE: 10

```
Ser Asp Gly Lys Val Ala Asp Glu Glu Lys Pro Lys Lys Ser Ser Leu
1               5                   10                  15

Cys Arg Thr Val Glu Gly Cys Arg Glu Glu Leu Gln Asn Gln Ala Asn
            20                  25                  30

Phe Ser Phe Ala Pro Leu Val Leu Asp Met Leu Asn Phe Leu Met Asp
        35                  40                  45

Ala Ile Gln Thr Asn Phe Gln Gln Ala Ser Ala Val Gly Ser Ser Ser
    50                  55                  60

Arg Ala Gln Gln Ala Leu Ser Glu Leu His Thr Val Glu Lys Ala Val
65                  70                  75                  80

Glu Met Thr Asp Gln Leu Met Val Pro Thr Leu Gly Ser Gln Glu Gly
                85                  90                  95

Ala Phe Glu Asn Val Arg Met Asn Tyr Ser Gly Asp Gln Gly Gln Thr
            100                 105                 110

Ile Arg Gln Leu Ile Ser Ala His Val Leu Arg Arg Val Ala Met Cys
        115                 120                 125

Val Leu Ser Ser Pro His Gly Arg Arg Gln His Leu Ala Val Ser His
    130                 135                 140

Glu Lys Gly Lys Ile Thr Val Leu Gln Leu Ser Ala Leu Leu Lys Gln
145                 150                 155                 160

Ala Asp Ser Ser Lys Arg Lys Leu Thr Leu Thr Arg Leu Ala Ser Ala
                165                 170                 175

Pro Val Pro Phe Thr Val Leu Ser Leu Thr Gly Asn Pro Cys Lys Glu
            180                 185                 190

Asp Tyr Leu Ala Val Cys Gly Leu Lys Asp Cys His Val Leu Thr Phe
        195                 200                 205

Ser Ser Ser Gly Ser Val Ser Asp His Leu Val Leu His Pro Gln Leu
    210                 215                 220

Ala Thr Gly Asn Phe Ile Ile Lys Ala Val Trp Leu Pro Gly Ser Gln
225                 230                 235                 240

Thr Glu Leu Ser Ile Val Thr Ala Asp Phe Val Lys Ile Tyr Asp Leu
                245                 250                 255

Cys Val Asp Ala Leu Ser Pro Thr Phe Tyr Phe Leu Leu Pro Ser Ser
            260                 265                 270
```

```
Lys Ile Arg Asp Val Thr Phe Leu Phe Asn Glu Glu Gly Lys Asn Ile
            275                 280                 285
Ile Val Ile Met Ser Ser Ala Gly Tyr Ile Tyr Thr Gln Leu Met Glu
290                 295                 300
Glu Ala Ser Ser Ala Gln Gln Gly Pro Phe Tyr Val Thr Asn Val Leu
305                 310                 315                 320
Glu Ile Asn His Glu Asp Leu Lys Asp Ser Asn Ser Gln Val Ala Gly
                325                 330                 335
Gly Gly Val Ser Val Tyr Tyr Ser His Val Leu Gln Met Leu Phe Phe
            340                 345                 350
Ser Tyr Cys Gln Gly Lys Ser Phe Ala Ala Thr Ile Ser Arg Thr Thr
        355                 360                 365
Leu Glu Val Leu Gln Leu Phe Pro Ile Asn Ile Lys Ser Ser Asn Gly
    370                 375                 380
Gly Ser Lys Thr Ser Pro Ala Leu Cys Gln Trp Ser Glu Val Met Asn
385                 390                 395                 400
His Pro Gly Leu Val Cys Cys Val Gln Gln Thr Thr Gly Val Pro Leu
                405                 410                 415
Val Val Met Val Lys Pro Asp Thr Phe Leu Ile Gln Glu Ile Lys Thr
            420                 425                 430
Leu Pro Ala Lys Ala Lys Ile Gln Asp Met Val Ala Ile Arg His Thr
        435                 440                 445
Ala Cys Asn Glu Gln Gln Arg Thr Thr Met Ile Leu Leu Cys Glu Asp
    450                 455                 460
Gly Ser Leu Arg Ile Tyr Met Ala Asn Val Glu Asn Thr Ser Tyr Trp
465                 470                 475                 480
Leu Gln Pro Ser Leu Gln Pro Ser Ser Val Ile Ser Ile Met Lys Pro
                485                 490                 495
Val Arg Lys Arg Lys Thr Ala Thr Ile Thr Thr Arg Thr Ser Ser Gln
            500                 505                 510
Val Thr Phe Pro Ile Asp Phe Phe Glu His Asn Gln Gln Leu Thr Asp
        515                 520                 525
Val Glu Phe Gly Gly Asn Asp Leu Leu Gln Val Tyr Asn Ala Gln Gln
    530                 535                 540
Ile Lys His Arg Leu Asn Ser Thr Gly Met Tyr Val Ala Asn Thr Lys
545                 550                 555                 560
Pro Gly Gly Phe Thr Ile Glu Ile Ser Asn Asn Asn Ser Thr Met Val
                565                 570                 575
Met Thr Gly Met Arg Ile Gln Ile Gly Thr Gln Ala Ile Glu Arg Ala
            580                 585                 590
Pro Ser Tyr Ile Glu Ile Phe Gly Arg Thr Met Gln Leu Asn Leu Ser
        595                 600                 605
Arg Ser Arg Trp Phe Asp Phe Pro Phe Thr Arg Glu Glu Ala Leu Gln
    610                 615                 620
Ala Asp Lys Lys Leu
625

<210> SEQ ID NO 11
<211> LENGTH: 2844
<212> TYPE: DNA
<213> ORGANISM: Homo sapiens

<400> SEQUENCE: 11
agtgatggaa aggttgctga cgaagagaag cccaagaaga gcagcctctg ccgcacagta    60
```

```
gagggctgcc gggaggaatt acagaaccag gccaatttct ccttcgctcc tctcgtgtta    120
gacatgctta atttccttat ggatgccatt cagaccaact tccagcaagc ttcagccgtc    180
gggagcagca gccgtgctca gcaagccctc agtgagctac acactgtgga aaggcagtg    240 gagatgacag accagctgat ggttcccacc ttagggtccc aggaaggtgc ctttgagaat    300
gtgcggatga attacagtgg agaccagggc cagaccatcc ggcagctgat cagtgctcat    360
gtgctcaggc gggtggctat gtgtgtgctc tcctctcccc atgggcgccg ccaacatttg    420
gctgtcagcc atgagaaggg caagatcacc gttctgcagc tctctgcact cctgaagcaa    480
gcagattcca gcaaaaggaa gttaactctg acccgcttgg cttctgcccc agttcctttt    540
actgtgttga gcctcacagg aaatccctgc aaggaagact acttggcggt tgtgggcta     600 aaggactgtc atgtgctcac ctttagtagc tcaggctctg tttcggatca cttggttttg    660
caccctcagt tggcaacggg gaacttcatc atcaaagccg tgtggttacc tggttcacag    720
accgagttat caattgtcac cgcagacttt gttaagattt atgacctgtg tgttgatgcc    780
ttgagtccaa ccttctattt tctcctgcca agctcaaaga taagagatgt taccttcctt    840
ttcaatgagg agggaaagaa catcattgtt ataatgtctt cggctgggta catctatact    900
cagcttatgg aagaggccag cagtgcccag cagggaccct tctatgtcac taatgtgttg    960
gaaatcaatc atgaggacct gaaggacagt aacagccagg tggcgggcgg tggtgtgtcc   1020
gtgtactact cccacgtgtt gcagatgttg ttcttcagct attgtcaagg caaatcattc   1080
gcagccacca tcagcaggac aaccctggag gtgttgcaac tcttccccat caacatcaaa   1140
agttccaatg gtggcagtaa gacttctcct gctctttgcc agtggtctga ggtgatgaac   1200
caccctggct tggtgtgctg tgtccagcaa actacagggg tgccgctggt agttatggtg   1260
aaaccagaca cttttcttat ccaggagatt aagactcttc ctgctaaagc gaagatccaa   1320
gacatggttg ctattaggca cacggcctgc aatgagcagc agcggacaac aatgattctg   1380
ctgtgtgagg atggcagcct gcgcatttac atggccaacg tggagaacac ctcctactgg   1440
ctgcagccat ccctgcagcc cagcagtgtc atcagcatca tgaagcctgt tcgaaagcgc   1500
aaaacagcta caatcacaac ccgcacgtct agccaggtga cttccccat tgactttttt    1560 gaacacaacc agcagctgac agatgtggag tttggtggta acgacctcct acaggtctat   1620
aatgcacaac agataaaaca ccggctgaat tccactggca tgtatgtggc caacaccaag   1680
cccggaggct tcaccattga gattagtaac aacaatagca ctatggtgat gacaggcatg   1740
cggatccaga ttgggactca agcaatagaa cgggccccgt catatatcga gatcttcggc   1800
agaactatgc agctcaacct gagtcgctca cgctggtttg acttcccctt caccagagaa   1860
gaagccctgc aggctgataa gaagctgaac ctcttcattg gggcctcggt ggaaccagca   1920
ggtgtcacca tgatagatgc tgtaaaaatt tatggcaaga ctaaggagca gtttggctgg   1980
cctgatgagc ccccagaaga attcccttct gcctctgtca gcaacatctg cccttcaaat   2040
ctgaaccaga gcaacggcac tggagatagc gactcagctg cccccactac gaccagtgga   2100
actgtcctgg agaggctggt tgtgagttct ttagaagccc tggaaagctg ctttgccgtt   2160
ggcccaatca tcgagaagga gagaaacaag aatgctgctc aggagctggc cactttgctg   2220
ttgtccctgc agcacctgc cagtgtccag cagcagtcca agagccttct ggccagcctg   2280
cacaccagcc gctcggccta ccacagccac aaggatcagg ccttgctgag caaagctgtg   2340
cagtgtctca acacatctag caaagagggc aaggatttgg accctgaggt gttccagagg   2400
```

```
ctagtgatca cagctcgctc cattgccatc atgcgcccca acaaccttgt ccactttacg    2460
gagtcaaagc tgccccagat ggaaacagaa ggaatggatg aagggaagga accgcagaag    2520
cagttggaag gagattgctg tagtttcatc acccagcttg tgaaccactt ctggaaactc    2580
catgcatcca aacccaagaa tgccttcttg gcacctgcct gccttccagg actaactcat    2640
attgaagcta ctgtcaatgc tctggtggac atcatccatg ctactgtac ctgtgagctg      2700 gattgtatta acacagcatc caagatctac atgcagatgc tcttgtgtcc tgatcctgct    2760
gtgagcttct cttgtaaaca agctctaatt cgagtcctaa ggcccaggaa caaacggaga    2820
catgtgactt taccctcttc ccct                                            2844
```

<210> SEQ ID NO 12
<211> LENGTH: 948
<212> TYPE: PRT
<213> ORGANISM: Homo sapiens

<400> SEQUENCE: 12

```
Ser Asp Gly Lys Val Ala Asp Glu Glu Lys Pro Lys Lys Ser Ser Leu
1               5                   10                  15

Cys Arg Thr Val Glu Gly Cys Arg Glu Glu Leu Gln Asn Gln Ala Asn
            20                  25                  30

Phe Ser Phe Ala Pro Leu Val Leu Asp Met Leu Asn Phe Leu Met Asp
        35                  40                  45

Ala Ile Gln Thr Asn Phe Gln Gln Ala Ser Ala Val Gly Ser Ser Ser
    50                  55                  60

Arg Ala Gln Gln Ala Leu Ser Glu Leu His Thr Val Glu Lys Ala Val
65                  70                  75                  80

Glu Met Thr Asp Gln Leu Met Val Pro Thr Leu Gly Ser Gln Glu Gly
                85                  90                  95

Ala Phe Glu Asn Val Arg Met Asn Tyr Ser Gly Asp Gln Gly Gln Thr
            100                 105                 110

Ile Arg Gln Leu Ile Ser Ala His Val Leu Arg Val Ala Met Cys
        115                 120                 125

Val Leu Ser Ser Pro His Gly Arg Arg Gln His Leu Ala Val Ser His
    130                 135                 140

Glu Lys Gly Lys Ile Thr Val Leu Gln Leu Ser Ala Leu Leu Lys Gln
145                 150                 155                 160

Ala Asp Ser Ser Lys Arg Lys Leu Thr Leu Thr Arg Leu Ala Ser Ala
                165                 170                 175

Pro Val Pro Phe Thr Val Leu Ser Leu Thr Gly Asn Pro Cys Lys Glu
            180                 185                 190

Asp Tyr Leu Ala Val Cys Gly Leu Lys Asp Cys His Val Leu Thr Phe
        195                 200                 205

Ser Ser Ser Gly Ser Val Ser Asp His Leu Val Leu His Pro Gln Leu
    210                 215                 220

Ala Thr Gly Asn Phe Ile Ile Lys Ala Val Trp Leu Pro Gly Ser Gln
225                 230                 235                 240

Thr Glu Leu Ser Ile Val Thr Ala Asp Phe Val Lys Ile Tyr Asp Leu
                245                 250                 255

Cys Val Asp Ala Leu Ser Pro Thr Phe Tyr Phe Leu Leu Pro Ser Ser
            260                 265                 270

Lys Ile Arg Asp Val Thr Phe Leu Phe Asn Glu Glu Gly Lys Asn Ile
        275                 280                 285

Ile Val Ile Met Ser Ser Ala Gly Tyr Ile Tyr Thr Gln Leu Met Glu
```

-continued

```
                290                 295                 300

Glu Ala Ser Ser Ala Gln Gln Gly Pro Phe Tyr Val Thr Asn Val Leu
305                 310                 315                 320

Glu Ile Asn His Glu Asp Leu Lys Asp Ser Asn Ser Gln Val Ala Gly
                325                 330                 335

Gly Gly Val Ser Val Tyr Tyr Ser His Val Leu Gln Met Leu Phe Phe
                340                 345                 350

Ser Tyr Cys Gln Gly Lys Ser Phe Ala Ala Thr Ile Ser Arg Thr Thr
                355                 360                 365

Leu Glu Val Leu Gln Leu Phe Pro Ile Asn Ile Lys Ser Ser Asn Gly
                370                 375                 380

Gly Ser Lys Thr Ser Pro Ala Leu Cys Gln Trp Ser Glu Val Met Asn
385                 390                 395                 400

His Pro Gly Leu Val Cys Cys Val Gln Thr Thr Gly Val Pro Leu
                405                 410                 415

Val Val Met Val Lys Pro Asp Thr Phe Leu Ile Gln Glu Ile Lys Thr
                420                 425                 430

Leu Pro Ala Lys Ala Lys Ile Gln Asp Met Val Ala Ile Arg His Thr
                435                 440                 445

Ala Cys Asn Glu Gln Gln Arg Thr Thr Met Ile Leu Leu Cys Glu Asp
                450                 455                 460

Gly Ser Leu Arg Ile Tyr Met Ala Asn Val Glu Asn Thr Ser Tyr Trp
465                 470                 475                 480

Leu Gln Pro Ser Leu Gln Pro Ser Ser Val Ile Ser Ile Met Lys Pro
                485                 490                 495

Val Arg Lys Arg Lys Thr Ala Thr Ile Thr Thr Arg Thr Ser Ser Gln
                500                 505                 510

Val Thr Phe Pro Ile Asp Phe Phe Glu His Asn Gln Gln Leu Thr Asp
                515                 520                 525

Val Glu Phe Gly Gly Asn Asp Leu Leu Gln Val Tyr Asn Ala Gln Gln
                530                 535                 540

Ile Lys His Arg Leu Asn Ser Thr Gly Met Tyr Val Ala Asn Thr Lys
545                 550                 555                 560

Pro Gly Gly Phe Thr Ile Glu Ile Ser Asn Asn Asn Ser Thr Met Val
                565                 570                 575

Met Thr Gly Met Arg Ile Gln Ile Gly Thr Gln Ala Ile Glu Arg Ala
                580                 585                 590

Pro Ser Tyr Ile Glu Ile Phe Gly Arg Thr Met Gln Leu Asn Leu Ser
                595                 600                 605

Arg Ser Arg Trp Phe Asp Phe Pro Phe Thr Arg Glu Glu Ala Leu Gln
610                 615                 620

Ala Asp Lys Lys Leu Asn Leu Phe Ile Gly Ala Ser Val Glu Pro Ala
625                 630                 635                 640

Gly Val Thr Met Ile Asp Ala Val Lys Ile Tyr Gly Lys Thr Lys Glu
                645                 650                 655

Gln Phe Gly Trp Pro Asp Glu Pro Pro Glu Glu Phe Pro Ser Ala Ser
                660                 665                 670

Val Ser Asn Ile Cys Pro Ser Asn Leu Asn Gln Ser Asn Gly Thr Gly
                675                 680                 685

Asp Ser Asp Ser Ala Ala Pro Thr Thr Thr Ser Gly Thr Val Leu Glu
                690                 695                 700

Arg Leu Val Val Ser Ser Leu Glu Ala Leu Glu Ser Cys Phe Ala Val
705                 710                 715                 720
```

Gly Pro Ile Ile Glu Lys Glu Arg Asn Lys Asn Ala Ala Gln Glu Leu
                725                 730                 735

Ala Thr Leu Leu Leu Ser Leu Pro Ala Pro Ala Ser Val Gln Gln Gln
            740                 745                 750

Ser Lys Ser Leu Leu Ala Ser Leu His Thr Ser Arg Ser Ala Tyr His
        755                 760                 765

Ser His Lys Asp Gln Ala Leu Leu Ser Lys Ala Val Gln Cys Leu Asn
    770                 775                 780

Thr Ser Ser Lys Glu Gly Lys Asp Leu Asp Pro Glu Val Phe Gln Arg
785                 790                 795                 800

Leu Val Ile Thr Ala Arg Ser Ile Ala Ile Met Arg Pro Asn Asn Leu
                805                 810                 815

Val His Phe Thr Glu Ser Lys Leu Pro Gln Met Glu Thr Glu Gly Met
            820                 825                 830

Asp Glu Gly Lys Glu Pro Gln Lys Gln Leu Glu Gly Asp Cys Cys Ser
        835                 840                 845

Phe Ile Thr Gln Leu Val Asn His Phe Trp Lys Leu His Ala Ser Lys
    850                 855                 860

Pro Lys Asn Ala Phe Leu Ala Pro Ala Cys Leu Pro Gly Leu Thr His
865                 870                 875                 880

Ile Glu Ala Thr Val Asn Ala Leu Val Asp Ile Ile His Gly Tyr Cys
                885                 890                 895

Thr Cys Glu Leu Asp Cys Ile Asn Thr Ala Ser Lys Ile Tyr Met Gln
            900                 905                 910

Met Leu Leu Cys Pro Asp Pro Ala Val Ser Phe Ser Cys Lys Gln Ala
        915                 920                 925

Leu Ile Arg Val Leu Arg Pro Arg Asn Lys Arg His Val Thr Leu
    930                 935                 940

Pro Ser Ser Pro
945

<210> SEQ ID NO 13
<211> LENGTH: 2154
<212> TYPE: DNA
<213> ORGANISM: Homo sapiens

<400> SEQUENCE: 13
gatttgcaca ccctggactc tcacgtgcgt gggatcaaga agctgctaga agagcagggg     60
atattcctcc gggcaagtgt ggttacagcc agctcaggct ccgccttgca atatgacaca    120
ctcatcagcc tgatggagca cctgaaagcc tgtgcagaga ttgccgccca gcgaaccatc    180
aactggcaga aattctgcat caaagatgac tccgtcctgt acttcctcct ccaagtcagt    240
ttccttgtgg atgagggcgt gtccccagtg ctgctgcaac tgctctcctg tgctctgtgc    300
ggcagcaagg tgctcgctgc actggcagcc tcttcgggat cctccagtgc ttcttcctcc    360
tcagcccctg tggctgccag ttctggacaa gccacaacac agtccaagtc ttccactaaa    420
aagagcaaga agaagagaaa agaaaaggag aaagatggtg agacctctgg cagccaggag    480
gaccagctgt gcacagctct ggtgaaccag ctgaacaaat tgccgataaa ggaaaccctg    540
atccagttcc tgcgttgttt cctgttagag tccaattctt cctcggtgcg ctggcaggcc    600
cactgtctga cactgcacat ctacagaaat tccagcaaat ctcaacagga gctcctgcta    660
gatctgatgt ggtccatctg gccagaactc ccagcctatg tcgtaaggc tgcccagttt    720 gtggacctac taggatattt ctccctgaaa actccacaaa cagagaagaa gttgaaggag    780

```
tattcacaga aggctgtgga gattctgcgg actcaaaacc atattcttac caaccacccc    840
aactcgaaca tttataacac tttgtctggc ttagtggagt ttgatggcta ttacctggag    900
agcgatccct gcctggtgtg taataacccg gaagtaccgt tctgttatat caagctgtct    960
tccattaaag tggacacgcg gtacaccacc acccagcagg ttgtgaagct cattggcagt   1020
cacaccatca gcaaagtgac agtgaaaatc ggggatctga acggaccaa gatggtgcgg    1080
accatcaacc tgtattataa caaccgaacc gtgcaggcca tcgtggagtt gaaaaacaag   1140
ccagctcgct ggcacaaagc caagaaggtt cagctgaccc ctggacagac agaggtgaag   1200
attgacctgc cgttgcccat tgtggcctcc aatctgatga ttgagtttgc agacttctat   1260
gaaaactacc aggcctccac agagaccctg cagtgccctc gctgtagtgc ctcggtccct   1320
gccaacccag gagtctgtgg caactgtgga gagaatgtgt accagtgtca caatgcaga    1380
tccatcaact acgatgaaaa ggatcccttc ctctgcaatg cctgtggctt ctgtaaatat   1440
gcccgcttcg acttcatgct ctatgccaag ccttgctgtg cagtggatcc cattgagaat   1500
gaagaagacc ggaagaaggc tgtatccaac atcaatacac ttttggacaa agctgatcga   1560
gtgtatcatc agctgatggg acaccggcca cagctggaga acctgctctg caaagtgaat   1620
gaggcagctc cagaaaagcc acaggatgac tcaggaacag caggggcat cagctccact   1680
tctgccagtg tgaatcgtta catcctgcag ttggctcagg agtattgtgg agactgcaag   1740
aactcttttg atgaactctc caaaatcatc cagaaagtct ttgcttcgcg caaagagttg   1800
ttggaatatg acctacagca gagggaagca gccactaaat catcccggac ctccgtgcag   1860
cccacattca ctgccagcca gtaccgtgcc ttatccgtcc tgggctgtgg ccacacatcc   1920
tccaccaagt gctatggctg cgcctcggct gtcacagaac attgtatcac actacttcgg   1980
gccctggcca ccaacccagc cttgaggcac atccttgtct cccagggcct tatccgggag   2040
ctctttgatt ataatcttcg ccgaggggct gcggccatgc gggaggaggt ccgccagctc   2100
atgtgcctcc taactcgaga caacccagaa gccacccaac agatgaatga cctg         2154
```

<210> SEQ ID NO 14
<211> LENGTH: 718
<212> TYPE: PRT
<213> ORGANISM: Homo sapiens

<400> SEQUENCE: 14

```
Asp Leu His Thr Leu Asp Ser His Val Arg Gly Ile Lys Lys Leu Leu
1               5                   10                  15

Glu Glu Gln Gly Ile Phe Leu Arg Ala Ser Val Val Thr Ala Ser Ser
            20                  25                  30

Gly Ser Ala Leu Gln Tyr Asp Thr Leu Ile Ser Leu Met Glu His Leu
        35                  40                  45

Lys Ala Cys Ala Glu Ile Ala Ala Gln Arg Thr Ile Asn Trp Gln Lys
    50                  55                  60

Phe Cys Ile Lys Asp Asp Ser Val Leu Tyr Phe Leu Gln Val Ser
65                  70                  75                  80

Phe Leu Val Asp Glu Gly Val Ser Pro Val Leu Gln Leu Ser
                85                  90                  95

Cys Ala Leu Cys Gly Ser Lys Val Leu Ala Ala Leu Ala Ala Ser Ser
            100                 105                 110

Gly Ser Ser Ser Ala Ser Ser Ser Ala Pro Val Ala Ala Ser Ser
        115                 120                 125
```

```
Gly Gln Ala Thr Thr Gln Ser Lys Ser Ser Thr Lys Lys Ser Lys Lys
    130                 135                 140

Glu Glu Lys Glu Lys Glu Lys Asp Gly Glu Thr Ser Gly Ser Gln Glu
145                 150                 155                 160

Asp Gln Leu Cys Thr Ala Leu Val Asn Gln Leu Asn Lys Phe Ala Asp
            165                 170                 175

Lys Glu Thr Leu Ile Gln Phe Leu Arg Cys Phe Leu Leu Glu Ser Asn
            180                 185                 190

Ser Ser Ser Val Arg Trp Gln Ala His Cys Leu Thr Leu His Ile Tyr
        195                 200                 205

Arg Asn Ser Ser Lys Ser Gln Gln Glu Leu Leu Asp Leu Met Trp
    210                 215                 220

Ser Ile Trp Pro Glu Leu Pro Ala Tyr Gly Arg Lys Ala Ala Gln Phe
225                 230                 235                 240

Val Asp Leu Leu Gly Tyr Phe Ser Leu Lys Thr Pro Gln Thr Glu Lys
                245                 250                 255

Lys Leu Lys Glu Tyr Ser Gln Lys Ala Val Glu Ile Leu Arg Thr Gln
            260                 265                 270

Asn His Ile Leu Thr Asn His Pro Asn Ser Asn Ile Tyr Asn Thr Leu
        275                 280                 285

Ser Gly Leu Val Glu Phe Asp Gly Tyr Tyr Leu Glu Ser Asp Pro Cys
    290                 295                 300

Leu Val Cys Asn Asn Pro Glu Val Pro Phe Cys Tyr Ile Lys Leu Ser
305                 310                 315                 320

Ser Ile Lys Val Asp Thr Arg Tyr Thr Thr Thr Gln Gln Val Val Lys
                325                 330                 335

Leu Ile Gly Ser His Thr Ile Ser Lys Val Thr Val Lys Ile Gly Asp
            340                 345                 350

Leu Lys Arg Thr Lys Met Val Arg Thr Ile Asn Leu Tyr Tyr Asn Asn
        355                 360                 365

Arg Thr Val Gln Ala Ile Val Glu Leu Lys Asn Lys Pro Ala Arg Trp
    370                 375                 380

His Lys Ala Lys Lys Val Gln Leu Thr Pro Gly Gln Thr Glu Val Lys
385                 390                 395                 400

Ile Asp Leu Pro Leu Pro Ile Val Ala Ser Asn Leu Met Ile Glu Phe
                405                 410                 415

Ala Asp Phe Tyr Glu Asn Tyr Gln Ala Ser Thr Glu Thr Leu Gln Cys
            420                 425                 430

Pro Arg Cys Ser Ala Ser Val Pro Ala Asn Pro Gly Val Cys Gly Asn
        435                 440                 445

Cys Gly Glu Asn Val Tyr Gln Cys His Lys Cys Arg Ser Ile Asn Tyr
    450                 455                 460

Asp Glu Lys Asp Pro Phe Leu Cys Asn Ala Cys Gly Phe Cys Lys Tyr
465                 470                 475                 480

Ala Arg Phe Asp Phe Met Leu Tyr Ala Lys Pro Cys Cys Ala Val Asp
                485                 490                 495

Pro Ile Glu Asn Glu Glu Asp Arg Lys Lys Ala Val Ser Asn Ile Asn
            500                 505                 510

Thr Leu Leu Asp Lys Ala Asp Arg Val Tyr His Gln Leu Met Gly His
        515                 520                 525

Arg Pro Gln Leu Glu Asn Leu Leu Cys Lys Val Asn Glu Ala Ala Pro
    530                 535                 540

Glu Lys Pro Gln Asp Asp Ser Gly Thr Ala Gly Gly Ile Ser Ser Thr
```

```
                545                 550                 555                 560
            Ser Ala Ser Val Asn Arg Tyr Ile Leu Gln Leu Ala Gln Glu Tyr Cys
                            565                 570                 575

Gly Asp Cys Lys Asn Ser Phe Asp Glu Leu Ser Lys Ile Ile Gln Lys
                        580                 585                 590

Val Phe Ala Ser Arg Lys Glu Leu Leu Glu Tyr Asp Leu Gln Gln Arg
                    595                 600                 605

Glu Ala Ala Thr Lys Ser Ser Arg Thr Ser Val Gln Pro Thr Phe Thr
                610                 615                 620

Ala Ser Gln Tyr Arg Ala Leu Ser Val Leu Gly Cys Gly His Thr Ser
            625                 630                 635                 640

Ser Thr Lys Cys Tyr Gly Cys Ala Ser Ala Val Thr Glu His Cys Ile
                            645                 650                 655

Thr Leu Leu Arg Ala Leu Ala Thr Asn Pro Ala Leu Arg His Ile Leu
                        660                 665                 670

Val Ser Gln Gly Leu Ile Arg Glu Leu Phe Asp Tyr Asn Leu Arg Arg
                    675                 680                 685

Gly Ala Ala Ala Met Arg Glu Glu Val Arg Gln Leu Met Cys Leu Leu
                690                 695                 700

Thr Arg Asp Asn Pro Glu Ala Thr Gln Gln Met Asn Asp Leu
            705                 710                 715

<210> SEQ ID NO 15
<211> LENGTH: 1764
<212> TYPE: DNA
<213> ORGANISM: Homo sapiens

<400> SEQUENCE: 15
gccacaacac agtccaagtc ttccactaaa aagagcaaga agaagaaaaa agaaaaggag      60
aaagatggtg agacctctgg cagccaggag gaccagctgt gcacagctct ggtgaaccag     120
ctgaacaaat ttgccgataa ggaaaccctg atccagttcc tgcgttgttt cctgttagag     180
tccaattctt cctcggtgcg ctggcaggcc cactgtctga cactgcacat ctacagaaat     240
tccagcaaat ctcaacagga gctcctgcta gatctgatgt ggtccatctg ccagaactc     300 ccagcctatg gtcgtaaggc tgcccagttt gtggacctac taggatattt ctccctgaaa     360
actccacaaa cagagaagaa gttgaaggag tattcacaga aggctgtgga gattctgcgg     420 actcaaaaacc atattcttac caaccacccc aactcgaaca tttataacac tttgtctggc     480
ttagtggagt ttgatggcta ttacctggag agcgatccct gcctggtgtg taataacccg     540
gaagtaccgt tctgttatat caagctgtct tccattaaag tggacacgcg gtacaccacc     600
acccagcagg ttgtgaagct cattggcagt cacaccatca gcaaagtgac agtgaaaatc     660
ggggatctga acggaccaa gatggtgcgg accatcaacc tgtattataa caaccgaacc     720
gtgcaggcca tcgtggagtt gaaaaacaag ccagctcgct ggcacaaagc caagaaggtt     780
cagctgaccc ctggacagac agaggtgaag attgacctgc cgttgcccat tgtggcctcc     840
aatctgatga ttgagtttgc agacttctat gaaaactacc aggcctccac agagaccctg     900
cagtgccctc gctgtagtgc ctcggtccct gccaacccag gagtctgtgg caactgtgga     960
gagaatgtgt accagtgtca caatgcagat ccatcaact acgatgaaaa ggatcccttc    1020
ctctgcaatg cctgtggctt ctgtaaatat gcccgcttcg acttcatgct ctatgccaag    1080
ccttgctgtg cagtggatcc cattgagaat gaagaagacc ggaagaaggc tgtatccaac    1140
atcaatacac ttttggacaa agctgatcga gtgtatcatc agctgatggg acaccggcca    1200
```

-continued

```
cagctggaga acctgctctg caaagtgaat gaggcagctc cagaaaagcc acaggatgac      1260
tcaggaacag caggggggcat cagctccact tctgccagtg tgaatcgtta catcctgcag     1320
ttggctcagg agtattgtgg agactgcaag aactcttttg atgaactctc caaaatcatc     1380
cagaaagtct ttgcttcgcg caaagagttg ttggaatatg acctacagca gagggaagca     1440
gccactaaat catcccggac ctccgtgcag cccacattca ctgccagcca gtaccgtgcc     1500
ttatccgtcc tgggctgtgg ccacacatcc tccaccaagt gctatggctg cgcctcgggct    1560 gtcacagaac attgtatcac actacttcgg gccctggcca ccaacccagc cttgaggcac     1620
atccttgtct cccagggcct tatccgggag ctctttgatt ataatcttcg ccagggggct     1680
gcggccatgc gggaggaggt ccgccagctc atgtgcctcc taactcgaga caacccagaa     1740
gccacccaac agatgaatga cctg                                            1764
```

<210> SEQ ID NO 16
<211> LENGTH: 588
<212> TYPE: PRT
<213> ORGANISM: Homo sapiens

<400> SEQUENCE: 16

```
Ala Thr Thr Gln Ser Lys Ser Ser Thr Lys Ser Lys Lys Glu Glu
1               5                   10                  15

Lys Glu Lys Glu Lys Asp Gly Glu Thr Ser Gly Ser Gln Glu Asp Gln
            20                  25                  30

Leu Cys Thr Ala Leu Val Asn Gln Leu Asn Lys Phe Ala Asp Lys Glu
        35                  40                  45

Thr Leu Ile Gln Phe Leu Arg Cys Phe Leu Glu Ser Asn Ser Ser
    50                  55                  60

Ser Val Arg Trp Gln Ala His Cys Leu Thr His Ile Tyr Arg Asn
65                  70                  75                  80

Ser Ser Lys Ser Gln Gln Glu Leu Leu Leu Asp Leu Met Trp Ser Ile
                85                  90                  95

Trp Pro Glu Leu Pro Ala Tyr Gly Arg Lys Ala Ala Gln Phe Val Asp
            100                 105                 110

Leu Leu Gly Tyr Phe Ser Leu Lys Thr Pro Gln Thr Glu Lys Lys Leu
        115                 120                 125

Lys Glu Tyr Ser Gln Lys Ala Val Glu Ile Leu Arg Thr Gln Asn His
    130                 135                 140

Ile Leu Thr Asn His Pro Asn Ser Asn Ile Tyr Asn Thr Leu Ser Gly
145                 150                 155                 160

Leu Val Glu Phe Asp Gly Tyr Tyr Leu Glu Ser Asp Pro Cys Leu Val
                165                 170                 175

Cys Asn Asn Pro Glu Val Pro Phe Cys Tyr Ile Lys Leu Ser Ser Ile
            180                 185                 190

Lys Val Asp Thr Arg Tyr Thr Thr Thr Gln Gln Val Val Lys Leu Ile
        195                 200                 205

Gly Ser His Thr Ile Ser Lys Val Thr Val Lys Ile Gly Asp Leu Lys
    210                 215                 220

Arg Thr Lys Met Val Arg Thr Ile Asn Leu Tyr Tyr Asn Asn Arg Thr
225                 230                 235                 240

Val Gln Ala Ile Val Glu Leu Lys Asn Lys Pro Ala Arg Trp His Lys
                245                 250                 255

Ala Lys Lys Val Gln Leu Thr Pro Gly Gln Thr Glu Val Lys Ile Asp
            260                 265                 270
```

```
Leu Pro Leu Pro Ile Val Ala Ser Asn Leu Met Ile Glu Phe Ala Asp
        275                 280                 285

Phe Tyr Glu Asn Tyr Gln Ala Ser Thr Glu Thr Leu Gln Cys Pro Arg
    290                 295                 300

Cys Ser Ala Ser Val Pro Ala Asn Pro Gly Val Cys Gly Asn Cys Gly
305                 310                 315                 320

Glu Asn Val Tyr Gln Cys His Lys Cys Arg Ser Ile Asn Tyr Asp Glu
                325                 330                 335

Lys Asp Pro Phe Leu Cys Asn Ala Cys Gly Phe Cys Lys Tyr Ala Arg
            340                 345                 350

Phe Asp Phe Met Leu Tyr Ala Lys Pro Cys Cys Ala Val Asp Pro Ile
        355                 360                 365

Glu Asn Glu Glu Asp Arg Lys Lys Ala Val Ser Asn Ile Asn Thr Leu
    370                 375                 380

Leu Asp Lys Ala Asp Arg Val Tyr His Gln Leu Met Gly His Arg Pro
385                 390                 395                 400

Gln Leu Glu Asn Leu Leu Cys Lys Val Asn Glu Ala Ala Pro Glu Lys
                405                 410                 415

Pro Gln Asp Asp Ser Gly Thr Ala Gly Gly Ile Ser Ser Thr Ser Ala
            420                 425                 430

Ser Val Asn Arg Tyr Ile Leu Gln Leu Ala Gln Glu Tyr Cys Gly Asp
        435                 440                 445

Cys Lys Asn Ser Phe Asp Glu Leu Ser Lys Ile Ile Gln Lys Val Phe
    450                 455                 460

Ala Ser Arg Lys Glu Leu Leu Glu Tyr Asp Leu Gln Gln Arg Glu Ala
465                 470                 475                 480

Ala Thr Lys Ser Ser Arg Thr Ser Val Gln Pro Thr Phe Thr Ala Ser
                485                 490                 495

Gln Tyr Arg Ala Leu Ser Val Leu Gly Cys Gly His Thr Ser Ser Thr
            500                 505                 510

Lys Cys Tyr Gly Cys Ala Ser Ala Val Thr Glu His Cys Ile Thr Leu
        515                 520                 525

Leu Arg Ala Leu Ala Thr Asn Pro Ala Leu Arg His Ile Leu Val Ser
    530                 535                 540

Gln Gly Leu Ile Arg Glu Leu Phe Asp Tyr Asn Leu Arg Arg Gly Ala
545                 550                 555                 560

Ala Ala Met Arg Glu Glu Val Arg Gln Leu Met Cys Leu Leu Thr Arg
                565                 570                 575

Asp Asn Pro Glu Ala Thr Gln Gln Met Asn Asp Leu
            580                 585

<210> SEQ ID NO 17
<211> LENGTH: 1866
<212> TYPE: DNA
<213> ORGANISM: Homo sapiens

<400> SEQUENCE: 17
ttagagtcca attcttcctc ggtgcgctgg caggcccact gtctgacact gcacatctac      60
agaaattcca gcaaatctca acaggagctc ctgctagatc tgatgtggtc catctggcca     120
gaactcccag cctatggtcg taaggctgcc cagtttgtgg acctactagg atatttctcc     180
ctgaaaactc cacaaacaga gaagaagttg aaggagtatt cacagaaggc tgtggagatt     240
ctgcggactc aaaaccatat tcttaccaac caccccaact cgaacattta taacactttg     300
```

```
tctggcttag tggagtttga tggctattac ctggagagcg atccctgcct ggtgtgtaat      360
aacccggaag taccgttctg ttatatcaag ctgtcttcca ttaaagtgga cacgcggtac      420
accaccaccc agcaggttgt gaagctcatt ggcagtcaca ccatcagcaa agtgacagtg      480
aaaatcgggg atctgaaacg gaccaagatg gtgcggacca tcaacctgta ttataacaac      540
cgaaccgtgc aggccatcgt ggagttgaaa acaagccag ctcgctggca caaagccaag      600
aaggttcagc tgacccctgg acagacagag gtgaagattg acctgccgtt gcccattgtg      660
gcctccaatc tgatgattga gtttgcagac ttctatgaaa actaccaggc tccacagag      720 accctgcagt gccctcgctg tagtgcctcg gtccctgcca accaggagt ctgtggcaac      780 tgtggagaga atgtgtacca gtgtcacaaa tgcagatcca tcaactacga tgaaaaggat      840
cccttcctct gcaatgcctg tggcttctgt aaatatgccc gcttcgactt catgctctat      900
gccaagcctt gctgtgcagt ggatcccatt gagaatgaag aagaccggaa gaaggctgta      960
tccaacatca atacactttt ggacaaagct gatcgagtgt atcatcagct gatgggacac     1020
cggccacagc tggagaacct gctctgcaaa gtgaatgagg cagctccaga aaagccacag     1080
gatgactcag aacagcagg gggcatcagc tccacttctg ccagtgtgaa tcgttacatc     1140
ctgcagttgg ctcaggagta ttgtgggagac tgcaagaact cttttgatga actctccaaa     1200
atcatccaga aagtctttgc ttcgcgcaaa gagttgttgg aatatgacct acagcagagg     1260
gaagcagcca ctaaatcatc ccggacctcc gtgcagccca cattcactgc cagccagtac     1320
cgtgccttat ccgtcctggg ctgtggccac acatcctcca ccaagtgcta ggctgcgcc      1380 tcggctgtca cagaacattg tatcacacta cttcgggccc tggccaccaa cccagccttg     1440
aggcacatcc ttgtctccca gggccttatc cgggagctct ttgattataa tcttcgccga     1500
ggggctgcgg ccatgcggga ggaggtccgc cagctcatgt gcctcctaac tcgagacaac     1560
ccagaagcca cccaacagat gaatgacctg attattggca aggtctccac agccctgaag     1620
agccactggg ccaaccccga tctggcaagt agcctgcagt atgaaatgct gctgctgacg     1680
gattctatct ccaaggagga cagctgctgg gagctccggt tacgctgtgc tctcagcctt     1740
ttcctcatgg ctgtgaacat taagactcct gtggtggttg aaaacattac cctcatgtgc     1800
ctgaggatct tgcagaagct gataaaacca cctgctccca ctagcaagaa gaacaaggat     1860
gtccccc                                                              1866
```

<210> SEQ ID NO 18
<211> LENGTH: 622
<212> TYPE: PRT
<213> ORGANISM: Homo sapiens

<400> SEQUENCE: 18

```
Leu Glu Ser Asn Ser Ser Ser Val Arg Trp Gln Ala His Cys Leu Thr
  1               5                  10                  15

Leu His Ile Tyr Arg Asn Ser Ser Lys Ser Gln Gln Glu Leu Leu Leu
             20                  25                  30

Asp Leu Met Trp Ser Ile Trp Pro Glu Leu Pro Ala Tyr Gly Arg Lys
         35                  40                  45

Ala Ala Gln Phe Val Asp Leu Leu Gly Tyr Phe Ser Leu Lys Thr Pro
     50                  55                  60

Gln Thr Glu Lys Lys Leu Lys Glu Tyr Ser Gln Lys Ala Val Glu Ile
 65                  70                  75                  80

Leu Arg Thr Gln Asn His Ile Leu Thr Asn His Pro Asn Ser Asn Ile
                 85                  90                  95
```

```
Tyr Asn Thr Leu Ser Gly Leu Val Glu Phe Asp Gly Tyr Tyr Leu Glu
            100                 105                 110

Ser Asp Pro Cys Leu Val Cys Asn Pro Glu Val Pro Phe Cys Tyr
            115                 120                 125

Ile Lys Leu Ser Ser Ile Lys Val Asp Thr Arg Tyr Thr Thr Thr Gln
            130                 135                 140

Gln Val Val Lys Leu Ile Gly Ser His Thr Ile Ser Lys Val Thr Val
145                 150                 155                 160

Lys Ile Gly Asp Leu Lys Arg Thr Lys Met Val Arg Thr Ile Asn Leu
                165                 170                 175

Tyr Tyr Asn Asn Arg Thr Val Gln Ala Ile Val Glu Leu Lys Asn Lys
                180                 185                 190

Pro Ala Arg Trp His Lys Ala Lys Lys Val Gln Leu Thr Pro Gly Gln
                195                 200                 205

Thr Glu Val Lys Ile Asp Leu Pro Leu Pro Ile Val Ala Ser Asn Leu
            210                 215                 220

Met Ile Glu Phe Ala Asp Phe Tyr Glu Asn Tyr Gln Ala Ser Thr Glu
225                 230                 235                 240

Thr Leu Gln Cys Pro Arg Cys Ser Ala Ser Val Pro Ala Asn Pro Gly
                245                 250                 255

Val Cys Gly Asn Cys Gly Glu Asn Val Tyr Gln Cys His Lys Cys Arg
            260                 265                 270

Ser Ile Asn Tyr Asp Glu Lys Asp Pro Phe Leu Cys Asn Ala Cys Gly
            275                 280                 285

Phe Cys Lys Tyr Ala Arg Phe Asp Phe Met Leu Tyr Ala Lys Pro Cys
            290                 295                 300

Cys Ala Val Asp Pro Ile Glu Asn Glu Glu Asp Arg Lys Lys Ala Val
305                 310                 315                 320

Ser Asn Ile Asn Thr Leu Leu Asp Lys Ala Asp Arg Val Tyr His Gln
                325                 330                 335

Leu Met Gly His Arg Pro Gln Leu Glu Asn Leu Leu Cys Lys Val Asn
                340                 345                 350

Glu Ala Ala Pro Glu Lys Pro Gln Asp Asp Ser Gly Thr Ala Gly Gly
            355                 360                 365

Ile Ser Ser Thr Ser Ala Ser Val Asn Arg Tyr Ile Leu Gln Leu Ala
            370                 375                 380

Gln Glu Tyr Cys Gly Asp Cys Lys Asn Ser Phe Asp Glu Leu Ser Lys
385                 390                 395                 400

Ile Ile Gln Lys Val Phe Ala Ser Arg Lys Glu Leu Leu Glu Tyr Asp
                405                 410                 415

Leu Gln Gln Arg Glu Ala Ala Thr Lys Ser Ser Arg Thr Ser Val Gln
            420                 425                 430

Pro Thr Phe Thr Ala Ser Gln Tyr Arg Ala Leu Ser Val Leu Gly Cys
            435                 440                 445

Gly His Thr Ser Ser Thr Lys Cys Tyr Gly Cys Ala Ser Ala Val Thr
            450                 455                 460

Glu His Cys Ile Thr Leu Leu Arg Ala Leu Ala Thr Asn Pro Ala Leu
465                 470                 475                 480

Arg His Ile Leu Val Ser Gln Gly Leu Ile Arg Glu Leu Phe Asp Tyr
                485                 490                 495

Asn Leu Arg Arg Gly Ala Ala Ala Met Arg Glu Glu Val Arg Gln Leu
            500                 505                 510
```

```
Met Cys Leu Leu Thr Arg Asp Asn Pro Glu Ala Thr Gln Gln Met Asn
            515                 520                 525

Asp Leu Ile Ile Gly Lys Val Ser Thr Ala Leu Lys Ser His Trp Ala
        530                 535                 540

Asn Pro Asp Leu Ala Ser Ser Leu Gln Tyr Glu Met Leu Leu Leu Thr
545                 550                 555                 560

Asp Ser Ile Ser Lys Glu Asp Ser Cys Trp Glu Leu Arg Leu Arg Cys
                565                 570                 575

Ala Leu Ser Leu Phe Leu Met Ala Val Asn Ile Lys Thr Pro Val Val
            580                 585                 590

Val Glu Asn Ile Thr Leu Met Cys Leu Arg Ile Leu Gln Lys Leu Ile
        595                 600                 605

Lys Pro Pro Ala Pro Thr Ser Lys Lys Asn Lys Asp Val Pro
610                 615                 620
```

<210> SEQ ID NO 19
<211> LENGTH: 2112
<212> TYPE: DNA
<213> ORGANISM: Homo sapiens

<400> SEQUENCE: 19

| | | | | | |
|---|---|---|---|---|---|
| gcccagtgtg | ggggcctgga | atgcatgctt | aacagactcg | cagggatcag | agatttcaag | 60 |
| cagggacgcc | accttctaac | agtgctactg | aaattgttca | gttactgcgt | gaaggtgaaa | 120 |
| gtcaaccggc | agcaactggt | caaactggaa | atgaacacct | tgaacgtcat | gctggggacc | 180 |
| ctaaacctgg | cccttgtagc | tgaacaagaa | agcaaggaca | gtgggggtgc | agctgtggct | 240 |
| gagcaggtgc | ttagcatcat | ggagatcatt | ctagatgagt | ccaatgctga | gcccctgagt | 300 |
| gaggacaagg | gcaacctcct | cctgacaggt | gacaaggatc | aactggtgat | gctcttggac | 360 |
| cagatcaaca | gcacctttgt | tcgctccaac | cccagtgtgc | tccagggcct | gcttcgcatc | 420 |
| atcccgtacc | tttcctttgg | agaggtggag | aaaatgcaga | tcttggtgga | gcgattcaaa | 480 |
| ccatactgca | actttgataa | atatgatgaa | gatcacagtg | gtgatgataa | agtcttcctg | 540 |
| gactgcttct | gtaaaatagc | tgctggcatc | aagaacaaca | gcaatgggca | ccagctgaag | 600 |
| gatctgattc | tccagaaggg | gatcacccag | aatgcacttg | actacatgaa | aaagcacatc | 660 |
| cctagcgcca | agaatttgga | tgccgacatc | tggaaaaagt | ttttgtctcg | cccagccttg | 720 |
| ccatttatcc | taaggctgct | tcggggcctg | gccatccagc | accctggcac | ccaggttctg | 780 |
| attggaactg | attccatccc | gaacctgcat | aagctggagc | aggtgtccag | tgatgagggc | 840 |
| attgggacct | tggcagagaa | cctgctggaa | gccctgcggg | aacaccctga | cgtaaacaag | 900 |
| aagattgacg | cagcccgcag | ggagacccgg | gcagagaaga | acgcatggc | catggcaatg | 960 |
| aggcagaagg | ccctgggcac | cctgggcatg | acgacaaatg | aaaagggcca | ggtcgtgacc | 1020 |
| aagacagcac | tcctgaagca | gatggaagag | ctgatcgagg | agcctggcct | cacgtgctgc | 1080 |
| atctgcaggg | agggatacaa | gttccagccc | acaaaggtcc | tgggcattta | accttcacg | 1140 |
| aagcgggtag | ccttggagga | gatggagaat | aagccccgga | acagcaggg | ctacagcacc | 1200 |
| gtgtcccact | tcaacattgt | gcactacgac | tgccatctgg | ctgccgtcag | gttggctcga | 1260 |
| ggccgggaag | agtgggagag | tgccgccctg | cagaatgcca | acaccaagtg | caacgggctc | 1320 |
| cttccggtct | ggggaccctca | tgtccctgaa | tcagcttttg | ccacttgctt | ggcaagacac | 1380 |
| aacacttacc | tccaggaatg | tacaggccag | cgggagccca | cgtatcagct | caacatccat | 1440 |
| gacatcaaac | tgctcttcct | gcgcttcgcc | atggagcagt | cgttcagcgc | agacactggc | 1500 |

```
ggggcgcc gggagagcaa catccacctg atcccgtaca tcattcacac tgtgctttac    1560
gtcctgaaca caacccgagc aacttcccga gaagagaaga acctccaagg ctttctggaa    1620
cagcccaagg agaagtgggt ggagagtgcc tttgaagtgg acgggcccta ctatttcaca    1680
gtcttggccc ttcacatcct gcccctgag cagtggagag ccacacgtgt ggaaatcttg    1740
cggaggctgt tggtgacctc gcaggctcgg gcagtggctc caggtggagc caccaggctg    1800
acagataagg cagtgaagga ctattccgct taccgttctt cccttctctt ttgggccctc    1860
gtcgatctca tttacaacat gtttaagaag gtgcctacca gtaacacaga gggaggctgg    1920
tcctgctctc tcgctgagta catccgccac aacgacatgc ccatctacga agctgccgac    1980
aaagccctga aaccttcca ggaggagttc atgccagtgg agaccttctc agagttcctc    2040
gatgtggccg tctttatc agaaatcacc gatccagaga gcttcctgaa ggacctgttg    2100
aactcagtcc cc                                                         2112
```

<210> SEQ ID NO 20
<211> LENGTH: 704
<212> TYPE: PRT
<213> ORGANISM: Homo sapiens

<400> SEQUENCE: 20

```
Ala Gln Cys Gly Gly Leu Glu Cys Met Leu Asn Arg Leu Ala Gly Ile
1               5                   10                  15

Arg Asp Phe Lys Gln Gly Arg His Leu Leu Thr Val Leu Leu Lys Leu
            20                  25                  30

Phe Ser Tyr Cys Val Lys Val Lys Val Asn Arg Gln Gln Leu Val Lys
        35                  40                  45

Leu Glu Met Asn Thr Leu Asn Val Met Leu Gly Thr Leu Asn Leu Ala
    50                  55                  60

Leu Val Ala Glu Gln Glu Ser Lys Asp Ser Gly Ala Ala Val Ala
65                  70                  75                  80

Glu Gln Val Leu Ser Ile Met Glu Ile Ile Leu Asp Glu Ser Asn Ala
                85                  90                  95

Glu Pro Leu Ser Glu Asp Lys Gly Asn Leu Leu Leu Thr Gly Asp Lys
            100                 105                 110

Asp Gln Leu Val Met Leu Leu Asp Gln Ile Asn Ser Thr Phe Val Arg
        115                 120                 125

Ser Asn Pro Ser Val Leu Gln Gly Leu Leu Arg Ile Ile Pro Tyr Leu
    130                 135                 140

Ser Phe Gly Glu Val Glu Lys Met Gln Ile Leu Val Glu Arg Phe Lys
145                 150                 155                 160

Pro Tyr Cys Asn Phe Asp Lys Tyr Asp Glu Asp His Ser Gly Asp Asp
                165                 170                 175

Lys Val Phe Leu Asp Cys Phe Cys Lys Ile Ala Ala Gly Ile Lys Asn
            180                 185                 190

Asn Ser Asn Gly His Gln Leu Lys Asp Leu Ile Leu Gln Lys Gly Ile
        195                 200                 205

Thr Gln Asn Ala Leu Asp Tyr Met Lys Lys His Ile Pro Ser Ala Lys
    210                 215                 220

Asn Leu Asp Ala Asp Ile Trp Lys Lys Phe Leu Ser Arg Pro Ala Leu
225                 230                 235                 240

Pro Phe Ile Leu Arg Leu Leu Arg Gly Leu Ala Ile Gln His Pro Gly
                245                 250                 255

Thr Gln Val Leu Ile Gly Thr Asp Ser Ile Pro Asn Leu His Lys Leu
```

-continued

```
              260                 265                 270
Glu Gln Val Ser Ser Asp Glu Gly Ile Gly Thr Leu Ala Glu Asn Leu
            275                 280                 285
Leu Glu Ala Leu Arg Glu His Pro Asp Val Asn Lys Lys Ile Asp Ala
        290                 295                 300
Ala Arg Arg Glu Thr Arg Ala Glu Lys Lys Arg Met Ala Met Ala Met
    305                 310                 315                 320
Arg Gln Lys Ala Leu Gly Thr Leu Gly Met Thr Thr Asn Glu Lys Gly
                325                 330                 335
Gln Val Val Thr Lys Thr Ala Leu Leu Lys Gln Met Glu Glu Leu Ile
                340                 345                 350
Glu Glu Pro Gly Leu Thr Cys Cys Ile Cys Arg Glu Gly Tyr Lys Phe
                355                 360                 365
Gln Pro Thr Lys Val Leu Gly Ile Tyr Thr Phe Thr Lys Arg Val Ala
            370                 375                 380
Leu Glu Glu Met Glu Asn Lys Pro Arg Lys Gln Gln Gly Tyr Ser Thr
385                 390                 395                 400
Val Ser His Phe Asn Ile Val His Tyr Asp Cys His Leu Ala Ala Val
                405                 410                 415
Arg Leu Ala Arg Gly Arg Glu Glu Trp Glu Ser Ala Ala Leu Gln Asn
                420                 425                 430
Ala Asn Thr Lys Cys Asn Gly Leu Leu Pro Val Trp Gly Pro His Val
            435                 440                 445
Pro Glu Ser Ala Phe Ala Thr Cys Leu Ala Arg His Asn Thr Tyr Leu
        450                 455                 460
Gln Glu Cys Thr Gly Gln Arg Glu Pro Thr Tyr Gln Leu Asn Ile His
465                 470                 475                 480
Asp Ile Lys Leu Leu Phe Leu Arg Phe Ala Met Glu Gln Ser Phe Ser
                485                 490                 495
Ala Asp Thr Gly Gly Gly Gly Arg Glu Ser Asn Ile His Leu Ile Pro
                500                 505                 510
Tyr Ile Ile His Thr Val Leu Tyr Val Leu Asn Thr Thr Arg Ala Thr
            515                 520                 525
Ser Arg Glu Glu Lys Asn Leu Gln Gly Phe Leu Glu Gln Pro Lys Glu
        530                 535                 540
Lys Trp Val Glu Ser Ala Phe Glu Val Asp Gly Pro Tyr Tyr Phe Thr
545                 550                 555                 560
Val Leu Ala Leu His Ile Leu Pro Pro Glu Gln Trp Arg Ala Thr Arg
                565                 570                 575
Val Glu Ile Leu Arg Arg Leu Leu Val Thr Ser Gln Ala Arg Ala Val
            580                 585                 590
Ala Pro Gly Gly Ala Thr Arg Leu Thr Asp Lys Ala Val Lys Asp Tyr
            595                 600                 605
Ser Ala Tyr Arg Ser Ser Leu Leu Phe Trp Ala Leu Val Asp Leu Ile
        610                 615                 620
Tyr Asn Met Phe Lys Lys Val Pro Thr Ser Asn Thr Glu Gly Gly Trp
625                 630                 635                 640
Ser Cys Ser Leu Ala Glu Tyr Ile Arg His Asn Asp Met Pro Ile Tyr
                645                 650                 655
Glu Ala Ala Asp Lys Ala Leu Lys Thr Phe Gln Glu Glu Phe Met Pro
                660                 665                 670
Val Glu Thr Phe Ser Glu Phe Leu Asp Val Ala Gly Leu Leu Ser Glu
            675                 680                 685
```

```
Ile Thr Asp Pro Glu Ser Phe Leu Lys Asp Leu Leu Asn Ser Val Pro
    690                 695                 700
```

<210> SEQ ID NO 21
<211> LENGTH: 1821
<212> TYPE: DNA
<213> ORGANISM: Homo sapiens

<400> SEQUENCE: 21

| | | | | | |
|---|---|---|---|---|---|
| cccctgagtg | aggacaaggg | caacctcctc | ctgacaggtg | acaaggatca | actggtgatg | 60 |
| ctcttggacc | agatcaacag | cacctttgtt | cgctccaacc | ccagtgtgct | ccagggcctg | 120 |
| cttcgcatca | tcccgtacct | ttcctttgga | gaggtggaga | aaatgcagat | cttggtggag | 180 |
| cgattcaaac | catactgcaa | ctttgataaa | tatgatgaag | atcacagtgg | tgatgataaa | 240 |
| gtcttcctgg | actgcttctg | taaaatagct | gctggcatca | gaacaacag | caatgggcac | 300 |
| cagctgaagg | atctgattct | ccagaagggg | atcacccaga | atgcacttga | ctacatgaaa | 360 |
| aagcacatcc | ctagcgccaa | gaatttggat | gccgacatct | ggaaaaagtt | tttgtctcgc | 420 |
| ccagccttgc | catttatcct | aaggctgctt | cggggcctgg | ccatccagca | ccctggcacc | 480 |
| caggttctga | ttggaactga | ttccatcccg | aacctgcata | agctggagca | ggtgtccagt | 540 |
| gatgagggca | ttgggacctt | ggcagagaac | ctgctggaag | ccctgcggga | cacccctgac | 600 |
| gtaaacaaga | agattgacgc | agcccgcagg | gagacccggg | cagagaagaa | acgcatggcc | 660 |
| atggcaatga | ggcagaaggc | cctgggcacc | ctgggcatga | cgacaaatga | aaagggccag | 720 |
| gtcgtgacca | agacagcact | cctgaagcag | atggaagagc | tgatcgagga | gcctggcctc | 780 |
| acgtgctgca | tctgcaggga | gggatacaag | ttccagccca | caaaggtcct | gggcatttat | 840 |
| accttcacga | agcgggtagc | cttggaggag | atggagaata | gccccggaa | acagcagggc | 900 |
| tacagcaccg | tgtcccactt | caacattgtg | cactacgact | gccatctggc | tgccgtcagg | 960 |
| ttggctcgag | gccggaaga | gtgggagagt | gccgccctgc | agaatgccaa | caccaagtgc | 1020 |
| aacgggctcc | ttccggtctg | ggaccctcat | gtccctgaat | cagcttttgc | cacttgcttg | 1080 |
| gcaagacaca | cacttacct | ccaggaatgt | acaggccagc | gggagcccac | gtatcagctc | 1140 |
| aacatccatg | acatcaaact | gctcttcctg | cgcttcgcca | tggagcagtc | gttcagcgca | 1200 |
| gacactggcg | ggggcggccg | ggagagcaac | atccacctga | tcccgtacat | cattcacact | 1260 |
| gtgctttacg | tcctgaacac | aacccgagca | acttcccgag | aagagaagaa | cctccaaggc | 1320 |
| tttctggaac | agcccaagga | gaagtgggtg | gagagtgcct | tgaagtgga | cgggccctac | 1380 |
| tatttcacag | tcttggccct | tcacatcctg | cccctgagc | agtggagagc | cacacgtgtg | 1440 |
| gaaatcttgc | ggaggctgtt | ggtgacctcg | caggctcggg | cagtggctcc | aggtggagcc | 1500 |
| accaggctga | cagataaggc | agtgaaggac | tattccgctt | accgttcttc | ccttctcttt | 1560 |
| tgggccctcg | tcgatctcat | ttacaacatg | tttaagaagg | tgcctaccag | taacacagag | 1620 |
| ggaggctggt | cctgctctct | cgctgagtac | atccgccaca | cgacatgcc | catctacgaa | 1680 |
| gctgccgaca | aagccctgaa | aaccttccag | gaggagttca | tgccagtgga | gaccttctca | 1740 |
| gagttcctcg | atgtggccgg | tcttttatca | gaaatcaccg | atccagagag | cttcctgaag | 1800 |
| gacctgttga | actcagtccc | c | | | | 1821 |

<210> SEQ ID NO 22
<211> LENGTH: 607
<212> TYPE: PRT
<213> ORGANISM: Homo sapiens

<400> SEQUENCE: 22

| | | | | | | | | | | | | | | |
|---|---|---|---|---|---|---|---|---|---|---|---|---|---|---|
| Pro | Leu | Ser | Glu | Asp | Lys | Gly | Asn | Leu | Leu | Thr | Gly | Asp | Lys | Asp |
| 1 | | | | 5 | | | | | 10 | | | | | 15 |
| Gln | Leu | Val | Met | Leu | Leu | Asp | Gln | Ile | Asn | Ser | Thr | Phe | Val | Arg | Ser |
| | | | 20 | | | | | 25 | | | | | 30 | | |
| Asn | Pro | Ser | Val | Leu | Gln | Gly | Leu | Leu | Arg | Ile | Ile | Pro | Tyr | Leu | Ser |
| | | 35 | | | | | 40 | | | | | 45 | | | |
| Phe | Gly | Glu | Val | Glu | Lys | Met | Gln | Ile | Leu | Val | Glu | Arg | Phe | Lys | Pro |
| | 50 | | | | | 55 | | | | | 60 | | | | |
| Tyr | Cys | Asn | Phe | Asp | Lys | Tyr | Asp | Glu | Asp | His | Ser | Gly | Asp | Asp | Lys |
| 65 | | | | | 70 | | | | | 75 | | | | | 80 |
| Val | Phe | Leu | Asp | Cys | Phe | Cys | Lys | Ile | Ala | Ala | Gly | Ile | Lys | Asn | Asn |
| | | | | 85 | | | | | 90 | | | | | 95 | |
| Ser | Asn | Gly | His | Gln | Leu | Lys | Asp | Leu | Ile | Leu | Gln | Lys | Gly | Ile | Thr |
| | | | 100 | | | | | 105 | | | | | 110 | | |
| Gln | Asn | Ala | Leu | Asp | Tyr | Met | Lys | Lys | His | Ile | Pro | Ser | Ala | Lys | Asn |
| | | | 115 | | | | | 120 | | | | | 125 | | |
| Leu | Asp | Ala | Asp | Ile | Trp | Lys | Lys | Phe | Leu | Ser | Arg | Pro | Ala | Leu | Pro |
| | 130 | | | | | 135 | | | | | 140 | | | | |
| Phe | Ile | Leu | Arg | Leu | Leu | Arg | Gly | Leu | Ala | Ile | Gln | His | Pro | Gly | Thr |
| 145 | | | | | 150 | | | | | 155 | | | | | 160 |
| Gln | Val | Leu | Ile | Gly | Thr | Asp | Ser | Ile | Pro | Asn | Leu | His | Lys | Leu | Glu |
| | | | | 165 | | | | | 170 | | | | | 175 | |
| Gln | Val | Ser | Ser | Asp | Glu | Gly | Ile | Gly | Thr | Leu | Ala | Glu | Asn | Leu | Leu |
| | | | 180 | | | | | 185 | | | | | 190 | | |
| Glu | Ala | Leu | Arg | Glu | His | Pro | Asp | Val | Asn | Lys | Lys | Ile | Asp | Ala | Ala |
| | | | 195 | | | | | 200 | | | | | 205 | | |
| Arg | Arg | Glu | Thr | Arg | Ala | Glu | Lys | Lys | Arg | Met | Ala | Met | Ala | Met | Arg |
| 210 | | | | | 215 | | | | | 220 | | | | | |
| Gln | Lys | Ala | Leu | Gly | Thr | Leu | Gly | Met | Thr | Thr | Asn | Glu | Lys | Gly | Gln |
| 225 | | | | | 230 | | | | | 235 | | | | | 240 |
| Val | Val | Thr | Lys | Thr | Ala | Leu | Leu | Lys | Gln | Met | Glu | Glu | Leu | Ile | Glu |
| | | | 245 | | | | | 250 | | | | | 255 | | |
| Glu | Pro | Gly | Leu | Thr | Cys | Cys | Ile | Cys | Arg | Glu | Gly | Tyr | Lys | Phe | Gln |
| | | | 260 | | | | | 265 | | | | | 270 | | |
| Pro | Thr | Lys | Val | Leu | Gly | Ile | Tyr | Thr | Phe | Thr | Lys | Arg | Val | Ala | Leu |
| | | 275 | | | | | 280 | | | | | 285 | | | |
| Glu | Glu | Met | Glu | Asn | Lys | Pro | Arg | Lys | Gln | Gly | Tyr | Ser | Thr | Val |
| | 290 | | | | | 295 | | | | | 300 | | | | |
| Ser | His | Phe | Asn | Ile | Val | His | Tyr | Asp | Cys | His | Leu | Ala | Ala | Val | Arg |
| 305 | | | | | 310 | | | | | 315 | | | | | 320 |
| Leu | Ala | Arg | Gly | Arg | Glu | Glu | Trp | Glu | Ser | Ala | Ala | Leu | Gln | Asn | Ala |
| | | | | 325 | | | | | 330 | | | | | 335 | |
| Asn | Thr | Lys | Cys | Asn | Gly | Leu | Leu | Pro | Val | Trp | Gly | Pro | His | Val | Pro |
| | | | 340 | | | | | 345 | | | | | 350 | | |
| Glu | Ser | Ala | Phe | Ala | Thr | Cys | Leu | Ala | Arg | His | Asn | Thr | Tyr | Leu | Gln |
| | | 355 | | | | | 360 | | | | | 365 | | | |
| Glu | Cys | Thr | Gly | Gln | Arg | Glu | Pro | Thr | Tyr | Gln | Leu | Asn | Ile | His | Asp |
| | 370 | | | | | 375 | | | | | 380 | | | | |
| Ile | Lys | Leu | Leu | Phe | Leu | Arg | Phe | Ala | Met | Glu | Gln | Ser | Phe | Ser | Ala |
| 385 | | | | | 390 | | | | | 395 | | | | | 400 |
| Asp | Thr | Gly | Gly | Gly | Gly | Arg | Glu | Ser | Asn | Ile | His | Leu | Ile | Pro | Tyr |

|  | 405 |  |  |  | 410 |  |  |  | 415 |  |  |
|---|---|---|---|---|---|---|---|---|---|---|---|

Ile Ile His Thr Val Leu Tyr Val Leu Asn Thr Thr Arg Ala Thr Ser
            420                 425                 430

Arg Glu Glu Lys Asn Leu Gln Gly Phe Leu Glu Gln Pro Lys Glu Lys
        435                 440                 445

Trp Val Glu Ser Ala Phe Glu Val Asp Gly Pro Tyr Tyr Phe Thr Val
    450                 455                 460

Leu Ala Leu His Ile Leu Pro Pro Glu Gln Trp Arg Ala Thr Arg Val
465                 470                 475                 480

Glu Ile Leu Arg Arg Leu Leu Val Thr Ser Gln Ala Arg Ala Val Ala
                485                 490                 495

Pro Gly Gly Ala Thr Arg Leu Thr Asp Lys Ala Val Lys Asp Tyr Ser
            500                 505                 510

Ala Tyr Arg Ser Ser Leu Leu Phe Trp Ala Leu Val Asp Leu Ile Tyr
        515                 520                 525

Asn Met Phe Lys Lys Val Pro Thr Ser Asn Thr Glu Gly Gly Trp Ser
    530                 535                 540

Cys Ser Leu Ala Glu Tyr Ile Arg His Asn Asp Met Pro Ile Tyr Glu
545                 550                 555                 560

Ala Ala Asp Lys Ala Leu Lys Thr Phe Gln Glu Phe Met Pro Val
                565                 570                 575

Glu Thr Phe Ser Glu Phe Leu Asp Val Ala Gly Leu Leu Ser Glu Ile
            580                 585                 590

Thr Asp Pro Glu Ser Phe Leu Lys Asp Leu Leu Asn Ser Val Pro
        595                 600                 605

<210> SEQ ID NO 23
<211> LENGTH: 1614
<212> TYPE: DNA
<213> ORGANISM: Homo sapiens

<400> SEQUENCE: 23

```
gggtcccagg aaggtgcctt tgagaatgtg cggatgaatt acagtggaga ccagggccag      60
accatccggc agctgatcag tgctcatgtg ctcaggcggg tggctatgtg tgtgctctcc     120
tctccccatg ggcgccgcca acatttggct gtcagccatg agaagggcaa gatcaccgtt     180
ctgcagctct ctgcactcct gaagcaagca gattccagca aaaggaagtt aactctgacc     240
cgcttggctt ctgccccagt tccttttact gtgttgagcc tcacaggaaa tccctgcaag     300
gaagactact ggcggtttg tgggctaaag actgtcatg tgctcacctt tagtagctca     360
ggctctgttt cggatcactt ggttttgcac cctcagttgg caacggggaa cttcatcatc     420
aaagccgtgt ggttacctgg ttcacagacc gagttatcaa ttgtcaccgc agactttgtt     480
aagatttatg acctgtgtgt tgatgccttg agtccaacct ctatttttct cctgccaagc     540
tcaaagataa gagatgttac cttccttttc aatgaggagg gaaagaacat cattgttata     600
atgtcttcgg ctgggtacat ctatactcag cttatggaag aggccagcag tgcccagcag     660
ggacccttct atgtcactaa tgtgttggaa atcaatcatg aggacctgaa ggacagtaac     720
agccaggtgg cgggcggtgg tgtgtccgtg tactactccc acgtgttgca gatgttgttc     780
ttcagctatt gtcaaggcaa atcattcgca gccaccatca gcaggacaac cctggaggtg     840
ttgcaactct tccccatcaa catcaaaagt tccaatggtg gcagtaagac ttctcctgct     900
cttttgccagt ggtctgaggt gatgaaccac cctggcttgg tgtgctgtgt ccagcaaact     960
acaggggtgc cgctggtagt tatggtgaaa ccagacactt ttcttatcca ggagattaag    1020
```

```
actcttcctg ctaaagcgaa gatccaagac atggttgcta ttaggcacac ggcctgcaat    1080
gagcagcagc ggacaacaat gattctgctg tgtgaggatg gcagcctgcg catttacatg    1140
gccaacgtgg agaacacctc ctactggctg cagccatccc tgcagccag cagtgtcatc     1200 agcatcatga agcctgttcg aaagcgcaaa acagctacaa tcacaacccg cacgtctagc    1260
caggtgactt tccccattga ctttttgaa cacaaccagc agctgacaga tgtggagttt     1320
ggtggtaacg acctcctaca ggtctataat gcacaacaga taaaacaccg gctgaattcc    1380
actggcatgt atgtggccaa caccaagccc ggaggcttca ccattgagat tagtaacaac    1440
aatagcacta tggtgatgac aggcatgcgg atccagattg ggactcaagc aatagaacgg    1500
gccccgtcat atatcgagat cttcggcaga actatgcagc tcaacctgag tcgctcacgc    1560
tggtttgact tccccttcac cagagaagaa gccctgcagg ctgataagaa gctg          1614
```

<210> SEQ ID NO 24
<211> LENGTH: 538
<212> TYPE: PRT
<213> ORGANISM: Homo sapiens

<400> SEQUENCE: 24

```
Gly Ser Gln Glu Gly Ala Phe Glu Asn Val Arg Met Asn Tyr Ser Gly
1               5                   10                  15

Asp Gln Gly Gln Thr Ile Arg Gln Leu Ile Ser Ala His Val Leu Arg
            20                  25                  30

Arg Val Ala Met Cys Val Leu Ser Ser Pro His Gly Arg Arg Gln His
        35                  40                  45

Leu Ala Val Ser His Glu Lys Gly Lys Ile Thr Val Leu Gln Leu Ser
    50                  55                  60

Ala Leu Leu Lys Gln Ala Asp Ser Ser Lys Arg Lys Leu Thr Leu Thr
65                  70                  75                  80

Arg Leu Ala Ser Ala Pro Val Pro Phe Thr Val Leu Ser Leu Thr Gly
                85                  90                  95

Asn Pro Cys Lys Glu Asp Tyr Leu Ala Val Cys Gly Leu Lys Asp Cys
            100                 105                 110

His Val Leu Thr Phe Ser Ser Ser Gly Ser Val Ser Asp His Leu Val
        115                 120                 125

Leu His Pro Gln Leu Ala Thr Gly Asn Phe Ile Ile Lys Ala Val Trp
    130                 135                 140

Leu Pro Gly Ser Gln Thr Glu Leu Ser Ile Val Thr Ala Asp Phe Val
145                 150                 155                 160

Lys Ile Tyr Asp Leu Cys Val Asp Ala Leu Ser Pro Thr Phe Tyr Phe
                165                 170                 175

Leu Leu Pro Ser Ser Lys Ile Arg Asp Val Thr Phe Leu Phe Asn Glu
            180                 185                 190

Glu Gly Lys Asn Ile Ile Val Ile Met Ser Ser Ala Gly Tyr Ile Tyr
        195                 200                 205

Thr Gln Leu Met Glu Glu Ala Ser Ser Ala Gln Gln Gly Pro Phe Tyr
    210                 215                 220

Val Thr Asn Val Leu Glu Ile Asn His Glu Asp Leu Lys Asp Ser Asn
225                 230                 235                 240

Ser Gln Val Ala Gly Gly Gly Val Ser Val Tyr Tyr Ser His Val Leu
                245                 250                 255

Gln Met Leu Phe Phe Ser Tyr Cys Gln Gly Lys Ser Phe Ala Ala Thr
            260                 265                 270
```

Ile Ser Arg Thr Thr Leu Glu Val Leu Gln Leu Phe Pro Ile Asn Ile
    275                 280                 285

Lys Ser Ser Asn Gly Gly Ser Lys Thr Ser Pro Ala Leu Cys Gln Trp
    290                 295                 300

Ser Glu Val Met Asn His Pro Gly Leu Val Cys Cys Val Gln Gln Thr
305                 310                 315                 320

Thr Gly Val Pro Leu Val Val Met Val Lys Pro Asp Thr Phe Leu Ile
                325                 330                 335

Gln Glu Ile Lys Thr Leu Pro Ala Lys Ala Lys Ile Gln Asp Met Val
            340                 345                 350

Ala Ile Arg His Thr Ala Cys Asn Glu Gln Gln Arg Thr Thr Met Ile
        355                 360                 365

Leu Leu Cys Glu Asp Gly Ser Leu Arg Ile Tyr Met Ala Asn Val Glu
    370                 375                 380

Asn Thr Ser Tyr Trp Leu Gln Pro Ser Leu Gln Pro Ser Ser Val Ile
385                 390                 395                 400

Ser Ile Met Lys Pro Val Arg Lys Arg Lys Thr Ala Thr Ile Thr Thr
                405                 410                 415

Arg Thr Ser Ser Gln Val Thr Phe Pro Ile Asp Phe Phe Glu His Asn
            420                 425                 430

Gln Gln Leu Thr Asp Val Glu Phe Gly Gly Asn Asp Leu Leu Gln Val
        435                 440                 445

Tyr Asn Ala Gln Gln Ile Lys His Arg Leu Asn Ser Thr Gly Met Tyr
    450                 455                 460

Val Ala Asn Thr Lys Pro Gly Gly Phe Thr Ile Glu Ile Ser Asn Asn
465                 470                 475                 480

Asn Ser Thr Met Val Met Thr Gly Met Arg Ile Gln Ile Gly Thr Gln
                485                 490                 495

Ala Ile Glu Arg Ala Pro Ser Tyr Ile Glu Ile Phe Gly Arg Thr Met
            500                 505                 510

Gln Leu Asn Leu Ser Arg Ser Arg Trp Phe Asp Phe Pro Phe Thr Arg
        515                 520                 525

Glu Glu Ala Leu Gln Ala Asp Lys Lys Leu
    530                 535

<210> SEQ ID NO 25
<211> LENGTH: 717
<212> TYPE: DNA
<213> ORGANISM: Homo sapiens

<400> SEQUENCE: 25
attgtcaccg cagactttgt taagatttat gacctgtgtg ttgatgcctt gagtccaacc      60
ttctattttc tcctgccaag ctcaaagata agagatgtta ccttcctttt caatgaggag     120
ggaaagaaca tcattgttat aatgtcttcg gctgggtaca tctatactca gcttatggaa     180
gaggccagca gtgcccagca gggacccttc tatgtcacta atgtgttgga aatcaatcat     240
gaggacctga aggacagtaa cagccaggtg gcgggcggtg gtgtgtccgt gtactactcc     300
cacgtgttgc agatgttgtt cttcagctat tgtcaaggca atcattcgc agccaccatc     360 agcaggacaa ccctggaggt gttgcaactc ttccccatca acatcaaaag ttccaatggt     420
ggcagtaaga cttctcctgc tctttgccag tggtctgagg tgatgaacca ccctggcttg     480
gtgtgctgtg tccagcaaac tacaggggtg ccgctggtag ttatggtgaa accagacact     540
tttcttatcc aggagattaa gactcttcct gctaaagcga agatccaaga catggttgct     600

-continued

```
attaggcaca cggcctgcaa tgagcagcag cggacaacaa tgattctgct gtgtgaggat    660
ggcagcctgc gcatttacat ggccaacgtg gagaacacct cctactggct gcagcca      717
```

<210> SEQ ID NO 26
<211> LENGTH: 239
<212> TYPE: PRT
<213> ORGANISM: Homo sapiens

<400> SEQUENCE: 26

```
Ile Val Thr Ala Asp Phe Val Lys Ile Tyr Asp Leu Cys Val Asp Ala
1               5                   10                  15

Leu Ser Pro Thr Phe Tyr Phe Leu Pro Ser Ser Lys Ile Arg Asp
            20                  25                  30

Val Thr Phe Leu Phe Asn Glu Glu Gly Lys Asn Ile Ile Val Ile Met
        35                  40                  45

Ser Ser Ala Gly Tyr Ile Tyr Thr Gln Leu Met Glu Glu Ala Ser Ser
    50                  55                  60

Ala Gln Gln Gly Pro Phe Tyr Val Thr Asn Val Leu Glu Ile Asn His
65                  70                  75                  80

Glu Asp Leu Lys Asp Ser Asn Ser Gln Val Ala Gly Gly Val Ser
                85                  90                  95

Val Tyr Tyr Ser His Val Leu Gln Met Leu Phe Phe Ser Tyr Cys Gln
            100                 105                 110

Gly Lys Ser Phe Ala Ala Thr Ile Ser Arg Thr Thr Leu Glu Val Leu
        115                 120                 125

Gln Leu Phe Pro Ile Asn Ile Lys Ser Ser Asn Gly Gly Ser Lys Thr
    130                 135                 140

Ser Pro Ala Leu Cys Gln Trp Ser Glu Val Met Asn His Pro Gly Leu
145                 150                 155                 160

Val Cys Cys Val Gln Gln Thr Thr Gly Val Pro Leu Val Val Met Val
                165                 170                 175

Lys Pro Asp Thr Phe Leu Ile Gln Glu Ile Lys Thr Leu Pro Ala Lys
            180                 185                 190

Ala Lys Ile Gln Asp Met Val Ala Ile Arg His Thr Ala Cys Asn Glu
        195                 200                 205

Gln Gln Arg Thr Thr Met Ile Leu Leu Cys Glu Asp Gly Ser Leu Arg
    210                 215                 220

Ile Tyr Met Ala Asn Val Glu Asn Thr Ser Tyr Trp Leu Gln Pro
225                 230                 235
```

<210> SEQ ID NO 27
<211> LENGTH: 1176
<212> TYPE: DNA
<213> ORGANISM: Homo sapiens

<400> SEQUENCE: 27

```
gggtcccagg aaggtgcctt tgagaatgtg cggatgaatt acagtggaga ccagggccag    60
accatccggc agctgatcag tgctcatgtg ctcaggcggg tggctatgtg tgtgctctcc    120
tctccccatg ggcgccgcca acatttggct gtcagccatg agaagggcaa gatcaccgtt    180
ctgcagctct ctgcactcct gaagcaagca gattccagca aaaggaagtt aactctgacc    240
cgcttggctt ctgccccagt tccttttact gtgttgagcc tcacaggaaa tccctgcaag    300
gaagactact tggcggtttg tgggctaaag gactgtcatg tgctcacctt tagtagctca    360
ggctctgttt cggatcactt ggttttgcac cctcagttgg caacggggaa cttcatcatc    420
```

```
aaagccgtgt ggttacctgg ttcacagacc gagttatcaa ttgtcaccgc agactttgtt      480
aagatttatg acctgtgtgt tgatgccttg agtccaacct tctatttttct cctgccaagc      540 tcaaagataa gagatgttac cttccttttc aatgaggagg gaaagaacat cattgttata      600
atgtcttcgg ctgggtacat ctatactcag cttatggaag aggccagcag tgcccagcag      660
ggacccttct atgtcactaa tgtgttggaa atcaatcatg aggacctgaa ggacagtaac      720
agccaggtgg cgggcggtgg tgtgtccgtg tactactccc acgtgttgca gatgttgttc      780
ttcagctatt gtcaaggcaa atcattcgca gccaccatca gcaggacaac cctggaggtg      840
ttgcaactct tccccatcaa catcaaaagt tccaatggtg gcagtaagac ttctcctgct      900
ctttgccagt ggtctgaggt gatgaaccac cctggcttgg tgtgctgtgt ccagcaaact      960 acagggtgc cgctggtagt tatggtgaaa ccagacactt ttcttatcca ggagattaag     1020
actcttcctg ctaaagcgaa gatccaagac atggttgcta ttaggcacac ggcctgcaat     1080
gagcagcagc ggacaacaat gattctgctg tgtgaggatg gcagcctgcg catttacatg     1140
gccaacgtgg agaacaccctc ctactggctg cagcca                              1176
```

<210> SEQ ID NO 28
<211> LENGTH: 392
<212> TYPE: PRT
<213> ORGANISM: Homo sapiens

<400> SEQUENCE: 28

```
Gly Ser Gln Glu Gly Ala Phe Glu Asn Val Arg Met Asn Tyr Ser Gly
1               5                   10                  15

Asp Gln Gly Gln Thr Ile Arg Gln Leu Ile Ser Ala His Val Leu Arg
            20                  25                  30

Arg Val Ala Met Cys Val Leu Ser Pro His Gly Arg Arg Gln His
        35                  40                  45

Leu Ala Val Ser His Glu Lys Gly Lys Ile Thr Val Leu Gln Leu Ser
    50                  55                  60

Ala Leu Leu Lys Gln Ala Asp Ser Ser Lys Arg Lys Leu Thr Leu Thr
65                  70                  75                  80

Arg Leu Ala Ser Ala Pro Val Pro Phe Thr Val Leu Ser Leu Thr Gly
                85                  90                  95

Asn Pro Cys Lys Glu Asp Tyr Leu Ala Val Cys Gly Leu Lys Asp Cys
            100                 105                 110

His Val Leu Thr Phe Ser Ser Gly Ser Val Ser Asp His Leu Val
        115                 120                 125

Leu His Pro Gln Leu Ala Thr Gly Asn Phe Ile Ile Lys Ala Val Trp
    130                 135                 140

Leu Pro Gly Ser Gln Thr Glu Leu Ser Ile Val Thr Ala Asp Phe Val
145                 150                 155                 160

Lys Ile Tyr Asp Leu Cys Val Asp Ala Leu Ser Pro Thr Phe Tyr Phe
                165                 170                 175

Leu Leu Pro Ser Ser Lys Ile Arg Asp Val Thr Phe Leu Phe Asn Glu
            180                 185                 190

Glu Gly Lys Asn Ile Ile Val Ile Met Ser Ser Ala Gly Tyr Ile Tyr
        195                 200                 205

Thr Gln Leu Met Glu Glu Ala Ser Ser Ala Gln Gln Gly Pro Phe Tyr
    210                 215                 220

Val Thr Asn Val Leu Glu Ile Asn His Glu Asp Leu Lys Asp Ser Asn
225                 230                 235                 240
```

```
Ser Gln Val Ala Gly Gly Val Ser Val Tyr Tyr Ser His Val Leu
                245                 250                 255

Gln Met Leu Phe Phe Ser Tyr Cys Gln Gly Lys Ser Phe Ala Ala Thr
            260                 265                 270

Ile Ser Arg Thr Thr Leu Glu Val Leu Gln Leu Phe Pro Ile Asn Ile
            275                 280                 285

Lys Ser Ser Asn Gly Gly Ser Lys Thr Ser Pro Ala Leu Cys Gln Trp
    290                 295                 300

Ser Glu Val Met Asn His Pro Gly Leu Val Cys Cys Val Gln Gln Thr
305                 310                 315                 320

Thr Gly Val Pro Leu Val Val Met Val Lys Pro Asp Thr Phe Leu Ile
                325                 330                 335

Gln Glu Ile Lys Thr Leu Pro Ala Lys Ala Lys Ile Gln Asp Met Val
            340                 345                 350

Ala Ile Arg His Thr Ala Cys Asn Glu Gln Gln Arg Thr Thr Met Ile
            355                 360                 365

Leu Leu Cys Glu Asp Gly Ser Leu Arg Ile Tyr Met Ala Asn Val Glu
    370                 375                 380

Asn Thr Ser Tyr Trp Leu Gln Pro
385                 390

<210> SEQ ID NO 29
<211> LENGTH: 1155
<212> TYPE: DNA
<213> ORGANISM: Homo sapiens

<400> SEQUENCE: 29
attgtcaccg cagactttgt taagatttat gacctgtgtg ttgatgcctt gagtccaacc      60
ttctattttc tcctgccaag ctcaaagata agagatgtta ccttccttt caatgaggag     120 ggaaagaaca tcattgttat aatgtcttcg gctgggtaca tctatactca gcttatggaa     180
gaggccagca gtgcccagca gggacccttc tatgtcacta atgtgttgga aatcaatcat     240
gaggacctga aggacagtaa cagccaggtg gcgggcggtg gtgtgtccgt gtactactcc     300
cacgtgttgc agatgttgtt cttcagctat tgtcaaggca aatcattcgc agccaccatc     360
agcaggacaa ccctggaggt gttgcaactc ttccccatca acatcaaaag ttccaatggt     420
ggcagtaaga cttctcctgc tctttgccag tggtctgagg tgatgaacca ccctggcttg     480
gtgtgctgtg tccagcaaac tacaggggtg ccgctggtag ttatggtgaa accagacact     540
tttcttatcc aggagattaa gactcttcct gctaaagcga agatccaaga catggttgct     600
attaggcaca cggcctgcaa tgagcagcag cggacaacaa tgattctgct gtgtgaggat     660
ggcagcctgc gcatttacat ggccaacgtg gagaacacct cctactggct gcagccatcc     720
ctgcagccca gcagtgtcat cagcatcatg aagcctgttc gaaagcgcaa aacagctaca     780
atcacaaccc gcacgtctag ccaggtgact ttccccattg acttttttga acacaaccag     840
cagctgacag atgtggagtt tggtggtaac gacctcctac aggtctataa tgcacaacag     900
ataaaacacc ggctgaattc cactggcatg tatgtggcca acaccaagcc cggaggcttc     960
accattgaga ttagtaacaa caatagcact atggtgatga caggcatgcg gatccagatt    1020
gggactcaag caatagaacg ggccccgtca tatatcgaga tcttcggcag aactatgcag    1080
ctcaacctga gtcgctcacg ctggtttgac ttccccttca ccagagaaga agccctgcag    1140
gctgataaga agctg                                                     1155
```

<210> SEQ ID NO 30
<211> LENGTH: 385
<212> TYPE: PRT
<213> ORGANISM: Homo sapiens

<400> SEQUENCE: 30

```
Ile Val Thr Ala Asp Phe Val Lys Ile Tyr Asp Leu Cys Val Asp Ala
1               5                   10                  15

Leu Ser Pro Thr Phe Tyr Phe Leu Leu Pro Ser Ser Lys Ile Arg Asp
            20                  25                  30

Val Thr Phe Leu Phe Asn Glu Glu Gly Lys Asn Ile Ile Val Ile Met
        35                  40                  45

Ser Ser Ala Gly Tyr Ile Tyr Thr Gln Leu Met Glu Glu Ala Ser Ser
50                  55                  60

Ala Gln Gln Gly Pro Phe Tyr Val Thr Asn Val Leu Glu Ile Asn His
65                  70                  75                  80

Glu Asp Leu Lys Asp Ser Asn Ser Gln Val Ala Gly Gly Val Ser
                85                  90                  95

Val Tyr Tyr Ser His Val Leu Gln Met Leu Phe Phe Ser Tyr Cys Gln
                100                 105                 110

Gly Lys Ser Phe Ala Ala Thr Ile Ser Arg Thr Thr Leu Glu Val Leu
            115                 120                 125

Gln Leu Phe Pro Ile Asn Ile Lys Ser Ser Asn Gly Gly Ser Lys Thr
130                 135                 140

Ser Pro Ala Leu Cys Gln Trp Ser Glu Val Met Asn His Pro Gly Leu
145                 150                 155                 160

Val Cys Cys Val Gln Gln Thr Gly Val Pro Leu Val Val Met Val
                165                 170                 175

Lys Pro Asp Thr Phe Leu Ile Gln Glu Ile Lys Thr Leu Pro Ala Lys
            180                 185                 190

Ala Lys Ile Gln Asp Met Val Ala Ile Arg His Thr Ala Cys Asn Glu
195                 200                 205

Gln Gln Arg Thr Thr Met Ile Leu Leu Cys Glu Asp Gly Ser Leu Arg
210                 215                 220

Ile Tyr Met Ala Asn Val Glu Asn Thr Ser Tyr Trp Leu Gln Pro Ser
225                 230                 235                 240

Leu Gln Pro Ser Ser Val Ile Ser Ile Met Lys Pro Val Arg Lys Arg
            245                 250                 255

Lys Thr Ala Thr Ile Thr Thr Arg Thr Ser Ser Gln Val Thr Phe Pro
            260                 265                 270

Ile Asp Phe Phe Glu His Asn Gln Gln Leu Thr Asp Val Glu Phe Gly
        275                 280                 285

Gly Asn Asp Leu Leu Gln Val Tyr Asn Ala Gln Ile Lys His Arg
290                 295                 300

Leu Asn Ser Thr Gly Met Tyr Val Ala Asn Thr Lys Pro Gly Gly Phe
305                 310                 315                 320

Thr Ile Glu Ile Ser Asn Asn Asn Ser Thr Met Val Met Thr Gly Met
                325                 330                 335

Arg Ile Gln Ile Gly Thr Gln Ala Ile Glu Arg Ala Pro Ser Tyr Ile
            340                 345                 350

Glu Ile Phe Gly Arg Thr Met Gln Leu Asn Leu Ser Arg Ser Arg Trp
        355                 360                 365

Phe Asp Phe Pro Phe Thr Arg Glu Glu Ala Leu Gln Ala Asp Lys Lys
370                 375                 380
```

Leu
385

<210> SEQ ID NO 31
<211> LENGTH: 2130
<212> TYPE: DNA
<213> ORGANISM: Homo sapiens

<400> SEQUENCE: 31

```
ggctccgagg gagaaggaga aggagaaact gaaggagatg tccacactag caacaggctg      60
cacatggtcc gtctaatgct gttggagaga ttactgcaga ccctgcctca attacgaaac     120
gttggcggtg tccgggccat cccatacatg caggtcattc taatgctcac tacagatctg     180
gatggagaag atgagaaaga caaggggggcc ctagacaacc tgctctccca gcttattgct     240
gagttgggta tggataaaaa ggatgtctcc aagaagaatg agcgcagcgc cctgaatgaa     300
gtccatctgg tagtaatgag actcctgagt gtcttcatgt cccgcaccaa atctggatcc     360
aagtcttcca tatgtgagtc atcttccctc atctccagtg ccacagcagc agctctactg     420
agctctgggg ctgtggacta ctgcctgcac gtgctcaaat cactgctgga atattggaag     480
agccaacaga atgacgagga gcctgtggct accagccagt gctgaaacc acatactacc     540
tcctccccac ctgacatgag cccattcttt ctccgccagt atgtgaaggg tcatgctgct     600
gatgtgtttg aggcctatac tcagcttcta acagaaatgg tactgaggct tccttaccaa     660
atcaaaaaga ttactgacac caattctcga atcccacctc ctgtctttga ccactcgtgg     720
ttttactttc tctccgagta cctcatgatc cagcagactc catttgtgcg ccgtcaagtc     780
cgcaaacttc tgctcttcat ctgtggatcc aaagagaagt accgccagct ccgggatttg     840
cacaccctgg actctcacgt gcgtgggatc aagaagctgc tagaagagca ggggatattc     900
ctccgggcaa gtgtggttac agccagctca ggctccgcct tgcaatatga cacactcatc     960
agcctgatgg agcacctgaa agcctgtgca gagattgccg cccagcgaac catcaactgg    1020
cagaaattct gcatcaaaga tgactccgtc ctgtacttcc tcctccaagt cagtttcctt    1080
gtggatgagg gcgtgtcccc agtgctgctg caactgctct cctgtgctct gtgcggcagc    1140
aaggtgctcg ctgcactggc agcctcttcg ggatcctcca gtgcttcttc ctcctcagcc    1200
cctgtggctg ccagttctgg acaagccaca acacagtcca agtcttccac taaaaagagc    1260
aagaaagaag aaaagaaaa ggagaaagat ggtgagacct ctggcagcca ggaggaccag    1320
ctgtgcacag ctctggtgaa ccagctgaac aaatttgccg ataaggaaac cctgatccag    1380
ttcctgcgtt gtttcctgtt agagtccaat tcttcctcgg tgcgctggca ggcccactgt    1440
ctgacactgc acatctacag aaattccagc aaatctcaac aggagctcct gctagatctg    1500
atgtggtcca tctggccaga actcccagcc tatggtcgta aggctgccca gtttgtggac    1560
ctactaggat atttctccct gaaaactcca caaacagaga agaagttgaa ggagtattca    1620
cagaaggctg tggagattct gcggactcaa aaccatattc ttaccaacca ccccaactcg    1680
aacatttata acactttgtc tggcttagtg gagtttgatg ctattaccct ggagagcgat    1740
ccctgcctgg tgtgtaataa cccggaagta ccgttctgtt atatcaagct gtcttccatt    1800
aaagtggaca cgcggtacac caccacccag caggttgtga agctcattgg cagtcacacc    1860
atcagcaaag tgacagtgaa aatcggggat ctgaaacgga ccaagatggt gcggaccatc    1920
aacctgtatt ataacaaccg aaccgtgcag gccatcgtgg agttgaaaaa caagccagct    1980
cgctggcaca agccaagaa ggttcagctg accctggac agacagaggt gaagattgac    2040
```

```
ctgccgttgc ccattgtggc ctccaatctg atgattgagt ttgcagactt ctatgaaaac    2100
taccaggcct ccacagagac cctgcagtgc                                    2130
```

<210> SEQ ID NO 32
<211> LENGTH: 710
<212> TYPE: PRT
<213> ORGANISM: Homo sapiens

<400> SEQUENCE: 32

| | | | | | | | | | | | | | | |
|---|---|---|---|---|---|---|---|---|---|---|---|---|---|---|
|Gly|Ser|Glu|Gly|Glu|Gly|Gly|Glu|Thr|Glu|Gly|Asp|Val|His|Thr|
|1| | | |5| | | |10| | | |15| | |
|Ser|Asn|Arg|Leu|His|Met|Val|Arg|Leu|Met|Leu|Leu|Glu|Arg|Leu|Leu|
| | | |20| | | |25| | | |30| | | |
|Gln|Thr|Leu|Pro|Gln|Leu|Arg|Asn|Val|Gly|Gly|Val|Arg|Ala|Ile|Pro|
| | | |35| | | |40| | | |45| | | |
|Tyr|Met|Gln|Val|Ile|Leu|Met|Leu|Thr|Thr|Asp|Leu|Asp|Gly|Glu|Asp|
| | |50| | | |55| | | |60| | | | |
|Glu|Lys|Asp|Lys|Gly|Ala|Leu|Asp|Asn|Leu|Leu|Ser|Gln|Leu|Ile|Ala|
|65| | | |70| | | |75| | | |80| | |
|Glu|Leu|Gly|Met|Asp|Lys|Lys|Asp|Val|Ser|Lys|Lys|Asn|Glu|Arg|Ser|
| | | | |85| | | |90| | | |95| | |
|Ala|Leu|Asn|Glu|Val|His|Leu|Val|Val|Met|Arg|Leu|Leu|Ser|Val|Phe|
| | | |100| | | |105| | | |110| | | |
|Met|Ser|Arg|Thr|Lys|Ser|Gly|Ser|Lys|Ser|Ser|Ile|Cys|Glu|Ser|Ser|
| | | |115| | | |120| | | |125| | | |
|Ser|Leu|Ile|Ser|Ser|Ala|Thr|Ala|Ala|Leu|Leu|Ser|Ser|Gly|Ala|
| | | |130| | | |135| | | |140| | | |
|Val|Asp|Tyr|Cys|Leu|His|Val|Leu|Lys|Ser|Leu|Leu|Glu|Tyr|Trp|Lys|
|145| | | |150| | | |155| | | |160| | |
|Ser|Gln|Gln|Asn|Asp|Glu|Glu|Pro|Val|Ala|Thr|Ser|Gln|Leu|Leu|Lys|
| | | |165| | | |170| | | |175| | | |
|Pro|His|Thr|Thr|Ser|Ser|Pro|Pro|Asp|Met|Ser|Pro|Phe|Phe|Leu|Arg|
| | | |180| | | |185| | | |190| | | |
|Gln|Tyr|Val|Lys|Gly|His|Ala|Ala|Asp|Val|Phe|Glu|Ala|Tyr|Thr|Gln|
| | | |195| | | |200| | | |205| | | |
|Leu|Leu|Thr|Glu|Met|Val|Leu|Arg|Leu|Pro|Tyr|Gln|Ile|Lys|Lys|Ile|
| | | |210| | | |215| | | |220| | | |
|Thr|Asp|Thr|Asn|Ser|Arg|Ile|Pro|Pro|Val|Phe|Asp|His|Ser|Trp|
|225| | | |230| | | |235| | | |240| | |
|Phe|Tyr|Phe|Leu|Ser|Glu|Tyr|Leu|Met|Ile|Gln|Gln|Thr|Pro|Phe|Val|
| | | |245| | | |250| | | |255| | | |
|Arg|Arg|Gln|Val|Arg|Lys|Leu|Leu|Leu|Phe|Ile|Cys|Gly|Ser|Lys|Glu|
| | | |260| | | |265| | | |270| | | |
|Lys|Tyr|Arg|Gln|Leu|Arg|Asp|Leu|His|Thr|Leu|Asp|Ser|His|Val|Arg|
| | | |275| | | |280| | | |285| | | |
|Gly|Ile|Lys|Lys|Leu|Leu|Glu|Glu|Gln|Gly|Ile|Phe|Leu|Arg|Ala|Ser|
| | | |290| | | |295| | | |300| | | |
|Val|Val|Thr|Ala|Ser|Ser|Gly|Ser|Ala|Leu|Gln|Tyr|Asp|Thr|Leu|Ile|
|305| | | |310| | | |315| | | |320| | |
|Ser|Leu|Met|Glu|His|Leu|Lys|Ala|Cys|Ala|Glu|Ile|Ala|Ala|Gln|Arg|
| | | |325| | | |330| | | |335| | | |
|Thr|Ile|Asn|Trp|Gln|Lys|Phe|Cys|Ile|Lys|Asp|Asp|Ser|Val|Leu|Tyr|
| | | |340| | | |345| | | |350| | | |

```
Phe Leu Leu Gln Val Ser Phe Leu Val Asp Glu Gly Val Ser Pro Val
            355                 360                 365
Leu Leu Gln Leu Leu Ser Cys Ala Leu Cys Gly Ser Lys Val Leu Ala
        370                 375                 380
Ala Leu Ala Ala Ser Ser Gly Ser Ser Ala Ser Ser Ser Ser Ser Ala
385                 390                 395                 400
Pro Val Ala Ala Ser Ser Gly Gln Ala Thr Thr Gln Ser Lys Ser Ser
                405                 410                 415
Thr Lys Lys Ser Lys Lys Glu Glu Glu Lys Glu Lys Asp Gly Glu
            420                 425                 430
Thr Ser Gly Ser Gln Glu Asp Gln Leu Cys Thr Ala Leu Val Asn Gln
        435                 440                 445
Leu Asn Lys Phe Ala Asp Lys Glu Thr Leu Ile Gln Phe Leu Arg Cys
450                 455                 460
Phe Leu Leu Glu Ser Asn Ser Ser Ser Val Arg Trp Gln Ala His Cys
465                 470                 475                 480
Leu Thr Leu His Ile Tyr Arg Asn Ser Ser Lys Ser Gln Glu Leu
                485                 490                 495
Leu Leu Asp Leu Met Trp Ser Ile Trp Pro Glu Leu Pro Ala Tyr Gly
            500                 505                 510
Arg Lys Ala Ala Gln Phe Val Asp Leu Leu Gly Tyr Phe Ser Leu Lys
        515                 520                 525
Thr Pro Gln Thr Glu Lys Lys Leu Lys Glu Tyr Ser Gln Lys Ala Val
        530                 535                 540
Glu Ile Leu Arg Thr Gln Asn His Ile Leu Thr Asn His Pro Asn Ser
545                 550                 555                 560
Asn Ile Tyr Asn Thr Leu Ser Gly Leu Val Glu Phe Asp Gly Tyr Tyr
                565                 570                 575
Leu Glu Ser Asp Pro Cys Leu Val Cys Asn Asn Pro Glu Val Pro Phe
            580                 585                 590
Cys Tyr Ile Lys Leu Ser Ser Ile Lys Val Asp Thr Arg Tyr Thr Thr
        595                 600                 605
Thr Gln Gln Val Val Lys Leu Ile Gly Ser His Thr Ile Ser Lys Val
610                 615                 620
Thr Val Lys Ile Gly Asp Leu Lys Arg Thr Lys Met Val Arg Thr Ile
625                 630                 635                 640
Asn Leu Tyr Tyr Asn Asn Arg Thr Val Gln Ala Ile Val Glu Leu Lys
                645                 650                 655
Asn Lys Pro Ala Arg Trp His Lys Ala Lys Val Gln Leu Thr Pro
            660                 665                 670
Gly Gln Thr Glu Val Lys Ile Asp Leu Pro Leu Pro Ile Val Ala Ser
        675                 680                 685
Asn Leu Met Ile Glu Phe Ala Asp Phe Tyr Glu Asn Tyr Gln Ala Ser
690                 695                 700
Thr Glu Thr Leu Gln Cys
705                 710
```

<210> SEQ ID NO 33
<211> LENGTH: 1296
<212> TYPE: DNA
<213> ORGANISM: Homo sapiens

<400> SEQUENCE: 33
gatttgcaca ccctggactc tcacgtgcgt gggatcaaga agctgctaga agagcagggg    60

| | |
|---|---|
| atattcctcc gggcaagtgt ggttacagcc agctcaggct ccgccttgca atatgacaca | 120 |
| ctcatcagcc tgatggagca cctgaaagcc tgtgcagaga ttgccgccca gcgaaccatc | 180 |
| aactggcaga aattctgcat caaagatgac tccgtcctgt acttcctcct ccaagtcagt | 240 |
| ttccttgtgg atgagggcgt gtccccagtg ctgctgcaac tgctctcctg tgctctgtgc | 300 |
| ggcagcaagg tgctcgctgc actggcagcc tcttcgggat cctccagtgc ttcttcctcc | 360 |
| tcagcccctg tggctgccag ttctggacaa gccacaacac agtccaagtc ttccactaaa | 420 |
| aagagcaaga aagaagaaaa agaaaaggag aaagatggtg agacctctgg cagccaggag | 480 |
| gaccagctgt gcacagctct ggtgaaccag ctgaacaaat tgccgataaa ggaaaccctg | 540 |
| atccagttcc tgcgttgttt cctgttagag tccaattctt cctcggtgcg ctggcaggcc | 600 |
| cactgtctga cactgcacat ctacagaaat ccagcaaat ctcaacagga gctcctgcta | 660 |
| gatctgatgt ggtccatctg ccagaactc ccagcctatg gtcgtaaggc tgcccagttt | 720 |
| gtggacctac taggatattt ctccctgaaa actccacaaa cagagaagaa gttgaaggag | 780 |
| tattcacaga aggctgtgga gattctgcgg actcaaaacc atattcttac caaccacccc | 840 |
| aactcgaaca tttataacac tttgtctggc ttagtggagt ttgatggcta ttacctggag | 900 |
| agcgatccct gcctggtgtg taataacccg gaagtaccgt tctgttatat caagctgtct | 960 |
| tccattaaag tggacacgcg gtacaccacc acccagcagg ttgtgaagct cattggcagt | 1020 |
| cacaccatca gcaaagtgac agtgaaaatc ggggatctga acggaccaa gatggtgcgg | 1080 |
| accatcaacc tgtattataa caaccgaacc gtgcaggcca tcgtggagtt gaaaaacaag | 1140 |
| ccagctcgct ggcacaaagc caagaaggtt cagctgaccc ctggacagac agaggtgaag | 1200 |
| attgacctgc cgttgcccat tgtggcctcc aatctgatga ttgagtttgc agacttctat | 1260 |
| gaaaactacc aggcctccac agagaccctg cagtgc | 1296 |

<210> SEQ ID NO 34
<211> LENGTH: 432
<212> TYPE: PRT
<213> ORGANISM: Homo sapiens

<400> SEQUENCE: 34

```
Asp Leu His Thr Leu Asp Ser His Val Arg Gly Ile Lys Lys Leu Leu
1               5                   10                  15

Glu Glu Gln Gly Ile Phe Leu Arg Ala Ser Val Val Thr Ala Ser Ser
            20                  25                  30

Gly Ser Ala Leu Gln Tyr Asp Thr Leu Ile Ser Leu Met Glu His Leu
        35                  40                  45

Lys Ala Cys Ala Glu Ile Ala Ala Gln Arg Thr Ile Asn Trp Gln Lys
    50                  55                  60

Phe Cys Ile Lys Asp Asp Ser Val Leu Tyr Phe Leu Gln Val Ser
65                  70                  75                  80

Phe Leu Val Asp Glu Gly Val Ser Pro Val Leu Gln Leu Ser
                85                  90                  95

Cys Ala Leu Cys Gly Ser Lys Val Leu Ala Ala Leu Ala Ala Ser Ser
            100                 105                 110

Gly Ser Ser Ser Ala Ser Ser Ser Ala Pro Val Ala Ala Ser Ser
        115                 120                 125

Gly Gln Ala Thr Thr Gln Ser Lys Ser Ser Thr Lys Lys Ser Lys
    130                 135                 140

Glu Glu Lys Glu Lys Glu Lys Asp Gly Glu Thr Ser Gly Ser Gln Glu
145                 150                 155                 160
```

Asp Gln Leu Cys Thr Ala Leu Val Asn Gln Leu Asn Lys Phe Ala Asp
                165                 170                 175
Lys Glu Thr Leu Ile Gln Phe Leu Arg Cys Phe Leu Leu Glu Ser Asn
            180                 185                 190
Ser Ser Ser Val Arg Trp Gln Ala His Cys Leu Thr Leu His Ile Tyr
        195                 200                 205
Arg Asn Ser Ser Lys Ser Gln Gln Glu Leu Leu Leu Asp Leu Met Trp
    210                 215                 220
Ser Ile Trp Pro Glu Leu Pro Ala Tyr Gly Arg Lys Ala Ala Gln Phe
225                 230                 235                 240
Val Asp Leu Leu Gly Tyr Phe Ser Leu Lys Thr Pro Gln Thr Glu Lys
                245                 250                 255
Lys Leu Lys Glu Tyr Ser Gln Lys Ala Val Glu Ile Leu Arg Thr Gln
            260                 265                 270
Asn His Ile Leu Thr Asn His Pro Asn Ser Asn Ile Tyr Asn Thr Leu
        275                 280                 285
Ser Gly Leu Val Glu Phe Asp Gly Tyr Tyr Leu Glu Ser Asp Pro Cys
    290                 295                 300
Leu Val Cys Asn Asn Pro Glu Val Pro Phe Cys Tyr Ile Lys Leu Ser
305                 310                 315                 320
Ser Ile Lys Val Asp Thr Arg Tyr Thr Thr Thr Gln Gln Val Val Lys
                325                 330                 335
Leu Ile Gly Ser His Thr Ile Ser Lys Val Thr Val Lys Ile Gly Asp
            340                 345                 350
Leu Lys Arg Thr Lys Met Val Arg Thr Ile Asn Leu Tyr Tyr Asn Asn
        355                 360                 365
Arg Thr Val Gln Ala Ile Val Glu Leu Lys Asn Lys Pro Ala Arg Trp
    370                 375                 380
His Lys Ala Lys Lys Val Gln Leu Thr Pro Gly Gln Thr Glu Val Lys
385                 390                 395                 400
Ile Asp Leu Pro Leu Pro Ile Val Ala Ser Asn Leu Met Ile Glu Phe
                405                 410                 415
Ala Asp Phe Tyr Glu Asn Tyr Gln Ala Ser Thr Glu Thr Leu Gln Cys
            420                 425                 430

<210> SEQ ID NO 35
<211> LENGTH: 942
<212> TYPE: DNA
<213> ORGANISM: Homo sapiens

<400> SEQUENCE: 35
gatttgcaca ccctggactc tcacgtgcgt gggatcaaga agctgctaga agagcagggg      60
atattcctcc gggcaagtgt ggttacagcc agctcaggct ccgccttgca atatgacaca     120
ctcatcagcc tgatggagca cctgaaagcc tgtgcagaga ttgccgccca gcgaaccatc     180
aactggcaga aattctgcat caaagatgac tccgtcctgt acttcctcct ccaagtcagt     240
ttccttgtgg atgagggcgt gtccccagtg ctgctgcaac tgctctcctg tgctctgtgc     300
ggcagcaagg tgctcgctgc actggcagcc tcttcgggat cctccagtgc ttcttcctcc     360
tcagcccctg tggctgccag ttctggacaa gccacaacac agtccaagtc ttccactaaa     420
aagagcaaga aagaagaaaa agaaaaggag aaagatggtg agacctctgg cagccaggag     480
gaccagctgt gcacagctct ggtgaaccag ctgaacaaat ttgccgataa ggaaccctg      540 atccagttcc tgcgttgttt cctgttagag tccaattctt cctcggtgcg ctggcaggcc     600

| | | |
|---|---|---|
| cactgtctga cactgcacat ctacagaaat tccagcaaat ctcaacagga gctcctgcta | 660 |
| gatctgatgt ggtccatctg gccagaactc ccagcctatg gtcgtaaggc tgcccagttt | 720 |
| gtggacctac taggatattt ctccctgaaa actccacaaa cagagaagaa gttgaaggag | 780 |
| tattcacaga aggctgtgga gattctgcgg actcaaaacc atattcttac caaccacccc | 840 |
| aactcgaaca tttataacac tttgtctggc ttagtggagt ttgatggcta ttacctggag | 900 |
| agcgatccct gcctggtgtg taataacccg gaagtaccgt tc | 942 |

<210> SEQ ID NO 36
<211> LENGTH: 314
<212> TYPE: PRT
<213> ORGANISM: Homo sapiens

<400> SEQUENCE: 36

Asp Leu His Thr Leu Asp Ser His Val Arg Gly Ile Lys Lys Leu Leu
1               5                   10                  15

Glu Glu Gln Gly Ile Phe Leu Arg Ala Ser Val Val Thr Ala Ser Ser
            20                  25                  30

Gly Ser Ala Leu Gln Tyr Asp Thr Leu Ile Ser Leu Met Glu His Leu
        35                  40                  45

Lys Ala Cys Ala Glu Ile Ala Ala Gln Arg Thr Ile Asn Trp Gln Lys
    50                  55                  60

Phe Cys Ile Lys Asp Asp Ser Val Leu Tyr Phe Leu Gln Val Ser
65                  70                  75                  80

Phe Leu Val Asp Glu Gly Val Ser Pro Val Leu Gln Leu Ser
                85                  90                  95

Cys Ala Leu Cys Gly Ser Lys Val Leu Ala Ala Leu Ala Ala Ser Ser
            100                 105                 110

Gly Ser Ser Ser Ala Ser Ser Ser Ala Pro Val Ala Ala Ser Ser
        115                 120                 125

Gly Gln Ala Thr Thr Gln Ser Lys Ser Ser Thr Lys Lys Ser Lys Lys
    130                 135                 140

Glu Glu Lys Glu Lys Glu Lys Asp Gly Glu Thr Ser Gly Ser Gln Glu
145                 150                 155                 160

Asp Gln Leu Cys Thr Ala Leu Val Asn Gln Leu Asn Lys Phe Ala Asp
                165                 170                 175

Lys Glu Thr Leu Ile Gln Phe Leu Arg Cys Phe Leu Leu Glu Ser Asn
            180                 185                 190

Ser Ser Ser Val Arg Trp Gln Ala His Cys Leu Thr Leu His Ile Tyr
        195                 200                 205

Arg Asn Ser Ser Lys Ser Gln Gln Glu Leu Leu Leu Asp Leu Met Trp
    210                 215                 220

Ser Ile Trp Pro Glu Leu Pro Ala Tyr Gly Arg Lys Ala Ala Gln Phe
225                 230                 235                 240

Val Asp Leu Leu Gly Tyr Phe Ser Leu Lys Thr Pro Gln Thr Glu Lys
                245                 250                 255

Lys Leu Lys Glu Tyr Ser Gln Lys Ala Val Glu Ile Leu Arg Thr Gln
            260                 265                 270

Asn His Ile Leu Thr Asn His Pro Asn Ser Asn Ile Tyr Asn Thr Leu
        275                 280                 285

Ser Gly Leu Val Glu Phe Asp Gly Tyr Tyr Leu Glu Ser Asp Pro Cys
    290                 295                 300

Leu Val Cys Asn Asn Pro Glu Val Pro Phe

<210> SEQ ID NO 37
<211> LENGTH: 1440
<212> TYPE: DNA
<213> ORGANISM: Homo sapiens

<400> SEQUENCE: 37

| | | | | | |
|---|---|---|---|---|---|
| gatttgcaca | ccctggactc | tcacgtgcgt | gggatcaaga | agctgctaga | agagcagggg | 60 |
| atattcctcc | gggcaagtgt | ggttacagcc | agctcaggct | ccgccttgca | atatgacaca | 120 |
| ctcatcagcc | tgatggagca | cctgaaagcc | tgtgcagaga | ttgccgccca | gcgaaccatc | 180 |
| aactggcaga | aattctgcat | caaagatgac | tccgtcctgt | acttcctcct | ccaagtcagt | 240 |
| ttccttgtgg | atgagggcgt | gtccccagtc | ctgctgcaac | tgctctcctg | tgctctgtgc | 300 |
| ggcagcaagg | tgctcgctgc | actggcagcc | tcttcgggat | cctccagtgc | ttcttcctcc | 360 |
| tcagcccctg | tggctgccag | ttctggacaa | gccacaacac | agtccaagtc | ttccactaaa | 420 |
| aagagcaaga | aagaagaaaa | agaaaaggag | aaagatggtg | agacctctgg | cagccaggag | 480 |
| gaccagctgt | gcacagctct | ggtgaaccag | ctgaacaaat | tgccgataa | ggaaaccctg | 540 |
| atccagttcc | tgcgttgttt | cctgttagag | tccaattctt | cctcggtgcg | ctggcaggcc | 600 |
| cactgtctga | cactgcacat | ctacagaaat | tccagcaaat | ctcaacagga | gctcctgcta | 660 |
| gatctgatgt | ggtccatctg | gccagaactc | ccagcctatg | tcgtaaggc | tgcccagttt | 720 |
| gtggacctac | taggatattt | ctccctgaaa | actccacaaa | cagagaagaa | gttgaaggag | 780 |
| tattcacaga | aggctgtgga | gattctgcgg | actcaaaacc | atattcttac | caaccacccc | 840 |
| aactcgaaca | tttataacac | tttgtctggc | ttagtggagt | ttgatggcta | ttacctggag | 900 |
| agcgatccct | gcctggtgtg | taataacccg | gaagtaccgt | tctgttatat | caagctgtct | 960 |
| tccattaaag | tggacacgcg | gtacaccacc | acccagcagg | ttgtgaagct | cattggcagt | 1020 |
| cacaccatca | gcaaagtgac | agtgaaaatc | ggggatctga | acggaccaa | gatggtgcgg | 1080 |
| accatcaacc | tgtattataa | caaccgaacc | gtgcaggcca | tcgtggagtt | gaaaaacaag | 1140 |
| ccagctcgct | ggcacaaagc | caagaaggtt | cagctgaccc | ctggacagac | agaggtgaag | 1200 |
| attgacctgc | cgttgcccat | tgtggcctcc | aatctgatga | ttgagtttgc | agacttctat | 1260 |
| gaaaactacc | aggcctccac | agagaccctg | cagtgcccctc | gctgtagtgc | ctcggtccct | 1320 |
| gccaacccag | gagtctgtgg | caactgtgga | gagaatgtgt | accagtgtca | caaatgcaga | 1380 |
| tccatcaact | acgatgaaaa | ggatcccttc | ctctgcaatg | cctgtggctt | ctgtaaatat | 1440 |

<210> SEQ ID NO 38
<211> LENGTH: 480
<212> TYPE: PRT
<213> ORGANISM: Homo sapiens

<400> SEQUENCE: 38

Asp Leu His Thr Leu Asp Ser His Val Arg Gly Ile Lys Lys Leu Leu
1               5                   10                  15

Glu Glu Gln Gly Ile Phe Leu Arg Ala Ser Val Thr Ala Ser Ser
            20                  25                  30

Gly Ser Ala Leu Gln Tyr Asp Thr Leu Ile Ser Leu Met Glu His Leu
        35                  40                  45

Lys Ala Cys Ala Glu Ile Ala Ala Gln Arg Thr Ile Asn Trp Gln Lys
    50                  55                  60

Phe Cys Ile Lys Asp Asp Ser Val Leu Tyr Phe Leu Leu Gln Val Ser

```
         65                  70                  75                  80
    Phe Leu Val Asp Glu Gly Val Ser Pro Val Leu Gln Leu Leu Ser
                     85                  90                  95

Cys Ala Leu Cys Gly Ser Lys Val Leu Ala Leu Ala Ala Ser Ser
                    100                 105                 110

Gly Ser Ser Ser Ala Ser Ser Ser Ala Pro Val Ala Ala Ser Ser
                    115                 120                 125

Gly Gln Ala Thr Thr Gln Ser Lys Ser Thr Lys Lys Ser Lys Lys
                130                 135                 140

Glu Glu Lys Glu Lys Glu Lys Asp Gly Glu Thr Ser Gly Ser Gln Glu
    145                 150                 155                 160

Asp Gln Leu Cys Thr Ala Leu Val Asn Gln Leu Asn Lys Phe Ala Asp
                    165                 170                 175

Lys Glu Thr Leu Ile Gln Phe Leu Arg Cys Phe Leu Leu Glu Ser Asn
                    180                 185                 190

Ser Ser Ser Val Arg Trp Gln Ala His Cys Leu Thr Leu His Ile Tyr
                    195                 200                 205

Arg Asn Ser Ser Lys Ser Gln Gln Glu Leu Leu Leu Asp Leu Met Trp
    210                 215                 220

Ser Ile Trp Pro Glu Leu Pro Ala Tyr Gly Arg Lys Ala Ala Gln Phe
    225                 230                 235                 240

Val Asp Leu Leu Gly Tyr Phe Ser Leu Lys Thr Pro Gln Thr Glu Lys
                    245                 250                 255

Lys Leu Lys Glu Tyr Ser Gln Lys Ala Val Glu Ile Leu Arg Thr Gln
                    260                 265                 270

Asn His Ile Leu Thr Asn His Pro Asn Ser Asn Ile Tyr Asn Thr Leu
                    275                 280                 285

Ser Gly Leu Val Glu Phe Asp Gly Tyr Tyr Leu Glu Ser Asp Pro Cys
                290                 295                 300

Leu Val Cys Asn Asn Pro Glu Val Pro Phe Cys Tyr Ile Lys Leu Ser
    305                 310                 315                 320

Ser Ile Lys Val Asp Thr Arg Tyr Thr Thr Thr Gln Gln Val Val Lys
                    325                 330                 335

Leu Ile Gly Ser His Thr Ile Ser Lys Val Thr Val Lys Ile Gly Asp
                    340                 345                 350

Leu Lys Arg Thr Lys Met Val Arg Thr Ile Asn Leu Tyr Tyr Asn Asn
                    355                 360                 365

Arg Thr Val Gln Ala Ile Val Glu Leu Lys Asn Lys Pro Ala Arg Trp
    370                 375                 380

His Lys Ala Lys Lys Val Gln Leu Thr Pro Gly Gln Thr Glu Val Lys
    385                 390                 395                 400

Ile Asp Leu Pro Leu Pro Ile Val Ala Ser Asn Leu Met Ile Glu Phe
                    405                 410                 415

Ala Asp Phe Tyr Glu Asn Tyr Gln Ala Ser Thr Glu Thr Leu Gln Cys
                    420                 425                 430

Pro Arg Cys Ser Ala Ser Val Pro Ala Asn Pro Gly Val Cys Gly Asn
                    435                 440                 445

Cys Gly Glu Asn Val Tyr Gln Cys His Lys Cys Arg Ser Ile Asn Tyr
    450                 455                 460

Asp Glu Lys Asp Pro Phe Leu Cys Asn Ala Cys Gly Phe Cys Lys Tyr
    465                 470                 475                 480

<210> SEQ ID NO 39
```

<211> LENGTH: 1452
<212> TYPE: DNA
<213> ORGANISM: Homo sapiens

<400> SEQUENCE: 39

```
cctagcgcca agaatttgga tgccgacatc tggaaaaagt ttttgtctcg cccagccttg     60
ccatttatcc taaggctgct tcggggcctg gccatccagc accctggcac ccaggttctg    120
attggaactg attccatccc gaacctgcat aagctggagc aggtgtccag tgatgagggc    180
attgggacct tggcagagaa cctgctggaa gccctgcggg aacaccctga cgtaaacaag    240
aagattgacg cagcccgcag ggagacccgg gcagagaaga aacgcatggc catggcaatg    300
aggcagaagg ccctgggcac cctgggcatg acgacaaatg aaagggccca ggtcgtgacc    360
aagacagcac tcctgaagca gatggaagag ctgatcgagg agcctggcct cacgtgctgc    420
atctgcaggg agggatacaa gttccagccc acaaaggtcc tgggcattta accttcacg    480
aagcgggtag ccttggagga gatggagaat aagccccgga acagcaggg ctacagcacc    540
gtgtcccact tcaacattgt gcactacgac tgccatctgg ctgccgtcag gttggctcga    600
ggccgggaag agtgggagag tgccgccctg cagaatgcca acaccaagtg caacgggctc    660
cttccggtct ggggacctca tgtccctgaa tcagcttttg ccacttgctt ggcaagacac    720
aacacttacc tccaggaatg tacaggccag cgggagccca cgtatcagct caacatccat    780
gacatcaaac tgctcttcct gcgcttcgcc atggagcagt cgttcagcgc agacactggc    840
gggggcggcc gggagagcaa catccacctg atcccgtaca tcattcacac tgtgctttac    900
gtcctgaaca caacccgagc aacttcccga gaagagaaga acctccaagg ctttctggaa    960
cagcccaagg agaagtgggt ggagagtgcc tttgaagtgg acgggcccta ctatttcaca   1020
gtcttggccc ttcacatcct gccccctgag cagtggagag ccacacgtgt ggaaatcttg   1080
cggaggctgt tggtgacctc gcaggctcgg gcagtggctc aggtggagc caccaggctg   1140
acagataagg cagtgaagga ctattccgct taccgttctt cccttctctt ttgggccctc   1200
gtcgatctca tttacaacat gtttaagaag gtgcctacca gtaacacaga gggaggctgg   1260
tcctgctctc tcgctgagta catccgccac aacgacatgc ccatctacga agctgccgac   1320
aaagccctga aaaccttcca ggaggagttc atgccagtgg agaccttctc agagttcctc   1380
gatgtggccg tcttttatc agaaatcacc gatccagaga gcttcctgaa ggacctgttg   1440
aactcagtcc cc                                                       1452
```

<210> SEQ ID NO 40
<211> LENGTH: 484
<212> TYPE: PRT
<213> ORGANISM: Homo sapiens

<400> SEQUENCE: 40

```
Pro Ser Ala Lys Asn Leu Asp Ala Asp Ile Trp Lys Lys Phe Leu Ser
1               5                   10                  15

Arg Pro Ala Leu Pro Phe Ile Leu Arg Leu Leu Arg Gly Leu Ala Ile
            20                  25                  30

Gln His Pro Gly Thr Gln Val Leu Ile Gly Thr Asp Ser Ile Pro Asn
        35                  40                  45

Leu His Lys Leu Glu Gln Val Ser Ser Asp Glu Gly Ile Gly Thr Leu
    50                  55                  60

Ala Glu Asn Leu Leu Glu Ala Leu Arg Glu His Pro Asp Val Asn Lys
65                  70                  75                  80
```

```
Lys Ile Asp Ala Ala Arg Arg Glu Thr Arg Ala Glu Lys Lys Arg Met
                85                  90                  95
Ala Met Ala Met Arg Gln Lys Ala Leu Gly Thr Leu Gly Met Thr Thr
            100                 105                 110
Asn Glu Lys Gly Gln Val Val Thr Lys Thr Ala Leu Leu Lys Gln Met
            115                 120                 125
Glu Glu Leu Ile Glu Glu Pro Gly Leu Thr Cys Cys Ile Cys Arg Glu
130                 135                 140
Gly Tyr Lys Phe Gln Pro Thr Lys Val Leu Gly Ile Tyr Thr Phe Thr
145                 150                 155                 160
Lys Arg Val Ala Leu Glu Glu Met Glu Asn Lys Pro Arg Lys Gln Gln
                165                 170                 175
Gly Tyr Ser Thr Val Ser His Phe Asn Ile Val His Tyr Asp Cys His
            180                 185                 190
Leu Ala Ala Val Arg Leu Ala Arg Gly Arg Glu Glu Trp Glu Ser Ala
            195                 200                 205
Ala Leu Gln Asn Ala Asn Thr Lys Cys Asn Gly Leu Leu Pro Val Trp
210                 215                 220
Gly Pro His Val Pro Glu Ser Ala Phe Ala Thr Cys Leu Ala Arg His
225                 230                 235                 240
Asn Thr Tyr Leu Gln Glu Cys Thr Gly Gln Arg Glu Pro Thr Tyr Gln
                245                 250                 255
Leu Asn Ile His Asp Ile Lys Leu Leu Phe Leu Arg Phe Ala Met Glu
            260                 265                 270
Gln Ser Phe Ser Ala Asp Thr Gly Gly Gly Arg Glu Ser Asn Ile
            275                 280                 285
His Leu Ile Pro Tyr Ile Ile His Thr Val Leu Tyr Val Leu Asn Thr
290                 295                 300
Thr Arg Ala Thr Ser Arg Glu Glu Lys Asn Leu Gln Gly Phe Leu Glu
305                 310                 315                 320
Gln Pro Lys Glu Lys Trp Val Glu Ser Ala Phe Glu Val Asp Gly Pro
                325                 330                 335
Tyr Tyr Phe Thr Val Leu Ala Leu His Ile Leu Pro Pro Glu Gln Trp
            340                 345                 350
Arg Ala Thr Arg Val Glu Ile Leu Arg Arg Leu Leu Val Thr Ser Gln
            355                 360                 365
Ala Arg Ala Val Ala Pro Gly Gly Ala Thr Arg Leu Thr Asp Lys Ala
370                 375                 380
Val Lys Asp Tyr Ser Ala Tyr Arg Ser Ser Leu Leu Phe Trp Ala Leu
385                 390                 395                 400
Val Asp Leu Ile Tyr Asn Met Phe Lys Lys Val Pro Thr Ser Asn Thr
                405                 410                 415
Glu Gly Gly Trp Ser Cys Ser Leu Ala Glu Tyr Ile Arg His Asn Asp
            420                 425                 430
Met Pro Ile Tyr Glu Ala Ala Asp Lys Ala Leu Lys Thr Phe Gln Glu
            435                 440                 445
Glu Phe Met Pro Val Glu Thr Phe Ser Glu Phe Leu Asp Val Ala Gly
            450                 455                 460
Leu Leu Ser Glu Ile Thr Asp Pro Glu Ser Phe Leu Lys Asp Leu Leu
465                 470                 475                 480
Asn Ser Val Pro

<210> SEQ ID NO 41
```

<211> LENGTH: 1923
<212> TYPE: DNA
<213> ORGANISM: Homo sapiens

<400> SEQUENCE: 41

```
gcccagtgtg ggggcctgga atgcatgctt aacagactcg cagggatcag agatttcaag      60
cagggacgcc accttctaac agtgctactg aaattgttca gttactgcgt gaaggtgaaa     120
gtcaaccggc agcaactggt caaactggaa atgaacacct tgaacgtcat gctgggacc      180
ctaaacctgg cccttgtagc tgaacaagaa agcaaggaca gtggggtgc agctgtggct      240
gagcaggtgc ttagcatcat ggagatcatt ctagatgagt ccaatgctga gccctgagt      300
gaggacaagg gcaacctcct cctgacaggt gacaaggatc aactggtgat gctcttggac     360
cagatcaaca gcacctttgt tcgctccaac cccagtgtgc tccagggcct gcttcgcatc     420
atcccgtacc tttcctttgg agaggtggag aaaatgcaga tcttggtgga gcgattcaaa     480
ccatactgca actttgataa atatgatgaa gatcacagtg gtgatgataa agtcttcctg     540
gactgcttct gtaaaatagc tgctggcatc aagaacaaca gcaatgggca ccagctgaag     600
gatctgattc tccagaaggg gatcacccag aatgcacttg actacatgaa aaagcacatc     660
cctagcgcca gaatttgga tgccgacatc tggaaaaagt ttttgtctcg cccagccttg      720
ccatttatcc taaggctgct tcggggcctg gccatccagc accctggcac ccaggttctg     780
attggaactg attccatccc gaacctgcat aagctggagc aggtgtccag tgatgagggc     840
attgggacct tggcagagaa cctgctggaa gccctgcggg aacaccctga cgtaaacaag     900
aagattgacg cagcccgcag ggagacccgg gcagagaaga acgcatggc catggcaatg     960
aggcagaagg ccctgggcac cctgggcatg acgacaaatg aaaagggcca ggtcgtgacc    1020
aagacagcac tcctgaagca gatggaagag ctgatcgagg agcctggcct cacgtgctgc    1080
atctgcaggg agggatacaa gttccagccc acaaaggtcc tgggcattta ccttcacg      1140
aagcgggtag ccttggagga gatggagaat aagccccga acagcaggg ctacagcacc     1200
gtgtcccact tcaacattgt gcactacgac tgccatctgg ctgccgtcag gttggctcga   1260
ggccgggaag agtgggagag tgccgccctg cagaatgcca acaccaagtg caacgggctc    1320
cttccggtct ggggacctca tgtccctgaa tcagcttttg ccacttgctt ggcaagacac    1380
aacacttacc tccaggaatg tacaggccag cgggagccca cgtatcagct caacatccat    1440
gacatcaaac tgctcttcct gcgcttcgcc atggagcagt cgttcagcgc agacactggc    1500
gggggcggcc gggagagcaa catccacctg atcccgtaca tcattcacac tgtgctttac    1560
gtcctgaaca caacccgagc aacttcccga gaagagaaga acctccaagg ctttctggaa    1620
cagcccaagg agaagtgggt ggagagtgcc tttgaagtgg acgggcccta ctatttcaca    1680
gtcttggccc ttcacatcct gccccctgag cagtggagag ccacacgtgt ggaaatcttg    1740
cggaggctgt tggtgacctc gcaggctcgg gcagtggctc aggtggagc caccaggctg     1800
acagataagg cagtgaagga ctattccgct taccgttctt cccttctctt ttgggccctc    1860
gtcgatctca tttacaacat gtttaagaag gtgcctacca gtaacacaga gggaggctgg    1920
tcc                                                                   1923
```

<210> SEQ ID NO 42
<211> LENGTH: 641
<212> TYPE: PRT
<213> ORGANISM: Homo sapiens

<400> SEQUENCE: 42

```
Ala Gln Cys Gly Gly Leu Glu Cys Met Leu Asn Arg Leu Ala Gly Ile
1               5                   10                  15

Arg Asp Phe Lys Gln Gly Arg His Leu Leu Thr Val Leu Leu Lys Leu
                20                  25                  30

Phe Ser Tyr Cys Val Lys Val Lys Val Asn Arg Gln Gln Leu Val Lys
            35                  40                  45

Leu Glu Met Asn Thr Leu Asn Val Met Leu Gly Thr Leu Asn Leu Ala
    50                  55                  60

Leu Val Ala Glu Gln Glu Ser Lys Asp Ser Gly Gly Ala Ala Val Ala
65                  70                  75                  80

Glu Gln Val Leu Ser Ile Met Glu Ile Ile Leu Asp Glu Ser Asn Ala
                85                  90                  95

Glu Pro Leu Ser Glu Asp Lys Gly Asn Leu Leu Leu Thr Gly Asp Lys
                100                 105                 110

Asp Gln Leu Val Met Leu Leu Asp Gln Ile Asn Ser Thr Phe Val Arg
        115                 120                 125

Ser Asn Pro Ser Val Leu Gln Gly Leu Leu Arg Ile Ile Pro Tyr Leu
    130                 135                 140

Ser Phe Gly Glu Val Glu Lys Met Gln Ile Leu Val Glu Arg Phe Lys
145                 150                 155                 160

Pro Tyr Cys Asn Phe Asp Lys Tyr Asp Glu Asp His Ser Gly Asp Asp
                165                 170                 175

Lys Val Phe Leu Asp Cys Phe Cys Lys Ile Ala Ala Gly Ile Lys Asn
                180                 185                 190

Asn Ser Asn Gly His Gln Leu Lys Asp Leu Ile Leu Gln Lys Gly Ile
    195                 200                 205

Thr Gln Asn Ala Leu Asp Tyr Met Lys Lys His Ile Pro Ser Ala Lys
    210                 215                 220

Asn Leu Asp Ala Asp Ile Trp Lys Lys Phe Leu Ser Arg Pro Ala Leu
225                 230                 235                 240

Pro Phe Ile Leu Arg Leu Leu Arg Gly Leu Ala Ile Gln His Pro Gly
                245                 250                 255

Thr Gln Val Leu Ile Gly Thr Asp Ser Ile Pro Asn Leu His Lys Leu
                260                 265                 270

Glu Gln Val Ser Ser Asp Glu Gly Ile Gly Thr Leu Ala Glu Asn Leu
    275                 280                 285

Leu Glu Ala Leu Arg Glu His Pro Asp Val Asn Lys Lys Ile Asp Ala
    290                 295                 300

Ala Arg Arg Glu Thr Arg Ala Glu Lys Lys Arg Met Ala Met Ala Met
305                 310                 315                 320

Arg Gln Lys Ala Leu Gly Thr Leu Gly Met Thr Thr Asn Glu Lys Gly
                325                 330                 335

Gln Val Val Thr Lys Thr Ala Leu Leu Lys Gln Met Glu Glu Leu Ile
                340                 345                 350

Glu Glu Pro Gly Leu Thr Cys Cys Ile Cys Arg Glu Gly Tyr Lys Phe
            355                 360                 365

Gln Pro Thr Lys Val Leu Gly Ile Tyr Thr Phe Thr Lys Arg Val Ala
    370                 375                 380

Leu Glu Glu Met Glu Asn Lys Pro Arg Lys Gln Gln Gly Tyr Ser Thr
385                 390                 395                 400

Val Ser His Phe Asn Ile Val His Tyr Asp Cys His Leu Ala Ala Val
                405                 410                 415
```

Arg Leu Ala Arg Gly Arg Glu Glu Trp Ser Ala Ala Leu Gln Asn
                420                 425                 430

Ala Asn Thr Lys Cys Asn Gly Leu Leu Pro Val Trp Gly Pro His Val
            435                 440                 445

Pro Glu Ser Ala Phe Ala Thr Cys Leu Ala Arg His Asn Thr Tyr Leu
450                 455                 460

Gln Glu Cys Thr Gly Gln Arg Glu Pro Thr Tyr Gln Leu Asn Ile His
465                 470                 475                 480

Asp Ile Lys Leu Leu Phe Leu Arg Phe Ala Met Glu Gln Ser Phe Ser
                485                 490                 495

Ala Asp Thr Gly Gly Gly Gly Arg Glu Ser Asn Ile His Leu Ile Pro
            500                 505                 510

Tyr Ile Ile His Thr Val Leu Tyr Val Leu Asn Thr Thr Arg Ala Thr
            515                 520                 525

Ser Arg Glu Glu Lys Asn Leu Gln Gly Phe Leu Glu Gln Pro Lys Glu
530                 535                 540

Lys Trp Val Glu Ser Ala Phe Glu Val Asp Gly Pro Tyr Tyr Phe Thr
545                 550                 555                 560

Val Leu Ala Leu His Ile Leu Pro Pro Glu Gln Trp Arg Ala Thr Arg
                565                 570                 575

Val Glu Ile Leu Arg Arg Leu Leu Val Thr Ser Gln Ala Arg Ala Val
            580                 585                 590

Ala Pro Gly Gly Ala Thr Arg Leu Thr Asp Lys Ala Val Lys Asp Tyr
            595                 600                 605

Ser Ala Tyr Arg Ser Ser Leu Leu Phe Trp Ala Leu Val Asp Leu Ile
610                 615                 620

Tyr Asn Met Phe Lys Lys Val Pro Thr Ser Asn Thr Glu Gly Gly Trp
625                 630                 635                 640

Ser

<210> SEQ ID NO 43
<211> LENGTH: 1434
<212> TYPE: DNA
<213> ORGANISM: Homo sapiens

<400> SEQUENCE: 43

| | | | | | |
|---|---|---|---|---|---|
| gcgagtcgca | aagatcctga | gttgttctta | ggtctggctt | ccaacatttt | gaacttcatc | 60 |
| acctcttcca | tgctgaactc | tcggaacaat | tttatccgaa | actatctgag | tgtatctctt | 120 |
| tcagaacacc | atatggccac | cctagccagt | atcatcaagg | aggtggacaa | agatggactc | 180 |
| aagggttcat | cagatgaaga | gtttgctgca | gctctctatc | acttcaacca | ctcactggta | 240 |
| acctctgacc | ttcagtcacc | taacctgcag | aacacactgt | tgcagcagct | aggagtggct | 300 |
| ccttttctg | agggcccttg | gcccttgtac | attcaccctc | aaagcctctc | tgtgctttca | 360 |
| cgcctcctgc | tcatctggca | acataaagcc | agtgctcaag | gtgaccctga | cgtcccagaa | 420 |
| tgccttaaag | tttgggacag | gttttttgtct | acaatgaagc | agaatgccct | gcaaggtgtg | 480 |
| gtgcccagtg | agacagagga | tctgaatgta | gaacacctgc | agatgctcct | cctcattttc | 540 |
| cacaatttca | ccgagacagg | ccggcgggcc | atattgtcgc | ttttttgtcca | gatcatccag | 600 |
| gagttgagcg | tcaacatgga | tgctcagatg | cgcttcgtgc | cgcttatctt | ggctcgcctc | 660 |
| cttctcatct | ttgattatct | gcttcatcag | tactccaaag | ccctgtgta | tctatttgag | 720 |
| caggtacagc | ataacctgct | aagtcctccc | tttgggtggg | caagtggatc | ccaggacagc | 780 |
| aacagccgcc | gggcaaccac | tcctctctat | catggattca | agaagtaga | agaaaactgg | 840 |

```
tctaagcatt tctcatcaga tgctgtccca caccccagat tctactgtgt cctgtcccca    900
gaagcctcag aggatgattt gaaccgactt gattctgtgg catgtgacgt ccttttctcc    960
aagcttgtca gtatgatga gctttatgct gcactgacag ccctgcttgc agctgggtcc    1020
cagcttgata cagttaggag aaaggaaaac aagaatgtaa cagccttgga ggcctgtgcc    1080
cttcaatatt acttcttgat actgtggagg atcctaggaa ttttaccacc atcaaagact    1140
tacattaacc agctatccat gaactcacct gagatgagcg aatgtgacat cttgcacact    1200
ctgcgatggt cttctcggct ccggatcagc tcctatgtca actggataaa ggatcacctt    1260
atcaaacagg gaatgaaggc tgagcatgct agctcgcttc tagaactggc atccaccact    1320
aagtgtagct cagtgaaata tgatgttgaa atagtagagg aatacttcgc tcgacagatc    1380
tcatccttct gtagtatcga ctgtaccacc atcttgcagc tgcatgaaat tccc          1434
```

<210> SEQ ID NO 44
<211> LENGTH: 478
<212> TYPE: PRT
<213> ORGANISM: Homo sapiens

<400> SEQUENCE: 44

```
Ala Ser Arg Lys Asp Pro Glu Leu Phe Leu Gly Leu Ala Ser Asn Ile
1               5                   10                  15

Leu Asn Phe Ile Thr Ser Ser Met Leu Asn Ser Arg Asn Asn Phe Ile
            20                  25                  30

Arg Asn Tyr Leu Ser Val Ser Leu Ser Glu His His Met Ala Thr Leu
        35                  40                  45

Ala Ser Ile Ile Lys Glu Val Asp Lys Asp Gly Leu Lys Gly Ser Ser
    50                  55                  60

Asp Glu Glu Phe Ala Ala Ala Leu Tyr His Phe Asn His Ser Leu Val
65                  70                  75                  80

Thr Ser Asp Leu Gln Ser Pro Asn Leu Gln Asn Thr Leu Leu Gln Gln
                85                  90                  95

Leu Gly Val Ala Pro Phe Ser Glu Gly Pro Trp Pro Leu Tyr Ile His
            100                 105                 110

Pro Gln Ser Leu Ser Val Leu Ser Arg Leu Leu Leu Ile Trp Gln His
        115                 120                 125

Lys Ala Ser Ala Gln Gly Asp Pro Asp Val Pro Glu Cys Leu Lys Val
    130                 135                 140

Trp Asp Arg Phe Leu Ser Thr Met Lys Gln Asn Ala Leu Gln Gly Val
145                 150                 155                 160

Val Pro Ser Glu Thr Glu Asp Leu Asn Val Glu His Leu Gln Met Leu
                165                 170                 175

Leu Leu Ile Phe His Asn Phe Thr Glu Thr Gly Arg Arg Ala Ile Leu
            180                 185                 190

Ser Leu Phe Val Gln Ile Ile Gln Glu Leu Ser Val Asn Met Asp Ala
        195                 200                 205

Gln Met Arg Phe Val Pro Leu Ile Leu Ala Arg Leu Leu Leu Ile Phe
    210                 215                 220

Asp Tyr Leu Leu His Gln Tyr Ser Lys Ala Pro Val Tyr Leu Phe Glu
225                 230                 235                 240

Gln Val Gln His Asn Leu Leu Ser Pro Pro Phe Gly Trp Ala Ser Gly
                245                 250                 255

Ser Gln Asp Ser Asn Ser Arg Arg Ala Thr Thr Pro Leu Tyr His Gly
            260                 265                 270
```

```
Phe Lys Glu Val Glu Glu Asn Trp Ser Lys His Phe Ser Ser Asp Ala
        275                 280                 285
Val Pro His Pro Arg Phe Tyr Cys Val Leu Ser Pro Glu Ala Ser Glu
        290                 295                 300
Asp Asp Leu Asn Arg Leu Asp Ser Val Ala Cys Asp Val Leu Phe Ser
305                 310                 315                 320
Lys Leu Val Lys Tyr Asp Glu Leu Tyr Ala Ala Leu Thr Ala Leu Leu
                325                 330                 335
Ala Ala Gly Ser Gln Leu Asp Thr Val Arg Arg Lys Glu Asn Lys Asn
            340                 345                 350
Val Thr Ala Leu Glu Ala Cys Ala Leu Gln Tyr Phe Leu Ile Leu
        355                 360                 365
Trp Arg Ile Leu Gly Ile Leu Pro Pro Ser Lys Thr Tyr Ile Asn Gln
370                 375                 380
Leu Ser Met Asn Ser Pro Glu Met Ser Glu Cys Asp Ile Leu His Thr
385                 390                 395                 400
Leu Arg Trp Ser Ser Arg Leu Arg Ile Ser Ser Tyr Val Asn Trp Ile
                405                 410                 415
Lys Asp His Leu Ile Lys Gln Gly Met Lys Ala Glu His Ala Ser Ser
            420                 425                 430
Leu Leu Glu Leu Ala Ser Thr Thr Lys Cys Ser Ser Val Lys Tyr Asp
        435                 440                 445
Val Glu Ile Val Glu Glu Tyr Phe Ala Arg Gln Ile Ser Ser Phe Cys
        450                 455                 460
Ser Ile Asp Cys Thr Thr Ile Leu Gln Leu His Glu Ile Pro
465                 470                 475

<210> SEQ ID NO 45
<211> LENGTH: 1122
<212> TYPE: DNA
<213> ORGANISM: Homo sapiens

<400> SEQUENCE: 45
ggcccttggc ccttgtacat tcaccctcaa agcctctctg tgctttcacg cctcctgctc      60
atctggcaac ataaagccag tgctcaaggt gaccctgacg tcccagaatg ccttaaagtt     120
tgggacaggt ttttgtctac aatgaagcag aatgccctgc aaggtgtggt gcccagtgag     180
acagaggatc tgaatgtaga cacctgcaga atgctcctcc tcattttcca caatttcacc     240
gagacaggcc ggcgggccat attgtcgctt tttgtccaga tcatccagga gttgagcgtc     300
aacatggatg ctcagatgcg cttcgtgccg cttatcttgg ctcgcctcct tctcatcttt     360
gattatctgc ttcatcagta ctccaaagcc cctgtgtatc tatttgagca ggtacagcat     420
aacctgctaa gtcctccctt tgggtgggca agtggatccc aggacagcaa cagccgccgg     480
gcaaccactc ctctctatca tggattcaaa gaagtagaag aaaactggtc taagcatttc     540
tcatcagatg ctgtcccaca ccccagattc tactgtgtcc tgtccccaga agcctcagag     600
gatgatttga accgacttga ttctgtggca tgtgacgtcc ttttctccaa gcttgtcaag     660
tatgatgagc tttatgctgc actgacagcc ctgcttgcag ctgggtccca gcttgataca     720
gttaggagaa aggaaaacaa gaatgtaaca gccttggagg cctgtgccct tcaatattac     780
ttcttgatac tgtggaggat cctaggaatt ttaccaccat caaagactta cattaaccag     840
ctatccatga actcacctga gatgagcgaa tgtgacatct gcacactct gcgatggtct     900
tctcggctcc ggatcagctc ctatgtcaac tggataaagg atcaccttat caaacaggga     960
```

```
atgaaggctg agcatgctag ctcgcttcta gaactggcat ccaccactaa gtgtagctca   1020
gtgaaatatg atgttgaaat agtagaggaa tacttcgctc gacagatctc atccttctgt   1080
agtatcgact gtaccaccat cttgcagctg catgaaattc cc                      1122
```

<210> SEQ ID NO 46
<211> LENGTH: 374
<212> TYPE: PRT
<213> ORGANISM: Homo sapiens

<400> SEQUENCE: 46

```
Gly Pro Trp Pro Leu Tyr Ile His Pro Gln Ser Leu Ser Val Leu Ser
1               5                   10                  15

Arg Leu Leu Ile Trp Gln His Lys Ala Ser Ala Gln Gly Asp Pro
            20                  25                  30

Asp Val Pro Glu Cys Leu Lys Val Trp Asp Arg Phe Leu Ser Thr Met
        35                  40                  45

Lys Gln Asn Ala Leu Gln Gly Val Val Pro Ser Glu Thr Glu Asp Leu
    50                  55                  60

Asn Val Glu His Leu Gln Met Leu Leu Leu Ile Phe His Asn Phe Thr
65                  70                  75                  80

Glu Thr Gly Arg Arg Ala Ile Leu Ser Leu Phe Val Gln Ile Gln
                85                  90                  95

Glu Leu Ser Val Asn Met Asp Ala Gln Met Arg Phe Val Pro Leu Ile
            100                 105                 110

Leu Ala Arg Leu Leu Leu Ile Phe Asp Tyr Leu Leu His Gln Tyr Ser
        115                 120                 125

Lys Ala Pro Val Tyr Leu Phe Glu Gln Val Gln His Asn Leu Leu Ser
    130                 135                 140

Pro Pro Phe Gly Trp Ala Ser Gly Ser Gln Asp Ser Asn Ser Arg Arg
145                 150                 155                 160

Ala Thr Thr Pro Leu Tyr His Gly Phe Lys Glu Val Glu Glu Asn Trp
                165                 170                 175

Ser Lys His Phe Ser Ser Asp Ala Val Pro His Pro Arg Phe Tyr Cys
            180                 185                 190

Val Leu Ser Pro Glu Ala Ser Glu Asp Asp Leu Asn Arg Leu Asp Ser
        195                 200                 205

Val Ala Cys Asp Val Leu Phe Ser Lys Leu Val Lys Tyr Asp Glu Leu
    210                 215                 220

Tyr Ala Ala Leu Thr Ala Leu Leu Ala Ala Gly Ser Gln Leu Asp Thr
225                 230                 235                 240

Val Arg Arg Lys Glu Asn Lys Asn Val Thr Ala Leu Glu Ala Cys Ala
                245                 250                 255

Leu Gln Tyr Tyr Phe Leu Ile Leu Trp Arg Ile Leu Gly Ile Leu Pro
            260                 265                 270

Pro Ser Lys Thr Tyr Ile Asn Gln Leu Ser Met Asn Ser Pro Glu Met
        275                 280                 285

Ser Glu Cys Asp Ile Leu His Thr Leu Arg Trp Ser Ser Arg Leu Arg
    290                 295                 300

Ile Ser Ser Tyr Val Asn Trp Ile Lys Asp His Leu Ile Lys Gln Gly
305                 310                 315                 320

Met Lys Ala Glu His Ala Ser Ser Leu Leu Glu Leu Ala Ser Thr Thr
                325                 330                 335

Lys Cys Ser Ser Val Lys Tyr Asp Val Glu Ile Val Glu Glu Tyr Phe
```

```
           340             345             350
Ala Arg Gln Ile Ser Ser Phe Cys Ser Ile Asp Cys Thr Thr Ile Leu
        355             360             365

Gln Leu His Glu Ile Pro
        370
```

<210> SEQ ID NO 47
<211> LENGTH: 1422
<212> TYPE: DNA
<213> ORGANISM: Homo sapiens

<400> SEQUENCE: 47

```
attttccaca atttcaccga gacaggccgg cgggccatat tgtcgctttt tgtccagatc    60
atccaggagt tgagcgtcaa catggatgct cagatgcgct tcgtgccgct tatcttggct   120
cgcctccttc tcatctttga ttatctgctt catcagtact ccaaagcccc tgtgtatcta   180
tttgagcagg tacagcataa cctgctaagt cctcccttttg ggtgggcaag tggatcccag   240
gacagcaaca gccgccgggc aaccactcct ctctatcatg gattcaaaga agtagaagaa   300
aactggtcta agcatttctc atcagatgct gtcccacacc ccagattcta ctgtgtcctg   360
tccccagaag cctcagagga tgatttgaac cgacttgatt ctgtggcatg tgacgtcctt   420
ttctccaagc ttgtcaagta tgatgagctt tatgctgcac tgacagccct gcttgcagct   480
gggtcccagc ttgatacagt taggagaaag gaaaacaaga atgtaacagc cttggaggcc   540
tgtgcccttc aatattactt cttgatactg tggaggatcc taggaatttt accaccatca   600
aagacttaca ttaaccagct atccatgaac tcacctgaga tgagcgaatg tgacatcttg   660
cacactctgc gatggtcttc tcggctccgg atcagctcct atgtcaactg gataaaggat   720
caccttatca acagggaat gaaggctgag catgctagct cgcttctaga actggcatcc   780
accactaagt gtagctcagt gaaatatgat gttgaaatag tagaggaata cttcgctcga   840
cagatctcat ccttctgtag tatcgactgt accaccatct gcagctgca tgaaattccc   900
agtctgcagt ccatctacac ccttgatgcc gcgatctcaa aggtccaggt ctctttggat   960
gagcattttt ctaagatggc tgctgagact gatcctcata gtcgtctga gattaccaag  1020
aacctacttc cagccacgct gcaactcatt gacacctatg catcgttcac cagagcctat  1080
ttgctgcaaa actttaatga agagggaaca actgagaaac cttccaagga gaaactgcaa  1140
ggctttgctg ctgttttggc tattggctct agcaggtgca aggcaaatac tctgggtccg  1200
acactggttc agaatttgcc atcgtcagtg cagactgtgt gtgagtcctg gaacaacatc  1260
aataccaatg aatttcccaa tattggatcc tggcgcaatg cctttgccaa tgacaccatc  1320
ccttcagaga gttatattag tgcagtgcag gctgcacacc tggggactct ctgtagccaa  1380
agtctgcccc tggctgcttc cctgaagcat accctcctct ca                    1422
```

<210> SEQ ID NO 48
<211> LENGTH: 474
<212> TYPE: PRT
<213> ORGANISM: Homo sapiens

<400> SEQUENCE: 48

```
Ile Phe His Asn Phe Thr Glu Thr Gly Arg Arg Ala Ile Leu Ser Leu
1               5                  10                  15

Phe Val Gln Ile Ile Gln Glu Leu Ser Val Asn Met Asp Ala Gln Met
            20                  25                  30

Arg Phe Val Pro Leu Ile Leu Ala Arg Leu Leu Leu Ile Phe Asp Tyr
```

```
            35                  40                  45
Leu Leu His Gln Tyr Ser Lys Ala Pro Val Tyr Leu Phe Glu Gln Val
 50                  55                  60

Gln His Asn Leu Leu Ser Pro Pro Phe Gly Trp Ala Ser Gly Ser Gln
65                   70                  75                  80

Asp Ser Asn Ser Arg Arg Ala Thr Thr Pro Leu Tyr His Gly Phe Lys
                85                  90                  95

Glu Val Glu Glu Asn Trp Ser Lys His Phe Ser Ser Asp Ala Val Pro
            100                 105                 110

His Pro Arg Phe Tyr Cys Val Leu Ser Pro Glu Ala Ser Glu Asp Asp
        115                 120                 125

Leu Asn Arg Leu Asp Ser Val Ala Cys Asp Val Leu Phe Ser Lys Leu
    130                 135                 140

Val Lys Tyr Asp Glu Leu Tyr Ala Ala Leu Thr Ala Leu Leu Ala Ala
145                 150                 155                 160

Gly Ser Gln Leu Asp Thr Val Arg Arg Lys Glu Asn Lys Asn Val Thr
                165                 170                 175

Ala Leu Glu Ala Cys Ala Leu Gln Tyr Tyr Phe Leu Ile Leu Trp Arg
            180                 185                 190

Ile Leu Gly Ile Leu Pro Pro Ser Lys Thr Tyr Ile Asn Gln Leu Ser
        195                 200                 205

Met Asn Ser Pro Glu Met Ser Glu Cys Asp Ile Leu His Thr Leu Arg
    210                 215                 220

Trp Ser Ser Arg Leu Arg Ile Ser Ser Tyr Val Asn Trp Ile Lys Asp
225                 230                 235                 240

His Leu Ile Lys Gln Gly Met Lys Ala Glu His Ala Ser Ser Leu Leu
                245                 250                 255

Glu Leu Ala Ser Thr Thr Lys Cys Ser Ser Val Lys Tyr Asp Val Glu
            260                 265                 270

Ile Val Glu Glu Tyr Phe Ala Arg Gln Ile Ser Ser Phe Cys Ser Ile
        275                 280                 285

Asp Cys Thr Thr Ile Leu Gln Leu His Glu Ile Pro Ser Leu Gln Ser
    290                 295                 300

Ile Tyr Thr Leu Asp Ala Ala Ile Ser Lys Val Gln Val Ser Leu Asp
305                 310                 315                 320

Glu His Phe Ser Lys Met Ala Ala Glu Thr Asp Pro His Lys Ser Ser
                325                 330                 335

Glu Ile Thr Lys Asn Leu Leu Pro Ala Thr Leu Gln Leu Ile Asp Thr
            340                 345                 350

Tyr Ala Ser Phe Thr Arg Ala Tyr Leu Leu Gln Asn Phe Asn Glu Glu
        355                 360                 365

Gly Thr Thr Glu Lys Pro Ser Lys Glu Lys Leu Gln Gly Phe Ala Ala
    370                 375                 380

Val Leu Ala Ile Gly Ser Ser Arg Cys Lys Ala Asn Thr Leu Gly Pro
385                 390                 395                 400

Thr Leu Val Gln Asn Leu Pro Ser Ser Val Gln Thr Val Cys Glu Ser
                405                 410                 415

Trp Asn Asn Ile Asn Thr Asn Glu Phe Pro Asn Ile Gly Ser Trp Arg
            420                 425                 430

Asn Ala Phe Ala Asn Asp Thr Ile Pro Ser Glu Ser Tyr Ile Ser Ala
        435                 440                 445

Val Gln Ala Ala His Leu Gly Thr Leu Cys Ser Gln Ser Leu Pro Leu
    450                 455                 460
```

Ala Ala Ser Leu Lys His Thr Leu Leu Ser
465                 470

<210> SEQ ID NO 49
<211> LENGTH: 753
<212> TYPE: DNA
<213> ORGANISM: Homo sapiens

<400> SEQUENCE: 49
tggctgagca gatgcaagaa atacctgtca cagaagaatg tagttgaaaa actgaatgcc      60
aatgtaatgc atggaaagca tgtgatgatc ttggagtgca catgccatat catgtcttac     120
ttggctgatg tcacgaatgc cctgagccag agtaatggtc aaggcccaag tcatctctca     180
gtggatgggg aagagcgggc cattgaagta gactcagact gggtggagga gttgcggtg     240
gaagaggaag attcccaggc tgaggattca gatgaagatt ctctttgcaa taaactctgc     300
acttttacga tcacacagaa agaattcatg aaccagcatt ggtaccactg tcacacctgt     360
aaaatggtgg atggcgtggg tgtctgcaca gtgtgtgcta aggtgtgcca caaggatcat     420
gagatttcct atgccaagta tggatccttc ttctgtgact gtggagccaa ggaagatggc     480
agctgtttgg ctctggtgaa gagaactcct agcagtggca tgagctctac catgaaggag     540
tcggcatttc agagtgaacc caggatttca gagagtctag tgcgtcatgc cagcacctcc     600
tcgccagctg acaaagccaa ggttaccatc agtgatggaa aggttgctga cgaagagaag     660
cccaagaaga gcagcctctg ccgcacagta gagggctgcc gggaggaatt acagaaccag     720
gccaatttct ccttcgctcc tctcgtgtta gac                                  753

<210> SEQ ID NO 50
<211> LENGTH: 251
<212> TYPE: PRT
<213> ORGANISM: Homo sapiens

<400> SEQUENCE: 50

Trp Leu Ser Arg Cys Lys Lys Tyr Leu Ser Gln Lys Asn Val Val Glu
1               5                   10                  15

Lys Leu Asn Ala Asn Val Met His Gly Lys His Val Met Ile Leu Glu
            20                  25                  30

Cys Thr Cys His Ile Met Ser Tyr Leu Ala Asp Val Thr Asn Ala Leu
        35                  40                  45

Ser Gln Ser Asn Gly Gln Gly Pro Ser His Leu Ser Val Asp Gly Glu
    50                  55                  60

Glu Arg Ala Ile Glu Val Asp Ser Asp Trp Val Glu Glu Leu Ala Val
65                  70                  75                  80

Glu Glu Glu Asp Ser Gln Ala Glu Asp Ser Asp Glu Asp Ser Leu Cys
                85                  90                  95

Asn Lys Leu Cys Thr Phe Thr Ile Thr Gln Lys Glu Phe Met Asn Gln
            100                 105                 110

His Trp Tyr His Cys His Thr Cys Lys Met Val Asp Gly Val Gly Val
        115                 120                 125

Cys Thr Val Cys Ala Lys Val Cys His Lys Asp His Glu Ile Ser Tyr
    130                 135                 140

Ala Lys Tyr Gly Ser Phe Phe Cys Asp Cys Gly Ala Lys Glu Asp Gly
145                 150                 155                 160

Ser Cys Leu Ala Leu Val Lys Arg Thr Pro Ser Ser Gly Met Ser Ser
                165                 170                 175

Thr Met Lys Glu Ser Ala Phe Gln Ser Glu Pro Arg Ile Ser Glu Ser
            180                 185                 190

Leu Val Arg His Ala Ser Thr Ser Pro Ala Asp Lys Ala Lys Val
            195                 200                 205

Thr Ile Ser Asp Gly Lys Val Ala Asp Glu Glu Lys Pro Lys Lys Ser
    210                 215                 220

Ser Leu Cys Arg Thr Val Glu Gly Cys Arg Glu Glu Leu Gln Asn Gln
225                 230                 235                 240

Ala Asn Phe Ser Phe Ala Pro Leu Val Leu Asp
            245                 250

<210> SEQ ID NO 51
<211> LENGTH: 1155
<212> TYPE: DNA
<213> ORGANISM: Homo sapiens

<400> SEQUENCE: 51

```
agtgatggaa aggttgctga cgaagagaag cccaagaaga gcagcctctg ccgcacagta      60
gagggctgcc gggaggaatt acagaaccag gccaatttct ccttcgctcc tctcgtgtta     120
gacatgctta atttccttat ggatgccatt cagaccaact tccagcaagc ttcagccgtc     180
gggagcagca gccgtgctca gcaagccctc agtgagctac acactgtgga aaggcagtg     240
gagatgacag accagctgat ggttcccacc ttagggtccc aggaaggtgc ctttgagaat     300
gtgcggatga attacagtgg agaccagggc cagaccatcc ggcagctgat cagtgctcat     360
gtgctcaggc gggtggctat gtgtgtgctc tcctctcccc atgggcgccg ccaacatttg     420
gctgtcagcc atgagaaggg caagatcacc gttctgcagc tctctgcact cctgaagcaa     480
gcagattcca gcaaaaggaa gttaactctg acccgcttgg cttctgcccc agttcctttt     540
actgtgttga gcctcacagg aaatccctgc aaggaagact acttggcggt tgtgggcta     600
aaggactgtc atgtgctcac ctttagtagc tcaggctctg tttcggatca cttggttttg     660
caccctcagt tggcaacggg gaacttcatc atcaaagccg tgtggttacc tggttcacag     720
accgagttat caattgtcac cgcagacttt gttaagattt atgacctgtg tgttgatgcc     780
ttgagtccaa ccttctattt tctcctgcca agctcaaaga taagagatgt taccttcctt     840
ttcaatgagg agggaaagaa catcattgtt ataatgtctt cggctgggta catctatact     900
cagcttatgg aagaggccag cagtgcccag cagggaccct tctatgtcac taatgtgttg     960
gaaatcaatc atgaggacct gaaggacagt aacagccagg tggcgggcgg tggtgtgtcc    1020
gtgtactact cccacgtgtt gcagatgttg ttcttcagct attgtcaagg caaatcattc    1080
gcagccacca tcagcaggac aaccctggag gtgttgcaac tcttccccat caacatcaaa    1140
agttccaatg gtggc                                                    1155
```

<210> SEQ ID NO 52
<211> LENGTH: 385
<212> TYPE: PRT
<213> ORGANISM: Homo sapiens

<400> SEQUENCE: 52

Ser Asp Gly Lys Val Ala Asp Glu Glu Lys Pro Lys Ser Ser Leu
1               5                   10                  15

Cys Arg Thr Val Glu Gly Cys Arg Glu Glu Leu Gln Asn Gln Ala Asn
            20                  25                  30

Phe Ser Phe Ala Pro Leu Val Leu Asp Met Leu Asn Phe Leu Met Asp
        35                  40                  45

```
Ala Ile Gln Thr Asn Phe Gln Gln Ala Ser Ala Val Gly Ser Ser Ser
     50                  55                  60

Arg Ala Gln Gln Ala Leu Ser Glu Leu His Thr Val Glu Lys Ala Val
 65                  70                  75                  80

Glu Met Thr Asp Gln Leu Met Val Pro Thr Leu Gly Ser Gln Glu Gly
                 85                  90                  95

Ala Phe Glu Asn Val Arg Met Asn Tyr Ser Gly Asp Gln Gly Gln Thr
                100                 105                 110

Ile Arg Gln Leu Ile Ser Ala His Val Leu Arg Arg Val Ala Met Cys
            115                 120                 125

Val Leu Ser Ser Pro His Gly Arg Arg Gln His Leu Ala Val Ser His
130                 135                 140

Glu Lys Gly Lys Ile Thr Val Leu Gln Leu Ser Ala Leu Leu Lys Gln
145                 150                 155                 160

Ala Asp Ser Ser Lys Arg Lys Leu Thr Leu Thr Arg Leu Ala Ser Ala
                165                 170                 175

Pro Val Pro Phe Thr Val Leu Ser Leu Thr Gly Asn Pro Cys Lys Glu
                180                 185                 190

Asp Tyr Leu Ala Val Cys Gly Leu Lys Asp Cys His Val Leu Thr Phe
        195                 200                 205

Ser Ser Ser Gly Ser Val Ser Asp His Leu Val Leu His Pro Gln Leu
    210                 215                 220

Ala Thr Gly Asn Phe Ile Ile Lys Ala Val Trp Leu Pro Gly Ser Gln
225                 230                 235                 240

Thr Glu Leu Ser Ile Val Thr Ala Asp Phe Val Lys Ile Tyr Asp Leu
                245                 250                 255

Cys Val Asp Ala Leu Ser Pro Thr Phe Tyr Phe Leu Pro Ser Ser
                260                 265                 270

Lys Ile Arg Asp Val Thr Phe Leu Phe Asn Glu Glu Gly Lys Asn Ile
            275                 280                 285

Ile Val Ile Met Ser Ser Ala Gly Tyr Ile Tyr Thr Gln Leu Met Glu
290                 295                 300

Glu Ala Ser Ser Ala Gln Gln Gly Pro Phe Tyr Val Thr Asn Val Leu
305                 310                 315                 320

Glu Ile Asn His Glu Asp Leu Lys Asp Ser Asn Ser Gln Val Ala Gly
                325                 330                 335

Gly Gly Val Ser Val Tyr Tyr Ser His Val Leu Gln Met Leu Phe Phe
                340                 345                 350

Ser Tyr Cys Gln Gly Lys Ser Phe Ala Ala Thr Ile Ser Arg Thr Thr
        355                 360                 365

Leu Glu Val Leu Gln Leu Phe Pro Ile Asn Ile Lys Ser Ser Asn Gly
    370                 375                 380

Gly
385

<210> SEQ ID NO 53
<211> LENGTH: 924
<212> TYPE: DNA
<213> ORGANISM: Homo sapiens

<400> SEQUENCE: 53
agtgatggaa aggttgctga cgaagagaag cccaagaaga gcagcctctg ccgcacagta      60
gagggctgcc gggaggaatt acagaaccag gccaatttct ccttcgctcc tctcgtgtta     120
```

```
gacatgctta atttccttat ggatgccatt cagaccaact tccagcaagc ttcagccgtc    180
gggagcagca gccgtgctca gcaagccctc agtgagctac acactgtgga aaggcagtg    240 gagatgacag accagctgat ggttcccacc ttagggtccc aggaaggtgc ctttgagaat    300
gtgcggatga attacagtgg agaccagggc cagaccatcc ggcagctgat cagtgctcat    360
gtgctcaggc gggtggctat gtgtgtgctc tcctctcccc atgggcgccg ccaacatttg    420
gctgtcagcc atgagaaggg caagatcacc gttctgcagc tctctgcact cctgaagcaa    480
gcagattcca gcaaaaggaa gttaactctg acccgcttgg cttctgcccc agttcctttt    540
actgtgttga gcctcacagg aaatccctgc aaggaagact acttggcggt tgtgggcta    600 aaggactgtc atgtgctcac ctttagtagc tcaggctctg tttcggatca cttggttttg    660
caccctcagt tggcaacggg gaacttcatc atcaaagccg tgtggttacc tggttcacag    720
accgagttat caattgtcac cgcagacttt gttaagattt atgacctgtg tgttgatgcc    780
ttgagtccaa ccttctattt tctcctgcca agctcaaaga taagagatgt taccttcctt    840
ttcaatgagg agggaaagaa catcattgtt ataatgtctt cggctgggta catctatact    900
cagcttatgg aagaggccag cagt                                           924

<210> SEQ ID NO 54
<211> LENGTH: 308
<212> TYPE: PRT
<213> ORGANISM: Homo sapiens

<400> SEQUENCE: 54

Ser Asp Gly Lys Val Ala Asp Glu Glu Lys Pro Lys Lys Ser Ser Leu
1               5                   10                  15

Cys Arg Thr Val Glu Gly Cys Arg Glu Glu Leu Gln Asn Gln Ala Asn
            20                  25                  30

Phe Ser Phe Ala Pro Leu Val Leu Asp Met Leu Asn Phe Leu Met Asp
        35                  40                  45

Ala Ile Gln Thr Asn Phe Gln Gln Ala Ser Ala Val Gly Ser Ser Ser
    50                  55                  60

Arg Ala Gln Gln Ala Leu Ser Glu Leu His Thr Val Glu Lys Ala Val
65                  70                  75                  80

Glu Met Thr Asp Gln Leu Met Val Pro Thr Leu Gly Ser Gln Glu Gly
                85                  90                  95

Ala Phe Glu Asn Val Arg Met Asn Tyr Ser Gly Asp Gln Gly Gln Thr
            100                 105                 110

Ile Arg Gln Leu Ile Ser Ala His Val Leu Arg Val Ala Met Cys
        115                 120                 125

Val Leu Ser Ser Pro His Gly Arg Arg Gln His Leu Ala Val Ser His
    130                 135                 140

Glu Lys Gly Lys Ile Thr Val Leu Gln Leu Ser Ala Leu Leu Lys Gln
145                 150                 155                 160

Ala Asp Ser Ser Lys Arg Lys Leu Thr Leu Thr Arg Leu Ala Ser Ala
                165                 170                 175

Pro Val Pro Phe Thr Val Leu Ser Leu Thr Gly Asn Pro Cys Lys Glu
            180                 185                 190

Asp Tyr Leu Ala Val Cys Gly Leu Lys Asp Cys His Val Leu Thr Phe
        195                 200                 205

Ser Ser Ser Gly Ser Val Ser Asp His Leu Val Leu His Pro Gln Leu
    210                 215                 220

Ala Thr Gly Asn Phe Ile Ile Lys Ala Val Trp Leu Pro Gly Ser Gln
```

```
                225                 230                 235                 240
Thr Glu Leu Ser Ile Val Thr Ala Asp Phe Val Lys Ile Tyr Asp Leu
                245                 250                 255

Cys Val Asp Ala Leu Ser Pro Thr Phe Tyr Phe Leu Leu Pro Ser Ser
            260                 265                 270

Lys Ile Arg Asp Val Thr Phe Leu Phe Asn Glu Gly Lys Asn Ile
        275                 280                 285

Ile Val Ile Met Ser Ser Ala Gly Tyr Ile Tyr Thr Gln Leu Met Glu
        290                 295                 300

Glu Ala Ser Ser
305

<210> SEQ ID NO 55
<211> LENGTH: 906
<212> TYPE: DNA
<213> ORGANISM: Homo sapiens

<400> SEQUENCE: 55
gccacaacac agtccaagtc ttccactaaa aagagcaaga aagaagaaaa agaaaaggag      60
aaagatggtg agacctctgg cagccaggag gaccagctgt gcacagctct ggtgaaccag     120
ctgaacaaat tgccgataaa ggaaaccctg atccagttcc tgcgttgttt cctgttagag     180
tccaattctt cctcggtgcg ctggcaggcc cactgtctga cactgcacat ctacagaaat     240
tccagcaaat ctcaacagga gctcctgcta gatctgatgt ggtccatctg ccagaactc      300 ccagcctatg tcgtaaggc tgcccagttt gtggacctac taggatattt ctccctgaaa      360
actccacaaa cagagaagaa gttgaaggag tattcacaga aggctgtgga gattctgcgg     420
actcaaaacc atattcttac caaccacccc aactcgaaca tttataacac tttgtctggc     480 ttagtgggagt ttgatggcta ttacctggag agcgatccct gcctggtgtg taataacccg    540
gaagtaccgt tctgttatat caagctgtct tccattaaag tggacacgcg gtacaccacc     600
acccagcagg ttgtgaagct cattggcagt cacaccatca gcaaagtgac agtgaaaatc     660
ggggatctga acggaccaa gatggtgcgg accatcaacc tgtattataa caaccgaacc      720
gtgcaggcca tcgtggagtt gaaaaacaag ccagctcgct ggcacaaagc caagaaggtt     780
cagctgaccc ctggacagac agaggtgaag attgacctgc cgttgcccat tgtggcctcc    840
aatctgatga ttgagtttgc agacttctat gaaaactacc aggcctccac agagaccctg    900
cagtgc                                                                906

<210> SEQ ID NO 56
<211> LENGTH: 302
<212> TYPE: PRT
<213> ORGANISM: Homo sapiens

<400> SEQUENCE: 56

Ala Thr Thr Gln Ser Lys Ser Ser Thr Lys Lys Ser Lys Lys Glu Glu
1               5                   10                  15

Lys Glu Lys Glu Lys Asp Gly Glu Thr Ser Gly Ser Gln Glu Asp Gln
            20                  25                  30

Leu Cys Thr Ala Leu Val Asn Gln Leu Asn Lys Phe Ala Asp Lys Glu
        35                  40                  45

Thr Leu Ile Gln Phe Leu Arg Cys Phe Leu Leu Glu Ser Asn Ser Ser
    50                  55                  60

Ser Val Arg Trp Gln Ala His Cys Leu Thr Leu His Ile Tyr Arg Asn
65                  70                  75                  80
```

```
Ser Ser Lys Ser Gln Gln Glu Leu Leu Leu Asp Leu Met Trp Ser Ile
                85                  90                  95
Trp Pro Glu Leu Pro Ala Tyr Gly Arg Lys Ala Ala Gln Phe Val Asp
            100                 105                 110
Leu Leu Gly Tyr Phe Ser Leu Lys Thr Pro Gln Thr Glu Lys Lys Leu
        115                 120                 125
Lys Glu Tyr Ser Gln Lys Ala Val Glu Ile Leu Arg Thr Gln Asn His
    130                 135                 140
Ile Leu Thr Asn His Pro Asn Ser Asn Ile Tyr Asn Thr Leu Ser Gly
145                 150                 155                 160
Leu Val Glu Phe Asp Gly Tyr Tyr Leu Glu Ser Asp Pro Cys Leu Val
            165                 170                 175
Cys Asn Asn Pro Glu Val Pro Phe Cys Tyr Ile Lys Leu Ser Ser Ile
            180                 185                 190
Lys Val Asp Thr Arg Tyr Thr Thr Thr Gln Gln Val Val Lys Leu Ile
        195                 200                 205
Gly Ser His Thr Ile Ser Lys Val Thr Val Lys Ile Gly Asp Leu Lys
    210                 215                 220
Arg Thr Lys Met Val Arg Thr Ile Asn Leu Tyr Tyr Asn Asn Arg Thr
225                 230                 235                 240
Val Gln Ala Ile Val Glu Leu Lys Asn Lys Pro Ala Arg Trp His Lys
            245                 250                 255
Ala Lys Lys Val Gln Leu Thr Pro Gly Gln Thr Glu Val Lys Ile Asp
            260                 265                 270
Leu Pro Leu Pro Ile Val Ala Ser Asn Leu Met Ile Glu Phe Ala Asp
        275                 280                 285
Phe Tyr Glu Asn Tyr Gln Ala Ser Thr Glu Thr Leu Gln Cys
    290                 295                 300

<210> SEQ ID NO 57
<211> LENGTH: 843
<212> TYPE: DNA
<213> ORGANISM: Homo sapiens

<400> SEQUENCE: 57
gatggtgaga cctctggcag ccaggaggac cagctgtgca cagctctggt gaaccagctg      60
aacaaatttg ccgataagga aaccctgatc cagttcctgc gttgtttcct gttagagtcc     120
aattcttcct cggtgcgctg gcaggccac tgtctgacac tgcacatcta cagaaattcc      180
agcaaatctc aacaggagct cctgctagat ctgatgtggt ccatctggcc agaactccca     240
gcctatggtc gtaaggctgc ccagtttgtg gacctactag atatttctc cctgaaaact      300 ccacaaacag agaagaagtt gaaggagtat tcacagaagg ctgtggagat tctgcggact     360
caaaaccata ttcttaccaa ccaccccaac tcgaacattt ataacacttt gtctggctta     420
gtggagtttg atggctatta cctggagagc gatccctgcc tggtgtgtaa taccccggaa     480
gtaccgttct gttatatcaa gctgtcttcc attaaagtgg acacgcggta caccaccacc     540
cagcaggttg tgaagctcat tggcagtcac accatcagca agtgacagt gaaaatcggg      600 gatctgaaac ggaccaagat ggtgcggacc atcaacctgt attataacaa ccgaaccgtg     660
caggccatcg tggagttgaa aaacaagcca gctcgctggc acaaagccaa gaaggttcag     720 ctgaccctg acagacaga ggtgaagatt gacctgccgt tgcccattgt ggcctccaat       780
ctgatgattg agtttgcaga cttctatgaa aactaccagg cctccacaga gaccctgcag     840
```

<210> SEQ ID NO 58
<211> LENGTH: 281
<212> TYPE: PRT
<213> ORGANISM: Homo sapiens

<400> SEQUENCE: 58

```
Asp Gly Glu Thr Ser Gly Ser Gln Glu Asp Gln Leu Cys Thr Ala Leu
1               5                   10                  15

Val Asn Gln Leu Asn Lys Phe Ala Asp Lys Glu Thr Leu Ile Gln Phe
            20                  25                  30

Leu Arg Cys Phe Leu Leu Glu Ser Asn Ser Ser Val Arg Trp Gln
        35                  40                  45

Ala His Cys Leu Thr Leu His Ile Tyr Arg Asn Ser Ser Lys Ser Gln
    50                  55                  60

Gln Glu Leu Leu Leu Asp Leu Met Trp Ser Ile Trp Pro Glu Leu Pro
65                  70                  75                  80

Ala Tyr Gly Arg Lys Ala Ala Gln Phe Val Asp Leu Leu Gly Tyr Phe
                85                  90                  95

Ser Leu Lys Thr Pro Gln Thr Gly Lys Lys Leu Lys Glu Tyr Ser Gln
            100                 105                 110

Lys Ala Val Glu Ile Leu Arg Thr Gln Asn His Ile Leu Thr Asn His
        115                 120                 125

Pro Asn Ser Asn Ile Tyr Asn Thr Leu Ser Gly Leu Val Glu Phe Asp
    130                 135                 140

Gly Tyr Tyr Leu Glu Ser Asp Pro Cys Leu Val Cys Asn Asn Pro Glu
145                 150                 155                 160

Val Pro Phe Cys Tyr Ile Lys Leu Ser Ser Ile Lys Val Asp Thr Arg
                165                 170                 175

Tyr Thr Thr Thr Gln Gln Val Val Lys Leu Ile Gly Ser His Thr Ile
            180                 185                 190

Ser Lys Val Thr Val Lys Ile Gly Asp Leu Lys Arg Thr Lys Met Val
        195                 200                 205

Arg Thr Ile Asn Leu Tyr Tyr Asn Asn Arg Thr Val Gln Ala Ile Val
    210                 215                 220

Glu Leu Lys Asn Lys Pro Ala Arg Trp His Lys Ala Lys Lys Val Gln
225                 230                 235                 240

Leu Thr Pro Gly Gln Thr Glu Val Lys Ile Asp Leu Pro Leu Pro Ile
                245                 250                 255

Val Ala Ser Asn Leu Met Ile Glu Phe Ala Asp Phe Tyr Glu Asn Tyr
            260                 265                 270

Gln Ala Ser Thr Glu Thr Leu Gln Cys
        275                 280
```

<210> SEQ ID NO 59
<211> LENGTH: 732
<212> TYPE: DNA
<213> ORGANISM: Homo sapiens

<400> SEQUENCE: 59

```
ttagagtcca attcttcctc ggtgcgctgg caggcccact gtctgacact gcacatctac      60
agaaattcca gcaaatctca acaggagctc ctgctagatc tgatgtggtc catctggcca     120
gaactcccag cctatggtcg taaggctgcc cagtttgtgg acctactagg atatttctcc     180
ctgaaaactc cacaaacaga gaagaagttg aaggagtatt cacagaaggc tgtggagatt     240
```

```
ctgcggactc aaaaccatat tcttaccaac cacccccaact cgaacattta taacactttg    300
tctggcttag tggagtttga tggctattac ctggagagcg atccctgcct ggtgtgtaat    360
aacccggaag taccgttctg ttatatcaag ctgtcttcca ttaaagtgga cacgcggtac    420
accaccaccc agcaggttgt gaagctcatt ggcagtcaca ccatcagcaa agtgacagtg    480
aaaatcgggg atctgaaacg gaccaagatg gtgcggacca tcaacctgta ttataacaac    540
cgaaccgtgc aggccatcgt ggagttgaaa aacaagccag ctcgctggca caaagccaag    600
aaggttcagc tgacccctgg acagacagag gtgaagattg acctgccgtt gcccattgtg    660
gcctccaatc tgatgattga gtttgcagac ttctatgaaa actaccaggc ctccacagag    720
accctgcagt gc                                                        732
```

<210> SEQ ID NO 60
<211> LENGTH: 244
<212> TYPE: PRT
<213> ORGANISM: Homo sapiens

<400> SEQUENCE: 60

```
Leu Glu Ser Asn Ser Ser Val Arg Trp Gln Ala His Cys Leu Thr
1               5                   10                  15

Leu His Ile Tyr Arg Asn Ser Lys Ser Gln Gln Glu Leu Leu Leu
                20                  25                  30

Asp Leu Met Trp Ser Ile Trp Pro Glu Leu Pro Ala Tyr Gly Arg Lys
            35                  40                  45

Ala Ala Gln Phe Val Asp Leu Leu Gly Tyr Phe Ser Leu Lys Thr Pro
        50                  55                  60

Gln Thr Glu Lys Lys Leu Lys Glu Tyr Ser Gln Lys Ala Val Glu Ile
65                  70                  75                  80

Leu Arg Thr Gln Asn His Ile Leu Thr Asn His Pro Asn Ser Asn Ile
                85                  90                  95

Tyr Asn Thr Leu Ser Gly Leu Val Glu Phe Asp Gly Tyr Tyr Leu Glu
            100                 105                 110

Ser Asp Pro Cys Leu Val Cys Asn Asn Pro Glu Val Pro Phe Cys Tyr
        115                 120                 125

Ile Lys Leu Ser Ser Ile Lys Val Asp Thr Arg Tyr Thr Thr Thr Gln
    130                 135                 140

Gln Val Val Lys Leu Ile Gly Ser His Thr Ile Ser Lys Val Thr Val
145                 150                 155                 160

Lys Ile Gly Asp Leu Lys Arg Thr Lys Met Val Arg Thr Ile Asn Leu
                165                 170                 175

Tyr Tyr Asn Asn Arg Thr Val Gln Ala Ile Val Glu Leu Lys Asn Lys
            180                 185                 190

Pro Ala Arg Trp His Lys Ala Lys Lys Val Gln Leu Thr Pro Gly Gln
        195                 200                 205

Thr Glu Val Lys Ile Asp Leu Pro Leu Pro Ile Val Ala Ser Asn Leu
    210                 215                 220

Met Ile Glu Phe Ala Asp Phe Tyr Glu Asn Tyr Gln Ala Ser Thr Glu
225                 230                 235                 240

Thr Leu Gln Cys
```

<210> SEQ ID NO 61
<211> LENGTH: 1236
<212> TYPE: DNA
<213> ORGANISM: Homo sapiens

<400> SEQUENCE: 61

```
tgtaataacc cggaagtacc gttctgttat atcaagctgt cttccattaa agtggacacg      60
cggtacacca ccacccagca ggttgtgaag ctcattggca gtcacaccat cagcaaagtg     120
acagtgaaaa tcggggatct gaaacggacc aagatggtgc ggaccatcaa cctgtattat     180
aacaaccgaa ccgtgcaggc catcgtggag ttgaaaaaca agccagctcg ctggcacaaa     240
gccaagaagg ttcagctgac ccctggacag acagaggtga agattgacct gccgttgccc     300
attgtggcct ccaatctgat gattgagttt gcagacttct atgaaaacta ccaggcctcc     360
acagagaccc tgcagtgccc tcgctgtagt gcctcggtcc ctgccaaccc aggagtctgt     420
ggcaactgtg gagagaatgt gtaccagtgt cacaaatgca gatccatcaa ctacgatgaa     480
aaggatccct cctctgcaa tgcctgtggc ttctgtaaat atgcccgctt cgacttcatg     540
ctctatgcca agccttgctg tgcagtggat cccattgaga atgaagaaga ccggaagaag     600
gctgtatcca acatcaatac acttttggac aaagctgatc gagtgtatca tcagctgatg     660
ggacaccggc cacagctgga gaacctgctc tgcaaagtga atgaggcagc tccagaaaag     720
ccacaggatg actcaggaac agcagggggc atcagctcca cttctgccag tgtgaatcgt     780
tacatcctgc agttggctca ggagtattgt ggagactgca agaactcttt tgatgaactc     840
tccaaaatca tccagaaagt ctttgcttcg cgcaaagagt tgttggaata tgacctacag     900
cagagggaag cagccactaa atcatcccgg acctccgtgc agcccacatt cactgccagc     960
cagtaccgtg ccttatccgt cctgggctgt ggccacacat cctccaccaa gtgctatggc    1020
tgcgcctcgg ctgtcacaga acattgtatc acactacttc gggccctggc caccaaccca    1080
gccttgaggc acatccttgt ctcccagggc cttatccggg agctctttga ttataatctt    1140
cgccgagggg ctgcggccat gcgggaggag gtccgccagc tcatgtgcct cctaactcga    1200
gacaacccag aagccaccca acagatgaat gacctg                               1236
```

<210> SEQ ID NO 62
<211> LENGTH: 412
<212> TYPE: PRT
<213> ORGANISM: Homo sapiens

<400> SEQUENCE: 62

```
Cys Asn Asn Pro Glu Val Pro Phe Cys Tyr Ile Lys Leu Ser Ser Ile
  1               5                  10                  15

Lys Val Asp Thr Arg Tyr Thr Thr Thr Gln Gln Val Val Lys Leu Ile
                 20                  25                  30

Gly Ser His Thr Ile Ser Lys Val Thr Val Lys Ile Gly Asp Leu Lys
             35                  40                  45

Arg Thr Lys Met Val Arg Thr Ile Asn Leu Tyr Tyr Asn Asn Arg Thr
         50                  55                  60

Val Gln Ala Ile Val Glu Leu Lys Asn Lys Pro Ala Arg Trp His Lys
 65                  70                  75                  80

Ala Lys Lys Val Gln Leu Thr Pro Gly Gln Thr Glu Val Lys Ile Asp
                 85                  90                  95

Leu Pro Leu Pro Ile Val Ala Ser Asn Leu Met Ile Glu Phe Ala Asp
                100                 105                 110

Phe Tyr Glu Asn Tyr Gln Ala Ser Thr Glu Thr Leu Gln Cys Pro Arg
            115                 120                 125

Cys Ser Ala Ser Val Pro Ala Asn Pro Gly Val Cys Gly Asn Cys Gly
        130                 135                 140
```

```
Glu Asn Val Tyr Gln Cys His Lys Cys Arg Ser Ile Asn Tyr Asp Glu
145                 150                 155                 160

Lys Asp Pro Phe Leu Cys Asn Ala Cys Gly Phe Cys Lys Tyr Ala Arg
            165                 170                 175

Phe Asp Phe Met Leu Tyr Ala Lys Pro Cys Cys Ala Val Asp Pro Ile
        180                 185                 190

Glu Asn Glu Glu Asp Arg Lys Lys Ala Val Ser Asn Ile Asn Thr Leu
    195                 200                 205

Leu Asp Lys Ala Asp Arg Val Tyr His Gln Leu Met Gly His Arg Pro
210                 215                 220

Gln Leu Glu Asn Leu Leu Cys Lys Val Asn Glu Ala Ala Pro Glu Lys
225                 230                 235                 240

Pro Gln Asp Asp Ser Gly Thr Ala Gly Gly Ile Ser Ser Thr Ser Ala
                245                 250                 255

Ser Val Asn Arg Tyr Ile Leu Gln Leu Ala Gln Glu Tyr Cys Gly Asp
            260                 265                 270

Cys Lys Asn Ser Phe Asp Glu Leu Ser Lys Ile Ile Gln Lys Val Phe
        275                 280                 285

Ala Ser Arg Lys Glu Leu Leu Glu Tyr Asp Leu Gln Gln Arg Glu Ala
    290                 295                 300

Ala Thr Lys Ser Ser Arg Thr Ser Val Gln Pro Thr Phe Thr Ala Ser
305                 310                 315                 320

Gln Tyr Arg Ala Leu Ser Val Leu Gly Cys Gly His Thr Ser Ser Thr
                325                 330                 335

Lys Cys Tyr Gly Cys Ala Ser Ala Val Thr Glu His Cys Ile Thr Leu
            340                 345                 350

Leu Arg Ala Leu Ala Thr Asn Pro Ala Leu Arg His Ile Leu Val Ser
        355                 360                 365

Gln Gly Leu Ile Arg Glu Leu Phe Asp Tyr Asn Leu Arg Arg Gly Ala
    370                 375                 380

Ala Ala Met Arg Glu Glu Val Arg Gln Leu Met Cys Leu Leu Thr Arg
385                 390                 395                 400

Asp Asn Pro Glu Ala Thr Gln Gln Met Asn Asp Leu
                405                 410

<210> SEQ ID NO 63
<211> LENGTH: 1026
<212> TYPE: DNA
<213> ORGANISM: Homo sapiens

<400> SEQUENCE: 63
cccttcctct gcaatgcctg tggcttctgt aaatatgccc gcttcgactt catgctctat       60
gccaagcctt gctgtgcagt ggatcccatt gagaatgaag aagaccggaa gaaggctgta      120
tccaacatca atacactttt ggacaaagct gatcgagtgt atcatcagct gatgggacac      180
cggccacagc tggagaacct gctctgcaaa gtgaatgagg cagctccaga aaagccacag      240
gatgactcag gaacagcagg gggcatcagc tccacttctg ccagtgtgaa tcgttacatc      300
ctgcagttgg ctcaggagta ttgtggagac tgcaagaact ttttgatga actctccaaa       360 atcatccaga aagtctttgc ttcgcgcaaa gagttgttgg aatatgacct acagcagagg      420
gaagcagcca ctaaatcatc ccggacctcc gtgcagccca cattcactgc agccagtac       480 cgtgccttat ccgtcctggg ctgtggccac acatcctcca ccaagtgcta tggctgcgcc      540
tcggctgtca cagaacattg tatcacacta cttcgggccc tggccaccaa cccagccttg      600
```

```
aggcacatcc ttgtctccca gggccttatc cgggagctct tgattataa tcttcgccga    660 ggggctgcgg ccatgcggga ggaggtccgc cagctcatgt gcctcctaac tcgagacaac    720
ccagaagcca cccaacagat gaatgacctg attattggca aggtctccac agccctgaag    780
agccactggg ccaaccccga tctggcaagt agcctgcagt atgaaatgct gctgctgacg    840
gattctatct ccaaggagga cagctgctgg gagctccggt tacgctgtgc tctcagcctt    900
ttcctcatgg ctgtgaacat taagactcct gtggtggttg aaaacattac cctcatgtgc    960
ctgaggatct tgcagaagct gataaaacca cctgctccca ctagcaagaa gaacaaggat   1020
gtcccc                                                              1026
```

<210> SEQ ID NO 64
<211> LENGTH: 342
<212> TYPE: PRT
<213> ORGANISM: Homo sapiens

<400> SEQUENCE: 64

```
Pro Phe Leu Cys Asn Ala Cys Gly Phe Cys Lys Tyr Ala Arg Phe Asp
 1               5                  10                  15

Phe Met Leu Tyr Ala Lys Pro Cys Cys Ala Val Asp Pro Ile Glu Asn
            20                  25                  30

Glu Glu Asp Arg Lys Lys Ala Val Ser Asn Ile Asn Thr Leu Leu Asp
        35                  40                  45

Lys Ala Asp Arg Val Tyr His Gln Leu Met Gly His Arg Pro Gln Leu
    50                  55                  60

Glu Asn Leu Leu Cys Lys Val Asn Glu Ala Ala Pro Glu Lys Pro Gln
65                  70                  75                  80

Asp Asp Ser Gly Thr Ala Gly Gly Ile Ser Ser Thr Ser Ala Ser Val
                85                  90                  95

Asn Arg Tyr Ile Leu Gln Leu Ala Gln Glu Tyr Cys Gly Asp Cys Lys
            100                 105                 110

Asn Ser Phe Asp Glu Leu Ser Lys Ile Ile Gln Lys Val Phe Ala Ser
        115                 120                 125

Arg Lys Glu Leu Leu Glu Tyr Asp Leu Gln Gln Arg Glu Ala Ala Thr
    130                 135                 140

Lys Ser Ser Arg Thr Ser Val Gln Pro Thr Phe Thr Ala Ser Gln Tyr
145                 150                 155                 160

Arg Ala Leu Ser Val Leu Gly Cys Gly His Thr Ser Thr Lys Cys
                165                 170                 175

Tyr Gly Cys Ala Ser Ala Val Thr Glu His Cys Ile Thr Leu Leu Arg
            180                 185                 190

Ala Leu Ala Thr Asn Pro Ala Leu Arg His Ile Leu Val Ser Gln Gly
        195                 200                 205

Leu Ile Arg Glu Leu Phe Asp Tyr Asn Leu Arg Arg Gly Ala Ala Ala
    210                 215                 220

Met Arg Glu Glu Val Arg Gln Leu Met Cys Leu Leu Thr Arg Asp Asn
225                 230                 235                 240

Pro Glu Ala Thr Gln Gln Met Asn Asp Leu Ile Ile Gly Lys Val Ser
                245                 250                 255

Thr Ala Leu Lys Ser His Trp Ala Asn Pro Asp Leu Ala Ser Ser Leu
            260                 265                 270

Gln Tyr Glu Met Leu Leu Leu Thr Asp Ser Ile Ser Lys Glu Asp Ser
        275                 280                 285
```

```
Cys Trp Glu Leu Arg Leu Arg Cys Ala Leu Ser Leu Phe Leu Met Ala
    290                 295                 300

Val Asn Ile Lys Thr Pro Val Val Val Glu Asn Ile Thr Leu Met Cys
305                 310                 315                 320

Leu Arg Ile Leu Gln Lys Leu Ile Lys Pro Pro Ala Pro Thr Ser Lys
                325                 330                 335

Lys Asn Lys Asp Val Pro
            340

<210> SEQ ID NO 65
<211> LENGTH: 1776
<212> TYPE: DNA
<213> ORGANISM: Homo sapiens

<400> SEQUENCE: 65
```

| | | |
|---|---|---|
| tttgattata atcttcgccg aggggctgcg gccatgcggg aggaggtccg ccagctcatg | 60 |
| tgcctcctaa ctcgagacaa cccagaagcc acccaacaga tgaatgacct gattattggc | 120 |
| aaggtctcca cagccctgaa gagccactgg gccaaccccg atctggcaag tagcctgcag | 180 |
| tatgaaatgc tgctgctgac ggattctatc tccaaggagg acagctgctg ggagctccgg | 240 |
| ttacgctgtg ctctcagcct ttttcctcatg gctgtgaaca ttaagactcc tgtggtggtt | 300 |
| gaaaacatta ccctcatgtg cctgaggatc ttgcagaagc tgataaaacc acctgctccc | 360 |
| actagcaaga gaacaaggga tgtccccgtc gaggccctca ccacggtgaa gccatactgc | 420 |
| aatgagatcc atgcccaggc tcaactgtgg ctcaagagag accccaaggc atcctatgat | 480 |
| gcctggaaga agtgtcttcc tatcagaggg atagatggca atgggaaagc ccccagcaaa | 540 |
| tcagagctcc gccatctcta tttgactgag aagtatgtgt ggaggtggaa acagttcctg | 600 |
| agtcgtcggg ggaagaggac ctccccccttg gatctcaaac tggggcataa caactggctg | 660 |
| cgacaagtgc ttttcactcc agcaacgcag gccgcacggc aggcagcctg taccattgtg | 720 |
| gaagctctag ccaccattcc cagccgcaag cagcaggtcc tggacctgct taccagttac | 780 |
| ctggatgagc tgagcatagc tggggagtgt gcagctgagt acctggctct ctaccagaag | 840 |
| ctcatcactt ctgcgcactg gaaagtctac ttggcagctc ggggagtcct acccctatgtg | 900 |
| ggcaacctca tcaccaagga aatagctcgt ctgctggccc tggaggaggc tacccctgagt | 960 |
| accgatctgc agcagggtta tgcccttaaa agtctcacag gccttctctc ctcctttgtt | 1020 |
| gaggtggaat ccatcaaaag acattttaaa agtcgcttgg tgggtactgt gctgaatgga | 1080 |
| tacctgtgct tgcggaagct ggtggtgcag aggaccaagc tgatcgatga gacgcaggac | 1140 |
| atgctgctgg agatgctgga ggacatgacc acaggtacag aatcagaaac caaggccttc | 1200 |
| atggctgtgt gcattgagac agccaagcgc tacaatctgg atgactaccg gaccccggtg | 1260 |
| ttcatcttcg agaggctctg cagcatcatt tatcctgagg agaatgaagt cactgagttc | 1320 |
| tttgtgaccc tggagaagga tccccaacaa gaagacttct tacagggcag gatgcctggg | 1380 |
| aacccgtata gcagcaatga gccaggcatc gggccgctga tgaggatat aaagaacaag | 1440 |
| atttgccagg actgtgactt agtggccctc ctggaagatg acagtggcat ggagcttcta | 1500 |
| gtgaacaata aaatcattag tttgaccctt cctgtggctg aagtttacaa gaaagtctgg | 1560 |
| tgtaccacga atgagggaga gcccatgagg attgtttatc gtatgcgggg gctgctgggc | 1620 |
| gatgccacag aggagttcat tgagtccctg gactctacta cagatgaaga agaagatgaa | 1680 |
| gaagaagtgt ataaaatggc tggtgtgatg gcccagtgtg ggggcctgga atgcatgctt | 1740 |
| aacagactcg cagggatcag agatttcaag caggga | 1776 |

<210> SEQ ID NO 66
<211> LENGTH: 592
<212> TYPE: PRT
<213> ORGANISM: Homo sapiens

<400> SEQUENCE: 66

```
Phe Asp Tyr Asn Leu Arg Arg Gly Ala Ala Met Arg Glu Glu Val
1               5                   10                  15

Arg Gln Leu Met Cys Leu Leu Thr Arg Asp Asn Pro Glu Ala Thr Gln
                20                  25                  30

Gln Met Asn Asp Leu Ile Ile Gly Lys Val Ser Thr Ala Leu Lys Ser
            35                  40                  45

His Trp Ala Asn Pro Asp Leu Ala Ser Ser Leu Gln Tyr Glu Met Leu
        50                  55                  60

Leu Leu Thr Asp Ser Ile Ser Lys Glu Asp Ser Cys Trp Glu Leu Arg
65                  70                  75                  80

Leu Arg Cys Ala Leu Ser Leu Phe Leu Met Ala Val Asn Ile Lys Thr
                85                  90                  95

Pro Val Val Glu Asn Ile Thr Leu Met Cys Leu Arg Ile Leu Gln
                100                 105                 110

Lys Leu Ile Lys Pro Pro Ala Pro Thr Ser Lys Lys Asn Lys Asp Val
            115                 120                 125

Pro Val Glu Ala Leu Thr Thr Val Lys Pro Tyr Cys Asn Glu Ile His
        130                 135                 140

Ala Gln Ala Gln Leu Trp Leu Lys Arg Asp Pro Lys Ala Ser Tyr Asp
145                 150                 155                 160

Ala Trp Lys Lys Cys Leu Pro Ile Arg Gly Ile Asp Gly Asn Gly Lys
                165                 170                 175

Ala Pro Ser Lys Ser Glu Leu Arg His Leu Tyr Leu Thr Glu Lys Tyr
            180                 185                 190

Val Trp Arg Trp Lys Gln Phe Leu Ser Arg Arg Gly Lys Arg Thr Ser
        195                 200                 205

Pro Leu Asp Leu Lys Leu Gly His Asn Asn Trp Leu Arg Gln Val Leu
210                 215                 220

Phe Thr Pro Ala Thr Gln Ala Ala Arg Gln Ala Ala Cys Thr Ile Val
225                 230                 235                 240

Glu Ala Leu Ala Thr Ile Pro Ser Arg Lys Gln Gln Val Leu Asp Leu
                245                 250                 255

Leu Thr Ser Tyr Leu Asp Glu Leu Ser Ile Ala Gly Glu Cys Ala Ala
            260                 265                 270

Glu Tyr Leu Ala Leu Tyr Gln Lys Leu Ile Thr Ser Ala His Trp Lys
        275                 280                 285

Val Tyr Leu Ala Ala Arg Gly Val Leu Pro Tyr Val Gly Asn Leu Ile
    290                 295                 300

Thr Lys Glu Ile Ala Arg Leu Leu Ala Leu Glu Ala Thr Leu Ser
305                 310                 315                 320

Thr Asp Leu Gln Gln Gly Tyr Ala Leu Lys Ser Leu Thr Gly Leu Leu
                325                 330                 335

Ser Ser Phe Val Glu Val Glu Ser Ile Lys Arg His Phe Lys Ser Arg
            340                 345                 350

Leu Val Gly Thr Val Leu Asn Gly Tyr Leu Cys Leu Arg Lys Leu Val
        355                 360                 365

Val Gln Arg Thr Lys Leu Ile Asp Glu Thr Gln Asp Met Leu Leu Glu
```

```
                370               375               380
Met Leu Glu Asp Met Thr Thr Gly Thr Glu Ser Glu Thr Lys Ala Phe
385               390               395               400

Met Ala Val Cys Ile Glu Thr Ala Lys Arg Tyr Asn Leu Asp Asp Tyr
                405               410               415

Arg Thr Pro Val Phe Ile Phe Glu Arg Leu Cys Ser Ile Ile Tyr Pro
            420               425               430

Glu Glu Asn Glu Val Thr Glu Phe Phe Val Thr Leu Glu Lys Asp Pro
        435               440               445

Gln Gln Glu Asp Phe Leu Gln Gly Arg Met Pro Gly Asn Pro Tyr Ser
    450               455               460

Ser Asn Glu Pro Gly Ile Gly Pro Leu Met Arg Asp Ile Lys Asn Lys
465               470               475               480

Ile Cys Gln Asp Cys Asp Leu Val Ala Leu Leu Glu Asp Asp Ser Gly
                485               490               495

Met Glu Leu Leu Val Asn Asn Lys Ile Ile Ser Leu Asp Leu Pro Val
            500               505               510

Ala Glu Val Tyr Lys Lys Val Trp Cys Thr Thr Asn Glu Gly Glu Pro
        515               520               525

Met Arg Ile Val Tyr Arg Met Arg Gly Leu Leu Gly Asp Ala Thr Glu
    530               535               540

Glu Phe Ile Glu Ser Leu Asp Ser Thr Thr Asp Glu Glu Glu Asp Glu
545               550               555               560

Glu Glu Val Tyr Lys Met Ala Gly Val Met Ala Gln Cys Gly Gly Leu
                565               570               575

Glu Cys Met Leu Asn Arg Leu Ala Gly Ile Arg Asp Phe Lys Gln Gly
            580               585               590

<210> SEQ ID NO 67
<211> LENGTH: 1410
<212> TYPE: DNA
<213> ORGANISM: Homo sapiens

<400> SEQUENCE: 67
gtgaccctgg agaaggatcc ccaacaagaa gacttcttac agggcaggat gcctgggaac      60
ccgtatagca gcaatgagcc aggcatcggg ccgctgatga gggatataaa gaacaagatt     120
tgccaggact gtgacttagt ggccctcctg gaagatgaca gtggcatgga gcttctagtg     180
aacaataaaa tcattagttt ggaccttcct gtggctgaag tttacaagaa agtctggtgt     240
accacgaatg agggagagcc catgaggatt gtttatcgta tgcgggggct gctgggcgat     300
gccacagagg agttcattga gtccctggac tctactacag atgaagaaga agatgaagaa     360
gaagtgtata aaatggctgg tgtgatggcc cagtgtgggg gcctggaatg catgcttaac     420
agactcgcag ggatcagaga tttcaagcag ggacgccacc ttctaacagt gctactgaaa     480
ttgttcagtt actgcgtgaa ggtgaaagtc aaccggcagc aactggtcaa actgaaaatg     540
aacaccttga acgtcatgct ggggacccta aacctggccc ttgtagctga acaagaaagc     600
aaggacagtg ggggtgcagc tgtggctgag caggtgctta gcatcatgga gatcattcta     660
gatgagtcca atgctgagcc cctgagtgag acaagggca acctcctcct gacaggtgac     720
aaggatcaac tggtgatgct cttggaccag atcaacagca cctttgttcg ctccaacccc     780
agtgtgctcc agggcctgct tcgcatcatc ccgtaccttt cctttggaga ggtggagaaa     840
atgcagatct tggtggagcg attcaaacca tactgcaact ttgataaata tgatgaagat     900
```

-continued

```
cacagtggtg atgataaagt cttcctggac tgcttctgta aaatagctgc tggcatcaag    960
aacaacagca atgggcacca gctgaaggat ctgattctcc agaagggggat cacccagaat   1020 gcacttgact acatgaaaaa gcacatccct agcgccaaga atttggatgc cgacatctgg   1080
aaaaagtttt tgtctcgccc agccttgcca tttatcctaa ggctgcttcg ggcctggcc    1140 atccagcacc ctggcaccca ggttctgatt ggaactgatt ccatcccgaa cctgcataag   1200
ctggagcagg tgtccagtga tgagggcatt gggaccttgg cagagaacct gctgaagcc    1260 ctgcgggaac accctgacgt aaacaagaag attgacgcag cccgcaggga gacccgggca   1320
gagaagaaac gcatggccat ggcaatgagg cagaaggccc tgggcaccct gggcatgacg   1380
acaaatgaaa agggccaggt cgtgaccaag                                     1410
```

<210> SEQ ID NO 68
<211> LENGTH: 470
<212> TYPE: PRT
<213> ORGANISM: Homo sapiens

<400> SEQUENCE: 68

```
Val Thr Leu Glu Lys Asp Pro Gln Gln Glu Asp Phe Leu Gln Gly Arg
1               5                   10                  15

Met Pro Gly Asn Pro Tyr Ser Ser Glu Pro Gly Ile Gly Pro Leu
            20                  25                  30

Met Arg Asp Ile Lys Asn Lys Ile Cys Gln Asp Cys Asp Leu Val Ala
        35                  40                  45

Leu Leu Glu Asp Asp Ser Gly Met Glu Leu Leu Val Asn Asn Lys Ile
    50                  55                  60

Ile Ser Leu Asp Leu Pro Val Ala Glu Val Tyr Lys Lys Val Trp Cys
65                  70                  75                  80

Thr Thr Asn Glu Gly Glu Pro Met Arg Ile Val Tyr Arg Met Arg Gly
                85                  90                  95

Leu Leu Gly Asp Ala Thr Glu Glu Phe Ile Glu Ser Leu Asp Ser Thr
            100                 105                 110

Thr Asp Glu Glu Glu Asp Glu Glu Val Tyr Lys Met Ala Gly Val
        115                 120                 125

Met Ala Gln Cys Gly Gly Leu Glu Cys Met Leu Asn Arg Leu Ala Gly
    130                 135                 140

Ile Arg Asp Phe Lys Gln Gly Arg His Leu Leu Thr Val Leu Leu Lys
145                 150                 155                 160

Leu Phe Ser Tyr Cys Val Lys Val Lys Val Asn Arg Gln Gln Leu Val
                165                 170                 175

Lys Leu Glu Met Asn Thr Leu Asn Val Met Leu Gly Thr Leu Asn Leu
            180                 185                 190

Ala Leu Ala Glu Gln Glu Ser Lys Asp Ser Gly Gly Ala Ala Val
        195                 200                 205

Ala Glu Gln Val Leu Ser Ile Met Glu Ile Ile Leu Asp Glu Ser Asn
    210                 215                 220

Ala Glu Pro Leu Ser Glu Asp Lys Gly Asn Leu Leu Leu Thr Gly Asp
225                 230                 235                 240

Lys Asp Gln Leu Val Met Leu Asp Gln Ile Asn Ser Thr Phe Val
                245                 250                 255

Arg Ser Asn Pro Ser Val Leu Gln Gly Leu Leu Arg Ile Ile Pro Tyr
            260                 265                 270

Leu Ser Phe Gly Glu Val Glu Lys Met Gln Ile Leu Val Glu Arg Phe
        275                 280                 285
```

```
Lys Pro Tyr Cys Asn Phe Asp Lys Tyr Asp Glu Asp His Ser Gly Asp
            290                 295                 300

Asp Lys Val Phe Leu Asp Cys Phe Cys Lys Ile Ala Ala Gly Ile Lys
305                 310                 315                 320

Asn Asn Ser Asn Gly His Gln Leu Lys Asp Leu Ile Leu Gln Lys Gly
                325                 330                 335

Ile Thr Gln Asn Ala Leu Asp Tyr Met Lys Lys His Ile Pro Ser Ala
            340                 345                 350

Lys Asn Leu Asp Ala Asp Ile Trp Lys Lys Phe Leu Ser Arg Pro Ala
            355                 360                 365

Leu Pro Phe Ile Leu Arg Leu Arg Gly Leu Ala Ile Gln His Pro
            370                 375                 380

Gly Thr Gln Val Leu Ile Gly Thr Asp Ser Ile Pro Asn Leu His Lys
385                 390                 395                 400

Leu Glu Gln Val Ser Ser Asp Glu Gly Ile Gly Thr Leu Ala Glu Asn
                405                 410                 415

Leu Leu Glu Ala Leu Arg Glu His Pro Asp Val Asn Lys Lys Ile Asp
            420                 425                 430

Ala Ala Arg Arg Glu Thr Arg Ala Glu Lys Lys Arg Met Ala Met Ala
            435                 440                 445

Met Arg Gln Lys Ala Leu Gly Thr Leu Gly Met Thr Thr Asn Glu Lys
450                 455                 460

Gly Gln Val Val Thr Lys
465                 470

<210> SEQ ID NO 69
<211> LENGTH: 2250
<212> TYPE: DNA
<213> ORGANISM: Homo sapiens

<400> SEQUENCE: 69
tttgattata atcttcgccg agggctgcg gccatgcggg aggaggtccg ccagctcatg      60
tgcctcctaa ctcgagacaa cccagaagcc acccaacaga tgaatgacct gattattggc    120
aaggtctcca cagccctgaa gagccactgg gccaaccccg atctggcaag tagcctgcag    180
tatgaaatgc tgctgctgac ggattctatc tccaaggagg acagctgctg ggagctccgg    240
ttacgctgtg ctctcagcct tttcctcatg gctgtgaaca ttaagactcc tgtggtggtt    300
gaaaacatta ccctcatgtg cctgaggatc ttgcagaagc tgataaaacc acctgctccc    360
actagcaaga agaacaagga tgtccccgtc gaggccctca ccacggtgaa gccatactgc    420
aatgagatcc atgcccaggc tcaactgtgg ctcaagagag accccaaggc atcctatgat    480
gcctggaaga agtgtcttcc tatcagaggg atagatggca atgggaaagc ccccagcaaa    540
tcagagctcc gccatctcta tttgactgag aagtatgtgt ggaggtggaa acagttcctg    600
agtcgtcggg ggaagaggac ctccccttg atctcaaac tggggcataa caactggctg      660
cgacaagtgc ttttcactcc agcaacgcag gccgcacggc aggcagcctg taccattgtg    720
gaagctctag ccaccattcc cagccgcaag cagcaggtcc tggacctgct taccagttac    780
ctggatgagc tgagcatagc tggggagtgt gcagctgagt acctggctct ctaccagaag    840
ctcatcactt ctgcgcactg gaaagtctac ttggcagctc ggggagtcct accctatgtg    900
ggcaacctca tcaccaagga aatagctcgt ctgctggccc tggaggaggc tacccctgagt    960 accgatctgc agcagggtta tgcccttaaa agtctcacag gccttctctc ctcctttgtt   1020
```

| | |
|---|---|
| gaggtggaat ccatcaaaag acattttaaa agtcgcttgg tgggtactgt gctgaatgga | 1080 |
| tacctgtgct tgcggaagct ggtggtgcag aggaccaagc tgatcgatga dacgcaggac | 1140 |
| atgctgctgg agatgctgga ggacatgacc acaggtacag aatcagaaac caaggccttc | 1200 |
| atggctgtgt gcattgagac agccaagcgc tacaatctgg atgactaccg dacccccggtg | 1260 |
| ttcatcttcg agaggctctg cagcatcatt tatcctgagg agaatgaagt cactgagttc | 1320 |
| tttgtgaccc tggagaagga tccccaacaa gaagacttct tacagggcag gatgcctggg | 1380 |
| aacccgtata gcagcaatga ccaggcatc gggccgctga tgagggatat aaagaacaag | 1440 |
| atttgccagg actgtgactt agtggccctc ctggaagatg acagtggcat ggagcttcta | 1500 |
| gtgaacaata aaatcattag tttggacctt cctgtggctg aagtttacaa gaaagtctgg | 1560 |
| tgtaccacga atgagggaga gcccatgagg attgtttatc gtatgcgggg gctgctgggc | 1620 |
| gatgccacag aggagttcat tgagtccctg gactctacta cagatgaaga agaagatgaa | 1680 |
| gaagaagtgt ataaaatggc tggtgtgatg gcccagtgtg ggggcctgga atgcatgctt | 1740 |
| aacagactcg cagggatcag agatttcaag cagggacgcc accttctaac agtgctactg | 1800 |
| aaattgttca gttactgcgt gaaggtgaaa gtcaaccggc agcaactggt caaactggaa | 1860 |
| atgaacacct tgaacgtcat gctggggacc ctaaacctgg cccttgtagc tgaacaagaa | 1920 |
| agcaaggaca gtgggggtgc agctgtggct gagcaggtgc ttagcatcat ggagatcatt | 1980 |
| ctagatgagt ccaatgctga gcccctgagt gaggacaagg gcaacctcct cctgacaggt | 2040 |
| gacaaggatc aactggtgat gctcttggac cagatcaaca gcacctttgt tcgctccaac | 2100 |
| cccagtgtgc tccagggcct gcttcgcatc atcccgtacc tttcctttgg agaggtggag | 2160 |
| aaaatgcaga tcttggtgga gcgattcaaa ccatactgca actttgataa atatgatgaa | 2220 |
| gatcacagtg gtgatgataa agtcttcctg | 2250 |

<210> SEQ ID NO 70
<211> LENGTH: 750
<212> TYPE: PRT
<213> ORGANISM: Homo sapiens

<400> SEQUENCE: 70

```
Phe Asp Tyr Asn Leu Arg Arg Gly Ala Ala Met Arg Glu Glu Val
1               5                   10                  15

Arg Gln Leu Met Cys Leu Leu Thr Arg Asp Asn Pro Glu Ala Thr Gln
            20                  25                  30

Gln Met Asn Asp Leu Ile Ile Gly Lys Val Ser Thr Ala Leu Lys Ser
        35                  40                  45

His Trp Ala Asn Pro Asp Leu Ala Ser Ser Leu Gln Tyr Glu Met Leu
    50                  55                  60

Leu Leu Thr Asp Ser Ile Ser Lys Glu Asp Ser Cys Trp Glu Leu Arg
65                  70                  75                  80

Leu Arg Cys Ala Leu Ser Leu Phe Leu Met Ala Val Asn Ile Lys Thr
                85                  90                  95

Pro Val Val Glu Asn Ile Thr Leu Met Cys Leu Arg Ile Leu Gln
            100                 105                 110

Lys Leu Ile Lys Pro Pro Ala Pro Thr Ser Lys Asn Lys Asp Val
        115                 120                 125

Pro Val Glu Ala Leu Thr Thr Val Lys Pro Tyr Cys Asn Glu Ile His
    130                 135                 140

Ala Gln Ala Gln Leu Trp Leu Lys Arg Asp Pro Lys Ala Ser Tyr Asp
145                 150                 155                 160
```

-continued

```
Ala Trp Lys Lys Cys Leu Pro Ile Arg Gly Ile Asp Gly Asn Gly Lys
                165                 170                 175
Ala Pro Ser Lys Ser Glu Leu Arg His Leu Tyr Leu Thr Glu Lys Tyr
            180                 185                 190
Val Trp Arg Trp Lys Gln Phe Leu Ser Arg Arg Gly Lys Arg Thr Ser
        195                 200                 205
Pro Leu Asp Leu Lys Leu Gly His Asn Asn Trp Leu Arg Gln Val Leu
    210                 215                 220
Phe Thr Pro Ala Thr Gln Ala Ala Arg Gln Ala Ala Cys Thr Ile Val
225                 230                 235                 240
Glu Ala Leu Ala Thr Ile Pro Ser Arg Lys Gln Gln Val Leu Asp Leu
                245                 250                 255
Leu Thr Ser Tyr Leu Asp Glu Leu Ser Ile Ala Gly Glu Cys Ala Ala
            260                 265                 270
Glu Tyr Leu Ala Leu Tyr Gln Lys Leu Ile Thr Ser Ala His Trp Lys
        275                 280                 285
Val Tyr Leu Ala Ala Arg Gly Val Leu Pro Tyr Val Gly Asn Leu Ile
    290                 295                 300
Thr Lys Glu Ile Ala Arg Leu Leu Ala Leu Glu Glu Ala Thr Leu Ser
305                 310                 315                 320
Thr Asp Leu Gln Gln Gly Tyr Ala Leu Lys Ser Leu Thr Gly Leu Leu
                325                 330                 335
Ser Ser Phe Val Glu Val Glu Ser Ile Lys Arg His Phe Lys Ser Arg
            340                 345                 350
Leu Val Gly Thr Val Leu Asn Gly Tyr Leu Cys Leu Arg Lys Leu Val
        355                 360                 365
Val Gln Arg Thr Lys Leu Ile Asp Glu Thr Gln Asp Met Leu Leu Glu
    370                 375                 380
Met Leu Glu Asp Met Thr Thr Gly Thr Glu Ser Glu Thr Lys Ala Phe
385                 390                 395                 400
Met Ala Val Cys Ile Glu Thr Ala Lys Arg Tyr Asn Leu Asp Asp Tyr
                405                 410                 415
Arg Thr Pro Val Phe Ile Phe Glu Arg Leu Cys Ser Ile Ile Tyr Pro
            420                 425                 430
Glu Glu Asn Glu Val Thr Glu Phe Phe Val Thr Leu Glu Lys Asp Pro
        435                 440                 445
Gln Gln Glu Asp Phe Leu Gln Gly Arg Met Pro Gly Asn Pro Tyr Ser
    450                 455                 460
Ser Asn Glu Pro Gly Ile Gly Pro Leu Met Arg Asp Ile Lys Asn Lys
465                 470                 475                 480
Ile Cys Gln Asp Cys Asp Leu Val Ala Leu Leu Glu Asp Asp Ser Gly
                485                 490                 495
Met Glu Leu Leu Val Asn Asn Lys Ile Ile Ser Leu Asp Leu Pro Val
            500                 505                 510
Ala Glu Val Tyr Lys Lys Val Trp Cys Thr Thr Asn Glu Gly Glu Pro
        515                 520                 525
Met Arg Ile Val Tyr Arg Met Arg Gly Leu Leu Gly Asp Ala Thr Glu
    530                 535                 540
Glu Phe Ile Glu Ser Leu Asp Ser Thr Thr Asp Glu Glu Glu Asp Glu
545                 550                 555                 560
Glu Glu Val Tyr Lys Met Ala Gly Val Met Ala Gln Cys Gly Gly Leu
                565                 570                 575
```

```
Glu Cys Met Leu Asn Arg Leu Ala Gly Ile Arg Asp Phe Lys Gln Gly
            580                 585                 590

Arg His Leu Leu Thr Val Leu Leu Lys Leu Phe Ser Tyr Cys Val Lys
        595                 600                 605

Val Lys Val Asn Arg Gln Gln Leu Val Lys Leu Glu Met Asn Thr Leu
    610                 615                 620

Asn Val Met Leu Gly Thr Leu Asn Leu Ala Leu Val Ala Glu Gln Glu
625                 630                 635                 640

Ser Lys Asp Ser Gly Gly Ala Ala Val Ala Gln Val Leu Ser Ile
                645                 650                 655

Met Glu Ile Ile Leu Asp Glu Ser Asn Ala Glu Pro Leu Ser Glu Asp
        660                 665                 670

Lys Gly Asn Leu Leu Leu Thr Gly Asp Lys Asp Gln Leu Val Met Leu
            675                 680                 685

Leu Asp Gln Ile Asn Ser Thr Phe Val Arg Ser Asn Pro Ser Val Leu
        690                 695                 700

Gln Gly Leu Leu Arg Ile Ile Pro Tyr Leu Ser Phe Gly Glu Val Glu
705                 710                 715                 720

Lys Met Gln Ile Leu Val Glu Arg Phe Lys Pro Tyr Cys Asn Phe Asp
                725                 730                 735

Lys Tyr Asp Glu Asp His Ser Gly Asp Asp Lys Val Phe Leu
            740                 745                 750

<210> SEQ ID NO 71
<211> LENGTH: 2373
<212> TYPE: DNA
<213> ORGANISM: Homo sapiens

<400> SEQUENCE: 71
aagagagacc ccaaggcatc ctatgatgcc tggaagaagt gtcttcctat cagagggata      60
gatggcaatg ggaaagcccc cagcaaatca gagctccgcc atctctattt gactgagaag     120
tatgtgtgga ggtggaaaca gttcctgagt cgtcggggga agaggacctc cccccttggat    180
ctcaaactgg gcataacaa ctggctgcga caagtgcttt tcactccagc aacgcaggcc      240
gcacggcagg cagcctgtac cattgtggaa gctctagcca ccattcccag ccgcaagcag     300
caggtcctgg acctgcttac cagttacctg gatgagctga gcatagctgg ggagtgtgca    360
gctgagtacc tggctctcta ccagaagctc atcacttctg cgcactggaa agtctacttg    420
gcagctcggg gagtcctacc ctatgtgggc aacctcatca ccaaggaaat agctcgtctg    480
ctggccctgg aggaggctac cctgagtacc gatctgcagc agggttatgc ccttaaaagt    540
ctcacaggcc ttctctcctc ctttgttgag gtggaatcca tcaaaagaca ttttaaaagt    600
cgcttggtgg gtactgtgct gaatggatac ctgtgcttgc ggaagctggt ggtgcagagg    660
accaagctga tcgatgagac gcaggacatg ctgctggaga tgctggagga catgaccaca    720
ggtacagaat cagaaaccaa ggccttcatg gctgtgtgca ttgagacagc caagcgctac    780
aatctggatg actaccggac cccggtgttc atcttcgaga ggctctgcag catcatttat    840
cctgaggaga atgaagtcac tgagttcttt gtgaccctgg agaaggatcc ccaacaagaa    900
gacttcttac agggcaggat gcctgggaac ccgtatagca gcaatgagcc aggcatcggg    960
ccgctgatga gggatataaa gaacaagatt tgccaggact gtgacttagt ggccctcctg   1020
gaagatgaca gtggcatgga gcttctagtg aacaataaaa tcattagttt ggaccttcct   1080
gtggctgaag tttacaagaa agtctggtgt accacgaatg agggagagcc catgaggatt   1140
```

```
gtttatcgta tgcgggggct gctgggcgat gccacagagg agttcattga gtccctggac   1200
tctactacag atgaagaaga agatgaagaa gaagtgtata aaatggctgg tgtgatggcc   1260
cagtgtgggg gcctggaatg catgcttaac agactcgcag ggatcagaga tttcaagcag   1320
ggacgccacc ttctaacagt gctactgaaa ttgttcagtt actgcgtgaa ggtgaaagtc   1380
aaccggcagc aactggtcaa actggaaatg aacaccttga acgtcatgct ggggacccta   1440
aacctggccc ttgtagctga caagaaaagc aaggacagtg ggggtgcagc tgtggctgag   1500
caggtgctta gcatcatgga gatcattcta gatgagtcca atgctgagcc cctgagtgag   1560
gacaagggca acctcctcct gacaggtgac aaggatcaac tggtgatgct cttggaccag   1620
atcaacagca cctttgttcg ctccaacccc agtgtgctcc agggcctgct tcgcatcatc   1680
ccgtaccttt cctttggaga ggtggagaaa atgcagatct tggtggagcg attcaaacca   1740
tactgcaact ttgataaata tgatgaagat cacagtggtg atgataaagt cttcctggac   1800
tgcttctgta aaatagctgc tggcatcaag aacaacagca atgggcacca gctgaaggat   1860
ctgattctcc agaagggat cacccagaat gcacttgact acatgaaaaa gcacatccct   1920
agcgccaaga atttggatgc cgacatctgg aaaaagtttt tgtctcgccc agccttgcca   1980
tttatcctaa ggctgcttcg gggcctggcc atccagcacc ctggcaccca ggttctgatt   2040
ggaactgatt ccatcccgaa cctgcataag ctggagcagg tgtccagtga tgagggcatt   2100
gggaccttgg cagagaacct gctggaagcc ctgcgggaac accctgacgt aaacaagaag   2160
attgacgcag cccgcaggga gacccgggca gagaagaaac gcatggccat ggcaatgagg   2220
cagaaggccc tgggcaccct gggcatgacg acaaatgaaa agggccaggt cgtgaccaag   2280
acagcactcc tgaagcagat ggaagagctg atcgaggagc ctggcctcac gtgctgcatc   2340
tgcagggagg gatacaagtt ccagcccaca aag                                2373
```

<210> SEQ ID NO 72
<211> LENGTH: 791
<212> TYPE: PRT
<213> ORGANISM: Homo sapiens

<400> SEQUENCE: 72

```
Lys Arg Asp Pro Lys Ala Ser Tyr Asp Ala Trp Lys Lys Cys Leu Pro
1               5                   10                  15

Ile Arg Gly Ile Asp Gly Asn Gly Lys Ala Pro Ser Lys Ser Glu Leu
            20                  25                  30

Arg His Leu Tyr Leu Thr Glu Lys Tyr Val Trp Arg Trp Lys Gln Phe
        35                  40                  45

Leu Ser Arg Arg Gly Lys Arg Thr Ser Pro Leu Asp Leu Lys Leu Gly
    50                  55                  60

His Asn Asn Trp Leu Arg Gln Val Leu Phe Thr Pro Ala Thr Gln Ala
65                  70                  75                  80

Ala Arg Gln Ala Ala Cys Thr Ile Val Glu Ala Leu Ala Thr Ile Pro
                85                  90                  95

Ser Arg Lys Gln Gln Val Leu Asp Leu Leu Thr Ser Tyr Leu Asp Glu
            100                 105                 110

Leu Ser Ile Ala Gly Glu Cys Ala Ala Glu Tyr Leu Ala Leu Tyr Gln
        115                 120                 125

Lys Leu Ile Thr Ser Ala His Trp Lys Val Tyr Leu Ala Ala Arg Gly
    130                 135                 140

Val Leu Pro Tyr Val Gly Asn Leu Ile Thr Lys Glu Ile Ala Arg Leu
145                 150                 155                 160
```

```
Leu Ala Leu Glu Glu Ala Thr Leu Ser Thr Asp Leu Gln Gln Gly Tyr
                165                 170                 175
Ala Leu Lys Ser Leu Thr Gly Leu Leu Ser Ser Phe Val Glu Val Glu
            180                 185                 190
Ser Ile Lys Arg His Phe Lys Ser Arg Leu Val Gly Thr Val Leu Asn
        195                 200                 205
Gly Tyr Leu Cys Leu Arg Lys Leu Val Val Gln Arg Thr Lys Leu Ile
    210                 215                 220
Asp Glu Thr Gln Asp Met Leu Leu Glu Met Leu Asp Met Thr Thr
225                 230                 235                 240
Gly Thr Glu Ser Glu Thr Lys Ala Phe Met Ala Val Cys Ile Glu Thr
                245                 250                 255
Ala Lys Arg Tyr Asn Leu Asp Asp Tyr Arg Thr Pro Val Phe Ile Phe
            260                 265                 270
Glu Arg Leu Cys Ser Ile Ile Tyr Pro Glu Glu Asn Glu Val Thr Glu
        275                 280                 285
Phe Phe Val Thr Leu Glu Lys Asp Pro Gln Gln Glu Asp Phe Leu Gln
    290                 295                 300
Gly Arg Met Pro Gly Asn Pro Tyr Ser Ser Asn Glu Pro Gly Ile Gly
305                 310                 315                 320
Pro Leu Met Arg Asp Ile Lys Asn Lys Ile Cys Gln Asp Cys Asp Leu
                325                 330                 335
Val Ala Leu Leu Glu Asp Asp Ser Gly Met Glu Leu Leu Val Asn Asn
            340                 345                 350
Lys Ile Ile Ser Leu Asp Leu Pro Val Ala Glu Val Tyr Lys Lys Val
        355                 360                 365
Trp Cys Thr Thr Asn Glu Gly Glu Pro Met Arg Ile Val Tyr Arg Met
    370                 375                 380
Arg Gly Leu Leu Gly Asp Ala Thr Glu Glu Phe Ile Glu Ser Leu Asp
385                 390                 395                 400
Ser Thr Thr Asp Glu Glu Asp Glu Glu Val Tyr Lys Met Ala
                405                 410                 415
Gly Val Met Ala Gln Cys Gly Gly Leu Glu Cys Met Leu Asn Arg Leu
            420                 425                 430
Ala Gly Ile Arg Asp Phe Lys Gln Gly Arg His Leu Leu Thr Val Leu
        435                 440                 445
Leu Lys Leu Phe Ser Tyr Cys Val Lys Val Lys Val Asn Arg Gln Gln
    450                 455                 460
Leu Val Lys Leu Glu Met Asn Thr Leu Asn Val Met Leu Gly Thr Leu
465                 470                 475                 480
Asn Leu Ala Leu Val Ala Glu Gln Ser Lys Asp Ser Gly Gly Ala
                485                 490                 495
Ala Val Ala Glu Gln Val Leu Ser Ile Met Glu Ile Ile Leu Asp Glu
            500                 505                 510
Ser Asn Ala Glu Pro Leu Ser Glu Asp Lys Gly Asn Leu Leu Leu Thr
        515                 520                 525
Gly Asp Lys Asp Gln Leu Val Met Leu Leu Asp Gln Ile Asn Ser Thr
    530                 535                 540
Phe Val Arg Ser Asn Pro Ser Val Leu Gln Gly Leu Leu Arg Ile Ile
545                 550                 555                 560
Pro Tyr Leu Ser Phe Gly Glu Val Glu Lys Met Gln Ile Leu Val Glu
                565                 570                 575
```

```
Arg Phe Lys Pro Tyr Cys Asn Phe Asp Lys Tyr Asp Glu Asp His Ser
            580                 585                 590
Gly Asp Asp Lys Val Phe Leu Asp Cys Phe Cys Lys Ile Ala Ala Gly
        595                 600                 605
Ile Lys Asn Asn Ser Asn Gly His Gln Leu Lys Asp Leu Ile Leu Gln
    610                 615                 620
Lys Gly Ile Thr Gln Asn Ala Leu Asp Tyr Met Lys Lys His Ile Pro
625                 630                 635                 640
Ser Ala Lys Asn Leu Asp Ala Asp Ile Trp Lys Lys Phe Leu Ser Arg
                645                 650                 655
Pro Ala Leu Pro Phe Ile Leu Arg Leu Leu Arg Gly Leu Ala Ile Gln
            660                 665                 670
His Pro Gly Thr Gln Val Leu Ile Gly Thr Asp Ser Ile Pro Asn Leu
        675                 680                 685
His Lys Leu Glu Gln Val Ser Ser Asp Glu Gly Ile Gly Thr Leu Ala
    690                 695                 700
Glu Asn Leu Leu Glu Ala Leu Arg Glu His Pro Asp Val Asn Lys Lys
705                 710                 715                 720
Ile Asp Ala Ala Arg Arg Glu Thr Arg Ala Glu Lys Lys Arg Met Ala
                725                 730                 735
Met Ala Met Arg Gln Lys Ala Leu Gly Thr Leu Gly Met Thr Thr Asn
            740                 745                 750
Glu Lys Gly Gln Val Val Thr Lys Thr Ala Leu Leu Lys Gln Met Glu
        755                 760                 765
Glu Leu Ile Glu Glu Pro Gly Leu Thr Cys Cys Ile Cys Arg Glu Gly
    770                 775                 780
Tyr Lys Phe Gln Pro Thr Lys
785                 790

<210> SEQ ID NO 73
<211> LENGTH: 1797
<212> TYPE: DNA
<213> ORGANISM: Homo sapiens

<400> SEQUENCE: 73
aagagagacc ccaaggcatc ctatgatgcc tggaagaagt gtcttcctat cagagggata      60
gatggcaatg ggaaagcccc cagcaaatca gagctccgcc atctctattt gactgagaag     120
tatgtgtgga ggtggaaaca gttcctgagt cgtcggggga agaggacctc ccccttggat     180
ctcaaactgg gcataacaa ctggctgcga caagtgcttt tcactccagc aacgcaggcc      240
gcacggcagg cagcctgtac cattgtggaa gctctagcca ccattcccag ccgcaagcag     300
caggtcctgg acctgcttac cagttacctg gatgagctga gcatagctgg ggagtgtgca     360
gctgagtacc tggctctcta ccagaagctc atcacttctg cgcactggaa agtctacttg     420
gcagctcggg gagtcctacc ctatgtgggc aacctcatca ccaaggaaat agctcgtctg     480
ctggccctgg aggaggctac cctgagtacc gatctgcagc agggttatgc ccttaaaagt     540
ctcacaggcc ttctctcctc ctttgttgag gtggaatcca tcaaaagaca ttttaaaagt     600
cgcttggtgg gtactgtgct gaatggatac ctgtgcttgc ggaagctggt ggtgcagagg     660
accaagctga tcgatgagac gcaggacatg ctgctggaga tgctggagga catgaccaca     720
ggtacagaat cagaaaccaa ggccttcatg gctgtgtgca ttgagacagc caagcgctac     780
aatctggatg actaccggac cccggtgttc atcttcgaga ggctctgcag catcattat      840 cctgaggaga atgaagtcac tgagttcttt gtgaccctgg agaaggatcc ccaacaagaa     900
```

```
gacttcttac agggcaggat gcctgggaac ccgtatagca gcaatgagcc aggcatcggg     960
ccgctgatga gggatataaa gaacaagatt tgccaggact gtgacttagt ggccctcctg    1020
gaagatgaca gtggcatgga gcttctagtg aacaataaaa tcattagttt ggaccttcct    1080
gtggctgaag tttacaagaa agtctggtgt accacgaatg agggagagcc catgaggatt    1140
gtttatcgta tgcgggggct gctgggcgat gccacagagg agttcattga gtccctggac    1200
tctactacag atgaagaaga agatgaagaa gaagtgtata aaatggctgg tgtgatggcc    1260
cagtgtgggg gcctggaatg catgcttaac agactcgcag ggatcagaga tttcaagcag    1320
ggacgccacc ttctaacagt gctactgaaa ttgttcagtt actgcgtgaa ggtgaaagtc    1380
aaccggcagc aactggtcaa actggaaatg aacaccttga acgtcatgct ggggaccta    1440
aacctggccc ttgtagctga acaagaaagc aaggacagtg ggggtgcagc tgtggctgag    1500
caggtgctta gcatcatgga gatcattcta gatgagtcca atgctgagcc cctgagtgag    1560
gacaagggca acctcctcct gacaggtgac aaggatcaac tggtgatgct cttggaccag    1620
atcaacagca cctttgttcg ctccaacccc agtgtgctcc agggcctgct tcgcatcatc    1680
ccgtaccttt cctttggaga ggtggagaaa atgcagatct tggtggagcg attcaaacca    1740
tactgcaact ttgataaata tgatgaagat cacagtggtg atgataaagt cttcctg      1797
```

<210> SEQ ID NO 74
<211> LENGTH: 599
<212> TYPE: PRT
<213> ORGANISM: Homo sapiens

<400> SEQUENCE: 74

```
Lys Arg Asp Pro Lys Ala Ser Tyr Asp Ala Trp Lys Lys Cys Leu Pro
1               5                   10                  15

Ile Arg Gly Ile Asp Gly Asn Gly Lys Ala Pro Ser Lys Ser Glu Leu
            20                  25                  30

Arg His Leu Tyr Leu Thr Glu Lys Tyr Val Trp Arg Trp Lys Gln Phe
        35                  40                  45

Leu Ser Arg Arg Gly Lys Arg Thr Ser Pro Leu Asp Leu Lys Leu Gly
    50                  55                  60

His Asn Asn Trp Leu Arg Gln Val Leu Phe Thr Pro Ala Thr Gln Ala
65                  70                  75                  80

Ala Arg Gln Ala Ala Cys Thr Ile Val Glu Ala Leu Ala Thr Ile Pro
                85                  90                  95

Ser Arg Lys Gln Gln Val Leu Asp Leu Leu Thr Ser Tyr Leu Asp Glu
            100                 105                 110

Leu Ser Ile Ala Gly Glu Cys Ala Ala Glu Tyr Leu Ala Leu Tyr Gln
        115                 120                 125

Lys Leu Ile Thr Ser Ala His Trp Lys Val Tyr Leu Ala Ala Arg Gly
    130                 135                 140

Val Leu Pro Tyr Val Gly Asn Leu Ile Thr Lys Glu Ile Ala Arg Leu
145                 150                 155                 160

Leu Ala Leu Glu Glu Ala Thr Leu Ser Thr Asp Leu Gln Gln Gly Tyr
                165                 170                 175

Ala Leu Lys Ser Leu Thr Gly Leu Leu Ser Ser Phe Val Glu Val Glu
            180                 185                 190

Ser Ile Lys Arg His Phe Lys Ser Arg Leu Val Gly Thr Val Leu Asn
        195                 200                 205

Gly Tyr Leu Cys Leu Arg Lys Leu Val Val Gln Arg Thr Lys Leu Ile
```

```
            210                 215                 220
Asp Glu Thr Gln Asp Met Leu Leu Glu Met Leu Glu Asp Met Thr Thr
225                 230                 235                 240

Gly Thr Glu Ser Glu Thr Lys Ala Phe Met Ala Val Cys Ile Glu Thr
                245                 250                 255

Ala Lys Arg Tyr Asn Leu Asp Asp Tyr Arg Thr Pro Val Phe Ile Phe
                260                 265                 270

Glu Arg Leu Cys Ser Ile Ile Tyr Pro Glu Glu Asn Glu Val Thr Glu
            275                 280                 285

Phe Phe Val Thr Leu Glu Lys Asp Pro Gln Gln Glu Asp Phe Leu Gln
        290                 295                 300

Gly Arg Met Pro Gly Asn Pro Tyr Ser Ser Asn Glu Pro Gly Ile Gly
305                 310                 315                 320

Pro Leu Met Arg Asp Ile Lys Asn Lys Ile Cys Gln Asp Cys Asp Leu
                325                 330                 335

Val Ala Leu Leu Glu Asp Asp Ser Gly Met Glu Leu Leu Val Asn Asn
                340                 345                 350

Lys Ile Ile Ser Leu Asp Leu Pro Val Ala Glu Val Tyr Lys Lys Val
            355                 360                 365

Trp Cys Thr Thr Asn Glu Gly Glu Pro Met Arg Ile Val Tyr Arg Met
        370                 375                 380

Arg Gly Leu Leu Gly Asp Ala Thr Glu Glu Phe Ile Glu Ser Leu Asp
385                 390                 395                 400

Ser Thr Thr Asp Glu Glu Glu Asp Glu Glu Val Tyr Lys Met Ala
                405                 410                 415

Gly Val Met Ala Gln Cys Gly Gly Leu Glu Cys Met Leu Asn Arg Leu
                420                 425                 430

Ala Gly Ile Arg Asp Phe Lys Gln Gly Arg His Leu Leu Thr Val Leu
            435                 440                 445

Leu Lys Leu Phe Ser Tyr Cys Val Lys Val Lys Val Asn Arg Gln Gln
450                 455                 460

Leu Val Lys Leu Glu Met Asn Thr Leu Asn Val Met Leu Gly Thr Leu
465                 470                 475                 480

Asn Leu Ala Leu Val Ala Glu Gln Glu Ser Lys Asp Ser Gly Gly Ala
                485                 490                 495

Ala Val Ala Glu Gln Val Leu Ser Ile Met Glu Ile Ile Leu Asp Glu
                500                 505                 510

Ser Asn Ala Glu Pro Leu Ser Glu Asp Lys Gly Asn Leu Leu Leu Thr
            515                 520                 525

Gly Asp Lys Asp Gln Leu Val Met Leu Leu Asp Gln Ile Asn Ser Thr
530                 535                 540

Phe Val Arg Ser Asn Pro Ser Val Leu Gln Gly Leu Leu Arg Ile Ile
545                 550                 555                 560

Pro Tyr Leu Ser Phe Gly Glu Val Glu Lys Met Gln Ile Leu Val Glu
                565                 570                 575

Arg Phe Lys Pro Tyr Cys Asn Phe Asp Lys Tyr Asp Glu Asp His Ser
                580                 585                 590

Gly Asp Asp Lys Val Phe Leu
            595

<210> SEQ ID NO 75
<211> LENGTH: 1506
<212> TYPE: DNA
<213> ORGANISM: Homo sapiens
```

<400> SEQUENCE: 75

```
gcccagtgtg ggggcctgga atgcatgctt aacagactcg cagggatcag agatttcaag    60
cagggacgcc accttctaac agtgctactg aaattgttca gttactgcgt gaaggtgaaa   120
gtcaaccggc agcaactggt caaactggaa atgaacacct tgaacgtcat gctggggacc   180
ctaaacctgg cccttgtagc tgaacaagaa agcaaggaca gtgggggtgc agctgtggct   240
gagcaggtgc ttagcatcat ggagatcatt ctagatgagt ccaatgctga gcccctgagt   300
gaggacaagg gcaacctcct cctgacaggt gacaaggatc aactggtgat gctcttggac   360
cagatcaaca gcacctttgt tcgctccaac cccagtgtgc tccagggcct gcttcgcatc   420
atcccgtacc tttcctttgg agaggtggag aaaatgcaga tcttggtgga gcgattcaaa   480
ccatactgca actttgataa atatgatgaa atcacagtg gtgatgataa agtcttcctg   540
gactgcttct gtaaaatagc tgctggcatc aagaacaaca gcaatgggca ccagctgaag   600
gatctgattc tccagaaggg gatcacccag aatgcacttg actacatgaa aaagcacatc   660
cctagcgcca agaatttgga tgccgacatc tggaaaaagt ttttgtctcg cccagccttg   720
ccatttatcc taaggctgct tcggggcctg gccatccagc accctggcac ccaggttctg   780
attggaactg attccatccc gaacctgcat aagctggagc aggtgtccag tgatgagggc   840
attgggacct tggcagagaa cctgctgaaa gccctgcggg aacaccctga cgtaaacaag   900
aagattgacg cagcccgcag ggagacccgg gcagagaaga acgcatggc catggcaatg   960
aggcagaagg ccctgggcac cctgggcatg acgacaaatg aaaagggcca ggtcgtgacc  1020
aagacagcac tcctgaagca gatggaagag ctgatcgagg agcctggcct cacgtgctgc  1080
atctgcaggg agggatacaa gttccagccc acaaaggtcc tgggcattta taccttcacg  1140
aagcgggtag ccttggagga gatggagaat aagccccgga acagcagggg ctacagcacc  1200
gtgtcccact tcaacattgt gcactacgac tgccatctgg ctgccgtcag gttggctcga  1260
ggccgggaag agtgggagag tgccgccctg cagaatgcca acaccaagtg caacgggctc  1320
cttccggtct ggggaccttca tgtccctgaa tcagcttttg ccacttgctt ggcaagacac  1380
aacacttacc tccaggaatg tacaggccag cgggagccca cgtatcagct caacatccat  1440
gacatcaaac tgctcttcct gcgcttcgcc atggagcagt cgttcagcgc agacactggc  1500
gggggc                                                              1506
```

<210> SEQ ID NO 76
<211> LENGTH: 502
<212> TYPE: PRT
<213> ORGANISM: Homo sapiens

<400> SEQUENCE: 76

```
Ala Gln Cys Gly Gly Leu Glu Cys Met Leu Asn Arg Leu Ala Gly Ile
  1               5                  10                  15

Arg Asp Phe Lys Gln Gly Arg His Leu Leu Thr Val Leu Leu Lys Leu
             20                  25                  30

Phe Ser Tyr Cys Val Lys Val Lys Val Asn Arg Gln Gln Leu Val Lys
         35                  40                  45

Leu Glu Met Asn Thr Leu Asn Val Met Leu Gly Thr Leu Asn Leu Ala
     50                  55                  60

Leu Val Ala Glu Gln Glu Ser Lys Asp Ser Gly Gly Ala Ala Val Ala
 65                  70                  75                  80

Glu Gln Val Leu Ser Ile Met Glu Ile Ile Leu Asp Glu Ser Asn Ala
```

-continued

```
                85                  90                  95
Glu Pro Leu Ser Glu Asp Lys Gly Asn Leu Leu Thr Gly Asp Lys
                100                 105                 110
Asp Gln Leu Val Met Leu Leu Asp Gln Ile Asn Ser Thr Phe Val Arg
                115                 120                 125
Ser Asn Pro Ser Val Leu Gln Gly Leu Leu Arg Ile Ile Pro Tyr Leu
                130                 135                 140
Ser Phe Gly Glu Val Glu Lys Met Gln Ile Leu Val Glu Arg Phe Lys
145             150                 155                 160
Pro Tyr Cys Asn Phe Asp Lys Tyr Asp Glu Asp His Ser Gly Asp Asp
                165                 170                 175
Lys Val Phe Leu Asp Cys Phe Cys Lys Ile Ala Ala Gly Ile Lys Asn
                180                 185                 190
Asn Ser Asn Gly His Gln Leu Lys Asp Leu Ile Leu Gln Lys Gly Ile
                195                 200                 205
Thr Gln Asn Ala Leu Asp Tyr Met Lys Lys His Ile Pro Ser Ala Lys
                210                 215                 220
Asn Leu Asp Ala Asp Ile Trp Lys Lys Phe Leu Ser Arg Pro Ala Leu
225             230                 235                 240
Pro Phe Ile Leu Arg Leu Leu Arg Gly Leu Ala Ile Gln His Pro Gly
                245                 250                 255
Thr Gln Val Leu Ile Gly Thr Asp Ser Ile Pro Asn Leu His Lys Leu
                260                 265                 270
Glu Gln Val Ser Ser Asp Glu Gly Ile Gly Thr Leu Ala Glu Asn Leu
                275                 280                 285
Leu Glu Ala Leu Arg Glu His Pro Asp Val Asn Lys Lys Ile Asp Ala
                290                 295                 300
Ala Arg Arg Glu Thr Arg Ala Glu Lys Lys Arg Met Ala Met Ala Met
305             310                 315                 320
Arg Gln Lys Ala Leu Gly Thr Leu Gly Met Thr Thr Asn Glu Lys Gly
                325                 330                 335
Gln Val Val Thr Lys Thr Ala Leu Leu Lys Gln Met Glu Glu Leu Ile
                340                 345                 350
Glu Glu Pro Gly Leu Thr Cys Cys Ile Cys Arg Glu Gly Tyr Lys Phe
                355                 360                 365
Gln Pro Thr Lys Val Leu Gly Ile Tyr Thr Phe Thr Lys Arg Val Ala
                370                 375                 380
Leu Glu Glu Met Glu Asn Lys Pro Arg Lys Gln Gln Gly Tyr Ser Thr
385             390                 395                 400
Val Ser His Phe Asn Ile Val His Tyr Asp Cys His Leu Ala Ala Val
                405                 410                 415
Arg Leu Ala Arg Gly Arg Glu Glu Trp Glu Ser Ala Ala Leu Gln Asn
                420                 425                 430
Ala Asn Thr Lys Cys Asn Gly Leu Leu Pro Val Trp Gly Pro His Val
                435                 440                 445
Pro Glu Ser Ala Phe Ala Thr Cys Leu Ala Arg His Asn Thr Tyr Leu
                450                 455                 460
Gln Glu Cys Thr Gly Gln Arg Glu Pro Thr Tyr Gln Leu Asn Ile His
465             470                 475                 480
Asp Ile Lys Leu Leu Phe Leu Arg Phe Ala Met Glu Gln Ser Phe Ser
                485                 490                 495
Ala Asp Thr Gly Gly Gly
                500
```

<210> SEQ ID NO 77
<211> LENGTH: 1668
<212> TYPE: DNA
<213> ORGANISM: Homo sapiens

<400> SEQUENCE: 77

```
gcccagtgtg ggggcctgga atgcatgctt aacagactcg cagggatcag agatttcaag      60
cagggacgcc accttctaac agtgctactg aaattgttca gttactgcgt gaaggtgaaa     120
gtcaaccggc agcaactggt caaactggaa atgaacacct tgaacgtcat gctggggacc     180
ctaaacctgg cccttgtagc tgaacaagaa agcaaggaca gtggggggtgc agctgtggct     240
gagcaggtgc ttagcatcat ggagatcatt ctagatgagt ccaatgctga gcccctgagt     300
gaggacaagg gcaacctcct cctgacaggt gacaaggatc aactggtgat gctcttggac     360
cagatcaaca gcacctttgt tcgctccaac cccagtgtgc tccagggcct gcttcgcatc     420
atcccgtacc tttcctttgg agaggtggag aaaatgcaga tcttggtgga gcgattcaaa     480
ccatactgca actttgataa atatgatgaa gatcacagtg gtgatgataa agtcttcctg     540
gactgcttct gtaaaatagc tgctggcatc aagaacaaca gcaatgggca ccagctgaag     600
gatctgattc tccagaaggg gatcacccag aatgcacttg actacatgaa aaagcacatc     660
cctagcgcca gaatttgga tgccgacatc tggaaaaagt ttttgtctcg cccagccttg     720
ccatttatcc taaggctgct tcggggcctg gccatccagc ccctggcac ccaggttctg     780
attggaactg attccatccc gaacctgcat aagctggagc aggtgtccag tgatgagggc     840
attgggacct tggcagagaa cctgctggaa gccctgcggg aacaccctga cgtaaacaag     900
aagattgacg cagcccgcag ggagacccgg cagagaaga aacgcatggc catggcaatg     960
aggcagaagg ccctgggcac cctgggcatg acgacaaatg aaaagggcca ggtcgtgacc    1020
aagacagcac tcctgaagca gatggaagag ctgatcgagg agcctggcct cacgtgctgc    1080
atctgcaggg agggatacaa gttccagccc acaaaggtcc tgggcattta taccttcacg    1140
aagcgggtag ccttggagga gatggagaat aagcccgga acagcaggg ctacagcacc    1200
gtgtcccact tcaacattgt gcactacgac tgccatctgg ctgccgtcag gttggctcga    1260
ggccgggaag agtgggagag tgccgccctg cagaatgcca acaccaagtg caacgggctc    1320
cttccggtct ggggacctca tgtccctgaa tcagcttttg ccacttgctt ggcaagacac    1380
aacacttacc tccaggaatg tacaggccag cgggagccca cgtatcagct caacatccat    1440
gacatcaaac tgctcttcct gcgcttcgcc atggagcagt cgttcagcgc agacactggc    1500
ggggcggcc gggagagcaa catccacctg atcccgtaca tcattcacac tgtgctttac    1560
gtcctgaaca caacccgagc aacttcccga gaagagaaga acctccaagg ctttctggaa    1620
cagcccaagg agaagtgggt ggagagtgcc tttgaagtgg acgggccc              1668
```

<210> SEQ ID NO 78
<211> LENGTH: 556
<212> TYPE: PRT
<213> ORGANISM: Homo sapiens

<400> SEQUENCE: 78

```
Ala Gln Cys Gly Gly Leu Glu Cys Met Leu Asn Arg Leu Ala Gly Ile
1               5                   10                  15

Arg Asp Phe Lys Gln Gly Arg His Leu Leu Thr Val Leu Leu Lys Leu
            20                  25                  30
```

```
Phe Ser Tyr Cys Val Lys Val Lys Val Asn Arg Gln Gln Leu Val Lys
            35                  40                  45

Leu Glu Met Asn Thr Leu Asn Val Met Leu Gly Thr Leu Asn Leu Ala
 50                  55                  60

Leu Val Ala Glu Gln Glu Ser Lys Asp Ser Gly Gly Ala Ala Val Ala
 65                  70                  75                  80

Glu Gln Val Leu Ser Ile Met Glu Ile Ile Leu Asp Glu Ser Asn Ala
                 85                  90                  95

Glu Pro Leu Ser Glu Asp Lys Gly Asn Leu Leu Leu Thr Gly Asp Lys
                100                 105                 110

Asp Gln Leu Val Met Leu Leu Asp Gln Ile Asn Ser Thr Phe Val Arg
            115                 120                 125

Ser Asn Pro Ser Val Leu Gln Gly Leu Leu Arg Ile Ile Pro Tyr Leu
130                 135                 140

Ser Phe Gly Glu Val Glu Lys Met Gln Ile Leu Val Glu Arg Phe Lys
145                 150                 155                 160

Pro Tyr Cys Asn Phe Asp Lys Tyr Asp Glu Asp His Ser Gly Asp Asp
                165                 170                 175

Lys Val Phe Leu Asp Cys Phe Cys Lys Ile Ala Ala Gly Ile Lys Asn
                180                 185                 190

Asn Ser Asn Gly His Gln Leu Lys Asp Leu Ile Leu Gln Lys Gly Ile
        195                 200                 205

Thr Gln Asn Ala Leu Asp Tyr Met Lys Lys His Ile Pro Ser Ala Lys
    210                 215                 220

Asn Leu Asp Ala Asp Ile Trp Lys Lys Phe Leu Ser Arg Pro Ala Leu
225                 230                 235                 240

Pro Phe Ile Leu Arg Leu Leu Arg Gly Leu Ala Ile Gln His Pro Gly
                245                 250                 255

Thr Gln Val Leu Ile Gly Thr Asp Ser Ile Pro Asn Leu His Lys Leu
                260                 265                 270

Glu Gln Val Ser Ser Asp Glu Gly Ile Gly Thr Leu Ala Glu Asn Leu
            275                 280                 285

Leu Glu Ala Leu Arg Glu His Pro Asp Val Asn Lys Lys Ile Asp Ala
290                 295                 300

Ala Arg Arg Glu Thr Arg Ala Glu Lys Lys Arg Met Ala Met Ala Met
305                 310                 315                 320

Arg Gln Lys Ala Leu Gly Thr Leu Gly Met Thr Thr Asn Glu Lys Gly
                325                 330                 335

Gln Val Val Thr Lys Thr Ala Leu Leu Lys Gln Met Glu Glu Leu Ile
                340                 345                 350

Glu Glu Pro Gly Leu Thr Cys Cys Ile Cys Arg Glu Gly Tyr Lys Phe
            355                 360                 365

Gln Pro Thr Lys Val Leu Gly Ile Tyr Thr Phe Thr Lys Arg Val Ala
    370                 375                 380

Leu Glu Glu Met Glu Asn Lys Pro Arg Lys Gln Gln Gly Tyr Ser Thr
385                 390                 395                 400

Val Ser His Phe Asn Ile Val His Tyr Asp Cys His Leu Ala Ala Val
                405                 410                 415

Arg Leu Ala Arg Gly Arg Glu Trp Glu Ser Ala Ala Leu Gln Asn
                420                 425                 430

Ala Asn Thr Lys Cys Asn Gly Leu Leu Pro Val Trp Gly Pro His Val
                435                 440                 445

Pro Glu Ser Ala Phe Ala Thr Cys Leu Ala Arg His Asn Thr Tyr Leu
```

```
                450             455             460
Gln Glu Cys Thr Gly Gln Arg Glu Pro Thr Tyr Gln Leu Asn Ile His
465                 470                 475                 480

Asp Ile Lys Leu Leu Phe Leu Arg Phe Ala Met Glu Gln Ser Phe Ser
                485                 490                 495

Ala Asp Thr Gly Gly Gly Arg Glu Ser Asn Ile His Leu Ile Pro
            500                 505                 510

Tyr Ile Ile His Thr Val Leu Tyr Val Leu Asn Thr Thr Arg Ala Thr
            515                 520                 525

Ser Arg Glu Glu Lys Asn Leu Gln Gly Phe Leu Glu Gln Pro Lys Glu
            530                 535                 540

Lys Trp Val Glu Ser Ala Phe Glu Val Asp Gly Pro
545                 550                 555

<210> SEQ ID NO 79
<211> LENGTH: 1791
<212> TYPE: DNA
<213> ORGANISM: Homo sapiens

<400> SEQUENCE: 79
```

| | | | | | |
|---|---|---|---|---|---|
| gcccagtgtg | ggggcctgga | atgcatgctt | aacagactcg | cagggatcag | agatttcaag | 60 |
| cagggacgcc | accttctaac | agtgctactg | aaattgttca | gttactgcgt | gaaggtgaaa | 120 |
| gtcaaccggc | agcaactggt | caaactggaa | atgaacacct | tgaacgtcat | gctgggggacc | 180 |
| ctaaacctgg | cccttgtagc | tgaacaagaa | agcaaggaca | gtgggggtgc | agctgtggct | 240 |
| gagcaggtgc | ttagcatcat | ggagatcatt | ctagatgagt | ccaatgctga | gccctgagt | 300 |
| gaggacaagg | gcaacctcct | cctgacaggt | gacaaggatc | aactggtgat | gctcttggac | 360 |
| cagatcaaca | gcacctttgt | tcgctccaac | cccagtgtgc | tccagggcct | gcttcgcatc | 420 |
| atcccgtacc | tttcctttgg | agaggtggag | aaaatgcaga | tcttggtgga | gcgattcaaa | 480 |
| ccatactgca | actttgataa | atatgatgaa | atcacagtg | gtgatgataa | agtcttcctg | 540 |
| gactgcttct | gtaaaatagc | tgctggcatc | aagaacaaca | gcaatgggca | ccagctgaag | 600 |
| gatctgattc | tccagaaggg | gatcacccag | aatgcacttg | actacatgaa | aaagcacatc | 660 |
| cctagcgcca | agaatttgga | tgccgacatc | tggaaaaagt | ttttgtctcg | cccagccttg | 720 |
| ccatttatcc | taaggctgct | tcggggcctg | gccatccagc | ccctggcac | ccaggttctg | 780 |
| attggaactg | attccatccc | gaacctgcat | aagctggagc | aggtgtccag | tgatgagggc | 840 |
| attgggacct | tggcagagaa | cctgctgaa | gccctgcggg | aacaccctga | cgtaaacaag | 900 |
| aagattgacg | cagcccgcag | ggagacccgg | gcagagaaga | acgcatggc | catggcaatg | 960 |
| aggcagaagg | ccctgggcac | cctgggcatg | acgacaaatg | aaaagggcca | ggtcgtgacc | 1020 |
| aagacagcac | tcctgaagca | gatggaagag | ctgatcgagg | agcctggcct | cacgtgctgc | 1080 |
| atctgcaggg | agggatacaa | gttccagccc | acaaaggtcc | tgggcattta | accttcacg | 1140 |
| aagcgggtag | ccttggagga | gatggagaat | aagcccggga | acagcaggg | ctacagcacc | 1200 |
| gtgtcccact | tcaacattgt | gcactacgac | tgccatctgg | ctgccgtcag | gttggctcga | 1260 |
| ggccgggaag | agtgggagag | tgccgccctg | cagaatgcca | acaccaagtg | caacgggctc | 1320 |
| cttccggtct | ggggacctca | tgtccctgaa | tcagcttttg | ccacttgctt | ggcaagacac | 1380 |
| aacacttacc | tccaggaatg | tacaggccag | cgggagccca | cgtatcagct | caacatccat | 1440 |
| gacatcaaac | tgctcttcct | gcgcttcgcc | atggagcagt | cgttcagcgc | agacactggc | 1500 |
| ggggcggcc | gggagagcaa | catccacctg | atcccgtaca | tcattcacac | tgtgctttac | 1560 |

```
gtcctgaaca acccccgagc aacttcccga gaagagaaga acctccaagg ctttctggaa    1620
cagcccaagg agaagtgggt ggagagtgcc tttgaagtgg acgggcccta ctatttcaca    1680
gtcttggccc ttcacatcct gcccctgag cagtggagag ccacacgtgt ggaaatcttg     1740
cggaggctgt tggtgacctc gcaggctcgg gcagtggctc caggtggagc c             1791
```

<210> SEQ ID NO 80
<211> LENGTH: 597
<212> TYPE: PRT
<213> ORGANISM: Homo sapiens

<400> SEQUENCE: 80

```
Ala Gln Cys Gly Gly Leu Glu Cys Met Leu Asn Arg Leu Ala Gly Ile
1               5                   10                  15

Arg Asp Phe Lys Gln Gly Arg His Leu Leu Thr Val Leu Leu Lys Leu
            20                  25                  30

Phe Ser Tyr Cys Val Lys Val Lys Val Asn Arg Gln Gln Leu Val Lys
        35                  40                  45

Leu Glu Met Asn Thr Leu Asn Val Met Leu Gly Thr Leu Asn Leu Ala
    50                  55                  60

Leu Val Ala Glu Gln Glu Ser Lys Asp Ser Gly Ala Ala Val Ala
65                  70                  75                  80

Glu Gln Val Leu Ser Ile Met Glu Ile Ile Leu Asp Glu Ser Asn Ala
                85                  90                  95

Glu Pro Leu Ser Glu Asp Lys Gly Asn Leu Leu Leu Thr Gly Asp Lys
            100                 105                 110

Asp Gln Leu Val Met Leu Leu Asp Gln Ile Asn Ser Thr Phe Val Arg
        115                 120                 125

Ser Asn Pro Ser Val Leu Gln Gly Leu Leu Arg Ile Ile Pro Tyr Leu
    130                 135                 140

Ser Phe Gly Glu Val Glu Lys Met Gln Ile Leu Val Glu Arg Phe Lys
145                 150                 155                 160

Pro Tyr Cys Asn Phe Asp Lys Tyr Asp Glu Asp His Ser Gly Asp Asp
                165                 170                 175

Lys Val Phe Leu Asp Cys Phe Cys Lys Ile Ala Ala Gly Ile Lys Asn
            180                 185                 190

Asn Ser Asn Gly His Gln Leu Lys Asp Leu Ile Leu Gln Lys Gly Ile
        195                 200                 205

Thr Gln Asn Ala Leu Asp Tyr Met Lys Lys His Ile Pro Ser Ala Lys
    210                 215                 220

Asn Leu Asp Ala Asp Ile Trp Lys Lys Phe Leu Ser Arg Pro Ala Leu
225                 230                 235                 240

Pro Phe Ile Leu Arg Leu Leu Arg Gly Leu Ala Ile Gln His Pro Gly
                245                 250                 255

Thr Gln Val Leu Ile Gly Thr Asp Ser Ile Pro Asn Leu His Lys Leu
            260                 265                 270

Glu Gln Val Ser Ser Asp Glu Gly Ile Gly Thr Leu Ala Glu Asn Leu
        275                 280                 285

Leu Glu Ala Leu Arg Glu His Pro Asp Val Asn Lys Lys Ile Asp Ala
    290                 295                 300

Ala Arg Arg Glu Thr Arg Ala Glu Lys Lys Arg Met Ala Met Ala Met
305                 310                 315                 320

Arg Gln Lys Ala Leu Gly Thr Leu Gly Met Thr Thr Asn Glu Lys Gly
                325                 330                 335
```

-continued

```
Gln Val Val Thr Lys Thr Ala Leu Leu Lys Gln Met Glu Glu Leu Ile
            340             345             350

Glu Glu Pro Gly Leu Thr Cys Cys Ile Cys Arg Glu Gly Tyr Lys Phe
        355             360             365

Gln Pro Thr Lys Val Leu Gly Ile Tyr Thr Phe Thr Lys Arg Val Ala
    370             375             380

Leu Glu Glu Met Glu Asn Lys Pro Arg Lys Gln Gln Gly Tyr Ser Thr
385             390             395             400

Val Ser His Phe Asn Ile Val His Tyr Asp Cys His Leu Ala Ala Val
            405             410             415

Arg Leu Ala Arg Gly Arg Glu Glu Trp Glu Ser Ala Ala Leu Gln Asn
        420             425             430

Ala Asn Thr Lys Cys Asn Gly Leu Leu Pro Val Trp Gly Pro His Val
        435             440             445

Pro Glu Ser Ala Phe Ala Thr Cys Leu Ala Arg His Asn Thr Tyr Leu
    450             455             460

Gln Glu Cys Thr Gly Gln Arg Glu Pro Thr Tyr Gln Leu Asn Ile His
465             470             475             480

Asp Ile Lys Leu Leu Phe Leu Arg Phe Ala Met Glu Gln Ser Phe Ser
            485             490             495

Ala Asp Thr Gly Gly Gly Arg Glu Ser Asn Ile His Leu Ile Pro
        500             505             510

Tyr Ile Ile His Thr Val Leu Tyr Val Leu Asn Thr Thr Arg Ala Thr
        515             520             525

Ser Arg Glu Glu Lys Asn Leu Gln Gly Phe Leu Glu Gln Pro Lys Glu
    530             535             540

Lys Trp Val Glu Ser Ala Phe Glu Val Asp Gly Pro Tyr Tyr Phe Thr
545             550             555             560

Val Leu Ala Leu His Ile Leu Pro Pro Glu Gln Trp Arg Ala Thr Arg
            565             570             575

Val Glu Ile Leu Arg Arg Leu Leu Val Thr Ser Gln Ala Arg Ala Val
        580             585             590

Ala Pro Gly Gly Ala
        595
```